US010174329B2

(12) United States Patent
Deng et al.

(10) Patent No.: US 10,174,329 B2
(45) Date of Patent: Jan. 8, 2019

(54) METHODS FOR INCREASING THE STABILITY OF PRODUCTION OF COMPOUNDS IN MICROBIAL HOST CELLS

(71) Applicant: Algenol Biotech LLC, Fort Myers, FL (US)

(72) Inventors: Ming-De Deng, Manitowoc, WI (US); Ulf Dühring, Berlin (DE); Frank Uliczka, Berlin (DE); Kimberly Lynn Anderson, Estero, FL (US)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

(21) Appl. No.: 15/622,637

(22) Filed: Jun. 14, 2017

(65) Prior Publication Data

US 2017/0283811 A1 Oct. 5, 2017

Related U.S. Application Data

(63) Continuation of application No. PCT/US2015/000210, filed on Dec. 23, 2015.

(Continued)

(51) Int. Cl.

| | |
|---|---|
| *C12P 7/00* | (2006.01) |
| *C12N 1/20* | (2006.01) |
| *C12N 15/00* | (2006.01) |
| *C12Q 1/68* | (2018.01) |
| *C07H 21/04* | (2006.01) |
| *C12N 15/74* | (2006.01) |
| *C07K 14/195* | (2006.01) |
| *C12N 15/52* | (2006.01) |
| *C12P 7/06* | (2006.01) |
| *C12N 9/04* | (2006.01) |

(Continued)

(52) U.S. Cl.

CPC ............ *C12N 15/74* (2013.01); *C07K 14/195* (2013.01); *C12N 9/0006* (2013.01); *C12N 9/0008* (2013.01); *C12N 9/0044* (2013.01); *C12N 15/52* (2013.01); *C12P 7/06* (2013.01); *C12P 7/065* (2013.01); *C12Y 101/01001* (2013.01); *C12Y 102/04001* (2013.01); *C12Y 107/07001* (2013.01); *Y02E 50/17* (2013.01)

(58) Field of Classification Search

None

See application file for complete search history.

(56) References Cited

U.S. PATENT DOCUMENTS

| | | | |
|---|---|---|---|
| 6,306,639 | B1 | 10/2001 | Woods et al. |
| 6,699,696 | B2 | 3/2004 | Woods et al. |

(Continued)

FOREIGN PATENT DOCUMENTS

| | | | |
|---|---|---|---|
| EP | 2285948 | B1 | 1/2014 |
| WO | WO/2008/106803 | | 9/2008 |

(Continued)

OTHER PUBLICATIONS

Deng, M.D. et al., (1999), “Ethanol Synthesis by Genetic Engineering in Cyanobacteria”, Applied and Environmental Microbiology, 65:523-52.

(Continued)

*Primary Examiner* — Yong D Pak

(57) ABSTRACT

Methods for increasing the genetic stability of genetically enhanced microbial host cells capable of producing a compound of interest are disclosed.

25 Claims, 16 Drawing Sheets

Specification includes a Sequence Listing.

pABICyano1-6.8 kb 6828 bp

1000

2000

3000

4000

5000

6000

Rep active site motif potential origin of replication

Related U.S. Application Data

(60) Provisional application No. 62/096,383, filed on Dec. 23, 2014.

(51) Int. Cl.
*C12N 9/02* (2006.01)
*C12N 9/06* (2006.01)

(56) References Cited

U.S. PATENT DOCUMENTS

| | | | | |
|---|---|---|---|---|
| 7,770,322 | B2 | 8/2010 | Huntley | |
| 7,794,969 | B1 | 9/2010 | Reppas et al. | |
| 7,968,321 | B1 | 6/2011 | Green et al. | |
| 7,981,647 | B2 | 7/2011 | Berry et al. | |
| 8,048,666 | B1 | 11/2011 | Green et al. | |
| 8,183,027 | B2 | 5/2012 | Reppas et al. | |
| 8,216,816 | B2 | 7/2012 | Green et al. | |
| 8,268,601 | B2 | 9/2012 | Huntley | |
| 8,304,232 | B2 | 11/2012 | Morgan et al. | |
| 8,404,466 | B2 | 3/2013 | Baier et al. | |
| 8,465,954 | B2 | 6/2013 | Green et al. | |
| 8,709,808 | B2 | 4/2014 | Cuello et al. | |
| 8,753,840 | B2 | 6/2014 | Vermaas | |
| 8,846,369 | B2 | 9/2014 | Piven et al. | |
| 8,986,964 | B2 | 3/2015 | Green et al. | |
| 9,127,297 | B2 | 9/2015 | Dühring et al. | |
| 9,157,101 | B2 | 10/2015 | Piven et al. | |
| 9,163,264 | B2 | 10/2015 | Green et al. | |
| 9,315,820 | B2 | 4/2016 | Dühring et al. | |
| 9,315,832 | B2 | 4/2016 | Piven et al. | |
| 9,476,067 | B2 * | 10/2016 | Wang | C12N 15/70 |
| 9,493,794 | B2 | 11/2016 | Dühring et al. | |
| 9,493,795 | B2 | 11/2016 | Dühring et al. | |
| 9,551,014 | B2 | 1/2017 | Dühring et al. | |
| 9,650,642 | B2 | 5/2017 | Woods et al. | |
| 9,765,364 | B2 | 9/2017 | Dühring et al. | |
| 9,862,974 | B2 * | 1/2018 | Wang | C12P 7/06 |
| 2010/0297736 | A1 | 11/2010 | Duhring et al. | |
| 2013/0143284 | A1 | 6/2013 | Roberts et al. | |
| 2014/0113342 | A1 | 4/2014 | Ziegler et al. | |
| 2014/0154762 | A1 | 6/2014 | Duehring et al. | |
| 2014/0178958 | A1 * | 6/2014 | Piven | C12P 7/065 435/161 |
| 2015/0211028 | A1 | 7/2015 | Chin et al. | |
| 2015/0232884 | A1 | 8/2015 | Duehring et al. | |
| 2017/0175148 | A1 | 6/2017 | Kramer et al. | |
| 2018/0112225 | A1 | 4/2018 | Roessler et al. | |

FOREIGN PATENT DOCUMENTS

| | | | |
|---|---|---|---|
| WO | WO/2009/111513 | 9/2009 | |
| WO | WO/2010/044960 | 4/2010 | |
| WO | WO/2011/029013 | 3/2011 | |
| WO | WO/2011/094457 | 8/2011 | |
| WO | WO/2012/000057 | 1/2012 | |
| WO | WO/2012/101459 | 8/2012 | |
| WO | WO/2014/100799 | 6/2014 | |
| WO | WO-2014100798 A1 * | 6/2014 | C12N 15/70 |
| WO | WO/2016105405 | 6/2016 | |
| WO | WO/2016105483 | 6/2016 | |

OTHER PUBLICATIONS

Blanch, H.W., (2012), "Bioprocessing for Biofuels", Current Opinion in Biotechnology, 23:390-395.
Wang, B., (2012), "Application of synthetic biology in cyanobacteria and algae", Frontiers in Microbiology, 3 (article 344): 1-15.
Shih, PM., (2013), "Improving the coverage of the cyanobacterial phylum using diversity-driven genome sequencing", Proceedings of the National Academy of Sciences, 110:1053-1058.
Rippka, R., (1979),"Generic assignments, strain histories and properties of pure cultures of cyanobacteria", Journal of General Microbiology, 111:1-61.
Helman et al., (2003), "Genes Encoding A-Type Flavoproteins are essential for Photoreduction of O2 in Cyanobacteria", Current Biology, 13:230-235.
Broun et al., (1998), "Catalytic plasticity of fatty acid modification enzymes underlying chemical diversity of plant lipids", Science, 282:1315-1317.
Chica et al., (2005), "Semi-rational approaches to engineering enzyme activity: combining the benefits of directed evolution and rational design", Curr. Opi. Biotechnol., 16:378-384.
Devos et al., (2000), "Practical limits of function prediction", Proteins: Structure, Function, and Genetics, 41:98-107.
Kisselev et al., (2002), "Polypeptide release factors in prokaryotes and eukaryotes: same function, different structure", Structure, 10:8-9.
Seffernick. et al., (2001), "Melamine deaminase and Atrazine chlorohydrolase; 98 percent identical but functionally different", J. Bacteriol., 183:2405-2410.
Whisstock et al., (2003), "Prediction of protein function from protein sequence", Q. Rev. Biophysics, 36:307-340.
Wishart et al., (1995), "A single mutation converts a novel phosphotyrosine binding domain into a dual-specificity phosphatase", J. Biol. Chem., 270:26782-26785.
Witkowski et al., (1999), "Conversion of b-ketoacyl synthase to a Malonyl Decarboxylase by replacement of the active cysteine with glutamine", Biochemistry, 38:11643-11650.
Trautmann et al., (2013), GenBank accession No. AGF53389.
Neale et al., (1993), GenBank accession No. AAA27697.
Sen et al., (2007), "Developments in Directed Evolution for Improving Enzyme Functions", Appl. Biochem. Biotechnol., 143:212-223.
Wilde et al., (2001), "Characterization of the Cyanobacterial ycf37: Mutation Decreases the Photosystem I Content", Biochemical Journal, 357:211-216.
Nakamura et al., (2002), "Complete Genome Structure of the Thermophilic Cyanobacterium Thermosynechococcus Elongatus BP-1", DNA Research, 9:123-130.
Kirkwood, D., (1993), "Nutrients: Practical Notes on their Determination in Seawater", HELCOM 1994; ICES/HELCOM Workshop on Quality Assurance of Chemical Analytical Procedures for the Baltic Monitoring Programme, Baltic Sea Environmental Proceedings of Oct. 5, 1993, 58:23-47.
Bass et al., (2002), "Isolation and Characterization of cIV25, a Bacteriodes fragilis Chromosomal Transfer Factor Resembling Multiple *Bacteriodes* sp. Mobilizable Transposons", Journal of Bacteriology, 184:1895-1904.
Kongsuwan et al, (2006), "The Plasmid RK2 Replication Initiator Protein (TrfA) Binds to the Sliding Clamp Beta Subunit of DNA Polymerase III: Implication for the Toxicity of a Peptide Derived From the Amino-Terminal Portion of 33-Kilodalton TrfA", Journal of Bacteriology, 188:5501-5509.
International Preliminary Report on Patentability (IPRP) and Written Opinion for International Patent Application No. PCT/US2015/000210, dated Jun. 27, 2017; 7 pages.
Pfleger et al., (2006), "Combinatorial engineering of intergenic regions in operons tunes expression of multiple genes", Nature Biotechnology, 24:1027-1032.
Moro et al., (2007), "Cyanobacterium aponinum, a new Cyanoprokaryote from the microbial mat of Euganean thermal springs (Padua, Italy)", Algological Studies, 123:1-15.
Chen et al. (2004), "Operon prediction by comparative genomics: an application to the *Synechococcus* sp. WH8102 genome", Nucleic Acids Research, 32:2147-2157.

* cited by examiner

```
aatatttttc gtcagatacg caaaccttac aaacataatt aacaactgaa actattgata     60
tgtctaggtt ttagctctat cacaggttgt tagacaccct gtcatgtatt ttatattatt    120
tatttcacca tacggattaa gtgaaaccta atgaaaatag tactttcgga gctttaactt    180
taatgaaggt atgttttttt atagacatcg atgtctggtt taacaatagg aaaaagtagc    240
taaaactccc atgaattaaa gaaataacaa ggtgtctaac aacctgttat taagaatgtt    300
agaaaagact taacatttgt gttgagtttt tatagacatt ggtgtctaga catacggtag    360
ataaggtttg ctcaaaaata aaataaaaaa agattggact aaaaaacatt taatttagta    420
caatttaatt agttattttt tcgtctcaaa ttttgctttg ttgagcagaa atttagataa    480
aaaaatcccc gtgatcagat tacaatgtcg ttcattgtac gatgtgtcga aaaatcttta    540
cgacactcta aactgaccac acgggggaaa aagaaaactg aactaataac atcatgatac    600
tcggaaaacc tagcaattct caacccctaa acaaaagaaa cttccaaaac cctgaccata    660
taaaggagtg gcaacaatca gcaatcagtc aagatttgat agcagaaaat cttgtatcgg    720
ttgctaatgg ttttgatgta ctatttatcg gcaataaata ccgaactaac acgggtgttc    780
tgtcacggca catattaaac tcctattctc atttagaaga tggtggttcg tatggtagaa    840
catttgaccc atttaccaat aaagaaatgc agtgggttca atttaaaccg aatagaccaa    900
gaaaaggttc tactggtaag gtaatcaaat atgaatcgcc aaaaggtgaa cctacaagag    960
ttctaatgcc gtttgtgcct atgaaaatat ggcaacggat tagcgataag ttcggagtac   1020
cgattaatcc gaaaaaagat actcactttt gggaatgggt aaagaataat ccatcgatac   1080
cgattgccat tacagaagga aataaaaaag ctaattgcct attatcctat ggctatcctg   1140
ctattgcctt tgtaggcatt tggaacggat tagagaaaat aaatgatttc tcgaaggaaa   1200
agcagttaaa agaggatttg aaatggttgt tatccaacgg caaccgaaat attaatatca   1260
tctttgacca agaccagaaa caaaaaactg taattaatgt aaacaaagct attttcgctt   1320
tatcttctct aataagtaga aatggtcata aagttaatat tgtgcaatgg ttgccgtcaa   1380
aaggtaaagg aatagatgat tatttggtag ctttaccttt tgagaaaaga gaaaatcatt   1440
tagacaactt aattaaaatt gcaccatcat ttaatttttg gtcaactaaa tacttattca   1500
agtgtcgtaa accagattta accgtaaatt gccgttattt gagcgatgca gtaaaagaat   1560
tacctcaaga ggatatagca ttaatagcac ctcacggcac gggtaaaact tcattagtag   1620
ctactcacgt taagaatcgg agttatcacg gaaggaaaac tatttcattg gtgcatcttg   1680
aaagtttagc caaagctaat ggcaacgcac ttggattata ttaccgaacc gaaaataata   1740
ttgaaaagca atatcttgga tttagcttat gtgtagatag ttgccgtgat aagattaacg   1800
gcattacaac tgatattatt tcaggtcaag attattgcct tttcattgat gaaattgacc   1860
aagtaattcc acacatcctt aacagtgaaa ctgaagtaag taagtataga tgcaccatca   1920
ttgacacttt ttctgaactg gtgagaaatg ctgaacaggt cattattgct gatgctgatt   1980
tatccgatgt gacgattgac ctaatagaaa acatcagagg taaaaaacta tatgtaatca   2040
agaatgaata tcagtatcag ggaatgactt ttaacgccgt tggttcacca ttagaaatga   2100
tggcaatgat gggaaaatcg gtgtcagaag gcaagaaatt atttattaac accacatccc   2160
aaaaggcaaa aagtaagtac ggcacaatcg ctcttgagtc ttatattttt ggtctaaata   2220
aagaagcaaa gatattaaga atagactctg aaaccactaa aaaccctgaa catccagcct   2280
ataaaatcat tgaccaagac ttaaataata tcctcaaaga ttatgattat gtcattgcct   2340
caccttgcct tcaaacaggt gtcagtatta ccttaaaagg gcattttgac cagcaattta   2400
acttttccag tggaaacatt acacctcatt gctttttaca gcaaatgtgg cggttgaggg   2460
atgcagaaat tgaaagattc tattatgtgc cgaactcatc taacctcaat ctcattggga   2520
ataagtcaag ttcaccatca gaccttctaa agagcaataa caagatggca acggcaacgg   2580
ttaacctttt gggtagaatc gactccgaat attccctaga gtatgaatcg cacggcattt   2640
ggcttgagac gtgggcaaaa ttatcagcac ggcataacag ttcaatgcgt tgttactctg   2700
aaattcttac ctatctaatt acgtctcaag ggcataaatt aaatatcaac attccctcac   2760
ctcttgcaga tattaagaag ctaaatgatg aggtaagtag taacagggaa aaggtaaaaa   2820
atgagagata ctctcagagg ttaaactcac cagatattaa cgatgcagaa gctaccatac   2880
tcgaatctaa agagcaaaaa atcggattga ctctcaatga gagatgcacc ctagaaaagc   2940
ataaagttaa gaagcggtat gggaatgtaa agatggatat tctcaccttt gatgatgatg   3000
gactataccc caaactcaga ctattttatt acctcaccat cggtaaacct catctcaagg   3060
ctaatgacag aaaagctatt gccaaaatgg gcaatgacaa taaaggcaag attctatcaa   3120
aagacttagt taataaaact tactccgctc gtgtgaaggt cttagagatt cttaaactaa   3180
```

FIG. 2

```
ctgactttat cgacaatctt agagatgaac tcttaataac tcccaataat ccagctatca     3240
ccgattttaa taatcttctg ctaagagcta agaaggattt aagagtatta ggagtcaaca     3300
tcggaaaata tccaatggcc aacattaatg ccgtacttac tctcattggt cacaaacttt     3360
ctgtaatgag agatgagttc ggaaaagaga aaaggataaa agtagatggt aaatcatacc     3420
gatgttatca acttgaaaca ttaccagatt ttaccaatga tactcttgac tactggttag     3480
aaaatgatag ccaaaaagaa gtaacagcaa cagaaaatta ctccgaaaat tttaaccctt     3540
caaatagcta caatccagac agtaagacac tttcagaggg tgcaaatttc ctatatataa     3600
ataaagaaga attgcatcca aataaattgc acctagaaat aaaagaaggt gctgaacttt     3660
ttttattcgg ggtaaaggtg attgtgaaag gaatcttgga cggggcagta actatattct     3720
ctatgggtca agaatacgat ttatccctca atgaactaga ggggatgtta acatcatgaa     3780
ctttacaaga atctttttaa agggcgatcg caccatgtta aatgatggta catttgttca     3840
gatatttgat atttaccatg accacgcatt gggagtgacc cttgacctta agacagaaaa     3900
aattatttcc gatgatgtta gggtaattac tgtcaaagac ttattgttcg atggcactta     3960
taaaggggta aaatctttta tgcccgataa tgcccgataa tgcccgattg atgctacaaa     4020
atcccataat cataagcgat aatcccctaa tagcttgtaa ttcttgaacc gtagcgattt     4080
tagagtattc caaaaagaag aaataaacac cgcaaaatgt cgtatttcac atatataaac     4140
caaggttttt tgccctaaaa tctttatgtt tgtagtgtga tgttgggtca aaatggtcag     4200
aaaagttgca aggtttttat ggatgcttac gcgcgcgagg ggtaagcatc cccaaatagt     4260
tactttatcc tagtccatgc ccatttattg ccgtcccgtt cggctttaaa aaagtgccaa     4320
aactcacaag gtgcaataaa aagttctgta cctttcgcaa ccctagataa tctttcaaca     4380
gttacttttt ttcctattat ctcggtacaa agtttggcta gtttctcttt tccctctttt     4440
tcaatcaagc cttcttgtat gcccaactca ttgattaatc tctctatttt taccattatt     4500
tcccgttcag gtagtttatc ccctaaatct tcatcggggg gcaatgtagg gcattctgaa     4560
ggggcttttt cttctgtctg gacattatct aatattgaag taaccaaact atcttcagtt     4620
ttttctattc ctattaattc atattcggtt actgtatccg tatcaatatc cgaataacta     4680
tctttatccg tattagctat tcggttaagt ttatccgtta actcagaaac aagactatat     4740
agcggtttta gcttttcttc tatcctgtta tctaatacgg ataagtttat acggttatca     4800
ttatccgtat tagtatcatt gggctttttt ggtagttcta ccccctcata aaccgctttt     4860
attcccaatt ccaacagact gataacagta tcctttataa tgggtttttt gctgatatgg     4920
tgaacttttg ccccttccat cattgcgata ctttctatct cactcatcaa cttatcgctt     4980
aagtgaatct cgtatctgtt taatccctta ctggttttat tcatatccgt ttactttatt     5040
cggttaacaa ttctatttta tacgaataaa atattatacg gttaacttta tacgtttaac     5100
tattttatct atacggataa cagtaataag ttattcgtat tagttatacg tttactttta     5160
tccaaataaa attagtgcat ttaaactaaa agaatgattt tatcggagtt gatagcattg     5220
gattaaccta aagatgttta taagctatat ctgataagta tttaaggtta ttttgttatt     5280
ctgtttattg acattatcag aataaaagaa tagaatataa ttgttgagag ataagaggtt     5340
taagtgatta tggttaagaa gttagttggt tatgtcaggg tcagtagtga atcgcaagag     5400
gataacacta gcttacagaa tcagatagag agaattgaag catattgtat ggcttttggt     5460
tatgagttgg taaaaatatt caaagaggtt gccactggta caaaagcaga tattgaaacc     5520
cgtcctattt ttaatgaagc tatagaatac ttgaaacagg ataatgctaa tggaattatt     5580
gccttgaagc tagaccgaat cgcacggaat gctttagatg tattgcgttt ggttcgtgaa     5640
accttagaac cacaaaataa aatgttagtg ttactagata ttcaggtaga tacttcgaca     5700
ccttcaggaa aaatgatttt aactgtaatg agtgccgttg ctgaactcga aagagacatg     5760
atctatgatc gcactcaggg gggtagaaag actaaagccc aaaagggcgg gtatgcctac     5820
gggaaaccta aatttggcta taagactgaa gaaaaggaac taaaagaaga ttcagcacaa     5880
caggaaacta ttaaactaat taagagacac cgtaggtcag ggaaaagcta ccagaaaata     5940
gctgattatc tcaatgccca aagtattccc actaaacaag gtaagaaatg gagttctagc     6000
gtcgtctatc gaatctgtca ggaaaaagct ggttaagtct gtttatagat atttagaatt     6060
tattgaataa aaatagtatg aacaataaat atttatggac taaccacgct cggaaacgtt     6120
taactgaacg atgggaaata aaagaatcat gggttattga taccatcgaa aatcctgaac     6180
gttcagaatt tattgttgat gagtcagggg aaaaatatca ttactataaa agaatagcta     6240
agtttaagaa tagagtgtta gaagtgataa cttctgccaa ctcaacaccc acaagaataa     6300
taacctttta ctttaaccgt aacatgagga aaaatttatg attgttactt acgataatga     6360
agttgacgca atttatttta agttaacgga aaataaaatt gatagcaccg aacctcaaac     6420
agacaggatt atcattgatt acgatgaaag taataatatt gttggcattg aggtattaga     6480
```

FIG. 2 continued

```
ttttaattat cttgtcaaga aaggtttaac cgttgctgat ttaccttttt ctgaagatga      6540
aagattaaca gcttctcaat attttaattt tcctgttgct atctaatcca gaaggggcaa      6600
taatcccctt ctttcatcga gttagactta atatcacaaa agtcattttc attttaccgt      6660
ttcttttcca cagcgtccgt acgcccctcg ttaaatctca aaaccgacaa tttatgatgt      6720
ttataaaaag ttactcactt taataagtat ttatactcat taaagggtta ttcttttttt      6780
gtagcctgat aggttgggaa ggaatatttc agattatcag atttgttg                   6828


ID   pABICyano1-6.8  standard; circular DNA;6828 BP.
DE   Complementary copy of pABICyano1-6.8 ano rc
FH   Key             Location/Qualifiers
FT   primer          complement(1859..1883)
FT                   /vntifkey="27"
FT                   /label=FB3
FT   CDS             594..3779
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   CDS             5350..6036
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             3815..4000
FT                   /vntifkey="4"
FT                   /label=ORF\2
FT                   /note="orf2"
FT   CDS             complement(4260..5024)
FT                   /vntifkey="4"
FT                   /label=ORF\3
FT                   /note="orf3"
FT   CDS             6078..6341
FT                   /vntifkey="4"
FT                   /label=ORF\5
FT                   /note="orf5"
FT   CDS             6338..6586
FT                   /vntifkey="4"
FT                   /label=ORF\6
FT                   /note="orf6"
FT   rep_origin      3375..3408
FT                   /vntifkey="33"
FT                   /label=Rep_Origin_1
FT                   /note="active site motif of Rep protein"
SQ   Sequence 6828 BP; 2360 A; 1153 C; 1212 G; 2103 t;
```

FIG. 2 continued

METHODS FOR INCREASING THE STABILITY OF PRODUCTION OF COMPOUNDS IN MICROBIAL HOST CELLS

CROSS-REFERENCE TO RELATED APPLICATIONS

This application is a continuation of International Application No. PCT/US2015/000210, filed Dec. 23, 2015, which claims the benefit of U.S. Provisional Application No. 62/096,383, filed on Dec. 23, 2014, the disclosures of which are hereby incorporated by reference.

STATEMENT REGARDING FEDERALLY SPONSORED RESEARCH

Not applicable.

REFERENCE TO SEQUENCE LISTING

This application contains a sequence listing submitted by EFS-Web, thereby satisfying the requirements of 37 C.F.R. § 1.821-1.825. The sequence listing file, named "Essential_operon_P0036_02_PCT_ST25", was created on Dec. 22, 2015, and is 191 kb in size.

FIELD OF THE INVENTION

The present invention relates to genetically enhancing microbes to produce compounds of interest.

BACKGROUND OF THE INVENTION

Cyanobacteria are prokaryotes capable of photoautotrophy. Cyanobacteria can be genetically enhanced to use light and $CO_2$ to produce compounds of interest such as biofuels, industrial chemicals, pharmaceuticals, nutrients, carotenoids, and food supplements. Various cyanobacterial strains have been genetically enhanced to produce compounds of interest. Carbon dioxide that is used by cyanobacteria can be derived from any source, such as a waste byproduct of industrial production. In this way, cyanobacteria can be used to recycle $CO_2$ to compounds of interest.

The cyanobacterial genus *Cyanobacterium* was first established in 1983 (see Rippka et al. (2001), Bergey's Manual of Systematic Bacteriology, Vol. 1, p. 497-498). Members of the *Cyanobacterium* genus are often found in thermal mats (Moro, et al., 2007, Algological Studies, 123: 1-15).

The transformation of the cyanobacterial genus *Cyanobacterium* with genes that encode enzymes that can produce ethanol for biofuel production has been described, for example, in U.S. Pat. No. 8,846,369 to Piven et al.

SUMMARY

The loss of expression of an exogenous pyruvate decarboxylase (pdc) gene, which is one of the production genes in non-naturally occurring ethanologenic cyanobacterial strains, results in loss of ethanol production. The loss of expression can occur quickly, so that by the end of a production run, very little ethanol is being produced. This has been found to be due to mutation based inactivation ("reversion") of the pdc gene itself, so that the cell doesn't produce the ethanol intermediate. To prevent this, an endogenous gene that is essential to the cyanobacterial cell's survival is modified so that it is tied to the correct expression of the production gene. If the production gene is not expressed, the essential gene is also not expressed, and the cell dies.

In an embodiment, a pdc-nirA operon was made essential to the survival of host cells when grown on nitrate as the nitrogen source. Non-naturally occurring ethanologenic cyanobacterial strains were created tying nirA expression to pdc expression in an operon in order to increase genetic stability. For these strains, a knockout out of pdc expression causes the loss of NirA activity. Because these strains lack a chromosomal copy of nirA, the lack of expression of the pdc-nirA operon results in cell death.

In another embodiment, using methods described herein, any gene useful for the production of a compound of interest can be made part of an essential operon containing another gene that complements an auxotrophic host cell. The resulting host-cells demonstrate increased genetic stability of the gene useful for the production of a compound of interest.

In an aspect, a non-naturally occurring auxotrophic microbe capable of production of a compound of interest via the expression of exogenous genes is disclosed wherein said microbe contains an extrachromosomal plasmid comprising at least one of said exogenous genes and a gene whose expression complements the auxotrophy of said non-naturally occurring auxotrophic microbe and wherein said at least one of said exogenous genes and said gene whose expression complements auxotrophy form a polycistronic operon wherein said at least one of said exogenous genes and said gene whose expression complements auxotrophy are both operably linked to a promoter such that expression of said gene whose expression complements auxotrophy cannot occur without expression of said at least one of said exogenous genes. In an embodiment, the non-naturally occurring auxotrophic microbe contains a promoter that is an inducible promoter. In another embodiment, the non-naturally occurring auxotrophic microbe contains a promoter that is light inducible. In an embodiment, the non-naturally occurring auxotrophic microbe of contains a promoter that is a constitutive promoter. In another embodiment, a non-naturally occurring auxotrophic microbe is disclosed that is a cyanobacterial host cell. In yet another embodiment, the non-naturally occurring auxotrophic microbe is a microbe that is an auxotroph derived from *Cyanobacterium* sp. ABICyano1 deposited in the American Type Tissue Collection (ATCC) as PTA-13311. In another embodiment, the non-naturally occurring auxotrophic microbe contains at least one inducible promoter operably linked to said polycistronic operon has at least 85% identity to a promoter selected from the group consisting of PnirA, PziaA, PsmtA, PcorT, PnrsB, PnrtA, PpetJ, PnarB, PmntC, Porf0221, Porf0223, Porf0316, Porf0128, Porf1486, Porf3164, Porf3293, Porf3621, Porf3635, Porf1071 (PmntC), Porf1072, Porf1074, Porf1075, Porf1542, Porf1823, Porf3126, Porf0222, Porf3126, Porf3232, Porf3749, PrbcL, PrnpA, PrpsL, PrpoA, PpsaA, PpsbA2, PpsbD, and PcpcB. In another embodiment, the non-naturally occurring auxotrophic microbe contains an extrachromosomal plasmid that has greater than 80% sequence identity to p6.8. In another embodiment, the non-naturally occurring auxotrophic microbe contains an extrachromosomal plasmid that is self-replicating within the microbe. In another embodiment, the non-naturally occurring auxotrophic microbe contains an extrachromosomal plasmid that contains a self-replicating origin of replication that has greater than 90% sequence identity to the origin of replication of p6.8. In another embodiment, the non-naturally occurring auxotrophic microbe has exogenous genes that are pyruvate decarboxylase and alcohol dehydrogenase. The non-naturally occurring auxotrophic microbe contains a gene whose expression complements the auxotrophy of the non-naturally occurring auxotrophic microbe being auxotrophic because it lacks a functional nirA, or narB, or nrtABCD gene. In another embodiment, the non-naturally occurring auxotrophic microbe contains a gene whose expression complements the auxotrophy of the non-naturally occurring auxotrophic microbe and the gene is selected from the group consisting of a urease subunit gene, a urease accessory gene and a urea uptake gene. In another embodiment, the non-naturally occurring auxotrophic microbe has a gene whose expression complements the auxotrophy of the non-naturally occurring auxotrophic microbe and is involved in vitamin B12 biosynthesis. In an embodiment, the non-naturally occurring auxotrophic microbe is capable of producing a compound of interest which is ethanol. In yet another embodiment, the non-naturally occurring auxotrophic microbe contains a polycistronic operon that has genes linked through intergenic sequences. The intergenic sequences can be derived from exogenous or endogenous sources. In an embodiment, the non-naturally occurring auxotrophic microbe contains a polycistronic operon that has genes linked through intergenic sequences derived from genes whose expression products are part of a photosynthetic apparatus.

In an another aspect, a non-naturally occurring auxotrophic microbe capable of production of a compound of interest via the expression of exogenous genes is disclosed wherein the microbe contains a chromosomal polynucleotide sequence comprising at least one of the exogenous genes and a gene whose expression complements the auxotrophy of the non-naturally occurring auxotrophic microbe and wherein the at least one of said exogenous genes and the gene whose expression complements auxotrophy form a polycistronic operon wherein the at least one of the exogenous genes and the gene whose expression complements auxotrophy are both operably linked to a promoter such that expression of the gene whose expression complements auxotrophy cannot occur without expression of the at least one of said exogenous genes.

In another aspect, a method for producing a compound of interest is disclosed wherein a non-naturally occurring auxotrophic microbe that is capable of producing the compound of interest produces the compound of interest via the expression of exogenous genes wherein the microbe contains an extrachromosomal plasmid comprising at least one of said exogenous genes and a gene whose expression complements the auxotrophy of said non-naturally occurring auxotrophic microbe and wherein the at least one of said exogenous genes and the gene whose expression complements auxotrophy form a polycistronic operon wherein the at least one of the exogenous genes and the gene whose expression complements auxotrophy are both operably linked to an inducible promoter such that expression of the gene whose expression complements auxotrophy cannot occur without expression of the at least one of said exogenous genes, the method comprising inducing the inducible promoter. In an embodiment, the method uses a microbe that is a cyanobacterial host cell. In another embodiment, the method uses a microbe that is an auxotroph derived from *Cyanobacterium* sp. ABICyano1 deposited in the American Type Tissue Collection (ATCC) as PTA-13311.

BRIEF DESCRIPTION OF THE DRAWINGS

FIG. 2 depicts the polynucleotide sequence of p6.8 (SEQ ID NO: 1) and depicts labels of various polynucleotide sequences.

FIG. 4A depicts $OD_{750}$ of ABICyano1:pAB722 (SEQ ID NO: 8), ABICyano1:pAB193 (SEQ ID NO: 9), ABICyano1:pAB194 (SEQ ID NO: 10), and ABICyano1:pAB195 (SEQ ID NO: 11). FIG. 4B depicts ethanol production (% v/v). FIG. 4C depicts VLE corrected ethanol production. FIG. 4D depicts the percentage of cells that “reverted” to non-ethanol producing cells over time, for either the control strain (722) or the nirA complementation strain (193).

DETAILED DESCRIPTION

Figure 1:
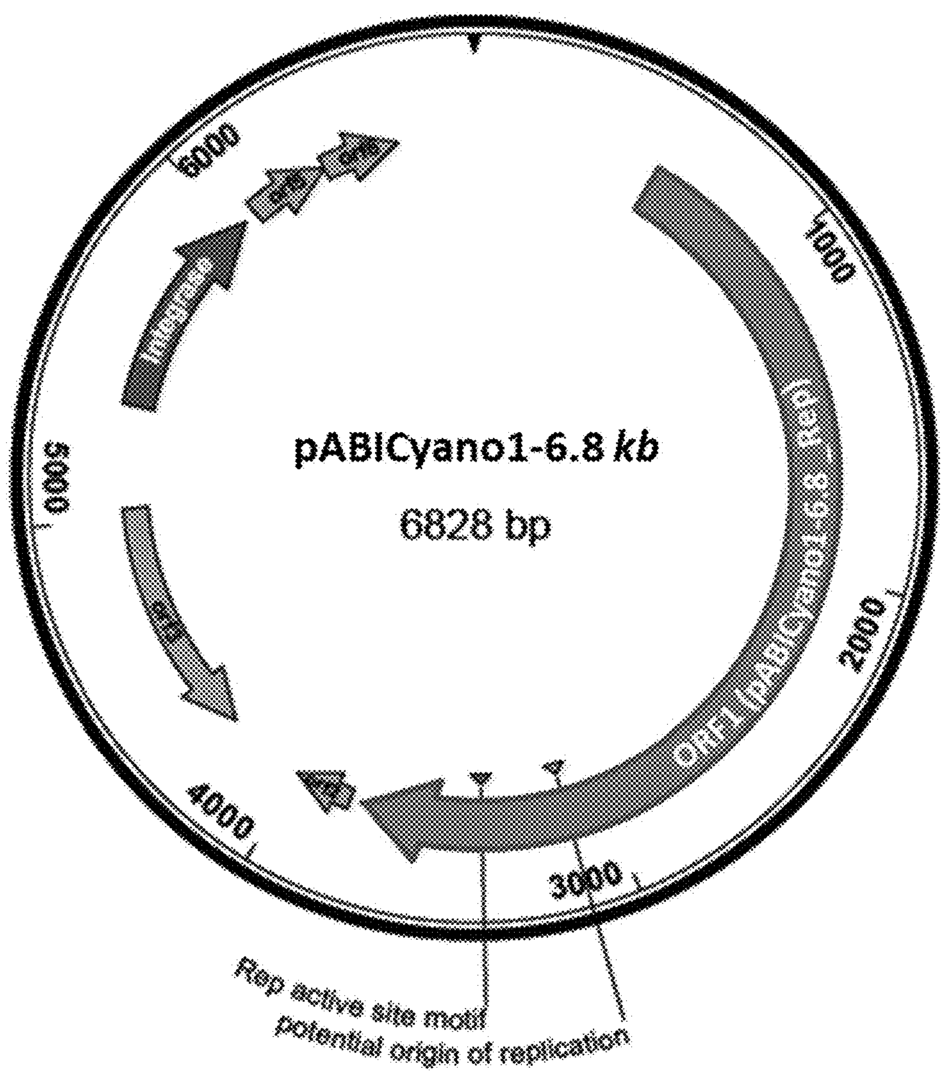
FIG. 1 depicts a plasmid map of a pABICyano1 6.8 kb endogenous plasmid from ABICyano1, alternately referred to as p6.8 (SEQ ID NO: 1; also depicted in FIG. 2). The plasmid p6.8 contains six open reading frames ORF 1 (SEQ ID NO: 2), ORF 2 (SEQ ID NO: 3), ORF 3 (SEQ ID NO: 4), ORF 4 (SEQ ID NO: 5), ORF 5 (SEQ ID NO: 6), and ORF 6 (SEQ ID NO: 7).

Presented herein are improved methods for making microbial host cells that have increased genetic stability for the expression of genes responsible for the production of compounds of interest. In an embodiment, the methods used to increase the genetic stability of host cells are applicable to all microbes: eukaryotic, prokaryotic and archaeal. In another embodiment, the methods disclosed herein are useful in microbes that lack functional and/or efficient homologous genetic recombination systems. In another embodiment, the methods disclosed herein are useful for creating non-naturally occurring photoautotrophic host cells, such as cyanobacterial host cells.

In one embodiment, the host cells are derived from an isolated strain of the *Cyanobacterium* genus. A species member of the *Cyanobacterium* genus is referred to as a *Cyanobacterium* sp. and includes several species and strains and have been found in a variety of environments including thermal mats in Italy (Moro, et al., 2007, Algological Studies, 123:1-15). In an embodiment, antibiotic resistance gene (ABR) free host cells generated using methods disclosed herein are a species of the *Cyanobacterium* genus, *Cyanobacterium* sp. ABICyano1 (referred to herein as "ABICyano1" or "AB1") which has been deposited in the American Type Tissue Collection (ATCC) as PTA-13311.

Genetically enhanced, non-naturally occurring ABICyano1 organisms disclosed herein are useful for the production of compounds of interest, such as ethanol, for example. Such genetic modifications can comprise heterologous genes for expression in the host cell in order to establish a foreign metabolic pathway for production of a product of interest. If the compound of interest is ethanol, then, in one embodiment, exogenous pyruvate decarboxylase (pdc) and alcohol dehydrogenase (adh) genes on an extrachromosomal plasmid can be introduced into a cyanobacterial host cell for phototrophic production of ethanol.

Definitions

Aspects of the disclosure encompass techniques and methods well known in molecular biology, microbiology and cell culture. Laboratory references for these types of methodologies are readily available to those skilled in the art, see, for example, Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; Handbook Of Microalgal Culture Biotechnology And Applied Phycology (2003) Richmond, A.; (ed.), Blackwell Publishing; and "The Cyanobacteria, Molecular Biology, Genomics and Evolution", Edited by Antonia Herrero and Enrique Flores, Caister Academic Press, Norfolk, U K, 2008.

All publications and patent applications mentioned in this specification are herein incorporated by reference to the same extent as if each individual publication or patent application was specifically and individually indicated to be incorporated by reference.

Unless defined otherwise, all technical and scientific terms used herein have the meaning commonly understood by a person skilled in the art to which this disclosure belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

It is well known to a person of ordinary skill in the art that large plasmids can be produced using techniques such as the ones described in the U.S. Pat. No. 6,472,184 B1 titled "Method for Producing Nucleic Acid Polymers" and U.S. Pat. No. 5,750,380 titled "DNA Polymerase Mediated Synthesis of Double Stranded Nucleic Acid Molecules", which are hereby incorporated by reference in their entirety.

Genes are disclosed as a three letter lower case name followed by a capitalized letter if more than one related gene exists, for example nirA. The respective protein encoded by that gene is denominated by the same name with the first letter capitalized, such as NirA, or all letters are capitalized.

The term "monocistronic" as used herein is an mRNA molecule that contains the genetic information to translate only a single protein chain.

The term "polycistronic" as used herein is an mRNA molecule that carries several open reading frames each of which is translated into a polypeptide. Dicistronic or bicistronic mRNA encodes only two proteins and may be referred to as polycistronic.

The term "operon" as used herein is a segment of genomic DNA that contains one or more genes under the control of a single promoter.

The term "essential gene" as used herein is a gene whose presence in the cell is required for the cell to remain viable.

The term "conditionally essential gene" as used herein is a type of essential gene where the presence of the gene in the cell is required under some conditions, but wherein the cell can survive if another condition is present. An example is nutrient utilization genes, where under certain conditions (such as the presence of an additional compound in the medium), another gene can functionally substitute for the missing gene. As used herein, a "conditionally essential gene" can also be referred to as an "essential gene".

The term "essential operon" as used herein refers to the nucleic acid-based linking of a production gene of interest so that it is located on the same mRNA transcript, immediately upstream of an essential gene. Thus, if the production gene is somehow mutated so that it is not expressed, the essential gene is also not expressed, and the cell dies. The genes are located on the same operon, under the control of one upstream promoter.

The term "conditionally essential operon" as used herein is an essential operon system whereby the essential gene is a conditionally essential gene. This allows for the cell to survive when certain conditions are met, but the cell dies when those conditions are not met.

Promoter sequences, which control the transcription of a gene, are given by a capitalized letter "P" followed by the subscripted gene name according to the above described nomenclature, for example "$P_{nirA}$" for the promoter controlling the transcription of the nirA gene. Promoter sequences may also be referred to without the gene name being subscripted, for example "PnirA".

Enzyme names can be given in a two or three letter code indicating the origin of the enzyme, followed by the above mentioned three letter code for the enzyme itself, such as SynAdh ($Zn^{2+}$ dependent Alcohol dehydrogenase from *Synechocystis* PCC 6803), ZmPdc (pyruvate decarboxylase from *Zymomonas mobilis*).

The term "Cyanobacteria" refers to a member from the group of photoautotrophic prokaryotic microorganisms which can utilize solar energy and fix carbon dioxide. Cyanobacteria are also referred to as blue-green algae.

The term "terminator" refers to a nucleic acid sequence, at which the transcription of an mRNA stops. Non-limiting examples are dsrA from *Escherichia coli* (*E. coli*), the oop terminator or the rho terminator.

The term "*Cyanobacterium* sp." refers to a member of the genus *Cyanobacterium*, as, for example, characterized by Rippka et al., 1983. Ann. Microbiol. (Inst. Pasteur) 134B: 32.

The term "BG-11" or "BG11" refers to a growth media used for growing cyanobacterial species as disclosed in Rippka, R. et al., "Generic Assignments, Strain Histories and Properties of Pure Cultures of Cyanobacteria." (1979) J. Gen. Microbiol. 111: 1-61.

The term "mBG-11" or "mBG11" refers to marine BG11 and in may alternatively be referred to as marine medium. mBG11 has from about 30 to about 38 psu (practical salinity units).

The terms "host cell" and "recombinant host cell" include a cell suitable for metabolic manipulation including, but not limited to, incorporating heterologous polynucleotide sequences and can be transformed. Host cell and recombinant host cell includes progeny of the cell originally transformed. In particular embodiments, the cell is a prokaryotic cell, such as a cyanobacterial cell. The term recombinant host cell is intended to include a cell that has already been engineered to have desirable properties and is suitable for further enhancement using the compositions and methods disclosed herein.

The terms "positive selection marker" or "positive marker" as used herein are selectable markers that confer a selective advantage to the host organism such as an antibiotic resistance gene which allows a host organism to survive antibiotic selection.

The term "negative selection marker" or "counterselectable marker" or "counter-selection marker" are selectable markers that eliminate or inhibit growth of the host organism upon selection. An example of a counter-selection marker is galK wherein expression of galK in the presence of a counter-selection compound, in this case 2-deoxy-galactose, causes the death of a host cell. Other counter-selection markers are well known in the art and include mazF and sacB, for example.

The term "positive and negative selectable marker" as used herein means markers that can serve as both a positive and a negative marker by conferring an advantage to the host under one condition, but inhibiting growth under a different condition. An example would be an enzyme that exhibits positive selection by being able to complement an auxotrophy in a first condition and in a second condition exhibits negative selection by converting a compound to a compound toxic to the host cell.

The term "screenable marker" refers to a marker that when expressed in a host cell confers a first condition and when not expressed in a host cell confers a second condition measurably different from the first condition. An example of a screenable marker is a gene that produces a colorometric difference between host cells containing the screenable marker and host cells that do not contain a functional screenable marker. An example of a screenable marker is the lacZ gene that can be used for blue/white screening when grown in the presence of X-gal and IPTG.

The term "cassette" or "gene cassette" as used herein refers to a manipulatable fragment of DNA carrying, and capable of expressing, one or more genes of interest between one or more sets of restriction sites.

The term "shuttle vector" refers to a vector, such as a plasmid, which can propagate in different host species. For example, a shuttle vector with a cyanobacterial origin of replication can be replicated and propagated in different cyanobacterial genera such as *Cyanobacterium, Synechococcus*, and *Synechocystis*. Alternatively, or additionally, a shuttle vector may also contain an origin of replication for different phyla of bacteria such as Enterobacteriaceae and Cyanobacteria, so that cloning/genetic enhancements can performed in *E. coli* and the recombinant plasmid can be expressed/maintained in cyanobacterial hosts. For example, in the latter case, in certain embodiments, the shuttle vector is either a broad host range vector whose origin of replication is recognized by *E. coli* and cyanobacteria, or a plasmid which contains at least two different origins of replication for the appropriate organism.

The term "genome" refers to the chromosomal genome as well as to extrachromosomal plasmids which are normally present in wild type cyanobacteria without having performed recombinant DNA technology.

"Competent to express" refers to a host cell that provides a sufficient cellular environment for expression of endogenous and/or exogenous polynucleotides.

As used herein, the term "genetically enhanced" refers to any change in the endogenous genome (chromosomal and plasmidial) of a wild type cell or to the addition of non-endogenous genetic code to a wild type cell, e.g., the introduction of a heterologous gene. Changes to the genome of various organisms disclosed herein are made by the hand of man through the use of various recombinant polynucleotide technologies and other techniques such as mutagenesis, for example. Included in changes to the genomes are changes in protein coding sequences or non-protein coding sequences, including regulatory sequences such as promoters, enhancers or other regulators of transcription.

The nucleic acids disclosed herein may be modified and/or contain non-natural nucleotide bases.

As used herein, "substantially similar" refers to nucleic acid fragments wherein changes in one or more nucleotide bases results in substitution of one or more amino acids, but do not affect the functional properties of the protein encoded by the DNA sequences. In certain embodiments, changes in one or more nucleotide bases do not change the encoded amino acid. Substantially similar also refers to modifications of the nucleic acid fragments such as substitution, deletion or insertion of one or more nucleotide bases that do not substantially affect the functional properties of the resulting transcript.

As used herein, in certain embodiments, homologous nucleic acid sequences have about 50%, 60%, 65%, 68%, 70%, 75%, 80%, 85%, 90%, 91%, 92%, 93%, 94%, 95%, 96%, 97%, 98%, 99%, 99.5%, 99.9%, 99.95% or even higher identity to nucleic acid sequences disclosed herein.

Similarly, homologous amino acid sequences can have a sequence identity that is at least, for example, 50%, 60%, 70%, 80% 90%, 95%, 99%, or 99.5% or more identical to the amino acid sequences disclosed herein.

The percentage of identity of two nucleic acid sequences or two amino acid sequences can be determined using the algorithm of Thompson et al. (CLUSTALW, 1994 Nucleic Acid Research 22: 4673-4, 680). A nucleotide sequence or an amino acid sequence can also be used as a so-called "query sequence" to perform a search against public nucleic acid or protein sequence databases in order, for example, to identify further unknown homologous sequences, which can also be used in embodiments of this disclosure.

Such searches can be performed using the algorithm of Karlin and Altschul (1990, Proceedings of the National Academy of Sciences U.S.A. 87:2,264-2,268), modified as in Karlin and Altschul (1993, Proceedings of the National Academy of Sciences U.S.A. 90: 5,873-5,877). Such an algorithm is incorporated in the BLASTN and BLASTX programs of Altschul et al. (1990, Journal of Molecular Biology 215:403-410). Suitable parameters for these database searches with these programs are, for example, a score of 100 and a word length of 12 for BLAST nucleotide searches as performed with the BLASTN program. BLAST protein searches are performed with the BLASTX program with a score of 50 and a word length of 3. Where gaps exist between two sequences, gapped BLAST is utilized as described in Altschul et al. (1997, Nucleic Acids Research, 25:3,389-3,402).

"Recombinant" refers to polynucleotides synthesized or otherwise manipulated in vitro or in vivo ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacteria." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "non-naturally occurring", when used in reference to a microbial organism or microorganism herein is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon such as regions associated with promoters, for example. Exemplary metabolic polypeptides include enzymes or proteins within an ethanologenic biosynthetic pathway resulting in the production of ethanol by a non-naturally occurring organism.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides).

The term "transformation" is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent cross-over events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics 36:361-388; 2002.

The term "non-homologous or random integration" refers to any process by which DNA is integrated into the genome that does not involve homologous recombination. It appears to be a random process in which incorporation can occur at any of a large number of genomic locations.

The term "vector" as used herein is intended to refer to a nucleic acid molecule (polynucleotides and oligonucleotides) capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Some vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

The term "promoter" is intended to include a polynucleotide segment that can transcriptionally control a gene of interest, e.g., a pyruvate decarboxylase gene that it does or does not transcriptionally control in nature. In one embodiment, the transcriptional control of a promoter results in an increase in expression of the gene of interest. In an embodiment, a promoter is placed 5' to the gene of interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters may also be inducible, meaning that certain exogenous stimuli (e.g., nutrient starvation, heat shock, mechanical stress, light exposure, etc.) will induce the promoter leading to the transcription of an operably linked gene.

The phrase "operably linked" means that the nucleotide sequence of the nucleic acid molecule or gene of interest is linked to the regulatory sequence(s), e.g., a promoter, in a manner which allows for regulation of expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

The term "non-naturally occurring microbe" as used herein included genetically engineered microbes, and also includes microbes demonstrating non-natural characteristics as a result of being exposed to mutagenic conditions.

The term "gene" refers to an assembly of nucleotides that encode for a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence.

The term "exogenous" as used herein is intended to mean that the referenced molecule or the referenced activity is introduced into the host microbial organism. The molecule can be introduced, for example, by introduction of an encoding nucleic acid into the host cell genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The term "fragment" refers to a nucleotide sequence of reduced length relative to the reference nucleic acid and comprising, over the common portion, a nucleotide sequence substantially identical to the reference nucleic acid. Such a nucleic acid fragment according to the disclosure may be included in a larger polynucleotide of which it is a constituent. Such fragments comprise, or alternatively consist of, oligonucleotides ranging in length from at least about 6 to about 1500 or more consecutive nucleotides of a polynucleotide according to the disclosure.

The term "open reading frame" abbreviated as "ORF," refers to a length of nucleic acid sequence, either DNA, cDNA or RNA that contains a translation start signal or initiation codon, such as an ATG or AUG, and a termination codon and can be potentially translated into a polypeptide sequence.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The terms "restriction endonuclease" and "restriction enzyme" refer to an enzyme that binds and cuts within a specific nucleotide sequence within double stranded DNA.

The term "expression" as used herein, refers to the transcription and stable accumulation mRNA derived from a nucleic acid or polynucleotide. Expression may also refer to translation of mRNA into a protein or polypeptide. Expression may also be used to refer to the process by which a gene's coded information is converted into the structures and functions of a cell, such as a protein, transfer RNA, or ribosomal RNA.

An "expression cassette" or "construct" refers to a series of polynucleotide elements that permit transcription of a gene in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

The term "codon bias" refers to the fact that different organisms use different codon frequencies.

The term "codon improvement" refers to the modification of at least some of the codons present in a heterologous gene sequence from a triplet code that is not generally used in the host organism to a triplet code that is more common in the particular host organism. This can result in a higher expression level of the gene of interest. The term "codon improvement" can also be used synonymously with codon optimization. Similarly, the term "codon improved gene" refers to a gene that has had its nucleic acid sequence modified so that it has higher expression in an organism.

The term "codon adaptation index" or "CAI" refers to a method of analyzing codon usage bias of an organism. One can alter the CAI of a heterologous gene (by altering the nucleic acid sequence) to result in more efficient translation that leads to a higher level of the protein encoded by the gene. A suitable CAI table for ABICyano1 is found in Table 2.

The term "reporter gene" refers to a nucleic acid encoding an identifying factor that can be identified based upon the reporter gene's effect, in order to determine or confirm that a cell or organism contains the nucleic acid of interest, and/or to measure gene expression induction or transcription.

The term "selectable marker" or "marker" means an identifying factor, usually an antibiotic, chemical resistance gene, or counter-selection gene, that is able to be selected for based upon the marker gene's effect, such as resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest.

A "heterologous protein" refers to a protein not naturally produced in the cell and that is produced from a heterologous gene.

An "isolated polypeptide" or "isolated protein" is a polypeptide or protein that is substantially free of those compounds that are normally associated therewith in its natural state (e.g., other proteins or polypeptides, nucleic acids, carbohydrates, lipids).

An "isolated organism" is an organism that is substantially free of other organisms that are normally associated therewith in its natural state.

The term "tolerate" refers to the ability of an organism to continue to grow after exposure to a condition. In one embodiment, "tolerate" is defined as the ability of an organism to grow after being exposed to an environmental condition after being exposed to the condition for at least 2 hours per day over a time period of at least 7 days. In another embodiment, "tolerate" is synonymous with withstand. In an embodiment ability of an organism to tolerate environmental conditions is referred to as "hardiness".

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements.

As used herein, the term "VLE" stands for vapor-liquid equilibrium. VLE is a method of determining ethanol concentration in a medium by measuring the ethanol concentration in a vapor over the medium. VLE relies upon the vapor pressure of ethanol in a medium and other variables such as temperature and exchange of other gasses in the vapor. In one embodiment, ethanol concentration of the vapor phase over the medium is measured by gas chromatagraphy. In another embodiment, Raman spectroscopy, infrared spectroscopy and other spectrographic analyses may be performed in order to determine the concentration of a compound of interest in the vapor phase over a medium.

As used herein, the phrase "increased activity" refers to any genetic modification resulting in increased levels of enzyme function in a host cell. As known to one of ordinary skill in the art, in certain embodiments, enzyme activity may be increased by increasing the level of transcription, either by modifying promoter function or by increasing gene copy number, increasing translational efficiency of an enzyme messenger RNA, e.g., by modifying ribosomal binding, or by increasing the stability of an enzyme, which increases the half-life of the protein, leading to the presence of more enzyme molecules in the cell. All of these represent non-limiting examples of increasing the activity of an enzyme, see for example, mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Biomedical Engineering Handbook (2000) Bronzino, J. D., Springer, ISBN 354066808X, all of which are incorporated by reference.

The terms "pyruvate decarboxylase", "Pdc" and "PDC" refer to an enzyme that catalyzes the decarboxylation of pyruvic acid to acetaldehyde and carbon dioxide. A "pdc gene" refers to the gene encoding an enzyme that catalyzes the decarboxylation of pyruvic acid to acetaldehyde and carbon dioxide.

The terms "alcohol dehydrogenase", "Adh" and "ADH" refer to an enzyme that catalyzes the interconversion between alcohols and aldehydes or ketones. An "adh gene" refers to the gene encoding an enzyme that catalyzes the interconversion between alcohols and aldehydes or ketones.

The term "pdc/adh" refers to the pdc and adh genes collectively. A "pdc/adh cassette" refers to a nucleic acid sequence encoding a PDC enzyme and an ADH enzyme.

The term "ethanologenic cassette" refers to any polynucleotide sequence that encodes for enzymes capable of producing ethanol alone or in combination with other exogenous or endogenous enzymes. In a certain embodiment, an ethanologenic cassette comprises genes encoding for an alcohol dehydrogenase and a pyruvate decarboxylase. In another embodiment, an ethanologenic cassette comprises genes encoding for a bifunctional alcohol/aldehyde dehydrogenase. In certain embodiments, an ethanologenic cassette comprises genes encoding for enzymes that are part of a biochemical pathway to generate precursors for alcohol dehydrogenases and pyruvate decarboxylases of an ethanologenic cassette.

The term "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

The term "polymerase chain reaction," also termed "PCR," refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

The term "three-component cassette" as used herein refers to three genes that are part of a polynucleotide sequence having a restriction enzyme target sequence on both a 5' and 3' end of the three-component cassette. In an embodiment, the three-component cassette contains a selection marker, a counter-selection marker, and a site-specific recombinase. In another embodiment, the selection marker is an antibiotic resistance gene.

The term "photobioreactor" or "PBR" refers to a growing container for the cyanobacterial cultures. A "vPBR" means a vertical photobioreactor. An outdoor, commercial scale vPBR can have a volume of up to 100 liters or more.

An "LvPBR" or "lab-scale vertical photobioreactor" refers to a lab scale vertical photobioreactor; typically this system holds a culture volume of about 1.2 liters. As used herein, the term "mLvPBR" or "mini lab-scale vertical photobioreactor" refers to a laboratory-sized vertical photobioreactor system; typically this system holds about 0.4 liters of culture.

Database entry numbers as used herein may be from the NCBI database (National Center for Biotechnology Information; http://www.ncbi.nlm.nih.gov) or from the CyanoBase, the genome database for cyanobacteria ((http://bacteria.kazusa.or.jp/cyanobase/index.html); Yazukazu et al. "CyanoBase, the genome database for *Synechocystis* sp. Strain PCC6803: status for the year 2000", Nucleic Acid Research, 2000, Vol. 18, page 72).

The enzyme commission numbers (EC numbers) cited throughout this patent application are numbers which are a numerical classification scheme for enzymes based on the chemical reactions which are catalyzed by the enzymes.

Growth of ABICyano1

In an embodiment, methods disclosed herein are used for making an ABICyano1 markerless host cell useful for the production of a compound or compounds of interest. In comparison to other cyanobacterial species, ABICyano1 grows quickly and can tolerate and grow over a large range of various environmental stresses related to temperature, salinity, light intensity, oxygen levels, pH and the presence of contaminants including chemical and microbial contaminants. ABICyano1's ability to tolerate wide-ranging environmental parameters makes it ideally suited to growth in cyanobacterial culture systems. ABICyano1 can be genetically enhanced to express endogenous and exogenous genes used for the production of compounds of interest, such as biofuels, and still tolerates and grows over a large range of various environmental stresses related to temperature, salinity, light intensity, oxygen levels, pH and the presence of various contaminants.

Methods for cultivation of cyanobacteria in liquid media and on agarose-containing plates are well known to those skilled in the art (see, e.g., websites associated with ATCC). Any of these methods or media maybe used to culture ABICyano1 or derivatives thereof. A number of known recipes for cyanobacterial growth medium can be used. In an embodiment, BG11 medium is used for growing ABICyano1, see Stanier, R. Y., et al., Bacteriol. Rev. 1971, 35: 171-205, which is hereby incorporated by reference.

In an embodiment, the cyanobacterial strain is a fresh water strain, and BG11 is used. In another embodiment, the cyanobacteria culture grows best in a marine (salt water) medium, by adding an amount of salt to the BG11 medium. In an embodiment, marine BG11 (mBG11) contains about 35 practical salinity units (psu), see Unesco, The Practical Salinity Scale 1978 and the International Equation of State of Seawater 1980. Tech. Pap. Mar. Sci., 1981, 36: 25 which is hereby incorporated by reference.

ABICyano1 Endogenous Plasmids

ABICyano1 contains at least three endogenous plasmids. In combination with other genotypic and phenotypic attributes, these endogenous plasmids differentiate ABICyano1 from other *Cyanobacterium* species.

One endogenous plasmid is 6828 base pairs (SEQ ID NO: 1). The 6828 bp endogenous plasmid is alternatively referred to herein as pABICyano1, p6.8 or 6.8. A plasmid map of the 6828 endogenous plasmid is depicted in FIG. 1. The polynucleotide sequence, including descriptors of various portions of the polynucleotide sequence of p6.8 is depicted in FIG. 2.

Although the p6.8 plasmid was used for most of the transformation and evaluation work shown herein, one can also utilize the other two endogenous plasmids, exogenously derived plasmids, or even the chromosomal DNA, for the purpose of this invention.

The ABICyano1 endogenous plasmid p6.8 contains six open reading frames ORF 1 (SEQ ID NO: 2), ORF 2 (SEQ ID NO: 3), ORF 3 (SEQ ID NO: 4), ORF 4 (SEQ ID NO: 5), ORF 5 (SEQ ID NO: 6), and ORF 6 (SEQ ID NO: 7). With respect to the nucleotide sequence of SEQ ID NO: 1 of p6.8, ORF 1 consists of nucleotides 594 to 3779, ORF 2 consists of nucleotides 3815 to 4000, ORF 3 consists of nucleotides 4260 to 5024, ORF 4 consists of nucleotides 5350 to 6036, ORF 5 consists of nucleotides 6078 to 6341, ORF 6 consists of nucleotides 6338 to 6586, and the origin of replication consists of nucleotides 3375 to 3408.

In an embodiment, a modified p6.8 as used herein includes none or any combination of the up to six open reading frames of the endogenous p6.8.

As disclosed herein, plasmid 6.8 has been modified in vivo and in vitro for use as an extrachromosomal plasmid vector containing a three-component cassette and genes of interest for the production of compounds of interest.

In an embodiment, a modified endogenous vector derived from p6.8 from ABICyano1 was developed. The modified endogenous vector from ABICyano1 can be used to transform cyanobacteria from a broad range of genera, including ABICyano1 itself.

In certain embodiments, the present invention includes the p6.8 plasmid and modified vectors comprising sequences of the p6.8 plasmid. In an embodiment, the modified endogenous vector contains at least one of the following: a recombinant gene that encodes at least one protein involved in a biosynthetic pathway for the production of a compound or a marker protein; and an origin of replication suitable for replication in ABICyano1.

In certain embodiments, a gene coding for a replication initiation factor that binds to the origin of replication can either be present on the modified endogenous vector or can be present in the chromosomes or other extrachromosomal plasmids of ABICyano1. An origin of replication suitable for replication in ABICyano1 and the gene coding for the replication initiation factor binding to that origin of replication ensure that the modified endogenous vector can be replicated in ABICyano1.

In an embodiment, the nucleotide sequence of an origin of replication of the modified endogenous plasmid vector can have at least 80%, 90%, and 95% identity or can be identical to the nucleotides 3375 to 3408 of the sequence of the endogenous 6.8 kb plasmid (SEQ ID NO: 1).

In an embodiment, the sequence of the gene coding for the replication initiation factor has at least 80%, 90%, and 95% identity or is identical to nucleotides 594 to 3779 of the sequence of the endogenous 6.8 kb plasmid (SEQ ID NO: 1). In an embodiment, the gene coding for the replication initiation factor codes for a protein having at least 80%, 90%, and 95% sequence identity or is identical to the protein coded by nucleotides 594 to 3779 of the sequence of the endogenous 6.8 kb plasmid (SEQ ID NO: 1) of ABICyano1. This putative initiation replication factor is thought to bind to the putative origin of replication, thereby ensuring the replication of a plasmid containing the initiation factor in ABICyano1.

In an embodiment, a modified endogenous plasmid vector can contain a sequence having at least 50%, at least 55%, at least 60%, at least 65%, at least 70%, at least 75%, at least 80%, at least 85%, at least 90% or at least 95% identity to the sequence of the endogenous 6.8 kb plasmid (SEQ ID NO: 1). In another embodiment, the modified endogenous vector contains the entire p6.8 endogenous plasmid from ABICyano1.

In another embodiment, gene delivery vehicles that are developed using the endogenous 6.8 kb plasmid (or a portion of the plasmid) containing characteristic portions of the endogenous 6.8 kb plasmid may be able to be efficiently transformed into a wide range of cyanobacteria. In an embodiment, characteristic portions of the 6.8 kb endogenous plasmid from ABICyano1 include portions that enable it to replicate in a host cell (origin of replication and replication initiation factor, for example) and can be referred to as the backbone of the endogenous 6.8 kb plasmid. Such vectors may also be able to efficiently produce heterologous proteins and other compounds of interest in cyanobacterial cultures.

In another embodiment, modifications starting with the backbone of the 6.8 kb endogenous plasmid from ABICyano1 are performed individually or together to increase transformation efficiency, increase the replication rate or plasmid copy number within the cell, and to increase the production of a desired product from the cyanobacterial cell. Suitable modifications include, for example, insertion of three-component cassettes, selection markers (such as antibiotic resistance genes), recombinant genes or cassettes for the production of a desired compound, and other modifications to increase the expression or stability of the plasmid in the cyanobacterial cell. In an embodiment, the invention includes cyanobacteria, e.g. ABICyano1, comprising a modified p6.8 plasmid having any of these improved characteristics.

In yet another embodiment, codon improvement of at least one recombinant gene is performed for improved expression in the cyanobacterial host cell. Codon improvement can also be performed by adapting the codon usage of at least one recombinant gene to the codon usage in *Cyanobacterium* sp., in particular ABICyano1. In an embodiment, the G and/or C wobble bases in the codons for the amino acids in at least one recombinant gene can be replaced by A and/or T because the GC content of the genome of ABICyano1 is relatively low at about 36%.

In an embodiment, only 2% to 6% or 1% to 10% of the codons of variants of recombinant genes are codon improved. In another embodiment, highly codon improved variants of recombinant genes, at least 25%, to at least 50%, 65% or even at least 70% of the codons have been changed. In another embodiment, recombinant genes are used which are not codon improved.

Transformation of ABICyano1

Methods for producing a genetically enhanced, non-naturally occurring *Cyanobacterium* sp. and ABICyano1 host cells are disclosed herein. In an embodiment, methods include introducing a recombinant nucleic acid sequence into a cyanobacterial host cell. At least one recombinant gene can be introduced into the host cells through the transformation of the host cell by an extrachromosomal plasmid. In an embodiment, the extrachromosomal plasmid can independently replicate in the host cell. In another embodiment, at least one recombinant gene can be introduced into the genome of the host cell. In yet another embodiment, at least one recombinant gene is introduced into the genome of the host cell by homologous recombination.

In an embodiment, a recombinant nucleic acid sequence can be provided as part of an extrachromosomal plasmid containing cyanobacterial nucleic acid sequences in order to increase the likelihood of success for the transformation.

In another embodiment, the method for producing a genetically enhanced *Cyanobacterium* sp. host cell uses an extrachromosomal plasmid derived from an endogenous plasmid of the host cell to introduce a recombinant nucleic acid sequence into the host cell. This endogenous plasmid can be, for example, an extrachromosomal plasmid derived from the 6.8 kb endogenous plasmid of ABICyano1.

In another embodiment, a method for producing a genetically enhanced microbial host cell uses an extrachromosomal plasmid derived from an endogenous plasmid of the host cell. In an embodiment, the extrachromosomal plasmid contains a three-component cassette. In another embodiment, the extrachromosomal plasmid is also capable of self-replication. In yet another embodiment, the extrachromosomal plasmid contains a toxin-antitoxin cassette.

In an embodiment, the ABICyano1 6.8 kb endogenous plasmid is used as a backbone for a plasmid vector used for transformation of *Cyanobacterium* sp. Since this is the endogenous vector from the species, it is likely to be more stable when transformed into the cell than plasmids derived from completely different organisms. In an embodiment, the entire p6.8 endogenous plasmid is inserted into a vector used for transformation. In another embodiment, a sequence of about 50%, 70%, 75%, 80% 85%, 90%, 95%, 98%, 99%, or 99.5% identity to the entire endogenous plasmid sequence is inserted into the extrachromosomal plasmid vector.

In another embodiment, the p6.8 derived plasmid vector also contains an origin of transfer (oriT) which is suitable for conjugation. In particular, the plasmid vector can contain a combined origin of replication and an origin of transfer (oriVT), which enables replication in Enterobacteriaceae, in particular *E. coli*, and which also enables conjugation with, for example, an *E. coli* donor strain and *Cyanobacterium* sp., in particular ABICyano1 as a recipient strain. Such an plasmid vector can be used for triparental mating wherein a conjugative plasmid present in one bacterial strain assists the transfer of a mobilizable plasmid, for example a plasmid vector disclosed herein, present in a second bacterial strain into a third recipient bacterial strain, which can be ABICyano1.

In an embodiment for transforming host cells with p6.8 derived vectors, a shuttle vector expresses a codon-optimized antibiotic resistance gene (ABR), such as codon improved kanamycin or gentamycin resistance genes. In an embodiment, the shuttle vector is constructed based on a modular basis so that all of the key elements (replication ori, ABR gene and reporter gene) are exchangeable via unique restriction sites thus providing versatile cloning options and facilitating the delivery of genes of interest to target organisms. Other antibiotic resistance genes can be used if desired. For example, genes conferring resistance to ampicillin, chloramphenicol, spectinomycin or other antibiotics can be inserted into the vector, under the control of a suitable promoter. In some embodiments, the vector contains more than one antibiotic resistance gene.

In yet another embodiment, the p6.8 derived vector is modified by several factors so that it is capable of efficient replication in multiple types of cyanobacterial species. In an embodiment, recombinant genes are present on an extrachromosomal plasmid containing a three-component cassette having multiple copies per cell. The plasmid can be present, for example, at about 1, 3, 5, 8, 10, 15, 20, 30, 40, 50, 60, 70, 80, 90, or more copies per cyanobacterial host cell. In an embodiment, the recombinant plasmids are fully segregated from the non-recombinant plasmids in the presence of a negative selection compound such as an antibiotic. In an embodiment the three-component cassette containing plasmids are fully segregated from the excised plasmids which do not contain a three-component cassette by the dual expression of the site-specific recombinase and the counter-selection marker in a medium containing a counter-selection compound.

Exemplary methods suitable for transformation of cyanobacteria include, as non-limiting examples, natural DNA uptake (Chung, et al. (1998) FEMS Microbiol. Lett. 164: 353-361; Frigaard, et al. (2004) Methods Mol. Biol. 274: 325-40; Zang, et al. (2007) J. Microbiol. 45: 241-245), conjugation, transduction, glass bead transformation (Kindle, et al. (1989) J. Cell Biol. 109: 2589-601; Feng, et al. (2009) Mol. Biol. Rep. 36: 1433-9; U.S. Pat. No. 5,661,017), silicon carbide whisker transformation (Dunahay, et al. (1997) Methods Mol. Biol. (1997) 62: 503-9), biolistics (Dawson, et al. (1997) Curr. Microbiol. 35: 356-62; Hallmann, et al. (1997) Proc. Natl. Acad. USA 94: 7469-7474; Jakobiak, et al. (2004) Protist 155:381-93; Tan, et al. (2005) J. Microbiol. 43: 361-365; Steinbrenner, et al. (2006) Appl Environ. Microbiol. 72: 7477-7484; Kroth (2007) Methods Mol. Biol. 390: 257-267; U.S. Pat. No. 5,661,017) electroporation (Kjaerulff, et al. (1994) Photosynth. Res. 41: 277-283; Iwai, et al. (2004) Plant Cell Physiol. 45: 171-5; Ravindran, et al. (2006) J. Microbiol. Methods 66: 174-6; Sun, et al. (2006) Gene 377: 140-149; Wang, et al. (2007) Appl. Microbiol. Biotechnol. 76: 651-657; Chaurasia, et al. (2008) J. Microbiol. Methods 73: 133-141; Ludwig, et al. (2008) Appl. Microbiol. Biotechnol. 78: 729-35), laser-mediated transformation, or incubation with DNA in the presence of or after pretreatment with any of poly(amidoamine) dendrimers (Pasupathy, et al. (2008) Biotechnol. J. 3: 1078-82), polyethylene glycol (Ohnuma, et al. (2008) Plant Cell Physiol. 49: 117-120), cationic lipids (Muradawa, et al. (2008) J. Biosci. Bioeng. 105: 77-80), dextran, calcium phosphate, or calcium chloride (Mendez-Alvarez, et al.

(1994) J. Bacteriol. 176: 7395-7397), optionally after treatment of the cells with cell wall-degrading enzymes (Perrone, et al. (1998) Mol. Biol. Cell 9: 3351-3365). Biolistic methods (see, for example, Ramesh, et al. (2004) Methods Mol. Biol. 274: 355-307; Doestch, et al. (2001) Curr. Genet. 39: 49-60; all of which are incorporated herein by reference in their entireties.

Knockout of Essential Genes in Cyanobacteria

There are many essential genes, as well as conditionally essential genes, in the cyanobacterial genome, in which their complete removal would be likely to cause cell death. In an embodiment, these essential genes are removed from their original location on the chromosomal DNA and are placed on an extrachromosomal plasmid downstream of a gene of interest (such as the ethanol production gene pdc). As shown in Example 3, the knockout of several different essential (or conditionally essential) genes of ABICyano1 was conducted by use of double homologous recombination. Integrative plasmids were prepared to target (and delete) a specific gene. The integrative plasmids contained long flanking regions homologous to the upstream or downstream region of the target DNA. An antibiotic resistance marker was used between the flanking regions. Upon transformation, cells could be selected with gentamycin to select for cells having successfully gone through the double homologous recombination (and thus "knockouts" for the target gene. After multiple selection rounds to be sure that all copies of the chromosome contained the specific knockout, the cyanobacterial cells were ready to test. Using this method, as shown in Example 3, gene knockouts of essential genes narB, nirA, ureC and cobK were performed in ABICyano1. Additionally, other suitable means of deleting target essential genes that are known in the art can be used.

Transformation of ABICyano1 by Conjugation

In an embodiment, transformation of ABICyano1 with exogenous polynucleotides is performed by the conjugation technique as described in Elhai and Wolk, 1988 by using a helper plasmid pRL528.

Transformation of Other Cyanobacteria with p6.8 Derived Plasmids

In another embodiment, the modified plasmid vector based on the endogenous 6.8 kb plasmid backbone from ABICyano1, in addition to being useful for transformation to other cyanobacterial and *Cyanobacterium* sp. host cells, is used to transform other microbes including Eubacteria, Archaea and Eukaryotes. As an example, a shuttle vector containing the 6.8 kb endogenous plasmid from ABICyano1 with a kanamycin resistance cassette ($Km^R$) and the oriVT for replication in *E. coli* is transformed into *Synechococcus* PCC 7002 by natural uptake.

In another embodiment, a modified extrachromosomal plasmid, based on the endogenous 6.8 kb plasmid from ABICyano1, containing a three-component cassette and genes whose expression products produce a compound or compounds of interest is transformed into other genera of cyanobacteria. Examples of cyanobacteria that can be transformed with extrachromosomal plasmids containing three-component cassettes disclosed herein include, but are not limited to, *Synechocystis, Synechococcus, Cyanobacterium, Acaryochloris, Anabaena, Thermosynechococcus, Chamaesiphon, Chroococcus, Cyanobium, Dactylococcopsis, Gloeobacter, Gloeocapsa, Gloeothece, Microcystis, Prochlorococcus, Prochloron, Chroococcidiopsis, Cyanocystis, Dermocarpella, Myxosarcina, Pleurocapsa, Stanieria, Xenococcus, Arthrospira, Borzia, Crinalium, Geitlerinema, Halospirulina, Leptolyngbya, Limnothrix, Lyngbya, Microcoleus, Cyanodictyon, Aphanocapsa, Oscillatoria, Planktothrix, Prochlorothrix, Pseudanabaena, Spirulina, Starria, Symploca, Trichodesmium, Tychonema, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis, Iyengariella, Stigonema, Rivularia, Scytonema, Tolypothrix, Cyanothece, Phormidium, Adrianema*, and the like.

Promoters

In an embodiment, any desired promoter can be used to regulate the expression of the genes for the production of a desired compound in ABICyano1, a counter-selection marker, an antibiotic resistance marker and a site-specific recombinase and may include both endogenous as well as exogenous promoters. Exemplary promoter types include but are not limited to, constitutive promoters, and inducible promoters induced by, for example, nutrient starvation, heat shock, mechanical stress, environmental stress, metal ion concentration, and light exposure. Additional promoters, both constitutive and inducible, are well-known in the art.

In an embodiment, recombinant genes are placed under the transcriptional control (operably linked) of one or more promoters selected from exogenous or endogenous $P_{rbcLS}$, $P_{ntcA}$, $P_{nblA}$, $P_{isiA}$, $P_{petJ}$, $P_{petE}$, $P_{corT}$, $P_{smtA}$, $P_{ziaA}$, $P_{sigB}$, $P_{lrtA}$, $P_{htpG}$, $P_{hspA}$, $P_{clpB1}$, $P_{hliB}$, $P_{ggpS}$, $P_{psbA2}$, $P_{psaA}$, $P_{nirA}$, $P_{narB}$, $P_{nrtA}$, $P_{isiB}$, $P_{nrsB}$, $P_{lrtA}$, $P_{mrgA}$, $P_{pstS}$, and $P_{crhC}$. In an embodiment, synthetic promoters are used.

Recombinant genes disclosed herein may be regulated by one promoter, or they can each be regulated by individual promoters. The promoters can be constitutive or inducible. The promoter sequences can be derived, for example, from the host cell, from another organism, or can be synthetically derived.

Exemplary promoters for expression in cyanobacteria include, but are not limited to, $P_{petJ}$, $P_{psbD}$, $P_{nblA}$, $P_{rpoA}$, $P_{isiB}$, $P_{rbcLS}$, $P_{ntcA}$, $P_{nblA}$, $P_{isiA}$, $P_{petJ}$, $P_{petE}$, $P_{corT}$, $P_{smtA}$, $P_{ziaA}$, $P_{sigB}$, $P_{lrtA}$, $P_{htpG}$, $P_{hspA}$, $P_{clpB1}$, $P_{hliB}$, $P_{ggpS}$, $P_{psbA2}$, $P_{psaA}$, $P_{nirA}$, $P_{narB}$, $P_{nrtA}$, $P_{crhC}$, and additional metal ion inducible promoters and the like. Examples of constitutive promoters that can be used include, but are not limited to, $P_{rbcL}$, $P_{mpA}$, $P_{rpsL}$, $P_{rpoA}$, $P_{psaA}$, $P_{psbA2}$, $P_{psbD}$, $P_{cpcB}$. Additional details of these promoters can be found, for example, in PCT/EP2009/060526, which is herein incorporated by reference in its entirety.

In an embodiment, truncated or partially truncated versions of promoters disclosed herein can be used including only a small portion of the native promoters upstream of the transcription start point, such as the region ranging from −35 to the transcription start. Furthermore, introducing nucleotide changes into the promoter sequence, e.g. into the TATA box, the operator sequence and/or the ribosomal binding site (RBS) can be used to tailor or improve the promoter strength and/or its induction conditions, e.g. the concentration of inductor required for induction. For example, the inducible promoter can be $P_{nirA}$, and can be $P_{nirA}$ from ABICyano1, which is repressed by ammonium and induced by nitrite. This promoter may contain nucleotide changes in either one of the ribosomal binding site, the TATA box, the operator, and the 5'-UTR (untranslated region).

In certain embodiments, the present invention includes a polynucleotide comprising or consisting of any of the promoter sequences described herein, or variants thereof, including those having at least 80%, at least 85%, at least 90%, at least 95%, at least 98%, or at least 99% identity to the reference promoter sequence.

In an embodiment, disclosed herein are recombinant genes of a shuttle vector that comprise or are operably linked to an inducible promoter and/or a constitutive promoter. The promoter can be upstream of one gene to regulate that gene, or the promoter can be upstream of several genes so that one promoter regulates the expression of more than one gene. Alternatively, in some embodiments, each recombinant gene can be regulated by a separate promoter. In an embodiment, the promoter can be derived from a cyanobacterial host cell, can be derived from another cyanobacterial species, or can be derived from another organism.

In an embodiment, a promoter disclosed herein can be an inducible promoter selected from the group consisting of $P_{nirA}$, $P_{nrtA}$, and $P_{narB}$ from ABICyano1, for example. In another embodiment, a promoter is a constitutive promoter selected from the group consisting of $P_{rpsL}$, PrbcL, and $P_{cpcB}$ which can all be endogenous promoters of ABICyano1, for example.

In an embodiment, more than one recombinant gene is used in a recombinant vector. In one embodiment, a first and second recombinant gene can be controlled by one promoter, thereby forming a transcriptional operon. In another embodiment, the first and second recombinant genes are controlled by different first and second promoters.

In an embodiment, the recombinant gene under control of the promoter is induced if a sufficiently high culture density of *Cyanobacterium* sp. is reached. In the case that the second recombinant gene codes for a protein catalyzing a chemical reaction present in the wild-type *Cyanobacterium* sp., such as alcohol dehydrogenase, the gene can be under the control of either an inducible or a constitutive promoter because it does not disturb the carbon flux to the same extent as the non-native protein encoded by the first recombinant gene. The second recombinant gene then may be under the control of constitutive promoters such as $P_{rbcL}$, $P_{cpcB}$ or $P_{rpsL}$, all from ABICyano1, for example.

In an embodiment, a transcription terminator is present between the first and second recombinant gene in order to ensure a separate transcriptional control of the first and second recombinant gene and to provide for a high production of a compound of interest, such as ethanol. In certain embodiments, the present invention includes ethanologenic cassettes. In an embodiment for an ethanologenic cassette used to produce ethanol as a compound of interest, a first recombinant gene encodes pyruvate decarboxylase and the second recombinant gene encodes alcohol dehydrogenase. The first recombinant gene (pdc) is under the transcriptional control of a first inducible promoter and the second recombinant gene (adh) is under the transcriptional control of a second constitutive promoter. The first inducible promoter can be selected from, for example, $P_{nirA}$, $P_{nirA}$ variants $P_{nirA*2}$, $P_{nirA*3}$, $P_{nirA*4}$, $P_{mntc}$, $P_{smtA}$ ($P_{orf3126}$), $P_{orf221}$, $P_{orf222}$, $P_{orf223}$, $P_{orf316}$, $P_{orf3232}$, and $P_{orf3461}$ and the second constitutive promoter can be selected from, for example, $P_{rpsL}$, $P_{rpsL*4}$, $P_{rbc*(optRBS)}$, and $P_{cpcB}$.

In an embodiment, a non-naturally occurring ABICyano1 host cell comprising any of the ethanologenic cassettes described herein produces ethanol in quantities of at least 0.016% (v/v) per day in 12 h/12 h day/night cycles and a photon flux density of 230 $\mu E\ m^{-2}s^{-1}$ during the daylight phase. In certain other embodiments, the transcription of both the first and second recombinant gene encoding the pyruvate decarboxylase enzyme and the recombinant gene encoding the alcohol dehydrogenase enzymes are controlled by the same single promoter. For these embodiments, an inducible promoter may be used.

Promoter elements disclosed herein may be operably linked with any genes encoding any enzymes useful for the production of compounds of interest by using standard molecular cloning techniques.

In an embodiment, multiple combinations of inducible and constitutive promoters of varying strengths are operably linked to all genes necessary for the production of a compound of interest as well as the antibiotic resistance gene, the site-specific recombinase and the counter-selection marker that make up the self-excision cassette within an extrachromosomal plasmid.

Endogenous Promoters from ABICyano1

In an embodiment, promoters used herein can be endogenous to ABICyano1. In another embodiment endogenous promoters from ABICyano1 can be modified in order to increase or decrease efficiency and/or promoter strength. In an embodiment, and as described in US 2014/0178958, which is hereby incorporated by reference, endogenous promoters used to control the expression of genes on vectors disclosed herein include, but are not limited to promoters for cpcB, nirA, narB, nrtA, copA, mntC, smtA, rbcL, rpsL, lrtA, mrgA, nblA, ggpS, petJ, ppsA, rnpA, and pstS from ABICyano1.

In an embodiment, metal-inducible promoters may be operably linked to any of the genes necessary for the production of a compound of interest as well as the antibiotic resistance gene, the site-specific recombinase and the counter-selection marker that make up the self-excising three-component cassette within an extrachromosomal plasmid. Metal inducible promoters from ABICyano1 include, but are not limited to those previously disclosed in US 2014/0178958, such as promoters for orf0128, orf1486, orf3164, orf3293, orf3621, orf3635, orf3858, orf1071, orf1072, orf1074, orf1075, orf1542, orf1823, orf1824, orf3126, orf3389, orf0221, orf0222, orf0223, orf0316, orf3232, orf3461, and orf3749.

Several suitable promoters which are endogenous to *Cyanobacterium* sp. ABICyano1 are listed in Table 1, below:

TABLE 1

*Cyanobacterium* sp. ABICyano1 endogenous promoter sequences

| Promoter | Sequence | SEQ ID NO: |
|---|---|---|
| PnirA | AATTAATAACTTCTTCCTGTACGGGCGAATGGCCATTTGCTCCTAAC TAACTCCGTACTGCTTTGCGGAACGAGCGTAGCGAACTCTCCGAATT ACTAAGCCTTCATCCCTGATAGATGCAAAAAACGAATTAAAATTATG TGTAAAAAGAAAATGTGTCTTTATTTAGTAGTCAAAGTTACAAAATA TTAAGAATCAAATTAATAATGTATTGGGCAGTTAAGTATATAAGTCT TTAAATATTTATTTGTATTCAATATATTAACCGAGGACAAATT | 16 |
| Porf3126 (PsmtA) | CCAATATCTTGTCATACATACTTATTTGCCTCACTATTAGCCCTATAT GTCTCTATTGTATTTTTCTTTTTCTCCTATTCCTAGATCTTGTAATGAA TCATTACTCTCTGAAATATAGCTACTAATTTTATGGTTGTTTGTAAAA TATATTAACAAATGAACAATAAATCATATTTTGTGTTAATCTAATTAT TAGACAACTACTGAATTTATATTCAGATATTCACAGATAGGAGAATT TTGATT | 17 |

TABLE 1-continued

| *Cyanobacterium* sp. ABICyano1 endogenous promoter sequences | | |
|---|---|---|
| Promoter | Sequence | SEQ ID NO: |
| PnrtA | TATTATTTTTCGTTTATATGCAGATTTAGAATAAACAAAATTCATTTA CTGCAAATTTTCAAAAAAATGTGACTAAACATACAAAATAAAGAAA AAATAAAGTTTTAAATTTATGTACATCAAACTTAAGAAATGTTTAAA TTACTTAGAAATTTATAGTTC | 18 |
| Porf3461 (petJ) | TTTATATATAAACTCGAATAAAATTATCAATATAAAGTCAAACTATA TCTATCCTATTTTAACTGCTATTGGTAAGTCCCTTAATTAGTGTTGGG GTGAATAGATTTTAAAAGGGCAAACCCCCCTTTATCCTCCCTCGAGA GGGGGGAGGGCAAAAGGCAAGGGGCAAGGGAAAAATTAAGAATTA AGAATTAAAAACTCCGAACACCTGTAGGGGCGAATAGCCATTCGCT TCCCCTCATCCCCCCATCTCCCCAACACCCTAAGCCCCTACTCGTTAC TCATTTATTTACATCATTTATTTACATCATTAAGAAAAGTAACAAATT TTGACAAGTAGTCTTTTGACAGGAAAAAGCAAATTCTCGAAGATGA AAACAATAGAAAAAAATTCAATCTTACAGTAACGATGAAAAAACTT TTAGGCTTAATT | 19 |
| PnarB | TGTCTCAAAAAGACAGGTTTTTTTTATGAAAGTAATAAGAAATAAGT AGAAGTGAGGAGTTGGAAAGATAGGATTAAGAATTAGGAGTTAACT ATTTTCATTCTTTATTCTTCCATTGCCCATTGAGAAATCATATCTAAA ATCAGCAACGCCAAATTTTAGATGCAAAATAACCATAAATAAAATG CAGAAAAAAGAATACTTTAGATCTTCCGTATCAGAAGATACATTTCT TAACAAAATCTGGTGACAAGATTAAACACACGAAATCCGAGGTTTT ATATATTGATTAGTCCTAG | 20 |
| Porf1071 (PmntC) | ATTCTGTGAATTGATTAGATTTGAGGTTTTTTAAGAGGTTGATTACCT TGCCTCCAAAAAAATCATAACACACTAATGCTCTATATGAAAGGGCT TTAGACCCATAGGTTTTTGAGAAAAAAACTTGCTAACTCTCGGACAA TGTCAGCATAACTAAAGTCAATTCTTTTCGTACTTTATAATTGTCTAT AATTTAATATACAACTGTTCTGAAACTAGTTTTTCTCTACATTCCTTA GTTTTATCTGAGTAAGGTTGCTTGTAACTTAACTTCGGTTGGGCCTAA AAATATCCGATTAGGAGCAGGTGTCAGACTTTAATTAATTATTAATT ATTAATTGCTTATTGCCAACCCTCGGCGACACCACTTTTTCATCAGCC CCAGATAAAGATTGATGTTTTAGTTTTGTTTCTTTTTATCCCCTAATT CAACTAATACAAGTAAAACTAAGGTTGTTTATCAAAAATGATGGTTG ATGTTTGGGTAAATTTTAAGATATTATGAAAAGAAAATGAATAAAA AATGAAAAATCTTT | 21 |
| Porf0221 | GAATATCTCATCCTTAGCTTCTACTTATACCTTCAGCATAGTTAAAAA TCATCCCTTTATTGATGGTAATAAAAGAACAGGTTTTATTAGTGGAG TAACCTTTTTAATGCTCAATGGTTCTCACTTTACTGCTTCTGAAGTGG AAGTAGTACATATCATCCAAACCTTAGCTAGTGGCAGAATTACCGAG GAAGAATTACAACAATGGTTCGTAAGGAAAAGTAAGCAGATGAATA ATTAAAGCATCATTTCATCCTCATTTCATATTCTCCTGTCACCATGGT ATGGAAGATTAGGTAAAAATGAGGAAAAAGTTTATT | 22 |
| Porf0223 | ATACATGGTTGGTTCACTGACTTTTACCCCAGTTTTCTCTTTGAACAA TTGGCATAACTCTGAAAAAATCAGATCGGGCTTTTGTTGAATTATTT GTTCAATCAAAGCAAAACCGTGATTGTCTATTTTCTTTTTTTTCCCAC CACTCATAGATAAAAATTTATCCCGAACTCAGGTTATATTAAGTTCG GATGATCACTTAAGATAATTGATCAGATTGGTTAAGATAGAGAAAA ATTCTTTTTCATAGTGATTTCATAATTGATAGTTACAATAACGATTAT TATTTAGTAAAAAGATTTTCAAATC | 23 |
| Porf0316 | TGGTCAAGTTACTATATGTTTAGAAACAACAAAAAAAGAAGTCATTA TAAAAATAATTGATACAGGAATTGGCATTAATAAAGAAGAACAAAA ATTAATTTTTAATCGTTTTTATCGAATCAATAAAGCAAGAAATAGAG AGAAAGGCAGTTGCGGATTAGGTTTAGCTATTGCAAATGCGATCGCG CTTAATCATGGTGGTAGAATAATTTTAGAAAGTCAAGAAAATCAAG GCAGTATTTTTACCGTTTATTTACCGAAAATCATTTCATCCTAATTTC ATATTCTTTTGACAGAATCAAAGGTAAAGATAAAAAGAGAGAAACA GTC | 24 |
| Porf0128 | CCTCAACTACAAGTTCTTTTATATATTACTTTAACCTGAGTTTTGGAT AAGCTGAAAGCATTATTTTCTCGTAGTCAGAAAACCTTATAGCTTCT TAGAAATAACGATAAAATTACCTTAATCCGAACTGACGTTAAATATA TTCACCCCTATCACCCCAAAACCCTAAGCCCCTACTTCCCCCTTTCCC TTCATCACCTCATCCCCCCATCCCCTAACACTTAACCTTATTCTTTAT TCTTAAACCGAACTGAGGTGAAGTTGCAGAATACCCATGGGGGGTT ACAGCATTGTAGAAAAATAAATATTCTTTCATTATTAAGGTTGTTTG GTAAAAATATGTGAAAACCCTAATAATT | 25 |

TABLE 1-continued

*Cyanobacterium* sp. ABICyano1 endogenous promoter sequences

| Promoter | Sequence | SEQ ID NO: |
|---|---|---|
| Porf1486 | GGGGACAGACATATTTTTATCATAATGGTAAATTCATAATAATTTTA<br>GACTTTTTTTTGCAAAAATTAATCTCACTCTCTTCTTTCCCTATCTCCC<br>ATTGTTTCTTATATCCCAATGCCCCAATACCCAAAGCTCAGAAAATA<br>GGTATTAGCGAAGAGGTGTTGATCCCCTCCCCTAGCAAAATATACTC<br>CTATATAGTAAAGTGAGAAAGTGAAGAAATAAGATCAAGTTCGCAA<br>TTT | 26 |
| Porf3293 | TTGACGATTGTATTGACTTACGCCAAATGGCTTACCCTCATAGTGAA<br>TAGTTGATAATTAAGAATTAAAAATCCCGTTCACGACAGAAGGGAG<br>TGTAAGAGCCTTCGGTGCGAACTCTCATCTTCCCTGAAACCTGACAC<br>CTGAAACCTGACACCTGAAACCTGACACCTCATCTCCCTAATCCCCT<br>AATTTTAATGAAAAAATACCCTGAGTGGGCATTGAAAAAAAAGAAA<br>AGTTGTTCGACTATGAAATAAGAATTCTGCACTTCGTGAGAAAAAAG<br>GAAATGAAAT | 27 |
| Porf3621 | CTATTTAACTAGGAAAAGGTAAAGTTAAAAGGACAAGGGTAAATAA<br>TTAAAAATTAAGAATTAAGAACTTCTAACTCTCATTACTCATTACTTA<br>TTTCCTCCTCTCACCCCTTCTCCTGATCACCTCTTCTCCTCAATACTCG<br>GAACTCATTTCCCCATGGTGTGACACTCAAATCAAAAGTCTGTTATT<br>GACTTTCAGATGAAATATTACTATGATAACAATATCCCCCCTATGGG<br>TATATAAAAATATGAGCGATATTAGTTAAAAATCAAATTTGGATTTT<br>TTTTCTGAAAATATTTTAAGATTAAGTAAAGATAAGTAAAGAAATTA<br>TAAGCAATTTTGTTAAATCATACC | 28 |
| Porf3635 | CTCACACTGAAAATATTGCCACAAGAAATAAAGATCAAGCAATAAT<br>CCTGACTAAAAAGGAATAAAGTAATTATCCTTTTCCTGATATGTTAT<br>CTGACTTGTTGTTTCTTAGTCATGTTCCTTCCATTTTTATTTTTGTTTTT<br>ATCATTTTTATTACAAAAATTTCTTAATAGGGCTAAAGCATTTAGTTA<br>GTTTTTTAGCTCTCAACAAGTTGACTAATCAATATAATGCCCTAAGTT<br>AATTTGCCCTTGGTTTGACGGAGGATATTGGAAAAAAGAAACTTCTC<br>GTTGTATTTCACAGGGAAAAGGGGGAAATTTTATTAATAACTAAACA<br>ATAGAAAATAATTATTTATTTATATTATTTTGTGAACAAATGTTCAAG<br>AATTAAAGTGTAATAAGAAAATTTATTTTTTTATATTTATTTAAAACT<br>TAGATATAAGCCTAAAGGTCTGAAATTATTATTAGACAATCAATTGA<br>TTCAGAGGTAATAGTTTTTTACTTAAAAATATTTTTTCAAAATTATCC<br>CCTATTTGGGTATTGAAAAATAAATAAATTCAAGTAATAATATACAG<br>AATAAAGGAAAATCTAATCTTAAAAATTTTGTGTGTGAGGAATTGAA<br>A | 29 |
| Porf3164 | CAAATCACGAGAATTTATGTAGGGACTATTTTGGGTTGACGGTGGAG<br>AGTATGTCGCCCTTGAATTATGACCCGAAGATGAAGATGTCGGGGA<br>GGTGGAAGGACGGTCTTTAAGAGGTTTAACATCAAAGTTGGTCATAA<br>TCTCTGTCCCTGTTTGATAACTACTATTTAATTTTGAGTTGTTTTAGGT<br>ACATCAAAATACCCAAATCCTTACTCTCCCCTCAATATACAACAAAA<br>AAAACTTTTTGATTCACTTTAGTCATAAAAATTAGAATTTATCTACCG<br>AAATATTACATAAATGTAATGTATATATTTTCTGATTTATTCCGTGTG<br>AGCCATGATTCATAATTTATAATTCATAATTTCTAAATATGCCCCTAC<br>AATGGATATAGAATGTCATTTTAATTATAGGTATCATAATCGTGGTA<br>GTTACTCCGGAAAAAACTATTGAATCAAATTCAGTCTCACCTGCTAC<br>AGATAGAGTAGCCGTTATTCTT | 30 |
| Porf1072 | CTACAGGGGCAAGATTTGGCGGAAATCTATATGTGGATTCTCTTTCA<br>AGTGAAGAAGGTGCAGTGCCGACTTATCTGGACTTATTAGAATACGA<br>TATTCGCACTATTACTAATGGTTTGTTAGCAGGAGTGAACAATTAAA<br>AATTTTTTCCTAATTGACGAATAAAAAATCAATGTCAACTAATAGTT<br>AACAATACTCTCTGAAAACCAAAAATTGTCAACCAAAACATAACAT<br>AATTTTTACCCAAAAACCTCATTTATAAACTTTAAGGATAAAATCAA<br>TG | 31 |
| Porf1074 | GGGATTAGAGAGTTCAAAGTTAGGAATGAGGTGTCAGGTTTTAGGTT<br>TCAGGTTTAGGGGAGCAATGAGAAAGAGGTTTCAGGTTTCAGGTGTC<br>AGGTTGCAGGTGTCACAGGTGATGAGGGGATGGGGGATGAGGGGGA<br>AACAAGTAAGTAATAAGTGTTCGGAGTTTTTAATTCTTAATTCTTAAT<br>TTTTCCTTTGCCTCTTGCCTTTTGCCTTGTCTTAATTACTAATTTCTAA<br>TTAAAATGATTGTGTTTTCTAGTTTAGTCTCATGGTTACTTGAACCCT<br>TACAGCATAGTTTT | 32 |

TABLE 1-continued

| *Cyanobacterium* sp. ABICyano1 endogenous promoter sequences | | |
|---|---|---|
| Promoter | Sequence | SEQ ID NO: |
| Porf01075 | TTACAAACGGCGGGAATTATTATGGTAGTAGCGATGTTAGTAACCCC GGGTGCGATCGCATATTTACTTACAGATCGTTTTGATCAAATGTTAA TCTTATCAATAGTTAGTAGTGTTCTATCTTGTGTTTTAGGCACTTATT TAAGTTATCATTTTGATGTTTCTACGGGGGGAAGTATTGTCGTTTTAA TGACCATAATTTTTATTTTAGCGATGATTTTTGCTCCTAAATATGGCA TCATCAATCAAAATACCAAAATATATTCTGCTTAACTTGTTTACTGAT ACTTCAAATAATCATATAACCTATCTTCCGAGTTAAAAATAATGGAT ATTATCCAACTGAGGTCGAGAATAGAGTTTCTTTTTTGATAGAATTTT TTTACACCAGTTATTCATTACTATCATGGGATAAT | 33 |
| Porf1542 | TAATATAGTGATTATTATATAAATGCAATGTGAATCAAACCTATATTTT ACCGTACATTGACCATGGAACTTAATTTGAGGTGATTAGTAGAGGGT GCGATCGCCCTATTTGTCAAATAATAAAGATAACATTTGACATTGCT GATTGAAGACATAAAACACAGAAAAAATCAGGTAAAAATATAAAGC TAAAGTCTAAATATGGTTTACTTTTGCCTTCGACTTACAACAAAAAA TCATAGCTAGAATCACCAACGCCTAATATTTTATTTAGCTGAAATTTT GGGATGAACTTTTTGTAAAAATCGGGGGTCTAAAAATATAGCAACC ACGATATTAAATAACTGAGTGATTATTTTAATCTATTGGGGGCTTATT AACTAAATACTTGCATTTTTATGGAGGGTTTTAATT | 34 |
| Porf1823 | AAAGATTATTTTCTACAGAAGCAACCCTTTCATCTTCCGAATTTTCAG GAATTTCCTGCTTTTGTTTCTGAATATTAGCATAGGCGGCTTTTGCCC ACTCTAAAGAAGGTTGAGACTGAATTTCTGAGGTTTCAGAAGGAGC ATTAGATTGTTTATCTTCAACAACAGGAGGTTTTTGTTCAATATTTTC CTTATTCTCTTTTTTACGGCGAAACCAATTAAACATAATGATTGTGCA TAAATATTCGTTAATATATTGTAACCCTAGAAAGGAATCGGTTTCAG GTTTATCCCCAGAGAATGTGAACCTTTACAGAAAGTAAAAAGTCTAA AATCGTAGCAACAATAAATCACAGAAATTGAG | 35 |
| Porf0222 | GCGATTATCAACCACGAAAACATACAATTATTATCAAACCTGCTGAG AAATTATCCACAGAAATAGATGTTTCTGCGAAGGGAAAATGGGCTTT TCATTGCCATTTAATGTATCACATGGATGTGGGAATGTTTCGGACTA TTAATGTTATTTCCTAAAAAATAATAGTATTAAAGCCTAAAATTTTTA TAAAAAAATTCATGTCTTTTATTAGGGTGAGCATTCTTCCTTTATGTC TCCTTATTTTACCTCTTTAGAGGTAACTACAAACTTAATCAAAAAATT TAGATAATTAATTATATCA | 36 |
| Porf3232 | CATCTTTACTTTTGACTAACATTTCATAGGTATCATGACGAAAATTTT TTAGTCTGTTATATTTGTTCATGTAGAGAGATTTTAATTTGTGATTAT TTTATTTTCTCTCTATTTTTCTTTTTTGTCTTGTCCTTCCTCATTTTTCT CTACATTTAGTCTAAACTACAGCTCTTTAATCTTCAGTTTCTCTTTCCT CCTCTTCCTCATCAAGGTAATCATCCCAATTAATATCTTCTTCTTGTT CTAATTTGGGTTGAGATTGTTGTTTATCAATCATATTTCATACTCCTA AAACTTTCTTACTTATTTATCAGTTACTTTTTACCCATTTATGCAATA GTGTAGAAATTTTTTTCGATCGAGTTAATTAATTTTTATTTCAACCAT ATCTAAATAATTCTTGATGGACATTCTAGTTAACTAGAAGGTTTAAG CTAAAAATAATTATTGATATTGCCTTCGGTATAACTAACTATATCCA GAGAAAAAG | 37 |
| Porf3749 | CTCAAGAGATAGTTAAAAAACAAATAGCTTTAGTCTATCAATTAATC GAATTATTTTTACAAACAAATTTTCATAAACCCATAGAACTAGAGGA GGAAGTTATTTATGTTTAAAAATCTAAAAGAGTTTTATATTCCCCTA AAACCCCCTTAGTAAGAGTGACTTTTTTCATCATTTGCCTGTAAATTC TCCTCTTTTAATAAGAGAGCTAGGGTGTTTTAAAAGAGGATTTTATT GCTTTCCAATTCTAACTACTTCAAAAACTTATTTTATACTCAATAATT TATTAATCAAGAGGAAATTACC | 38 |
| PrbcL (Prbc) | TCGAGCGCTCGTTCCGCAAAGCGGTACGGAGTTAGTTAGGGGCTAAT GGGCATTCTCCCGTACAGGAAAGAGTTAGAAGTTATTAATTATCAAC AATTCTCCTTTGCCTAGTGCATCGTTACCTTTTTAATTAAAACATAAG GAAAACTAATAATCGTAATAATTTAACCTCAAAGTGTAAAGAAATGT GAAATTCTGACTTTTATAACGTTAAAGAGGGAAAAATTAGCAGTTTA AAATACCTAGAGAATAGTCTGGGGTAAGCATAGAGAATTAGATTAG TTAAGTTAATCAAATTCAGAAAAAATAATAATCGTAAATAGTTAATC TGGGTGTATAGAAAATGATCCCCTTCATGATAAGATTTAAACTCGAA AAGCAAAAGCCAAAAAACTAACTTCCATTAAAAGAAGTTGTTACAT ATAACGCTATAAAGAAAATTTATATATTTGGAGGATACCAAC | 39 |

TABLE 1-continued

*Cyanobacterium* sp. ABICyano1 endogenous promoter sequences

| Promoter | Sequence | SEQ ID NO: |
|---|---|---|
| PrnpA | AATAGTTGATAATTACTCGTTACTCATTACTCACTTAAACCTGCCACC<br>TGATACCTGCCACCTCTCCCCCCATCACCTCATCCCCTCAACATTCCG<br>AACCCCTTGACACTTTGAACTAAAATTGTATTAAAGTGCAAATCTGG<br>ACGGGGTTAACCAGTGTGACTTATAATAGTAAACGCTGTTTTTTATA<br>ATAAATAAGCTAAATATTTAAAAACTATGAGTAAATATACACTAAAT<br>GGTACTAGACGTAAGCAGAAAAGAACCTCCGGTTTCCGCGCCCGTA<br>TGAGAACCAAAAATGGTAGAAAAGTAATTCAAGCTCGTCGTAATAA<br>GGGTAGAAAAAGATTAGCAGTATAAAATTACTGTTAAATAAGGAAG<br>CTAAGTTTAGCATTTTAAGTTTGATATTACTAATCATTAAATTTACTG<br>TGAAATATAGGTGGGACTACCATCAAAGCATCGACTGAAACGGCGT<br>TTAAATTTCCAATCTGTTTATCAACAGGGTATTCGCCGCTCTAGTCGT<br>TATTTTATTGTCCGAGGGTTACGG | 40 |
| PrpsL | CTCCGCTTAAAAAATTTCATTTTTCGATCAAAAAAGACAAATTATTA<br>CTAATTAGCTCATGGCAATAAATAATCAGTAGTAATCTGTTTTCACA<br>TTTTATTGTTAATTTTTATTATTGCTAATATCAACCTTTTCTACTTCTG<br>CTTAATATTTTATTTATGCTCAATGGGAAAATCTGAAATAAGATTGA<br>GAACAGTGTTACCAATAGAAGTATTTAAGGTTTAAAGCATACCTTAA<br>AGATAACATTTTTTTTTGAAAAGAGTCAAATTATTTTTGAAAGGCTG<br>ATATTTTTGATATTTACTAATATTTTATTTATTTCTTTTTCCCTTAAAA<br>TAAGAGCTAAATCTGTTTTTATTATCATTTATCAAGCTCTATTAATAC<br>CTCAACTTTTTCAAGAAAAAATAATAATAATTTTTCCCTCTATTCTCA<br>TGACCTTTTAGGAAAATTAATTTTAGAAAAACTATTGACAAACCCAT<br>AAAAAATGAGATAAGATTATAGATTGTCACTGGTATTTTATACTAGA<br>GGCAAATTATATTTATATATACAAAAATGCTGTATAAAAAACATCT | 41 |
| PrpoA | AGTAAAGATTATCACCAACATCTGAAACCTGACTTCATCAACTGAGG<br>AAATAACCACTGTGGCTGTGTTTAAAATCGACTGCGTAGCAAGTAAA<br>ACTCAAAAAAATCAAGGTCAATACGGAAAGTTTGTGCTTGAACCCTT<br>AGAAAAAGGACAAGGCATAACT | 42 |
| PpsaA | CTACATCAACTAATCAAAAGTTAAGAAAAAAGATAGAAACGCCCAT<br>GAATATTAAAGATTAATCTGTGTCCTTTAACTTTTTATCCCCTTAAAA<br>GAGCATAACTAAAACATTGATAGATTTTATAAAGAAAAGTAACAAA<br>ATCTTGACTTAAATGAGAAAGGATTAAAAACCAAAGCCTTATCTGAG<br>GGAATGTTAAACAAATTTTAAATATTGTTAAGCAAGAACCACAATGG<br>TGACAAATAGCCCTTATCATCTTCAGTAATGTAGTAGTTTAAGTATTT<br>GTCGAGAGAGGAATCCCTC | 43 |
| PpsbA2 | GATCGAATTTTTGACTATTTAATAATTTCTTTACTATTCATAATATCT<br>CAAAAGACTTCTATCTTTTTAAGTAAACTACCTCCTCTAAGAATAAA<br>CACTTATTGACTATATTCCTTTTTAGTTATAAAATGGCATTTAAAGTT<br>ACTCAAAATATTTGCAATCATTCTACAAAACATAGTGTATTTCCTTGT<br>ATTAAGCGTATTGTGTCCTGTTAGATAATGTAGGAAAGATTGTGAGT<br>TGATAGGTGATAAATACATAACTCATTAGACAACAAGATAAAGTTGT<br>AGGAGTTCTAAATT | 44 |
| PpsbD | AAGAGTTTGGCATTTTTATTGGTAAGACTATTCTGAGAAAAATGTGA<br>CAATTTGTTAAAATATTTGCTAGAAATAGAAAAAGTAATTTGGCAAA<br>GATACTTAAATCGTATCGAAAAACGGAGTTACATTAACTCTAACTCA<br>TGCTATATTAAGAAAAGTTAATTGCAGATCAGTATTATTGCTGAGTA<br>GCAGTGCCGTCTCCAATAATATAAAGAGAGACAATATAAAAGTAAA<br>ACTTGACAAGTTAAAAAAAGAAAGATT | 45 |
| PcpcB | AACTTTAGATATTCGTAGTTGGCAATGTCGTAAATGCGGAACAATAC<br>ATGGAAAACATATAGATTTGTAATGAGAAAAAGTGTAAACAAATAT<br>TAAGAAAAAGATCAGAAAAATTTAACAACACGTAATAAAAAAATGC<br>GTCACTACGGGTTATAAATTTACATGAAAGGTTAAAACACTTTTCTG<br>AGACGATTTTGATAAAAAAGTTGTCAAAAAATTAAGTTTCTTTACAA<br>ATGCTTAACAAAAACTTGGTTTTAAGCACAAAATAAGAGAGACTAA<br>TTTGCAGAAGTTTTACAAGGAAATCTTGAAGAAAAAGATCTAAGTA<br>AAACGACTCTGTTTAACCAAAATTTAACAAATTTAACAAAACAAACT<br>AAATCTATTAGGAGATTAACTACA | 46 |

Codon Improvement of Recombinant Genes

At least some of the nucleic acid sequences to be expressed in cyanobacterial host cells can be codon improved for optimal expression in the target cyanobacterial strain. The underlying rationale is that the codon usage frequency of highly expressed genes is generally correlated to the host cognate tRNA abundance. (Bulmer, Nature 325:728-730; 1987). Codon improvement (sometimes referred to as codon optimization or codon adaptation) can be performed to increase the expression level of foreign genes such as antibiotic resistance genes, ethanologenic (or other compounds of interest) cassettes, and any other expressed genes on a plasmid, for example.

In an embodiment, the nucleic acid sequences of the recombinant genes are modified so that they will have improved expression in cyanobacteria. For example, the selectable marker gene that confers gentamycin or kanamycin resistance was codon optimized for higher expression in cyanobacteria. Additionally, the selectable marker gene that confers kanamycin resistance was codon optimized for higher expression in cyanobacteria. In an embodiment, as a result of codon improvement, the GC % of the antibiotic resistance genes decreased from 40-53% to 33-40%, which is similar to that of ABICyano1 coding genes (about 36% on average). The codon adaptation index (CAI) of the codon improved antibiotic resistance genes is significantly improved from less than 0.4 to greater than 0.8, which is similar to that of ABICyano1 endogenous genes.

In an embodiment, the CAI of a recombinant gene is codon improved for enhancing translation by having a codon adaptation index (CAI) of ≥0.60, preferably ≥0.70, most preferred ≥0.80 based on the codon usage table of the host cell. Table 2, below, depicts the codon usage statistics within ABICyano1.

TABLE 2

| Amino Acid | Codon | Fraction | Number | Frequency (/1000) |
|---|---|---|---|---|
| Ala | GCA | 0.293 | 20724 | 18.356 |
| Ala | GCC | 0.214 | 15144 | 13.414 |
| Ala | GCG | 0.14 | 9870 | 8.742 |
| Ala | GCT | 0.353 | 24915 | 22.068 |
| Arg | AGA | 0.347 | 16040 | 14.207 |
| Arg | AGG | 0.09 | 4158 | 3.683 |
| Arg | CGA | 0.106 | 4886 | 4.328 |
| Arg | CGC | 0.131 | 6043 | 5.353 |
| Arg | CGG | 0.039 | 1813 | 1.606 |
| Arg | CGT | 0.288 | 13329 | 11.806 |
| Asn | AAC | 0.22 | 14609 | 12.94 |
| Asn | AAT | 0.78 | 51712 | 45.804 |
| Asp | GAC | 0.193 | 11063 | 9.799 |
| Asp | GAT | 0.807 | 46399 | 41.098 |
| Cys | TGC | 0.218 | 2501 | 2.215 |
| Cys | TGT | 0.782 | 8976 | 7.95 |
| Gln | CAA | 0.806 | 43747 | 38.749 |
| Gln | CAG | 0.194 | 10554 | 9.348 |
| Glu | GAA | 0.787 | 60690 | 53.756 |
| Glu | GAG | 0.213 | 16451 | 14.571 |
| Gly | GGA | 0.324 | 22709 | 20.114 |
| Gly | GGC | 0.125 | 8720 | 7.724 |
| Gly | GGG | 0.151 | 10542 | 9.338 |
| Gly | GGT | 0.401 | 28065 | 24.859 |
| His | CAC | 0.251 | 4859 | 4.304 |
| His | CAT | 0.749 | 14516 | 12.858 |

TABLE 2-continued

| Amino Acid | Codon | Fraction | Number | Frequency (/1000) |
|---|---|---|---|---|
| Ile | ATA | 0.195 | 18334 | 16.239 |
| Ile | ATC | 0.19 | 17872 | 15.83 |
| Ile | ATT | 0.616 | 57964 | 51.342 |
| Leu | CTA | 0.088 | 10776 | 9.545 |
| Leu | CTC | 0.058 | 7129 | 6.314 |
| Leu | CTG | 0.033 | 4040 | 3.578 |
| Leu | CTT | 0.116 | 14162 | 12.544 |
| Leu | TTA | 0.571 | 69559 | 61.612 |
| Leu | TTG | 0.133 | 16235 | 14.38 |
| Lys | AAA | 0.836 | 59396 | 52.61 |
| Lys | AAG | 0.164 | 11694 | 10.358 |
| Met | ATG | 1 | 20093 | 17.797 |
| Phe | TTC | 0.172 | 8420 | 7.458 |
| Phe | TTT | 0.828 | 40450 | 35.829 |
| Pro | CCA | 0.169 | 7746 | 6.861 |
| Pro | CCC | 0.275 | 12613 | 11.172 |
| Pro | CCG | 0.066 | 3012 | 2.668 |
| Pro | CCT | 0.491 | 22560 | 19.982 |
| Ser | AGC | 0.088 | 6435 | 5.7 |
| Ser | AGT | 0.306 | 22393 | 19.835 |
| Ser | TCA | 0.14 | 10217 | 9.05 |
| Ser | TCC | 0.102 | 7465 | 6.612 |
| Ser | TCG | 0.044 | 3196 | 2.831 |
| Ser | TCT | 0.321 | 23473 | 20.791 |
| Thr | ACA | 0.26 | 15649 | 13.861 |
| Thr | ACC | 0.236 | 14251 | 12.623 |
| Thr | ACG | 0.083 | 5024 | 4.45 |
| Thr | ACT | 0.42 | 25340 | 22.445 |
| Trp | TGG | 1 | 14964 | 13.254 |
| Tyr | TAC | 0.187 | 7364 | 6.523 |
| Tyr | TAT | 0.813 | 31912 | 28.266 |
| Val | GTA | 0.28 | 18541 | 16.423 |
| Val | GTC | 0.117 | 7778 | 6.889 |
| Val | GTG | 0.184 | 12184 | 10.792 |
| Val | GTT | 0.419 | 27713 | 24.547 |
| End | TAA | 0.63 | 2495 | 2.23 |
| End | TAG | 0.22 | 848 | 0.76 |
| End | TGA | 0.15 | 591 | 0.53 |

Transformed ABICyano1

In an embodiment, genetically enhanced *Cyanobacterium* sp. host cells that lack antibiotic resistance markers, in particular ABICyano1 host cells, include at least one recombinant gene encoding at least one protein that is involved in a biosynthetic pathway for the production of a compound or marker protein. In certain embodiments, they comprise an ethanologenic cassette. In certain embodiments, the genetically enhanced *Cyanobacterium* host cells can be used for the production of various compounds of interest by culturing the host cells under harsh conditions of high temperature, high oxygen levels and in the case of the compound being ethanol, under high levels of ethanol in the medium. In an embodiment, a marker protein, or reporter protein, can be a fluorescent protein, such as a red or green fluorescent protein. In an embodiment, a marker protein, or reporter protein, can be a marker gene conferring resistance to a biocide such as an antibiotic which can be used to select for and maintain cultures of *Cyanobacterium* sp. host cells in the presence of other bacterial contaminating strains.

In another embodiment, a recombinant gene is present on an extrachromosomal plasmid that can replicate independently from the chromosomes of the *Cyanobacterium* sp. host cells such as ABICyano1. In an embodiment, the extrachromosomal plasmids described herein are present in high copy numbers in the host cells so that a compound of interest can be produced in a high yield.

Genetically enhanced *Cyanobacterium* sp., for example ABICyano1 host cells, can include further genetic enhancements such as partial deletions of endogenous genes of *Cyanobacterium* sp. or other recombinant genes which can increase the overall yield of the compound being produced by the host cells. For example, if the compound to be produced is ethanol, the genetic enhancements can relate to the knock out of endogenous genes coding for enzymes converting pyruvate or acetyl-CoA into a reserve or storage compound. In another embodiment, if the compound to be produced is ethanol, the genetic enhancements can relate to the overexpression of enzymes of the glycolysis pathway, Calvin cycle, amino acid metabolism, the fermentation pathway, the citric acid cycle, and other intermediate steps of metabolism in order to increase the production of ethanol by the *Cyanobacterium* sp. host cells. Examples of such genetic enhancements are described in PCT patent publication number WO 2009/098089, which is hereby incorporated by reference for this purpose.

In another embodiment, genetic enhancements of the genes encoding enzymes of the carbon fixation and subsequent carbohydrate metabolism (for example, pathways which compete with an ethanol production pathway) can be genetically enhanced to further increase the production of a compound of interest. Genetic enhancement targets include, but are not limited to, components of the photosystems (antennas and pigment modification), and components of the photosynthetic and respiratory electron transport systems as well as of the Calvin cycle. Genetic enhancement targets include local and global regulatory factors including, but not limited to, the two component system, sigma factors, small regulating RNAs and antisense RNAs.

In an embodiment, *Cyanobacterium* sp. host cells, e.g., ABICyano1 host cells, contain knockout mutations of endogenous genes that do not affect the toleration of being cultured in at least one of the following conditions: 1% (v/v) ethanol in the medium for at least 6, 12 or 16 weeks; 48° C., 50° C., 53 to 55° C. for at least 2 hours per day over a time period of at least 7 days, purging with 60% to 80% (v/v) oxygen (resulting in oxygen concentrations of up to 1000 µmol/L in the culture during the day).

Compounds of Interest Produced by ABICyano1

In certain embodiments, a variety of different compounds of interest can be produced using genetically enhanced ABICyano1 host cells. Plasmid vectors disclosed herein (e.g., derivatives of p6.8) can be used to carry a gene or genes involved in various biosynthetic pathways that produce a compound of interest in the ABICyano1 cell. Exemplary compounds of interest include, but are not limited to, organic carbon compounds, alcohols, fatty acids, oils, carotenoids, proteins, enzymes, biofuels, nutraceuticals, pharmaceuticals, and the like. Additional information on compounds that can be produced from cyanobacteria can be found, for example, in PCT/EP2009/000892 and in PCT/EP2009/060526, both of which are incorporated by reference herein in their entirety. Genes involved in the biosynthetic pathway for the production of a compound of interest can be inserted into the vector.

In one embodiment, propanol, 1,2-propanediol, 1,3-propanediol, butanol and their isomers are compounds of interest. In certain embodiments, genes encoding enzymes involved in isopropanol and isobutanol fermentation are incorporated into recombinant vectors and transformed into ABICyano1. Examples of enzymes involved in isopropanol fermentation include acetyl-CoA acetyltransferase (EC 2.3.1.9), acetyl-CoA:acetoacetyl-CoA transferase (EC 2.8.3.8), acetoacetate decarboxylase (EC 4.1.1.4) and isopropanol dehydrogenase (EC 1.1.1.80). Examples of enzymes involved in isobutanol fermentation include acetolactate synthase (EC 2.2.1.6), acetolactate reductoisomerase (EC 1.1.1.86), 2,3-dihydroxy-3-methylbutanoate dehydratase (EC 4.2.1.9), α-ketoisovalerate decarboxylase (EC 4.1.1.74), and alcohol dehydrogenase (EC 1.1.1.1).

In another embodiment, ethylene is produced as a compound of interest. In an embodiment, at least one recombinant gene encodes an enzyme for ethylene formation. Examples of enzymes involved in the production of ethylene include ethylene forming enzyme 1-aminocyclopropane-1-carboxylate oxidase (EC 1.14.17.4), which catalyzes the last step of ethylene formation, the oxidation of 1-aminocyclopropane-1-carboxylic acid to ethylene. The substrate for the ethylene forming enzyme is synthesized by the enzyme 1-aminocyclopropane-1-carboxylic acid synthase (EC 4.4.1.14) from the amino acid methionine.

In another embodiment, the compound of interest is isoprene. In an embodiment the recombinant vector used to transform a cyanobacterial host cell for the production of isoprene includes at least one recombinant gene encoding an enzyme such as isoprene synthase. Isoprene synthase (EC 4.2.3.27) catalyzes the chemical reaction from dimethylallyl diphosphate to isoprene and pyrophosphate.

In another embodiment, compounds of interest are terpenes and terpenoids. Terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are modified chemically, such as by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl diphosphate synthase (EC 2.5.1.1), which catalyzes the reaction of dimethylallyl diphosphate and isopentenyl diphosphate yielding farnesyl diphosphate. Another example is geranylgeranyl diphosphate synthase (EC 2.5.1.29), which catalyzes the reaction between transfarnesyl diphosphate and isopentenyl diphosphate yielding pyrophosphate and geranylgeranyl diphosphate.

In an embodiment, the compound of interest is hydrogen, and the recombinant genes can, for example, encode for hydrogenase. In an embodiment, hydrogenase is an enzyme catalyzing the following reaction: $12H^{+}+12X_{reduced}\rightarrow 6H_2+12X_{ocidized}$, where X is an electron carrier such as ferredoxin.

In an embodiment, examples of compounds of interest include non-ribosomal peptides (NRP) and the polyketides (PK). In another embodiment, alkaloids are compounds of interest.

In yet another embodiment, vitamins are compounds of interest. Vitamins are organic compounds that are essential nutrients for certain organisms and act mainly as cofactors in enzymatic reactions but can also have further importance, e.g. as antioxidants. In plants, vitamin C can be made via the L-ascorbic acid (L-AA) biosynthetic pathway starting from D-glucose. In an embodiment, recombinant genes encoding for enzymes involved in vitamin C synthesis are disclosed and include hexokinase, glucose-6-phosphate isomerase, mannose-6-phosphate isomerase, phosphomannomutase, mannose-1-phosphate guanylyltransferase, GDP-mannose-3,5-epimerase, GDP-L-galactose phosphorylase, L-galactose 1-phosphate phosphatase, L-galactose dehydrogenase, and L-galactono-1,4-lactone dehydrogenase.

In another embodiment amino acids are compounds of interest. Amino acids as compounds of interest include naturally occurring amino acids as well as amino acid derivatives.

In an embodiment, lactams are compounds of interest. In another embodiment, ethers are compounds of interest.

In yet another embodiment, alkanes (also known as saturated hydrocarbons) are compounds of interest. In an embodiment, these genes may be part of the recombinant vector and include genes encoding for acyl-ACP reductase (EC 1.3.1.9) which converts a fatty acyl-ACP into a fatty aldehyde that may subsequently be converted into an alkane/alkene by an aldehyde decarbonylase (EC 4.1.99.5).

In an embodiment, biopolymers such as polyhydroxyalkanoates (PHAs) are compounds of interest. The simplest and most commonly occurring form of PHA is the fermentative production of poly-3-hydroxybutyrate (P3HB) but many other polymers of this class are produced by a variety of organisms. PHAs include poly-4-hydroxybutyrate (P4HB), polyhydroxyvalerate (PHV), polyhydroxyhexanoate (PHH), polyhydroxyoctanoate (PHO) and their copolymers. In an embodiment, recombinant genes encoding for enzymes involved in P3HB synthesis are part of recombinant vectors. These genes include genes encoding β-ketothiolase (EC 2.3.1.9) that produces acetoacetyl-CoA which is converted to (R)-3-hydroxybutyryl-CoA (3HBCoA) by NADPH-dependent acetoacetyl-CoA reductase (EC 1.1.1.36). The 3HBCoA is subsequently polymerized by poly(3-hydroxyalkanoate) synthase (EC 2.3.1) and is converted to P3HB.

In an embodiment, esters, including fatty acid esters, are a compound of interest. Simple esters with lower chain alcohols (methyl-, ethyl-, n-propyl-, isopropyl- and butyl esters) are used as emollients in cosmetics and other personal care products and as lubricants.

In an embodiment, *Cyanobacterium* sp. host cells naturally contain the entire sequences of recombinant genes coding for enzymes used for the production of a compound of interest. In another embodiment, the *Cyanobacterium* sp. host cell contains the entire sequences of recombinant genes that encode for all of the enzymes used in a cascade of enzymatically catalyzed reactions that results in the production of a compound of interest.

In an embodiment, a first protein encoded by a first recombinant gene can produce a first intermediate which is further converted by a second protein encoded by a second recombinant gene into a second intermediate, which then in turn is further converted by a third protein encoded by a third recombinant gene into a third intermediate such that a sequence of reactions provide intermediates for the next enzyme leading to the eventual production of a compound of interest. In an embodiment, the recombinant genes encoding for the enzymes that catalyze the sequence of reactions can be introduced into ABICyano1 or other *Cyanobacterium* sp. host cells.

In an embodiment, the compounds of interest that are produced from recombinant ABICyano1 can be removed intermittently and/or continuously as the culture grows, or the compounds can be separated at the end of a batch growth period. The cultures can be grown indoors, or can be grown outdoors in enclosed containers such as bioreactors, or in another suitable type of container.

Production of Ethanol in ABICyano1

In an embodiment, the 6.8 kb endogenous plasmid vector from ABICyano1 is genetically enhanced to include recombinant genes encoding for enzymes that produce a compound of interest.

In an embodiment, a compound of interest is ethanol, and the genetic enhancements to ABICyano1 include transforming with a p6.8 based vector that comprises one or more recombinant genes encoding for an enzyme used in ethanol production. In an embodiment, the genes are adh and pdc. The gene pdc encodes for pyruvate decarboxylase (PDC), which catalyzes the interconversion between pyruvate and acetaldehyde. The gene adh encodes for alcohol dehydrogenase (Adh) which catalyzes the interconversion between acetaldehyde and ethanol. Thus, Pdc and Adh act in concert to produce ethanol. In another embodiment, the gene is adhE which encodes for AdhE enzyme (alcohol dehydrogenase E) which catalyzes the interconversion between acetyl-coenzyme A and ethanol.

Ethanol produced by non-naturally occurring ABICyano1 organisms can be measured by any means well known in the art. In an embodiment, ethanol produced by ethanologenic non-naturally occurring ABICyano1 organisms is measured using gas chromatographic analysis of a growth media and/or the headspace above a growth media.

In an embodiment, the pdc-encoding gene is from *Zymomonas mobilis*. In a further embodiment, the pdc-encoding gene is codon optimized for optimal expression in the host organism, such as AB1Cyano1. The pdc gene can be the codon optimized *Zymomonas mobilis* sequence of SEQ ID NO: 47. In another embodiment, the pdc gene can have a sequence identity of at least 85%, 90%, 95%, 97%, 99%, 99.5%, or greater in identity to SEQ ID NO: 47.

The Pdc protein can be, for example, the *Zymomonas mobilis* Pdc sequence (SEQ ID NO: 48). The gene encoding PDC can also be derived from other organisms. The Pdc enzyme can have a sequence identity of at least 85%, 90%, 95%, 97%, 99%, 99.5%, or greater in identity to SEQ ID NO: 48.

In an embodiment, Pdc activity is measured by a photometric kinetic reaction that can be monitored at 340 nm using a spectrophotometer. Pyruvate is enzymatically converted to acetaldehyde by pyruvate decarboxylase, which is reduced to ethanol by ethanol dehydrogenase under NADH oxidation. In an embodiment, the Pdc enzyme activity is related to the protein content and expressed as the specific activity of Pdc.

The Adh enzyme can be derived from numerous source organisms, and can be codon-optimized for optimal expression in the host cell, if desired. An exemplary adh gene from *Synechocystis* PCC 6803 is shown in SEQ NO: 49. The corresponding protein sequence is shown in SEQ ID NO: 50. A codon optimized version of the adh gene is present in SEQ ID NO: 51. The corresponding protein sequence is shown in SEQ ID NO: 52. Another example of an alcohol dehydrogenase gene that can be used is derived from Lyngbya sp. The codon-optimized DNA sequence is shown in SEQ ID NO: 53, wherease the corresponding protein sequence is shown in SEQ ID NO: 54.

In particular embodiments, the Adh enzyme is, for example, a $Zn^{2+}$-dependent alcohol dehydrogenase such as AdhI from *Zymomonas mobilis* (ZmAdh) or the Adh enzyme from *Synechocystis* PCC 6803 (SynAdh encoded by the synadh gene). Alternatively or in addition, the enzyme is an iron-dependent alcohol dehydrogenase (e.g. AdhII from *Z. mobilis*). The $Zn^{2+}$-dependent alcohol dehydrogenase can, for example, be an alcohol dehydrogenase enzyme having at least 60%, 70%, 80%, 90% or even more than 90% sequence identity to the amino acid sequence of $Zn^{2+}$ dependent alcohol dehydrogenase from *Synechocystis* PCC 6803. Relative to other alcohol dehydrogenases, SynAdh (annotated open reading frame slr1192 from the *Synechocystis* PCC 6803 genome) favors higher overall ethanol production because the reduction of acetaldehyde to ethanol is preferred to the reaction from ethanol to acetaldehyde. Thus, in an embodiment, a SynAdh encoding recombinant gene is useful for production of ethanol in a host cell.

AdhE is an iron-dependent, bifunctional enzyme that interconverts acetyl coenzyme A to ethanol. One characteristic of iron-dependent alcohol dehydrogenases (e.g. AdhE and AdhII) is their sensitivity to oxygen. In an embodiment, AdhE used to transform ABICyano1 is derived from thermophilic organisms such as *Thermosynechococcus elongatus* BP-1. In another embodiment, AdhE is from *E. coli*. In the case of AdhE from *E. coli*, a mutant was described that exhibited alcohol dehydrogenase activity under aerobic conditions, see Holland-Staley et al. (2000), J. Bacteriol. 182: 6049-6054. The E568K AdhE mutant of the *E. coli* AdhE was active both aerobically and anaerobically. Thus, in an embodiment, site-directed mutants of various AdhE enzymes could impart catalytic function to AdhE enzymes under both aerobic and anaerobic conditions in genetically enhanced ABICyano1 host cells.

In an embodiment, pyruvate decarboxylase can, for example, be from *Zymomonas mobilis, Zymobacter palmae*, or *Saccharomyces cerevisiae*. Nucleic acid sequences, protein sequences and properties of ethanologenic enzymes such as alcohol dehydrogenases and pyruvate decarboxylases disclosed herein, can be found, for example, in International Patent Application Publication No. WO2009098089, International Patent Application Publication No. WO2014198964, U.S. Pat. No. 9,157,101, and U.S. Pat. No. 9,127,297.

Non-Naturally Occurring, Genetically-Stable Ethanologenic Cyanobacterial Host Cells Genetic instability of ethanologenic cyanobacterial strains plays a key role in the loss of productivity of strains in indoor and outdoor bioreactors. Increased genetic stability helps keep production potential stable during scale up and throughout the duration of production in bioreactors. It also offers the ability to dilute cultures, often multiple times, after they enter the ethanol production phase, which saves on capital costs, scale up efforts, and material costs, and is a feasible outdoor strategy.

Ethanologenic cyanobacterial strains show a heavy bias for revertant cells in which the pdc is inactivated. In an embodiment, the pdc, or other gene responsible for the production of a compound of interest, may be inactivated through mutations in an operably linked promoter. In an embodiment, the pdc, or other gene responsible for the production of a compound of interest, may be inactivated through mutations in the gene. In an embodiment, the pdc, or other gene responsible for the production of a compound of interest, may be inactivated through mutations in the gene resulting in insertions and/or deletions. In an embodiment, the pdc, or other gene responsible for the production of a compound of interest, may be inactivated through mutations that result in truncation of the gene. In another embodiment, inactivation of the pdc, or other gene responsible for the production of a compound of interest, is by transposon insertions, primarily by the transposon ABIcyano1_orf0173 in the promoter or pdc coding sequence.

One method for mediating this type of reversion event is to couple the expression of pdc with an essential gene for selection against non-producer mutants. Transposon insertion in the promoter that drives pdc expression leads to the loss of expression of both pdc and the essential gene while transposon insertion in the pdc coding sequence will separate the promoter of the operon from the essential gene coding sequence. In both cases, the essential gene will not be expressed due to transposon inactivation. As a result, nonproducer mutants will not survive. Cyanobacterial cells have many genes that are essential to the cell's survival. In an embodiment, one or more of these essential genes can be chosen to be modified to produce more genetically stable cyanobacterial production cells.

Knockout of an Essential Gene

In an embodiment, a gene that is essential to the host cell survival can be deleted from its original location in a cell ("knockout") using DNA technology, such as double homologous recombination, or by other means. Because the endogenous essential gene is often present in the cell in multiple copies, a full "knockout" of all of its copies in a cell is typically employed. The essential gene can then be linked to a production gene of interest. Thus, typically, the gene is still present in the cell, but has been moved to a new location with different neighboring genes. In an embodiment, the production genes are located upstream of the essential gene in one operon, so that they must be transcribed correctly in order for the essential gene to be transcribed. This allows the cells containing active production genes to reverse the competitive disadvantage that they may have.

Knockout of Conditionally Essential Gene nirA

In an embodiment, the essential gene encodes nitrite reductase (nirA). ABICyano1 host cells are made auxotrophic for nitrate assimilation by knocking out a chromosomal copy of nirA which encodes for nitrite reductase. Thus, in an embodiment, nirA is encoded for on extrachromosomal plasmids as an essential gene operon fused to pdc through various naturally and non-naturally occurring intergenic sequences. Loss of nirA expression blocks the nitrate assimilation pathway. This makes the cell unable to grow on nitrate as the sole nitrogen source. Moreover, nitrite derived from nitrate assimilation is cytotoxic. This cytotoxicity makes the selection pressure against cells that do not express active nitrite reductase from an exogenous nirA even stronger.

In an embodiment, a knockout of the nirA gene (ABICyano1 orf0468) was made in ABICyano1 and labelled as AB0057. AB0057 is unable to grow on nitrate. To complement AB0057, multiple constructs were made in which pdc was expressed in an operon with nirA. The constructs had different intergenic sequences present between pdc and nirA. In one embodiment, different intergenic sequences between the pdc and nirA genes on the operon were tested to improve expression of the second gene in the operon, nirA.

Addition of Intergenic Sequences to Improve Expression of Downstream Genes in the Operon In polycistronic ethanologenic cassettes, genes located downstream of pdc often have different expression strengths depending on the intergenic sequence. Translation of the proteins encoded by the second and subsequent genes in an operon are affected by the neighboring genes in the operon and by the intergenic sequences in between the genes, see Pfleger et al., (2006) “Combinational engineering of intergenic regions in operons tunes expression of multiple genes” Nat. Biotech. 24:1027-1032. Pfleger et al. described a method for tuning the expression of multiple genes within operons in *E. coli* by generating libraries of tunable intergenic regions (TIGRs), recombining various post-transcriptional control elements and screening for the desired relative expression levels. TIGRs can vary the relative expression of two reporter genes over a 100-fold range and balance expression of three genes in an operon that encodes a heterologous mevalonate biosynthetic pathway, resulting in a seven-fold increase in mevalonate production. In an embodiment, a TIGR (p70rg-15) that leads to high expression of a second gene was used in an essential gene operon that contained a ribosome-binding site (RBS) that was replaced with a cyanobacterial RBS, such as that of PnirA*2. This intergenic sequence is referred to herein as a synthetic intergenic sequence (SIS).

Intergenic sequences from ABICyano1 operons that encode for naturally abundant proteins were used to improve the expression of genes in engineered operons. In an embodiment, genes that encode proteins used in the photosynthetic apparatus provide useful intergenic regions to help improve expression of all genes in an engineered operon. In one embodiment, intergenic sequences are derived from the alpha and beta subunits of phycocyanin, encoded by the cpcB-cpcA operon. Because cpcB and cpcA form heterodimers, the second gene (cpcA for the alpha subunit) of the operon should be translated as efficiently as cpcB, the first gene (beta subunit). The intergenic region cpcB-cpcA is 67 bp long. As with cpcBA, the intergenic sequence from psaAB is also useful for improving the expression of genes in an engineered polycistronic operon.

Construction and Analysis of the Essential Gene Operon Pdc-nirA

Figure 3:
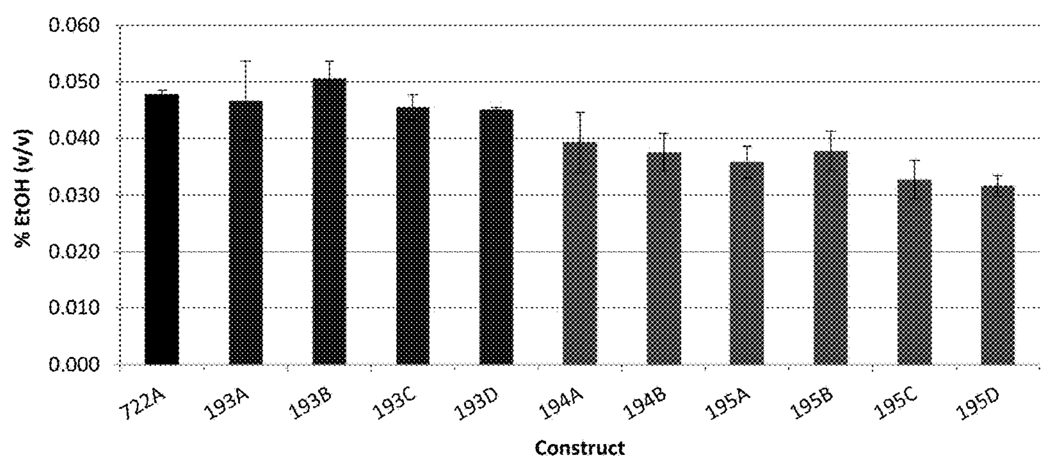
FIG. 3 is a bar graph depicting ethanol production of different nirA complementation constructs in a GC vial assay. The production is calculated as ethanol percentage per $OD_{750}$ per day.

The nirA knockout strain AB0057 was complemented with plasmids bearing the pdc gene tied to nirA such that expression of pdc was required for expression of nirA. The three constructs evaluated for increases in genetic stability have different intergenic sequences between the PDC and nirA in order to improve the expression of genes in operon form (Table 3). Three different intergenic sequences were used: 1) cpcBA intergenic sequence from ABICyano1 (pAB193), 2) psaAB intergenic sequence from ABICyano1 (pAB194) and 3) a synthetic intergenic sequence from *E. coli* using the optimized RBS from PnirA*2 (pAB195). These three constructs were transformed into AB0057 and evaluated for ethanol production and growth characteristics. FIG. 3 depicts ethanol production of different nirA complementation constructs. pAB193 produced a similar level of ethanol as the control strain pAB722, while pAB194 and pAB195 produced slightly less ethanol than the control.

Figure 4A:
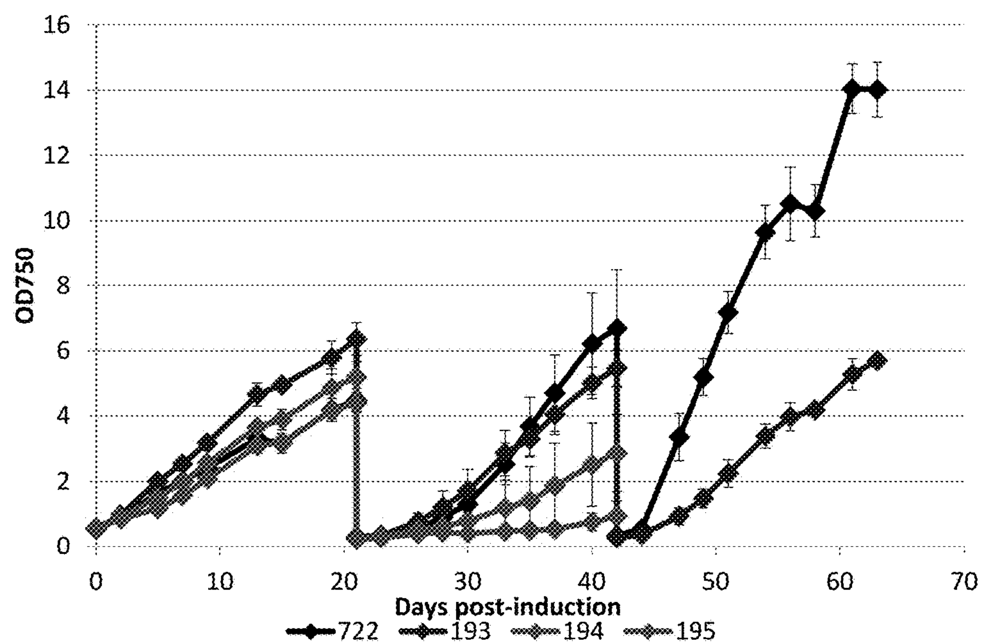
FIGS. 4A, 4B, 4C, and 4D depict average $OD_{750}$, ethanol, VLE corrected ethanol, and the percentage of revertant cells, respectively, of the nirA complementation strains and control strains in mLvPBRs.
Figure 4B:
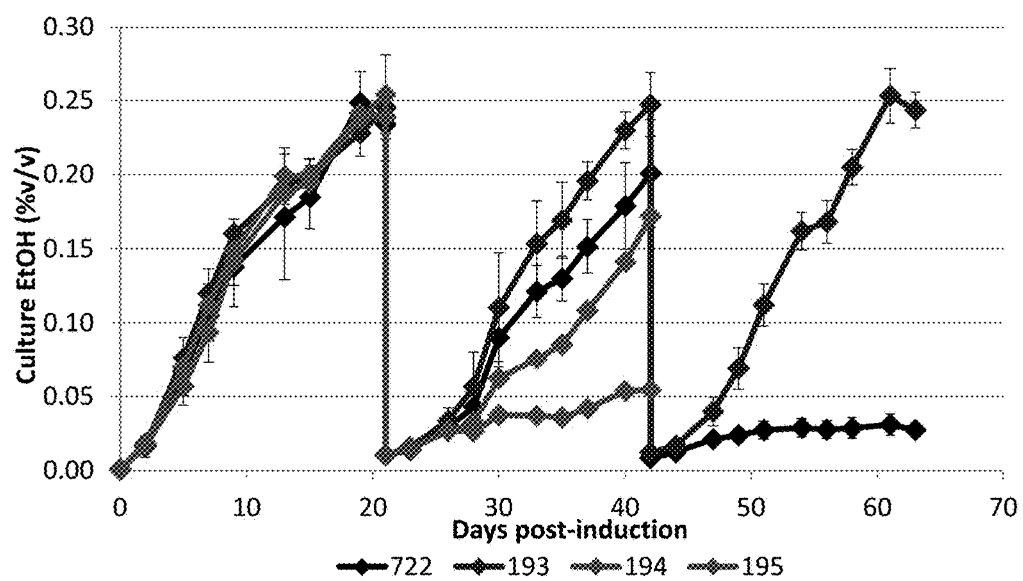
Figure 4C:
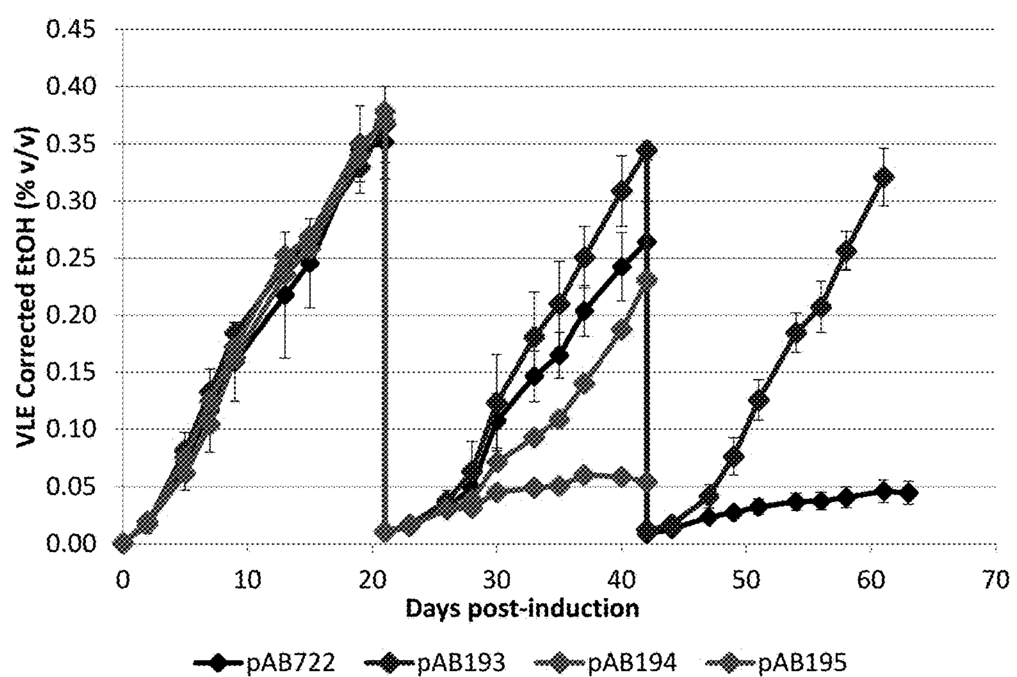

Once the constructs were evaluated in GC vials, they were then prepared for evaluation in mLvPBRs. For mLvPBR evaluation of genetic stability and ethanol production, each candidate strain was streaked out to isolate single colonies of three strains with the lowest reversion percentages. These three clones were used as biological replicates in mLvPBRs.

mLvPBRs were sampled three times a week for OD and ethanol percentages, and the VLE-corrected ethanol was calculated from the percentage of ethanol produced (FIGS. 4A, 4B and 4C). For all four strains (three isolates and a control pAB722 which is derived from p6.8 and does not contain a pdc-nirA fusion operon), the growth in the first 21-day batches as measured by $OD_{750}$ was similar (FIG. 4A). pAB193 did show better growth than the other two test strains and the control pAB722. The ethanol produced during the first batch was also similar among the four strains (FIGS. 4B and 4C). However, after the first 20:1 dilution step, pAB194 and pAB195 appeared to experience a lag in growth. Due to this lag in growth, only pAB722 and pAB193 were carried through the second dilution and into the third batch. However, even in the second 21-day batch, the control pAB722 was showing faster growth and lower ethanol production, indicating an increasing revertant percentage within these mLvPBRs. All three replicates of pAB193, in contrast, showed similar growth and ethanol production in all three 21-day batch cultures.

TABLE 3

| Construct | Description of Essential Gene/ pdc construct | Intergenic Sequence | Plasmid SEQ ID NO: | Source of Intergenic Sequence |
|---|---|---|---|---|
| pAB193 | 722-PnirA*2-pdc-IScpcBA-nirA | ABICyano1 cpcBA, 67 bp | 9 | ABICyano1 operon cpcBA |
| pAB194 | 722-PnirA*2-pdc-ISpsaAB-nirA | ABICyano1 psaAB, 283 bp | 10 | ABICyano1 operon psaAB |
| pAB195 | 722-PnirA*2-pdc-SIS-nirA | synthetic intergenic sequence with PnirA*2 RBS, 187 bp | 11 | Synthetic |

Figure 5:
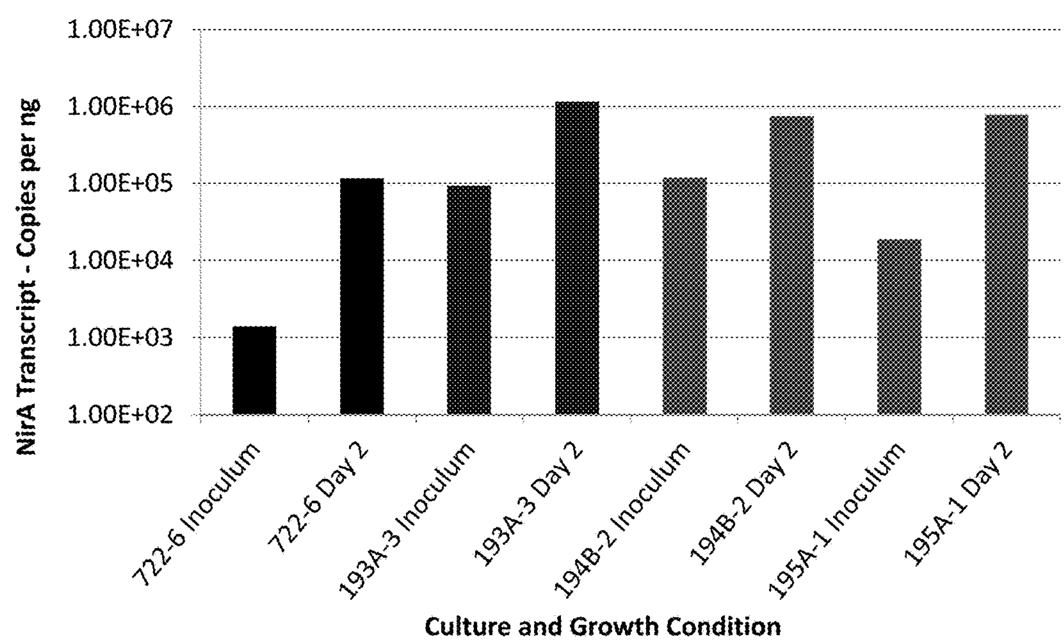
FIG. 5 is a bar graph depicting qRT-PCR quantitation of nirA gene expression in ABICyano1:pAB722 (SEQ ID NO: 8), ABICyano1:pAB193 (SEQ ID NO: 9), ABICyano1: pAB194 (SEQ ID NO: 10) and ABICyano1:pAB195 (SEQ ID NO: 11). Samples were taken from repressed inoculum and from mLvPBR evaluations on day 2.

The strains were also assayed for gene expression using qRT-PCR. Previous experiments have indicated that RNA levels peaked about 2 days after nitrate induction and steadily decline thereafter in systems driven by the PnirA*2 promoter. To assay the gene expression of the nirA, samples were taken from the repressed inoculum and from the mLvPBRs on day 2. Gene expression analysis shows an increase in gene copy number from the inoculum to day 2 for all three constructs (FIG. 5). There is also an increase in nirA expression in the control pAB722, which is to be expected with the switch from urea to nitrate as the nitrogen source. This data shows that nirA expression is induced by nitrate in all nirA complementation/genetic stability strains.

Figure 6A:
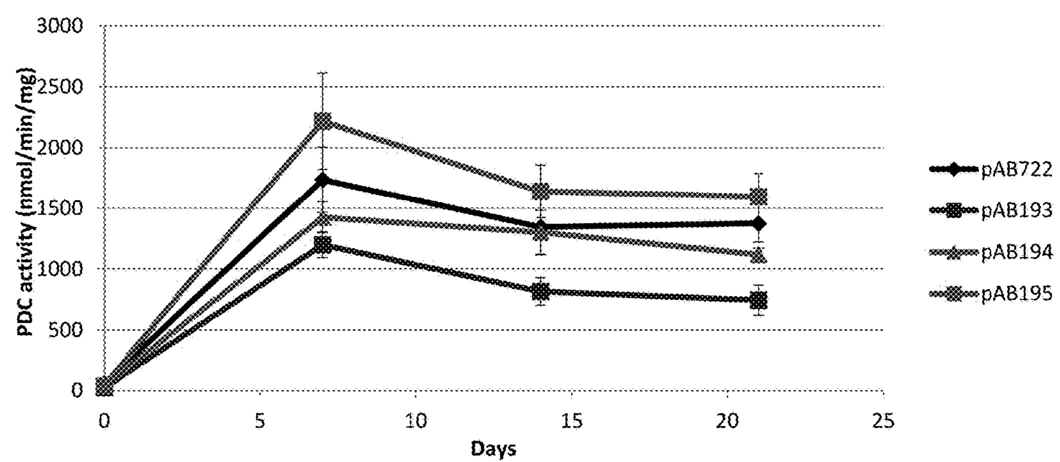
FIGS. 6A and 6B depict Pdc and Adh specific activity (nmol/min/mg), respectively, for nirA complementation strains in an mLvPBR evaluation for a first 21 day batch.
Figure 6B:
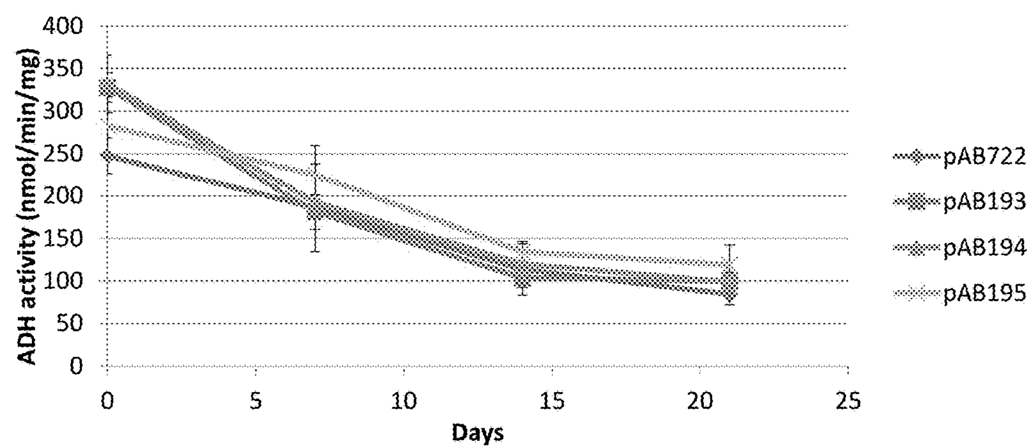
Figure 7A:
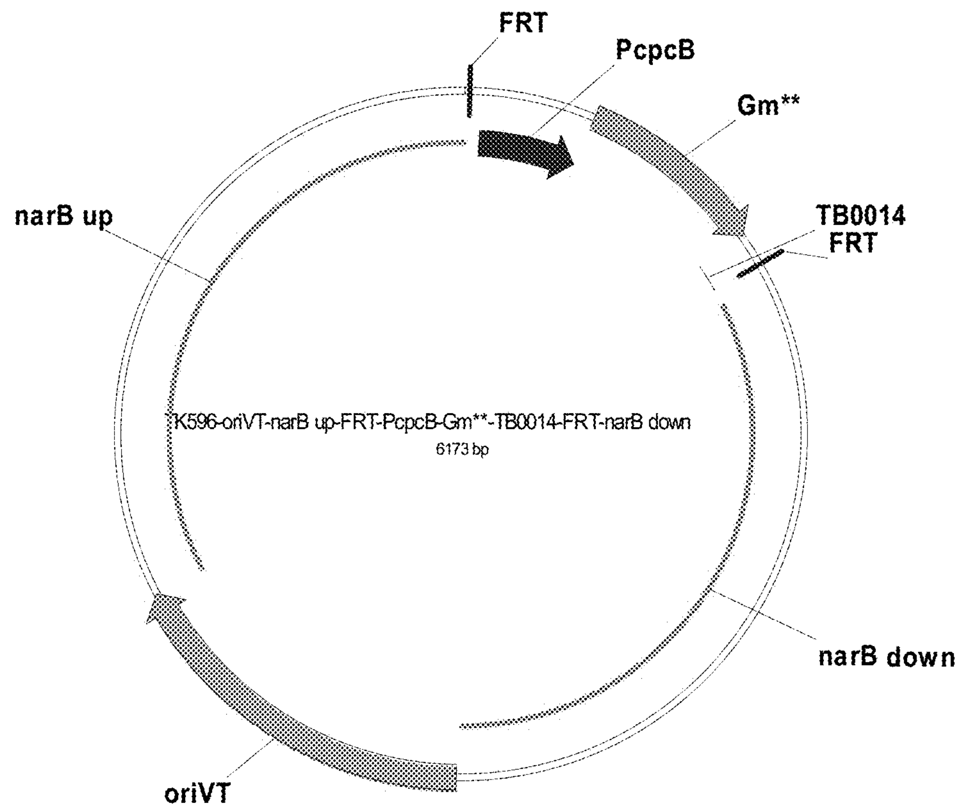
FIG. 7A is a map of plasmid #TK596 (SEQ ID NO: 12) (TK596\oriVT-narB_up-FRT-PcpcB-Gm**-TB0014-FRT-narB_down), which is an integrative construct designed for the deletion (knockout) of the nitrate reductase gene narB from the cyanobacterial genome.
Figure 7B:
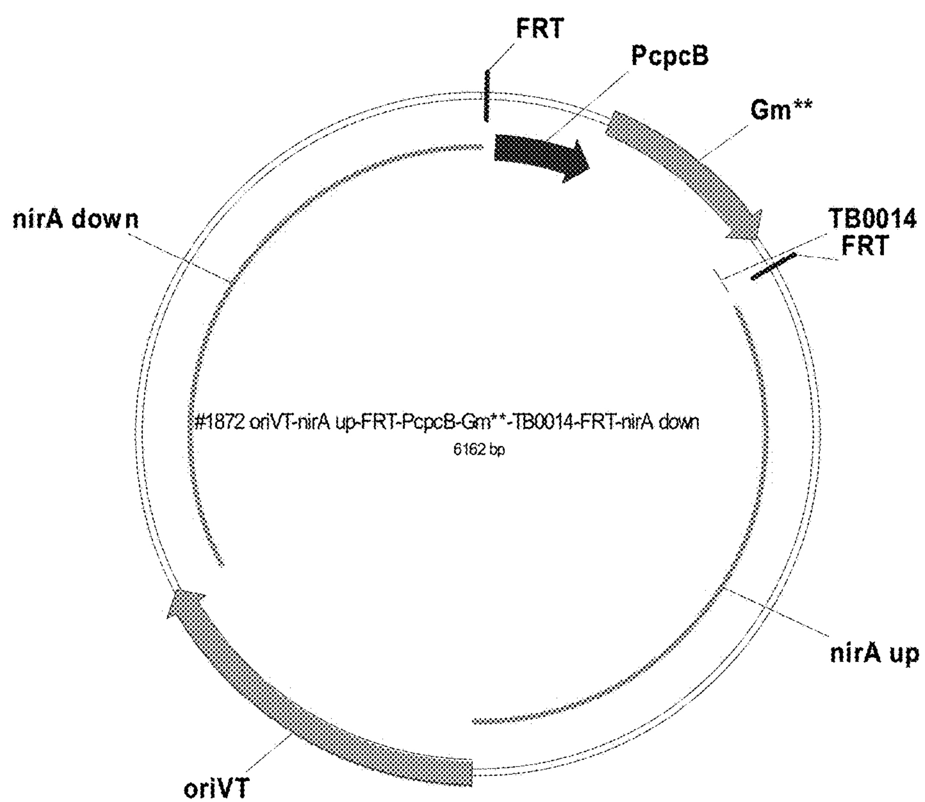
FIG. 7B is a map of plasmid #1872 (SEQ ID NO:13), (#1872\oriVT-nirA_up-FRT-PcpcB-Gm**-TB0014-FRT-nirA_down), which is an integrative construct designed for the deletion (knockout) of the nitrite reductase gene nirA from the cyanobacterial genome.
Figure 7C:
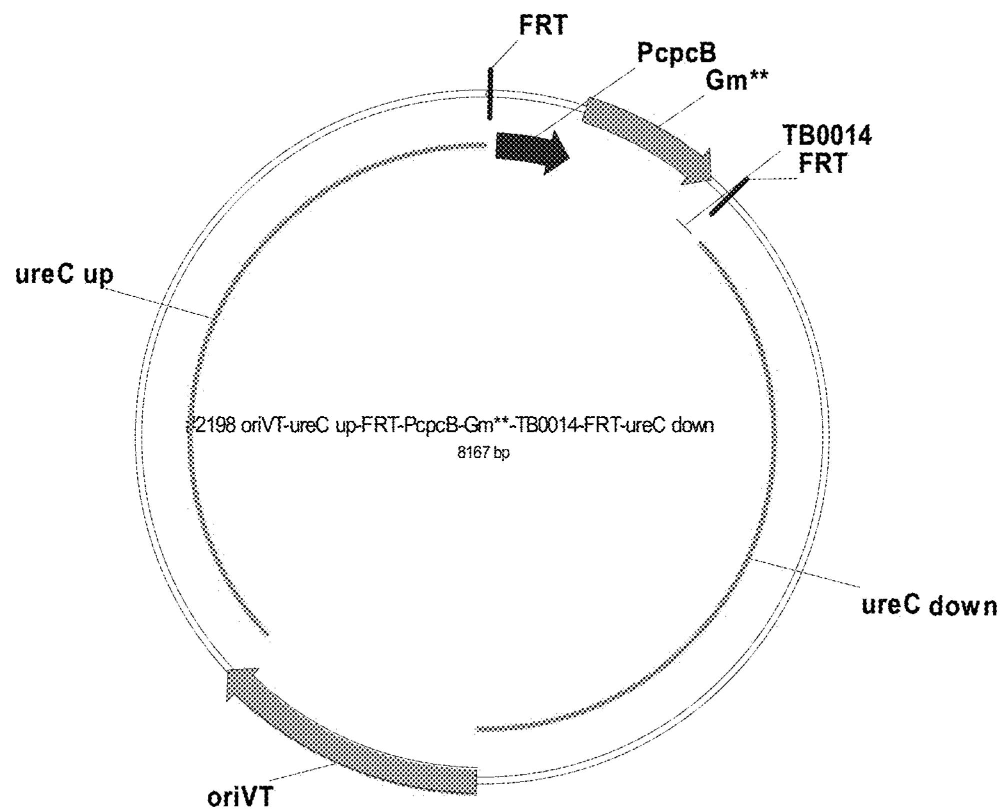
FIG. 7C is a map of plasmid #2198 (SEQ ID NO: 14), (#2198\oriVT-ureC_up-FRT-PcpcB-Gm**-TB0014-FRT-ureC_down), which is an integrative construct designed for the deletion (knockout) of the urease gene ureC from the cyanobacterial genome.
Figure 7D:
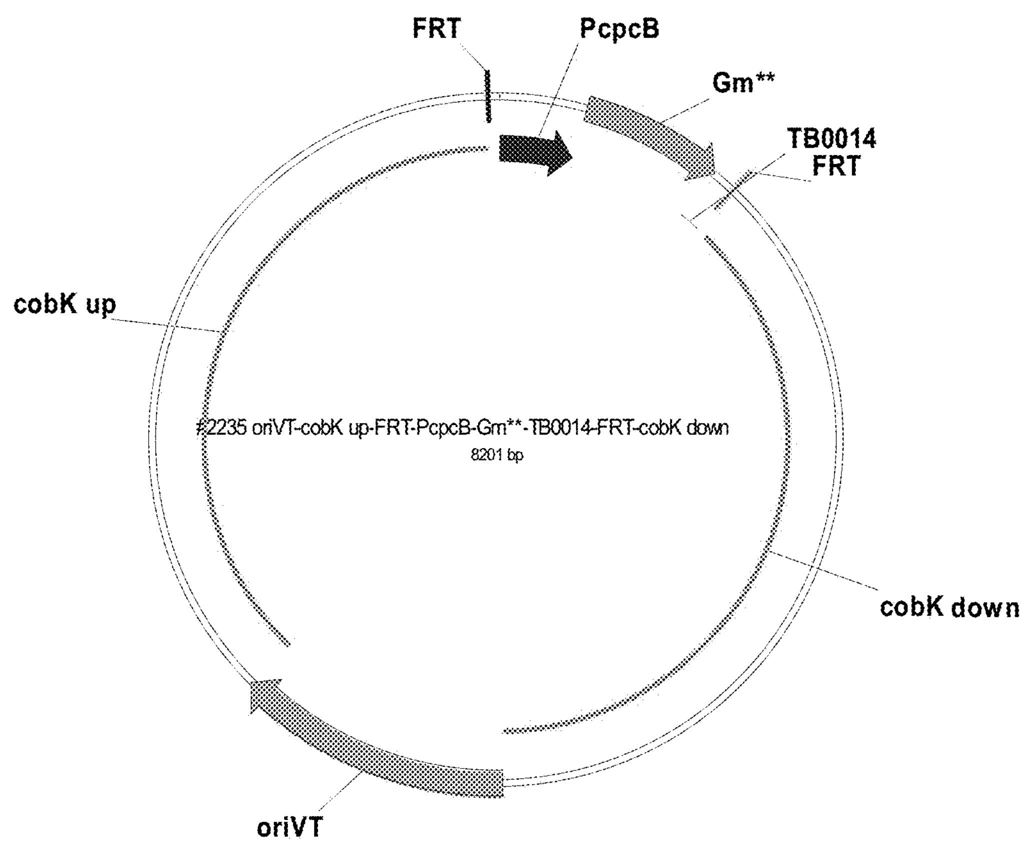
FIG. 7D is a map of plasmid #2235 (SEQ ID NO: 15) (#2235\oriVT-cobK_up-FRT-PcpcB-Gm**-TB0014-FRT-cobK_down), which is an integrative construct designed for the deletion (knockout) of the vitamin $B_{12}$ gene cobK from the cyanobacterial genome.

Pdc and Adh activity were measured weekly in the first 21-day batch for all strains, see FIGS. 6A and 6B, respectively. Pdc activity increased from the inoculum samples to day 7, then leveled off over the remaining 14 days, see FIG. 6A. Pdc levels were highest in pAB195 cultures. pAB722 (SEQ ID NO: 8) and pAB194 ((SEQ ID NO: 10) cultures had similar levels of Pdc, whereas pAB193 (SEQ ID NO: 9) showed the lowest levels of Pdc over time. The higher Pdc activity exhibited by pAB195 could be manifesting as slower growth that is seen in these cultures, while the lower Pdc activity of pAB193 could be allowing this strain to grow faster than the others. Interestingly, pAB193 grew to a higher cell density while maintaining ethanol production at a level as high as the control, implying higher carbon fixation in pAB193.

For Adh activity levels (FIG. 6B), all of the cultures showed similar activities, with the highest activity shown earlier on in the batch culture. The adh gene in these constructs is driven by PrbcL, which is responsive to light conditions. In a non-limiting embodiment, the highest activity being earlier in the batch culture can be due to an increase in culture density over time, so that less light is able to penetrate, resulting in lower Adh activity.

Thus, in an embodiment, genetic stability of ethanologenic cyanobacterial host cells has been improved, resulting in an increase in the duration of ethanol production.

Multiple Production Genes can be Present in the Essential Operon

In another embodiment, more than one gene of interest can be placed upstream of the essential gene in the essential gene operon. For example, both pdc and adh can be placed directly upstream of the nirA gene, so that all of the genes involved in ethanol production are expressed under the control of one promoter upstream of pdc. Thus, both pdc and adh would be expressed in order for the essential gene nirA to be expressed. Example 8 shows the construction of this system to produce ethanol. The method can be used to produce other desired compounds, such as, for example, 1,2-propanediol or 1,3-propanediol, by placing one to several of the production genes upstream of the essential gene, where all of the genes are controlled by the same promoter. The number of genes that can be placed upstream of the essential (or conditionally essential) gene can be, for example, from 1, 2, 3, 4, 5, 6, 7, 8, 9, 10, or more.

Other Essential Genes

In an embodiment, other genes can be made essential and then are engineered to become tied to the expression of a gene responsible for the production of a compound of interest.

In an embodiment, a non-naturally occurring ABICyano1 host cell bearing a nitrate reductase (narB) knockout can be made. Example 3 describes the construction of an integrative plasmid, as well as the transformation and selection method, that can be used to create a narB knockout strain. The narB gene can then be inserted into an operon of a plasmid that contains the pdc-adh ethanologenic construct. The narB gene can be placed immediately downstream of the pdc gene, so that it is not expressed if the pdc gene is not expressed. Similar to the method used for the nirA knockout and complementation system described above, the narB system can be utilized in cyanobacteria to create ethanologenic strains that are more stable.

In one embodiment, an ethanologenic vector contains a "pdc-urease" operon driven by a copper inducible promoter in an ABICyano1 host bearing a urease gene knock-out. An active urease requires at least seven genes: ureA, ureB and ureC encode the subunits (alpha, beta and gamma) while ureD, ureE, ureF and ureG encode for accessory peptides required for the assembly of the $Ni^{2+}$ metallocenter. In an embodiment, ureA, ureB or ureC gene could be knocked out on the chromosome and linked to pdc to form an operon in an ethanol cassette. Example 3 describes the construction of an integrative plasmid, as well as the transformation and selection method, that can be used to create the ureC knockout strain.

In an embodiment, a non-naturally occurring ABICyano1 host cell bearing a urease gene knock-out could be grown in a nitrate-containing medium with a low level of copper to repress ethanol production. Ethanol production can be induced by dilution into a medium containing a high level of copper and urea as the sole nitrogen source. In an embodiment, cells that will have lost ethanol production capacity because of transposon inactivation of the pdc-urease operon will not be able to survive in medium containing primarily only urea as a nitrogen source.

In another embodiment, cobK, a gene used for vitamin B12 biosynthesis, would be knocked out in a host cell and biosynthesis is restored by an essential operon containing a pdc gene and cobK. ABICyano1 contains an open reading frame (ABICyano1 orf3616) whose knock out can create a vitamin B12 auxotrophy in ABICyano1. Example 3 describes the construction of an integrative plasmid, as well as the transformation and selection method, that can be used to create a cobK knockout strain.

For complementation and in order to further increase genetic stability, a bicistronic essential operon can complement the auxotrophy. All complemented strains will be tested for the ability to grow without vitamin B12 supplementation and to make ethanol. Thus, in an embodiment, the essential operon approach using an ABICyano1-cobK knockout strain complemented with a plasmid such as pABICyano1_6.8::Porf0316-pdc-cobK, could significantly increase genetic stability of an ethanologenic ABICyano1 host cell.

The Essential Operon can be Located on the Chromosomal DNA

In another embodiment, the host cell can be modified so that the chosen essential gene remains present on the chromosomal DNA, but the production gene of interest is inserted directly upstream of the essential gene, so that the production gene and the essential gene are on one operon, under the control of a promoter upstream of the production gene. The production gene insertion can be performed, for example, using homologous recombination. A selectable marker can be inserted along with the production gene to allow for full segregation of the multiple chromosomal copies.

Kits for Producing Compounds of Interest

In an embodiment, a kit for producing a compound of interest includes genetically enhanced ABICyano1 host cells, a vessel for culturing the host cells and a means for illumination of the host cells. In an embodiment, the host cells of the kit produce ethanol and the means for illumination is photosynthetically active radiation from the sun. In an embodiment, the means for illumination of the host cells include lamps or light emitting diodes or a combination thereof. The vessel of the kit can be a photobioreactor which is at least partly transparent for the radiation emitted by the means for illumination of the host cells. In particular embodiments, any of the photobioreactors disclosed in the PCT application WO 2008/055190 A2, which is hereby incorporated in its entirety by reference, can be used. Furthermore the kit also can also include means for separating the compound, preferably ethanol from the growth medium as, for example, disclosed in the PCT application WO 2011/103277 A1, which is hereby incorporated in its entirety by reference.

The present disclosure is further described by the following non-limiting examples. However, it will be appreciated that those skilled in the art, on consideration of this disclosure, may make modifications and improvements within the spirit and scope of the present disclosure.

EXAMPLES

Example 1

Bacterial Strains, Growth Conditions, Selection of Transformants, and General Procedures

*Escherichia coli* (*E. coli*) strains HB101 (Promega), XL10-Gold (Stratagene), α-select (Bioline) and NEB Turbo (NEB) were grown in Luria-Bertani (LB) medium at 37° C. Ampicillin (100 μg/ml), kanamycin (25-50 μg/ml), gentamycin (15 μg/ml) and chloramphenicol (34 μg/ml) were used when appropriate. Cultures were continuously shaken overnight at 200 rpm. ABICyano1 was cultured at 30° C. in liquid BG11 fresh water medium on a reciprocal shaker at 150 rpm under continuous illumination of approximately 30-40 μmol photons/$m^{-2}$ $s^{-1}$. Cyanobacterial transformants were selected on solid BG11 medium containing 10-20 μg/ml kanamycin, gentamycin or chloramphenicol and were maintained on BG11 plates containing 20-100 μg/ml kanamycin, gentamycin or chloramphenicol.

Example 2

Preparation of Cyanobacterial Culture Medium

BG-11 stock solution was purchased from Sigma Aldrich (Sigma Aldrich, St. Louis, Mo.). Stock solutions of the antibiotics spectinomycin (100 mg/mL) and kanamycin (50 mg/mL) were purchased from Teknova (Teknova, Hollister, Calif.). Stock solution of the antibiotic gentamycin (10 mg/mL) was purchased from MP Biomedicals (MP Biomedicals, Solon, Ohio). Marine BG-11 (mBG-11) was prepared by dissolving 35 g Crystal Sea Marinemix (Marine Enterprises International, Inc., MD) in 1 L water and supplementing with BG-11 stock solution. mBG-11(IO) was prepared by dissolving 35 g Instant Ocean in 1 L water and supplementing with BG-11 stock solution. Vitamin B12 (Sigma Aldrich) was supplemented to mBG-11 to achieve a final concentration of 1 μg/L, as needed.

Example 3

Chromosomal Knockout of Target Cyanobacterial Essential Genes

Knockout of target essential genes of ABICyano1 was conducted with the help of integrative plasmids. The oriVT based plasmids contain flanking regions homologous to the up- and downstream region of the target gene of ABIcyanol. A gentamycin resistance gene is positioned in between the flanking regions in order to integrate the gentamycin resistance marker via double homologous recombination into the genome.

In order to knockout narB, nirA, ureC and cobK, ABICyano1 was conjugated with *E. coli* bearing the integrative constructs TK596 (narB) (SEQ ID NO: 12), #1872 (nirA) (SEQ ID NO: 13), #2198 (ureC) (SEQ ID NO: 14) and #2235 (cobK) (SEQ ID NO: 15). These integrative plasmids were inserted via double-crossover integration in the genome of ABICyano1, to result in a complete deletion (knockout) of the gene. Selection was conducted on BG11 plates containing gentamycin 10 μg/ml. Obtained clones were tested by PCR for double crossover integration of the gentamycin resistance marker.

Knockout of narB:

Positive clones of ABICyano1::TK596 were picked and streaked out for several rounds on nitrate free BG11 agar plates containing urea/ammonia (3 mM each) and increasing concentrations of gentamycin up to 200 μg/ml in order to force segregation. Deletion of the narB gene was verified by PCR, followed by agarose gel analysis, to determine the segregation status using specific PCR primers to detect the nirA gene.

Knockout of nirA:

Positive clones of ABICyano1::#1872 were picked and streaked out for several rounds on nitrate free BG11 plates containing urea/ammonia (3 mM each) and increasing concentrations of gentamycin up to 200 μg/ml in order to force segregation. Deletion of the nirA gene was verified by PCR, followed by agarose gel analysis, to determine the segregation status using specific PCR primers to detect the nirA gene.

Knockout of ureC:

In order to delete the ureC gene in ABICyano1, the integrative plasmid #2198 was inserted via double-crossover integration in the genome of ABICyano1. Positive clones of ABICyano1::#2198 were transferred several rounds onto BG11 plates with increasing concentrations of gentamycin up to 200 μg/ml. Segregation status was verified by PCR with specific primers to detect the ureC gene. Complete deletion of ureC was successfully achieved Knockout of cobK:

Partial knockout of the cobK gene in ABICyano1 was achieved after double-crossover integration of plasmid #2235 into the genome of ABICyano1. Positive clones of ABICyano1::#2235 were transferred several rounds on BG11 plates containing 40 μg/L vitamin B12 and gentamycin 75 μg/ml. However, complete segregation of the cobK deletion was not achieved in ABICyano1, indicating that cobK is essential under the tested selection conditions despite vitamin B12 addition.

Example 4

Transformation of ABICyano1 by Conjugation

Gene transfer to ABICyano1 was performed using conjugation. Generated plasmids containing oriVT were used for conjugation. The shuttle vectors were transformed into ABICyano1 following a modified conjugation protocol which includes the pretreatment of ABICyano1 to reduce its EPS layer. Some plasmids used in this project are listed in Table 4, below.

TABLE 4

| Plasmid | Genotype | Resistance Marker | Source |
|---|---|---|---|
| RP4 | Encodes necessary proteins for conjugation of oriT based plasmids | Amp, Kan | Fürste et al., 1989 |
| pRL528 | Helper plasmid for conjugal transfer, M. AvaI, M. AvaII | Chl | Elhai & Wolk, 1988 |

For triparental mating, *E. coli* strain J53 bearing a conjugative RP4 plasmid and *E. coli* strain HB101 harboring the cargo and the pRL528 helper plasmid (for in vivo methylation) were used (Table 2). *E. coli* strains were grown in 20 ml LB to exponential growth phase, washed twice with LB medium and resuspended in 200 μl LB medium. Then, *E.*

*coli* strains were mixed for triparental mating, centrifuged and resuspended in 100 μl BG11 medium.

For each conjugation, 25 ml of exponentially growing cyanobacterial culture ($OD_{750\ nm}$>0.5<1) was incubated with N-acetylcysteine for 24 hours at 16° C. in the dark (end concentration: 0.1 mg/ml) without shaking. This pretreatment was followed by several steps to degrade the EPS and to weaken the cell wall: the pretreated culture was pelleted at 4,600 rpm and washed with 0.9% NaCl containing 8 mM EDTA. After a second wash step with 0.5 M NaCl, the cell pellet was resuspended in 0.5 M sucrose and incubated 30-60 min at 28° C. with slow shaking (80-90 rpm). Cells were washed with 20 ml 50 mM Tris (pH 8.0), 10 mM EDTA (pH 8.0), 4% sucrose and 10 μg/ml lysozyme. After incubation at RT for 10-15 min, 20 ml TES was added to reduce/stop lysis. Then, cells were centrifuged and washed twice using i) 50 mM Tris containing 2% sucrose and 1 mM EDTA, and ii) BG11. All centrifugation steps were performed at 3,200 rpm for 10 min at 4-10° C. Resuspended cells were used for conjugation.

One hundred μl resuspended cyanobacterial and *E. coli* cultures were mixed and applied to a membrane filter (Millipore GVWP, 0.22 μm pore size) placed on the surface of solid BG11 medium supplemented with 5% LB. Petri dishes were incubated under dim light (5 μmol photons/$m^{-2}$ $s^{-1}$) for 2 days. Cells were then resuspended in fresh BG11 medium and plated onto selective medium containing 10-20 μg/ml kanamycin/gentamycin/chloramphenicol, respectively. Selection conditions were: light intensity approximately at 20-40 μmol photons/$m^{-2}$ $s^{-1}$, temperature at approximately 30° C. Once transformants were visible (approx. after 5-7 days), colonies were transferred on new plates containing 10-50 μg/ml kanamycin/gentamycin/chloramphenicol.

Example 5

Plasmids Containing Pdc-nirA Operons

Respective intergenic sequences and nirA were cloned into an ethanologenic plasmid backbone using PCR-based cloning techniques and the Invitrogen GENEART® Seamless Cloning and Assembly Kit from Life Technologies (Carlsbad, Calif., USA). The ethanologenic plasmid backbone used was pAB722 (SEQ ID NO: 8), a pABICYANO1-6.8-based vector constructed, with the following description: pABICYANO1_6.8::PnirA*2-pdc (ABICYANO1opt1)-TdsrA-Prbc*(optRBS)-synADH-Toop containing a kanamycin resistance marker. The three intergenic sequences used were the intergenic sequence from the operon cpcB-cpcA (ABICYANO1_orf2472-2471), the intergenic sequence from the operon psaA-psaB (ABICYANO1_orf3243-3241) and a synthetic intergenic sequence (SIS) known as p70rg-15 containing a cyanobacterial RBS (Pfleger et al., 2006).

Construct plasmid maps were designed using DNAStar software and pAB722 as the vector. pAB722 contains a SacI cutting site located at 22 bp downstream from the stop codon of the pdc sequence and immediately upstream of the dsrA terminator.

The PCR template for producing the nirA sequence was pAB183 plasmid, a pABICYANO1-6.8-based vector based on AB0419 in which the nirA is expressed in an operon with a codon optimized pdc gene (pdc-ABICyano1(opt1). The PCR template for each intergenic sequence was chemically synthesized by IDT DNA Technologies as either a single-stranded oligo or a gBlock. Respective oligo or gBlock sequences can be referred to in Table 5. PCR primers were designed for each respective template following manufacturer's guidelines for the Invitrogen GENEART® Seamless Cloning and Assembly Kit from Life Technologies (see Table 6 for PCR primers and associated sequences). PCR products were generated and gel purified for the nirA sequence and each respective intergenic sequence. Subsequent PCR reactions were carried out to combine respective inserts into one larger resulting insert (cpcBA-nirA, psaAB-nirA and SIS-nirA) and the resulting PCR products for the combined inserts were gel purified. The pAB722 plasmid was digested with SacI-HF restriction digest enzyme from New England Biolabs according to manufacturer's instructions to produce the linearized plasmid.

Following the manufacturer's protocol for the Invitrogen GENEART® Seamless Cloning and Assembly Kit from Life Technologies (Carlsbad, Calif., USA), the reaction was carried out for each respective combined insert as listed above with the AB0419 vector digested with SacI. The resultant constructs were transformed into *E. coli* XL10-Gold Ultracompetent Cells from Agilent Technologies. Transformed *E. coli* cultures were plated and quadrant streaked onto LBK agar plates with 50 μg/ml kanamycin (LKBm50). Plates were incubated at 37° C. overnight. Following overnight incubation, 20 colonies per construct were picked and patched onto fresh LBKm50 agar plates and allowed to incubate overnight at 37° C. Colony PCR was carried out on 8 clones of each construct and subsequent plasmid mini-preps were carried out on 3 positive clones of each construct. Plasmids were sequenced. One clone of each construct was confirmed, chosen and transformed into competent cells (*E. coli* cells (*E. coli* Top10+pRL528+pRL443 CmCb) by electroporation for subsequent transformation into ABICyano1.

TABLE 5

Intergenic Sequence PCR Templates

| Name | Sequence (5' → 3') | SEQ ID NO: |
|---|---|---|
| IScpcBA oligo | GTAATTTTTGGGGATCAATTCGAGCTCTTTAAACC AAGATTAGAAAATCCATTTCATTAACGTAAACCA ACATAATTAGGAGAAATTAATTACAATGCAAT | 55 |
| ISpsaAB_gBlock | GTAATTTTTGGGGATCAATTCGAGCTCGAATGTAA ACTTTCACTAATTTAGTGGGAAAATCTACGGCAAA ATAAGTTATAAAATAACAGATAAAGCCGTTTTTAC TAACAATAATTGTTAATAGTTGAAAGTCTATATTT ATCTTAGATTCTTCACTATTAACTAACATTTAAAA ATCAATTTAATTCCTTGCCTAGTTTCTTTTAAAGAA ATTTAATTCCGAGGGCTAGGCAAGATAAAATCCA AAATTGACCAGCGTATTTTAAACGTTGACTCTGAT TGTGTAACAGGAGAATTCCTAAAAAAAGCTATGC AA | 56 |

TABLE 5-continued

| Intergenic Sequence PCR Templates | | |
|---|---|---|
| Name | Sequence (5' → 3') | SEQ ID NO: |
| SIS_gBlock | GTAATTTTTGGGGATCAATTCGAGCTCATCTCCTG ATCCACACCCGGACATCTCCATAGTCTGGGCCAGT CTGAGGACTGGTGGATCAGGGCCGTGAATTTACA GTATTTCAGTTACCGCTCTATCCTTATCCTTATCCG CTCAAGAGCAGAGAGTTAATAGGATCCGCTAGGA TATCGGTACCGTATTTTGGATGATAAGGAGGATCA GCCTTATGCAA | 57 |

TABLE 6

| Primer names and sequences | | |
|---|---|---|
| Primer Name | Sequence (5' → 3') | SEQ ID NO: |
| IScpcBA FWD | TTTGGGGATCAATTCGAGCTCTTTAAACCAAGAT TAGAA | 58 |
| IScpcBA nirA REV | GTATTTACAGCAACAACCATTGTAATTAATTTCT CCTAA | 59 |
| ISpsaAB FWD | TTGGGGATCAATTCGAGCTCGAATGTAAACTTTC ACTAAT | 60 |
| ISpsaAB nirA REV | GTATTTACAGCAACAACCATAGCTTTTTTTAGGA ATTCTCCTGTTACACAA | 61 |
| SIS FWD | GGATCAATTCGAGCTCATCTCCTGATCCACACCC G | 62 |
| SIS nirA REV | GTATTTACAGCAACAACCATAAGGCTGATCCTCC TTATCATCCAAA | 63 |
| nirA IScpcBA FWD | TTAGGAGAAATTAATTACAATGGTTGTTGCTGTA AATACC | 64 |
| nirA ISpsaAB FWD | GAGAATTCCTAAAAAAAGCTATGGTTGTTGCTGT AAATAC | 65 |
| nirA SIS FWD | TGATAAGGAGGATCAGCCTTATGGTTGTTGCTGT AAATAC | 66 |
| nirA dsrA REV | GGTCGGGATGAAACTTGCTGAGCTCTTATTTAAC TGTTGC | 67 |

Once the plasmids were constructed, they were transformed into ABICyano1 by conjugation as described in the above examples. After transformation, candidates were repeatedly plated onto repressed medium (mBG11 nitrate free with 2 mM urea and 2 mM ammonium and 150 µg/ml kanamycin) until the cultures were cleaned of *E. coli*. Once axenic, the candidates were PCR confirmed to contain the appropriate plasmid.

Example 6

Determination of Ethanol Production Using Gas Chromatography

Two kinds of GC headspace measurements were performed:

a) REPPA (applied for clone testing and short-term characterizations of cultures cultivated in GC vials with a duration of 24 hours, and b) single GC single measurements (applied for measurements of EtOH concentrations in samples daily taken from PBR cultures) by measuring the ethanol content after transferring 0.5 mL of the PBR cultures into GC vials after certain points of time of cultivation in the photobioreactor.

Ethanol production potential for individual transformant clones was completed via REPPA—relative ethanol production potential assay. Transformant clone patches were cultured up in liquid medium of nitrate-free mBG11 (IO, instant ocean salt mixture) supplemented with 150 µg/ml kanamycin, 2 mM urea and 2 mM ammonium. After sufficient growth under light at 37° C. with shaking (120 rpm), cultures were induced for 20 hours in a vented 50-mL falcon tube. Cultures were induced by spinning the cultures down and resuspending the cells to 0.8 OD ($OD_{start}$) in 15-mL mBG11(IO). GC vial assays were then carried out the next day by resuspending the pellets to a 0.8 OD in 11-mL fresh mBG11(IO) with 90 mM sodium bicarbonate. GC vials were then incubated at 37° C. with 24-hours continuous ~90-100 µmol photons $m^{-2}s^{-1}$ light. There were 5 vials per culture (four for GC analysis and one for OD measurement). Each vial had 4 mL of air removed from and 4 mL of pure $CO_2$ directly added to the headspace. The OD at the end of incubation ($OD_{end}$) was measured from one vial; and, the average of $OD_{start}$ and $OD_{end}$ was used to report ethanol productivity as % (v/v) per $OD_{avg}$ per 24 hours.

GC single measurements did not involve the cultivation of the strains in the GC vials. GC single measurements were performed in order to characterize the long-term ethanol production of strains which were already known to produce ethanol in sufficient quantities in REPPA assays. GC single measurements further differed from REPPA measurements in the volume of the culture (2 mL in REPPA and 0.5 mL aliquots taken from a photobioreactor culture in GC single measurements). In single GC measurements only the absolute amount of ethanol produced at a certain point of time was determined, whereas the REPPA measurements determines the course of ethanol production during a certain period of time up to 24 hours of growing the cells a GC vial under constant illumination.

Headspace GC measurement of ethanol was performed for both REPPA and single gc measurements using an Agilent 7890A gas chromatograph with split/splitless (SSL) inlet and flame ionization detector coupled to an Agilent 7697A headspace autosampler. An Agilent DB-ALC1 capillary column (30 m×0.32 mm×1.8 µm) was maintained at 40° C. at 3.5 mL/min constant flow of helium and held isothermally for 5.5 minutes for separation and quantitation of the ethanol concentration in the sample. A calibration curve was constructed before each analysis using integrated peak areas resulting from ethanol standards prepared gravimetrically in 35 psu seawater in concentrations of 0.001% v, 0.01% v, 0.1% v, and 1% v using a 1/x weighted linear fit. Samples were introduced via automated headspace sampling after incubation at 85° C. for 30 minutes with high stirring into a 1 mL loop maintained at 85° C. Timing of the headspace sample introduction was as follows: 0.2 min vial pressurization to 15.1 psi, 0.2 min of loop fill, 0.05 min of loop equilibration, and 0.5 min of inject time. The headspace sample was then transferred to the GC via a 125° C. capillary transfer line into the SSL inlet at a temperature of 250° C. and a split ratio of 25:1. Detection was performed with a flame ionization detector held at 300° C. with a fuel gas flow of 30 mL/min, an air flow of 300 mL/min, and a makeup gas flow of 25 mL/min. The ethanol concentration of the sample was calculated from the peak area obtained compared to the aforementioned calibration curve.

Example 7

Evaluation of nirA Complementation/Essential Gene Operon Strains

AB1Cyano1:pAB193 (SEQ ID NO: 9), AB1Cyano1:pAB194 (SEQ ID NO: 10), and AB1Cyano1:pAB195 (SEQ ID NO: 11) were evaluated in photobioreactors (mLvPBRs) in comparison with a control strain AB1Cyano1:pAB722 (SEQ ID NO: 8). All cultures were streaked onto mBG11 nitrate free, 2 mM ammonium, and 2 mM urea plates with 150 μg/mL kanamycin directly from cryo preserved cultures. Six single colonies for each of the strains were patched onto the same medium, and then tested for the presence of the pdc/nirA operon. Strains that lacked a functional pdc/nirA operon were labelled as revertants. As an example, the presence or absence of the pdc/nirA operon could be detected through immunofluorescence techniques. The three candidates with the lowest revertant percentages were spread-plated onto the same repression medium described above. The plate cultures were then scraped into 150 mL bottles with natural well water (NWW) supplemented with nitrate-free (NF) BG-11 nutrients containing 5.5 mM Urea and 150 μg/mL kanamycin. The bottles were grown for 5 days with constant 1% $CO_2$ bubbling before being used to inoculate the mLvPBRs.

The following procedure describes the standard lab conditions under which a 0.4 L "mini lab vertical photobioreactor" (mLvPBR) was operated as well as the necessary parts, ports, etc. to construct this 0.4 L vPBR. mLvPBRs were made from the fusion of 5 cm inner diameter, 5.7 cm outer diameter Pyrex tubing (National Scientific Company, Inc.) and Corning Pyrex 100-mL screw cap media storage bottles (Fisher Scientific 16157-103). A 20.3 cm section of Pyrex tubing was welded between the bottom 1.3 cm and top 6.4 cm of the bottle (including the screw cap threads). Eagle Laboratory Glass Company (Painesville, Ohio) performed all glassware fabrication. The filling volume was about 0.4 L leading to a liquid height of about 21.5 cm and a headspace of about 4.5 cm. Caps were fitted with straight tapered ⅛" to 7/32" barbed polypropylene couplings (Fisher Scientific 15-315-28A), one each for gas inflow, gas outflow, and sampling. The diffuser consisted of a 1.5" section of EPDM 3/16" inner diameter tubing, which was perforated 12 times per inch by a standard sewing machine with a 60 gauge needle and attached to a polypropylene elbow fitting at the end of a section of tubing extending to the bottom of the reactor. On one side of the mLvPBR, a uniform 230 μmol $m^{-2}s^{-1}$ light surface generated by a light panel of 4×T5HO 54 W 6500K fluorescent bulbs operating in a 12/12 hour day/night cycle. The temperature was set to 30° C.±4° C. during day/night from light source heating/cooling. Culture mixing and introduction of gasses was attained by constant air bubbling through perforated EPDM tubing. Gas flow was delivered at ~22 mL $min^{-1}$ to each reactor via a set of 30 μm machined restriction orifice with a head pressure set at 27 psiG. Gas flow operated in constant sparging mode (day and night) with a fixed $CO_2$ supply of 0.25% at night and 0.5-6.0% supply during the day depending on growth and pH. The standard cell density for starting a cultivation experiment $OD_{750\ nm}$=0.2 in 35 psu natural well water amended with BG11 nutrients, 17 mM Nitrate and 0.75 mM Urea.

Each culture was inoculated into one mLvPBR, so each strain was evaluated using three biological replicates. Strains were inoculated by dilution of cultures into mLvPBRs to an initial Optical Density ($OD_{750}$) of 0.3 with an initial culture volume of ~400 mL. Cultures were maintained at ambient air with a range of 25 to 28° C. during the night with an increase to ~33° C. during the photoperiod (due to heating from the light source). Light was supplied from one side of the reactor with a homogeneous light field set to 230 μmol photons/$m^{-2}$ $s^{-1}$ to approximate the average annual irradiance observed at a 4:1 height to space ratio from outdoor vPBR cultures. Introduction of gasses was done via the same type of tubing currently in use in large-scale vPBRs (smooth EPDM). The length of gas tubing (ca. 4 cm) in each reactor was representative of the length per chamber in a 17 L-vPBR. Gas flow was set 30 mL $min^{-1}$ (scaled to match 0.5 L min-1 for a 17 L-vPBR) and delivered through machined restriction orifices to eliminate the need for mass flow controllers. $CO_2$ was delivered constantly from 0.5-5%; and, the percentage was controlled based on OD and pH over time. The standard cell density for starting a cultivation experiment $OD_{750\ nm}$=0.2 in 35 psu natural well water amended with BG11 nutrients, 17 mM Nitrate and 0.75 mM Urea.

After initial inoculation, cultures were grown in a 21-day batch. At day 21, cultures were diluted 20:1 into new mLvPBRs. The second batch was also grown for 21 days, after which a second 20:1 dilution step was performed. The third batch was 21 days in length as well, for a total of 9 weeks of cultivation. The effect of these several dilutions on various measurements, such as OD, ethanol levels, and the percentage of cells that were no longer able to produce ethanol, can be found in FIGS. 4A, 4B, 4C, and 4D.

The same strains were evaluated twice in mLvPBRs. For the first round of evaluation, 17 mM nitrate was used. The second round of evaluations used 23 mM nitrate. For both evaluations, OD and ethanol measurements were taken three times per week.

Samples for Pdc activity (FIG. 6A) and Adh activity (FIG. 6B) were taken weekly for the first three weeks of the evaluation.

Ethanol in the culture (FIG. 4B) was quantified by headspace analysis via gas chromatography as described in the examples above. To correct for ethanol loss due to venting, ethanol concentration in the headspace was assumed to be in equilibrium with ethanol or acetaldehyde in the culture. Ethanol losses to the vapor phase were estimated using a vapor-liquid equilibrium (VLE) model. The venting-loss corrected ethanol data was calculated by adding the ethanol venting loss and the culture ethanol concentration. Data generated were then presented as VLE-corrected ethanol (%, v/v) (FIG. 4C).

Cell population analysis (FIG. 4D) was performed every week, utilizing either colony counting on a solid medium plate (for the first two weeks) or by immunofluorescence techniques. For the plate counting method, cultures were diluted to an $OD_{750}$ of 1.0, then serially diluted to appropriate levels for obtaining countable numbers of revertant cells. The diluted samples were plated onto mBG11 plates containing Instant Ocean sea salt (Spectrum Brands, Blacksburg, Va., USA). Revertant cells were defined as colony forming units (CFUs) that appeared larger than other colonies. The larger colonies indicate the loss of ethanol production and thus were able to grow faster and produce larger colonies (as found by previous research, data not shown). The total number of cells plated was obtained by counting the lowest dilution, usually $10^{-4}$ or $10^{-5}$.

An immunofluorescence method was used after the first two weeks of culture growth. This method used flow cytometry to determine the percentage of cells still producing the PDC enzyme. For this method, samples were fixed, immunostained to recognize the PDC protein, and then analyzed by use of flow cytometry.

Results:

Host Cell Growth Rate:

As shown in FIG. 4A, the control strain had a higher growth rate over time (as measured by $OD_{750}$), particularly during the later stages of the culture. By the third dilution, the effect was particularly pronounced.

Ethanol Production:

As shown in FIG. 4B, however, ethanol production was higher in the nirA complementation strain than in the control strain. Again, the difference became more pronounced during the later stages of the culture. A similar result was seen when the ethanol was corrected for vapor loss ("VLE corrected"). Thus, the nirA complementation strain was capable of producing much more ethanol over a longer time than the control strain. In fact, the control strain produced very little ethanol by the end of the run. This data clearly shows that the nirA complementation method, as an essential gene system, does indeed result in an increased stability of ethanol production in the cyanobacterial cells. The increased ethanol level in comparison to the control was particularly strong after several dilutions of the culture, as can be seen in FIG. 4B and FIG. 4C.

Figure 4D:
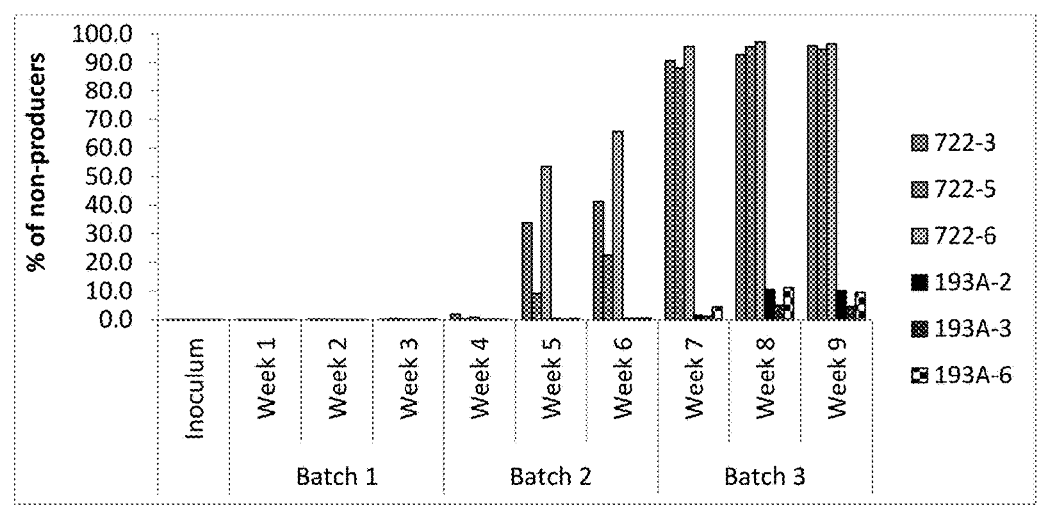

Genetic Stability of Production Gene(s):

A significant reason for this difference in ethanol production can be seen in FIG. 4D, showing that the control strain had a higher percentage of cells that were no longer making ethanol, which became more pronounced throughout the run. These cells had reverted by mutations (often in or upstream of the pdc gene) that inactivated the ethanol producing cassette. While the nirA complementation strains were likely to have a similar mutation rate as the control strains, the cells (in the nirA complementation strains) that mutated to inactivate ethanol production were also unable to express nirA, so those cells died, rather than being able to grow faster, as in the control strains. Because these cells could grow faster than the ethanol producing cells, they were capable of taking over the entire control culture by the end of the run: by week 9, the reversion rate of the control strain was almost 100%. Again, the difference between the induced culture having the essential operon system and the control became more pronounced over time, particularly after several culture dilutions occurred (FIG. 4D). The data shows that the nirA gene works well as an essential gene, and that the essential gene operon method is capable of increasing the stability of the ethanol producing cells over time. This is particularly useful for outdoor, long-term commercial growth of the cyanobacterial cultures to produce a product, such as ethanol.

Example 8

Three Gene nirA Complementation/Essential Gene Operon Strains

The use of the essential operon system, with nirA as the essential gene, was also demonstrated with both ethanol production genes pdc and adh located immediately upstream of the nirA gene on the same operon. This gene arrangement generally necessitates that both pdc and adh be adequately expressed in order for the nirA gene to be expressed.

Respective pdc, adh, and nirA genes were cloned into an ethanologenic plasmid backbone. The ethanologenic plasmid backbone used was a pABICYANO1-6.8-based vector containing a kanamycin resistance marker. The promoter PnirA*2, pdc, intergenic sequence IScpcBA*1, adh, and nirA genes were PCR-amplified using plasmid vectors that contain the elements as templates. All of the PCR products were cloned into the pABICYANO1-6.8-based vector containing a kanamycin resistance marker to create plasmid #2286.

The nirA complement strain AB1Cyano1:#2286 (SEQ ID NO: 68) was evaluated in photobioreactors (LvPBRs). All cultures were grown in 20 mL mBG11 nitrate free (NF), 2 mM ammonium, and 2 mM urea directly from cryo preserved cultures. The cultures were then inoculated into 50 mL of the same medium. 50 mL cultures were then inoculated into 700 mL bottles with natural well water supplemented with BG-11 nutrients containing 5.5 mM Urea to a starting density of $OD_{750}$ of 0.2. The bottles were grown for 5 days with constant 1% $CO_2$ bubbling before being used to inoculate the LvPBRs.

The following procedure describes the standard lab conditions under which a 1.2 L "vertical photobioreactor" (LvPBR) was operated as well as the necessary parts, ports, etc. to construct this 1.2 L vPBR. LvPBRs were constructed via fusion of 5 cm inner diameter, 5.7 cm outer diameter Pyrex tubing (National Scientific Company, Inc.) and Corning Pyrex 100-mL screw cap media storage bottles (Fisher Scientific 16157-103). A 28" section of Pyrex tubing was fused between the two top halves of a 100 mL glass media bottle including the screw cap threads so that port caps could be constructed on the bottom and top of the reator. An additional glass pH probe port was fused into the middle of the glass reactor at an angle. Eagle Laboratory Glass Company (Painesville, Ohio) performed all glassware fabrication. The filling volume was about 1.2 L. The LvPBR was equipped with several ports for operation: a sampling port (on the top of the LvPBR), a $gas_{in}$ port (on the bottom of the LvPBR), a pH probe port, a $medium_{in}$ port (on the top of the LvPBR), a $medium_{out}$ port (on the bottom of the LvPBR) and a $gas_{out}$ port (on the top of the LvPBR). The standard light conditions was a uniform light field from one side with 350 $\mu mol\ m^{-2}s^{-1}$ at the LvPBR surface generated by a light panel which consists of 8 T5 54 W 6500K fluorescent bulbs operating in a 12/12 hour day/night cycle. Introduction of gasses was done via a diffuser on the bottom reactor cap, which consisted of a 1.5" section of EPDM 3/16" inner diameter tubing, which was perforated 12 times in a concentric circle around the diffuser then attached to the reactor cap via a polypropylene luer fitting.

The mixing was realized via the ascending air bubbles through the liquid culture. The gas flow was operating in a constant sparging mode (day and night) with air enriched with max 4% $CO_2$ introduced on demand via pH control (pH setpoint=7.3, day and night) and a flow rate of 38 mL min'. The standard cell density for starting a cultivation experiment $OD_{750}$ nm=0.2 in 35 psu natural well water amended with BG11 nutrients, 17 mM Nitrate and 0.75 mM Urea.

Each culture was inoculated into three LvPBR. Strains were inoculated by dilution of cultures into LvPBRs to an initial $OD_{750}$ of 0.2 with an initial culture volume of ~1.2 L. Cultures were maintained at ambient air with a range of 25 to 28° C. during the night with an increase to ~33° C. during the photoperiod (due to heating from the light source). Light was supplied from one side of the reactor with a homogeneous light field set to 350 μmol photons $m^{-2}s^{-1}$. Introduction of gasses was done via medium walled EPDM diffusers. Gas flow was set 30 mL $min^{-1}$. $CO_2$ was delivered constantly from 0.5-5%; and, the percentage was controlled based on pH over time. After initial inoculation, cultures were grown in a 31-day batch.

Example 9

The Essential Gene Operon can be Located on the Chromosomal DNA

The production gene can also be inserted into the host cell chromosome, so that it is positioned directly upstream of the chosen essential gene. Using nirA as an example of the essential gene, a construct for homologous recombination is prepared based on the known sequence surrounding the chosen essential gene. The construct is designed so that once it is positioned in the cell, it will replace the promoter of the endogenous nirA gene. An inducible promoter is present upstream of the production gene. A kanamycin resistance gene is placed in the construct. After transformation, selection for the transformed sequence is performed by adding kanamycin, and selection for full segregation is performed by a sequential series of plating onto agar plates with increasing amounts of kanamycin. Full segregation is verified by PCR and agarose gel electrophoresis. The modified host cells are tested for their ability to make the product, as well as long term stability of the gene insertion in the host cell.

Example 10

RNA Extraction and qRT-PCR

Cultures were sampled into 15 mL or 50 mL centrifuge tubes cooled on ice. When sampling respective culture, a total of approximately 15.2 $OD_{750}$ was collected. Samples were centrifuged at 12,000×g for 10 minutes at 4° C. and placed back on ice once centrifugation was complete. The supernatant was pipetted off and discarded. Pellets were resuspended in 300 μL of RNA Resuspension Buffer (10 mM sodium acetate, 200 mM sucrose, 5 mM EDTA) and placed back on ice. Once all pellets were resuspended, samples were transferred off of ice. A volume of 900 μL of Z6 Extraction Buffer (8M guanidine hydrochloride, 50 mM β-mercaptoethanol, 20 mM EDTA, 20 mM MES, pH7.0) was added and samples were incubated for 5 minutes at room temperature. During the incubation, samples were mixed by inverting (15 mL tubes) or swirling (50 mL tubes) the tubes three times every 1 minute. Each culture suspension was transferred to a 1.5 mL screw cap microcentrifuge tube, flash frozen using liquid nitrogen, and then stored at −80° C. until extraction.

Total RNA was extracted using known RNA extraction protocols. For this method, the previously processed frozen culture suspension was thawed on ice. Once thawed, each culture suspension was mixed well by pipetting then divided and transferred into 2×1.5 mL screw cap microcentrifuge tubes. To each tube, 300 μL of hot (65° C.) Acidic Phenol was added and incubated for 15 minutes at 65° C. in an Eppendorf Thermomixer at 1,400 rpm. Following the incubation, tubes were centrifuged for 2 minutes at 17,000×g at 4° C. Each supernatant was transferred into a fresh 2.0 mL screw cap microcentrifuge tube. To each supernatant transferred, 0.5 volume of chloroform:isoamyl alcohol (24:1) was added for phase extraction. Tubes were shaken vigorously by hand for 15 seconds to mix, then centrifuged for 5 minutes at 17,000×g at 4° C. The aqueous phase was transferred to a new 2.0 mL screw cap microcentrifuge tube and 1 volume of phenol:chloroform:isoamyl alcohol (25:24:1) was added. Tubes were shaken vigorously by hand for 15 seconds to mix, then centrifuged for 5 minutes at 17,000×g at 4° C. The aqueous phase was transferred to a new 2.0 mL screw cap microcentrifuge tube and 1 volume of chloroform:isoamyl alcohol (24:1) was added. Tubes were shaken vigorously by hand for 15 seconds to mix, then centrifuged for 5 minutes at 17,000×g at 4° C. The aqueous phase was transferred to a new 2.0 mL screw cap microcentrifuge tube and 1 volume of chloroform:isoamyl alcohol (24:1) was added. Tubes were shaken vigorously by hand for 15 seconds to mix, then centrifuged for 5 minutes at 17,000×g at 4° C. The replicate aqueous phases were transferred and combined at this step into one fresh 2.0 mL screw cap microcentrifuge tube and 1 volume of chloroform:isoamyl alcohol (24:1) was added. Tubes were shaken vigorously by hand for 15 seconds to mix. Tubes were centrifuged for 5 minutes at 17,000×g at 4° C. The aqueous phase was transferred to a fresh 2.0 mL round bottom flip snap-cap microcentrifuge tube and 1 volume of 100% isopropanol was added and pipetted up and down to mix. In order to precipitate the RNA, tubes were incubated at −20° C. for a minimum of 2 hours.

Following the precipitation incubation, tubes were centrifuged for 30 minutes at 17,000×g at 4° C. The supernatant was removed and the pellet was washed with 1 mL of 75% Ethanol. Tubes were centrifuged for 5 minutes at 13,000×g at 4° C. The ethanol wash step was repeated for a total of 3 times. Following the removal of the ethanol after the last wash step, tubes were left open to air dry the pellet at room temperature for approximately 5 minutes. The pellet was resuspended in 75 μL nuclease-free water and transferred to a fresh 1.5 mL V-bottom flip snap-cap microcentrifuge tube. RNA samples were kept on ice. The concentration (ng/μL), 260/280 and 260/230 ratios were recorded using the NanoDrop. 260/280 ratio values were expected to be between 1.8 and 2.2, whereas 260/230 ratios were expected to be greater than 1.

RNA samples were treated with DNase and cleaned using the Invitrogen TURBO DNA-free kit from Life Technologies. qPCR using Applied Biosystems Power SYBR Green PCR Master Mix from Life Technologies was performed with primers specific to the ABICyano1 enolase gene (refer to Table 5) to check for any residual genomic DNA contamination in the RNA samples. All RNA samples resulted in no amplification above threshold level and were deemed to be clear of DNA. Synthesis of cDNA was performed using the Invitrogen Superscript VILO cDNA Synthesis Kit from Life Technologies that utilizes random hexamer primers.

The expression of pdc and nirA was quantified using SYBR green based qRT-PCR. qRT-PCR reactions were carried out using Applied Biosystems Power SYBR Green PCR Master Mix from Life Technologies. Primers and sequences used for pdc and nirA can be referred to in Table 7. A single-stranded oligo (ssDNA equivalent to each respective cDNA) of pdc and nirA was chemically synthesized by IDT DNA Technologies. Respective oligo sequences can be referred to in Table 8. Each respective ssDNA oligo was dissolved and the stock was used to prepare solutions at 12 concentrations. A volume of 2.5 μL of the standard at each concentration was used in qRT-PCR per reaction in duplicate to generate the standard curve. The final standard curve concentration range for each oligo was $5\times10^7$ copies to $1\times10^2$ copies. A volume of 2.5 μL of each sample was used as template such that cDNA was tested in duplicate and controls were tested singly. Transcript levels were expressed as copies per nanogram of total RNA, which was based on the respective standard curve generated using qRT-PCR from the known quantity of ssDNA oligo of the target gene as described above (FIG. 5).

TABLE 7

Primer names, respective targets and sequences

| Primer Name | Target | Sequence (5' → 3') | SEQ ID NO: |
|---|---|---|---|
| ABICyano1 eno 713F | Enolase (genomic) | CCGGCACAGATGTAGCTTTA | 69 |
| ABICyano1 eno 794R | Enolase (genomic) | AAACTCACTGGGAGAATGGG | 70 |
| PDCmax 629F | PDC | GCGATAAAGTTGCCGTGTTA | 71 |
| PDCmax 697R | PDC | CCACCTAAAGCATCAGCAAA | 72 |
| ABICyano1 nirA 752F | nirA | AATTATGCGCGGCTATTCTT | 73 |
| ABICyano1 nirA 823R | nirA | AACCACATTAAACGGGCTTT | 74 |

TABLE 8 ssDNA Oligo names and sequences

| ssDNA Oligo Name | Sequence (5' → 3') | SEQ ID NO: |
|---|---|---|
| PDCopt1 oligo | GAA GAA ACC TTA AAA TTT ATT GCC AAT CGC GAT AAA GTT GCC GTG TTA GTT GGT TCT AAA TTA AGA GCT GCT GGT GCT GAA GAA GCT GCT GTT AAA TTT GCT GAT GCT TTA GGT GGT GCA GTT GCT ACT ATG GCT GCT GCC AAA TCT T | 75 |
| nirA_ Oligo | ATG AAG AAG TAT TGA AAT TAT GCG CGG CTA TTC TTA GTG TTT ATA GTG AGT GTG CAT TGG AAG AAG GTT TGA GGG AAA ATA GAG CAA AAG CCC GTT TAA TGT GGT TAA TTG ATA AAT GGG GT | 76 |

What is claimed is:

1. A non-naturally occurring auxotrophic cyanobacterial cell capable of production of a compound of interest via the expression of at least one exogenous gene wherein the auxotrophic cyanobacterial cell contains an extrachromosomal plasmid comprising the at least one exogenous gene and a gene whose expression complements the auxotrophy of the non-naturally occurring auxotrophic cyanobacterial cell and wherein the at least one exogenous gene and the gene whose expression complements auxotrophy form a polycistronic operon wherein the at least one exogenous gene and the gene whose expression complements auxotrophy are both operably linked to a promoter such that expression of the gene whose expression complements auxotrophy cannot occur without expression of the at least one exogenous gene, further wherein the at least one exogenous gene and the gene whose expression complements auxotrophy are linked by an intergenic sequence that is not a promoter, further wherein the gene whose expression complements auxotrophy is a nitrogen assimilation gene, further wherein cell death occurs if a mutation occurs so that the exogenous gene is not expressed, further wherein more of the compound of interest is produced after either 50 days of growth or after a third dilution than if the genes are located on separate operons.

2. The non-naturally occurring auxotrophic cyanobacterial cell of claim 1 wherein the promoter is an inducible promoter.

3. The non-naturally occurring auxotrophic cyanobacterial cell of claim 1, wherein the nitrogen assimilation gene is a nitrate assimilation gene.

4. The non-naturally occurring auxotrophic cyanobacterial cell of claim 1, wherein the cyanobacterial cell is an auxotroph derived from *Cyanobacterium* sp. ABICyano1 deposited in the American Type Tissue Collection (ATCC) as PTA-13311.

5. The non-naturally occurring auxotrophic cyanobacterial cell of claim 1, wherein the promoter operably linked to the polycistronic operon has a sequence identity of at least 85% to a promoter selected from the group consisting of PnirA (SEQ ID NO: 16), PziaA, PsmtA, PcorT, PnrsB, PnrtA (SEQ ID NO: 18), PpetJ (SEQ ID NO: 19), PnarB (SEQ ID NO: 20), Porf0221 (SEQ ID NO: 22), Porf0223 (SEQ ID NO: 23), Porf0316 (SEQ ID NO: 24), Porf0128 (SEQ ID NO: 25), Porf1486 (SEQ ID NO: 26), Porf3164 (SEQ ID NO: 30), Porf3293 (SEQ ID NO: 27), Porf3621 (SEQ ID NO: 28), Porf3635 (SEQ ID NO: 29), Porf1071 (PmntC) (SEQ ID NO: 21), Porf1072 (SEQ ID NO: 31), Porf1074 (SEQ ID NO: 32), Porf1075 (SEQ ID NO: 33), Porf1542 (SEQ ID NO: 34), Porf1823 (SEQ ID NO: 35), Porf0222 (SEQ ID NO: 36), Porf3126 (SEQ ID NO: 17), Porf3232 (SEQ ID NO: 37), Porf3749 (SEQ ID NO: 38), PrbcL (SEQ ID NO: 39), PrnpA (SEQ ID NO: 40), PrpsL (SEQ ID NO: 41), PrpoA (SEQ ID NO: 42), PpsaA (SEQ ID NO: 43), PpsbA2 (SEQ ID NO: 44), PpsbD (SEQ ID NO: 45), and PcpcB (SEQ ID NO: 46).

6. The non-naturally occurring auxotrophic cyanobacterial cell of claim 1, wherein the extrachromosomal plasmid has greater than 80% sequence identity to plasmid p6.8 (SEQ ID NO: 1).

7. The non-naturally occurring auxotrophic cyanobacterial cell of claim 1, wherein the extrachromosomal plasmid contains a self-replicating origin of replication that has greater than 90% sequence identity to the origin of replication of plasmid p6.8 (nucleotides #3375-#3408 of SEQ ID NO: 1).

8. The non-naturally occurring auxotrophic cyanobacterial cell of claim 1, wherein the at least one exogenous gene comprises pyruvate decarboxylase, and wherein the compound of interest is ethanol.

9. The non-naturally occurring auxotrophic cyanobacterial cell of claim 3, wherein the nitrate assimilation gene is selected from the group consisting of nitrite reductase (nirA), nitrate reductase (narB), and the nitrate transporter nrtABCD.

10. The non-naturally occurring auxotrophic cyanobacterial cell of claim 9, wherein the nitrate assimilation gene is nirA.

11. The non-naturally occurring auxotrophic cyanobacterial cell of claim 1, wherein the polycistronic operon comprises genes linked through at least one intergenic sequence having at least 80% sequence identity to a sequence selected from the group consisting of SEQ ID NO: 77, SEQ ID NO: 78, and SEQ ID NO: 79.

12. The non-naturally occurring auxotrophic cyanobacterial cell of claim 1, wherein the cyanobacterial cell lacks an antibiotic resistance marker due to use of a three-component selection cassette for marker removal.

13. A method for producing a compound of interest, comprising growing the auxotrophic cyanobacterial cell of claim 1 under conditions to express the at least one exogenous gene.

14. A non-naturally occurring nitrite-auxotrophic cyanobacterial cell capable of production of a compound of interest, comprising:

an extrachromosomal plasmid comprising a polycistronic operon comprising a promoter operably linked to at least one exogenous production gene and a nitrite reductase (nirA) gene whose expression complements the auxotrophy of the non-naturally occurring auxotrophic cyanobacterial cell;

wherein the at least one exogenous production gene and the nitrite reductase gene are linked by an intergenic sequence that is from about 1 bp to about 300 bp in length, further wherein said intergenic sequence does not have transcriptional regulatory regions, further wherein cell death occurs if a mutation occurs so that the exogenous production gene is not expressed, further wherein cultures of the cells have a lower amount of non product-producing (revertant) cells than when the exogenous production gene and the nitrite reductase gene are located on separate operons.

15. The non-naturally occurring auxotrophic cyanobacterial cell of claim 14, wherein the intergenic sequence has at least 80% sequence identity to an intergenic sequence from an endogenous polycistronic cyanobacterial operon.

16. The non-naturally occurring auxotrophic cyanobacterial cell of claim 15, wherein the endogenous polycistronic cyanobacterial operon encodes proteins involved in the photosynthetic apparatus.

17. The non-naturally occurring auxotrophic cyanobacterial cell of claim 14, wherein said intergenic sequence has at least 80% sequence identity to SEQ ID NO: 77, SEQ ID NO: 78, or SEQ ID NO: 79.

18. The non-naturally occurring auxotrophic cyanobacterial cell of claim 14, wherein said intergenic sequence contains a ribosomal binding site (RBS).

19. The non-naturally occurring auxotrophic cyanobacterial cell of claim 14 wherein the promoter is an inducible promoter.

20. The non-naturally occurring auxotrophic cyanobacterial cell of claim 14, wherein the intergenic sequence contains a cyanobacterial ribosomal binding site.

21. The non-naturally occurring auxotrophic cyanobacterial cell of claim 20, wherein the cyanobacterial cell is an auxotroph derived from *Cyanobacterium* sp. ABICyano1 deposited in the American Type Tissue Collection (ATCC) as PTA-13311.

22. The non-naturally occurring auxotrophic cyanobacterial cell of claim 14, wherein the promoter operably linked to the polycistronic operon has a sequence identity of at least 85% to a promoter selected from the group consisting of PnirA (SEQ ID NO: 16), PziaA, PsmtA, PcorT, PnrsB, PnrtA (SEQ ID NO: 18), PpetJ (SEQ ID NO: 19), PnarB (SEQ ID NO: 20), Porf0221 (SEQ ID NO: 22), Porf0223 (SEQ ID NO: 23), Porf0316 (SEQ ID NO: 24), Porf0128 (SEQ ID NO: 25), Porf1486 (SEQ ID NO: 26), Porf3164 (SEQ ID NO: 30), Porf3293 (SEQ ID NO: 27), Porf3621 (SEQ ID NO: 28), Porf3635 (SEQ ID NO: 29), Porf1071 (PmntC) (SEQ ID NO: 21), Porf1072 (SEQ ID NO: 31), Porf1074 (SEQ ID NO: 32), Porf1075 (SEQ ID NO: 33), Porf1542 (SEQ ID NO: 34), Porf1823 (SEQ ID NO: 35), Porf0222 (SEQ ID NO: 36), Porf3126 (SEQ ID NO: 17), Porf3232 (SEQ ID NO: 37), Porf3749 (SEQ ID NO: 38), PrbcL (SEQ ID NO: 39), PrnpA (SEQ ID NO: 40), PrpsL (SEQ ID NO: 41), PrpoA (SEQ ID NO: 42), PpsaA (SEQ ID NO: 43), PpsbA2 (SEQ ID NO: 44), PpsbD (SEQ ID NO: 45), and PcpcB (SEQ ID NO: 46).

23. The non-naturally occurring auxotrophic cyanobacterial cell of claim 14, wherein the at least one exogenous gene comprises pyruvate decarboxylase, and wherein the compound of interest is ethanol.

24. The non-naturally occurring auxotrophic cyanobacterial cell of claim 14, wherein the nitrate assimilation gene is selected from the group consisting of nirA, narB, and nrtABCD.

25. The non-naturally occurring auxotrophic cyanobacterial cell of claim 14, wherein the cyanobacterial cell lacks an antibiotic resistance marker due to use of a three-component selection cassette for marker removal.

* * * * *

SEQUENCE LISTING

```
<160> NUMBER OF SEQ ID NOS: 79

<210> SEQ ID NO 1
<211> LENGTH: 6828
<212> TYPE: DNA
<213> ORGANISM: Cyanobacterium sp. ABICyano1

<400> SEQUENCE: 1

aatatttttc gtcagatacg caaaccttac aaacataatt aacaactgaa actattgata      60

tgtctaggtt ttagctctat cacaggttgt tagacaccct gtcatgtatt ttatattatt     120

tatttcacca tacggattaa gtgaaaccta atgaaaatag tactttcgga gctttaactt     180

taatgaaggt atgttttttt atagacatcg atgtctggtt taacaatagg aaaaagtagc     240

taaaactccc atgaattaaa gaaataacaa ggtgtctaac aacctgttat taagaatgtt     300

agaaaagact taacatttgt gttgagtttt tatagacatt ggtgtctaga catacggtag     360

ataaggtttg ctcaaaaata aaataaaaaa agattggact aaaaaacatt taatttagta     420
```

-continued

```
caatttaatt agttattttt tcgtctcaaa ttttgctttg ttgagcagaa atttagataa    480
aaaaatcccc gtgatcagat tacaatgtcg ttcattgtac gatgtgtcga aaaatcttta    540
cgacactcta aactgaccac acgggggaaa aagaaaactg aactaataac atcatgatac    600
tcggaaaacc tagcaattct caacccctaa acaaaagaaa cttccaaaac cctgaccata    660
taaaggagtg gcaacaatca gcaatcagtc aagatttgat agcagaaaat cttgtatcgg    720
ttgctaatgg ttttgatgta ctatttatcg gcaataaata ccgaactaac acgggtgttc    780
tgtcacggca catattaaac tcctattctc atttagaaga tggtggttcg tatggtagaa    840
catttgaccc atttaccaat aaagaaatgc agtgggttca atttaaaccg aatagaccaa    900
gaaaaggttc tactggtaag gtaatcaaat atgaatcgcc aaaaggtgaa cctacaagag    960
ttctaatgcc gtttgtgcct atgaaaatat ggcaacggat tagcgataag ttcggagtac   1020
cgattaatcc gaaaaaagat actcactttt gggaatgggt aaagaataat ccatcgatac   1080
cgattgccat tacagaagga aataaaaaag ctaattgcct attatcctat ggctatcctg   1140
ctattgcctt tgtaggcatt tggaacggat tagagaaaat aaatgatttc tcgaaggaaa   1200
agcagttaaa agaggatttg aaatggttgt tatccaacgg caaccgaaat attaatatca   1260
tctttgacca agaccagaaa caaaaaactg taattaatgt aaacaaagct attttcgctt   1320
tatcttctct aataagtaga aatggtcata aagttaatat tgtgcaatgg ttgccgtcaa   1380
aaggtaaagg aatagatgat tatttggtag ctttaccttt tgagaaaaga gaaaatcatt   1440
tagacaactt aattaaaatt gcaccatcat ttaatttttg gtcaactaaa tacttattca   1500
agtgtcgtaa accagattta accgtaaatt gccgttattt gagcgatgca gtaaaagaat   1560
tacctcaaga ggatatagca ttaatagcac ctcacggcac gggtaaaact tcattagtag   1620
ctactcacgt taagaatcgg agttatcacg gaaggaaaac tatttcattg gtgcatcttg   1680
aaagtttagc caaagctaat ggcaacgcac ttggattata ttaccgaacc gaaaataata   1740
ttgaaaagca atatcttgga tttagcttat gtgtagatag ttgccgtgat aagattaacg   1800
gcattacaac tgatattatt tcaggtcaag attattgcct tttcattgat gaaattgacc   1860
aagtaattcc acacatcctt aacagtgaaa ctgaagtaag taagtataga tgcaccatca   1920
ttgacacttt ttctgaactg gtgagaaatg ctgaacaggt cattattgct gatgctgatt   1980
tatccgatgt gacgattgac ctaatagaaa acatcagagg taaaaaacta tatgtaatca   2040
agaatgaata tcagtatcag ggaatgactt ttaacgccgt tggttcacca ttagaaatga   2100
tggcaatgat gggaaaatcg gtgtcagaag gcaagaaatt atttattaac accacatccc   2160
aaaaggcaaa aagtaagtac ggcacaatcg ctcttgagtc ttatattttt ggtctaaata   2220
aagaagcaaa gatattaaga atagactctg aaaccactaa aaaccctgaa catccagcct   2280
ataaaatcat tgaccaagac ttaaataata tcctcaaaga ttatgattat gtcattgcct   2340
caccttgcct tcaaacaggt gtcagtatta ccttaaaagg gcattttgac cagcaattta   2400
acttttccag tggaaacatt acacctcatt gctttttaca gcaaatgtgg cggttgaggg   2460
atgcagaaat tgaaagattc tattatgtgc cgaactcatc taacctcaat ctcattggga   2520
ataagtcaag ttcaccatca gaccttctaa agagcaataa caagatggca acggcaacgg   2580
ttaacctttt gggtagaatc gactccgaat attccctaga gtatgaatcg cacggcattt   2640
ggcttgagac gtgggcaaaa ttatcagcac ggcataacag ttcaatgcgt tgttactctg   2700
aaattcttac ctatctaatt acgtctcaag ggcataaatt aaatatcaac attccctcac   2760
ctcttgcaga tattaagaag ctaaatgatg aggtaagtag taacagggaa aaggtaaaaa   2820
```

```
atgagagata ctctcagagg ttaaactcac cagatattaa cgatgcagaa gctaccatac   2880
tcgaatctaa agagcaaaaa atcggattga ctctcaatga gagatgcacc ctagaaaagc   2940
ataaagttaa gaagcggtat gggaatgtaa agatggatat tctcaccttt gatgatgatg   3000
gactataccc caaactcaga ctattttatt acctcaccat cggtaaacct catctcaagg   3060
ctaatgacag aaaagctatt gccaaaatgg gcaatgacaa taaaggcaag attctatcaa   3120
aagacttagt taataaaact tactccgctc gtgtgaaggt cttagagatt cttaaactaa   3180
ctgactttat cgacaatctt agagatgaac tcttaataac tcccaataat ccagctatca   3240
ccgattttaa taatcttctg ctaagagcta agaaggattt aagagtatta ggagtcaaca   3300
tcggaaaata tccaatggcc aacattaatg ccgtacttac tctcattggt cacaaacttt   3360
ctgtaatgag agatgagttc ggaaaagaga aaaggataaa agtagatggt aaatcatacc   3420
gatgttatca acttgaaaca ttaccagatt ttaccaatga tactcttgac tactggttag   3480
aaaatgatag ccaaaaagaa gtaacagcaa cagaaaatta ctccgaaaat tttaaccctt   3540
caaatagcta caatccagac agtaagacac tttcagaggg tgcaaatttc ctatatataa   3600
ataaagaaga attgcatcca aataaattgc acctagaaat aaaagaaggt gctgaacttt   3660
ttttattcgg ggtaaaggtg attgtgaaag gaatcttgga cggggcagta actatattct   3720
ctatgggtca agaatacgat ttatccctca atgaactaga ggggatgtta acatcatgaa   3780
ctttacaaga atctttttaa agggcgatcg caccatgtta aatgatggta catttgttca   3840
gatatttgat atttaccatg accacgcatt gggagtgacc cttgacctta agacagaaaa   3900
aattatttcc gatgatgtta gggtaattac tgtcaaagac ttattgttcg atggcactta   3960
taaaggggta aaatctttta tgcccgataa tgcccgataa tgcccgattg atgctacaaa   4020
atcccataat cataagcgat aatcccctaa tagcttgtaa ttcttgaacc gtagcgattt   4080
tagagtattc caaaaagaag aaataaacac cgcaaaatgt cgtatttcac atatataaac   4140
caaggttttt tgccctaaaa tctttatgtt tgtagtgtga tgttgggtca aaatggtcag   4200
aaaagttgca aggtttttat ggatgcttac gcgcgcgagg ggtaagcatc cccaaatagt   4260
tactttatcc tagtccatgc ccatttattg ccgtcccgtt cggctttaaa aaagtgccaa   4320
aactcacaag gtgcaataaa aagttctgta cctttcgcaa ccctagataa tctttcaaca   4380
gttacttttt ttcctattat ctcggtacaa agtttggcta gtttctcttt tccctctttt   4440
tcaatcaagc cttcttgtat gcccaactca ttgattaatc tctctatttt taccattatt   4500
tcccgttcag gtagtttatc ccctaaatct tcatcggggg gcaatgtagg gcattctgaa   4560
ggggcttttt cttctgtctg gacattatct aatattgaag taaccaaact atcttcagtt   4620
ttttctattc ctattaattc atattcggtt actgtatccg tatcaatatc cgaataacta   4680
tctttatccg tattagctat tcggttaagt ttatccgtta actcagaaac aagactatat   4740
agcggtttta gcttttcttc tatcctgtta tctaatacgg ataagtttat acggttatca   4800
ttatccgtat tagtatcatt gggctttttt ggtagttcta ccccctcata aaccgctttt   4860
attcccaatt ccaacagact gataacagta tcctttataa tgggtttttt gctgatatgg   4920
tgaacttttg ccccttccat cattgcgata ctttctatct cactcatcaa cttatcgctt   4980
aagtgaatct cgtatctgtt taatccctta ctggttttat tcatatccgt ttactttatt   5040
cggttaacaa ttctatttta tacgaataaa atattatacg gttaacttta tacgtttaac   5100
tattttatct atacggataa cagtaataag ttattcgtat tagttatacg tttactttta   5160
tccaaataaa attagtgcat ttaaactaaa agaatgattt tatcggagtt gatagcattg   5220
```

```
gattaaccta aagatgttta taagctatat ctgataagta tttaaggtta ttttgttatt   5280
ctgtttattg acattatcag aataaaagaa tagaatataa ttgttgagag ataagaggtt   5340
taagtgatta tggttaagaa gttagttggt tatgtcaggg tcagtagtga atcgcaagag   5400
gataacacta gcttacagaa tcagatagag agaattgaag catattgtat ggcttttggt   5460
tatgagttgg taaaaatatt caaagaggtt gccactggta caaaagcaga tattgaaacc   5520
cgtcctattt ttaatgaagc tatagaatac ttgaaacagg ataatgctaa tggaattatt   5580
gccttgaagc tagaccgaat cgcacggaat gctttagatg tattgcgttt ggttcgtgaa   5640
accttagaac cacaaaataa aatgttagtg ttactagata ttcaggtaga tacttcgaca   5700
ccttcaggaa aaatgatttt aactgtaatg agtgccgttg ctgaactcga aagagacatg   5760
atctatgatc gcactcaggg gggtagaaag actaaagccc aaaagggcgg gtatgcctac   5820
gggaaaccta aatttggcta taagactgaa gaaaaggaac taaaagaaga ttcagcacaa   5880
caggaaacta ttaaactaat taagagacac cgtaggtcag ggaaaagcta ccagaaaata   5940
gctgattatc tcaatgccca aagtattccc actaaacaag gtaagaaatg gagttctagc   6000
gtcgtctatc gaatctgtca ggaaaaagct ggttaagtct gtttatagat atttagaatt   6060
tattgaataa aaatagtatg aacaataaat atttatggac taaccacgct cggaaacgtt   6120
taactgaacg atgggaaata aaagaatcat gggttattga taccatcgaa aatcctgaac   6180
gttcagaatt tattgttgat gagtcagggg aaaaatatca ttactataaa agaatagcta   6240
agtttaagaa tagagtgtta gaagtgataa cttctgccaa ctcaacaccc acaagaataa   6300
taacctttta ctttaaccgt aacatgagga aaaatttatg attgttactt acgataatga   6360
agttgacgca atttatttta agttaacgga aaataaaatt gatagcaccg aacctcaaac   6420
agacaggatt atcattgatt acgatgaaag taataatatt gttggcattg aggtattaga   6480
ttttaattat cttgtcaaga aaggtttaac cgttgctgat ttaccttttt ctgaagatga   6540
aagattaaca gcttctcaat attttaattt tcctgttgct atctaatcca gaaggggcaa   6600
taatcccctt ctttcatcga gttagactta atatcacaaa agtcattttc attttaccgt   6660
ttcttttcca cagcgtccgt acgcccctcg ttaaatctca aaaccgacaa tttatgatgt   6720
ttataaaaag ttactcactt taataagtat ttatactcat taaagggtta ttcttttttt   6780
gtagcctgat aggttgggaa ggaatatttc agattatcag atttgttg                 6828
```

<210> SEQ ID NO 2
<211> LENGTH: 2271
<212> TYPE: DNA
<213> ORGANISM: Cyanobacterium sp. ABICyano1

<400> SEQUENCE: 2

```
ttggtagctt tacctttttga gaaaagagaa aatcatttag acaacttaat taaaattgca     60
ccatcattta atttttggtc aactaaatac ttattcaagt gtcgtaaacc agatttaacc    120
gtaaattgcc gttatttgag cgatgcagta aaagaattac ctcaagagga tatagcatta    180
atagcacctc acggcacggg taaaacttca ttagtagcta ctcacgttaa gaatcggagt    240
tatcacggaa ggaaaactat ttcattggtg catcttgaaa gtttagccaa agctaatggc    300
aacgcacttg gattatatta ccgaaccgaa aataatattg aaaagcaata tcttggattt    360
agcttatgtg tagatagttg ccgtgataag attaacggca ttacaactga tattatttca    420
ggtcaagatt attgcctttt cattgatgaa attgaccaag taattccaca catccttaac    480
agtgaaactg aagtaagtaa gtatagatgc accatcattg acactttttc tgaactggtg    540
```

-continued

```
agaaatgctg aacaggtcat tattgctgat gctgatttat ccgatgtgac gattgaccta    600
atagaaaaca tcagaggtaa aaaactatat gtaatcaaga atgaatatca gtatcaggga    660
atgactttta acgccgttgg ttcaccatta gaaatgatgg caatgatggg aaaatcggtg    720
tcagaaggca agaaattatt tattaacacc acatcccaaa aggcaaaaag taagtacggc    780
acaatcgctc ttgagtctta tatttttggt ctaaataaag aagcaaagat attaagaata    840
gactctgaaa ccactaaaaa ccctgaacat ccagcctata aaatcattga ccaagactta    900
aataatatcc tcaaagatta tgattatgtc attgcctcac cttgccttca aacaggtgtc    960
agtattacct taaaagggca ttttgaccag caatttaact tttccagtgg aaacattaca   1020
cctcattgct tttacagcaa aatgtggcgg ttgagggatg cagaaattga aagattctat   1080
tatgtgccga actcatctaa cctcaatctc attgggaata agtcaagttc accatcagac   1140
cttctaaaga gcaataacaa gatggcaacg gcaacggtta accttttggg tagaatcgac   1200
tccgaatatt ccctagagta tgaatcgcac ggcatttggc ttgagacgtg ggcaaaatta   1260
tcagcacggc ataacagttc aatgcgttgt tactctgaaa ttcttaccta tctaattacg   1320
tctcaagggc ataaattaaa tatcaacatt ccctcacctc ttgcagatat taagaagcta   1380
aatgatgagg taagtagtaa cagggaaaag gtaaaaaatg agagatactc tcagaggtta   1440
aactcaccag atattaacga tgcagaagct accatactcg aatctaaaga gcaaaaaatc   1500
ggattgactc tcaatgagag atgcacccta gaaaagcata aagttaagaa gcggtatggg   1560
aatgtaaaga tggatattct cacctttgat gatgatggac tataccccaa actcagacta   1620
ttttattacc tcaccatcgg taaacctcat ctcaaggcta atgacagaaa agctattgcc   1680
aaaatgggca atgacaataa aggcaagatt ctatcaaaag acttagttaa taaaacttac   1740
tccgctcgtg tgaaggtctt agagattctt aaactaactg actttatcga caatcttaga   1800
gatgaactct taataactcc caataatcca gctatcaccg attttaataa tcttctgcta   1860
agagctaaga aggatttaag agtattagga gtcaacatcg gaaaatatcc aatggccaac   1920
attaatgccg tacttactct cattggtcac aaactttctg taatgagaga tgagttcgga   1980
aaagagaaaa ggataaaagt agatggtaaa tcataccgat gttatcaact tgaaacatta   2040
ccagatttta ccaatgatac tcttgactac tggttagaaa atgatagcca aaaagaagta   2100
acagcaacag aaaattactc cgaaaatttt aacccttcaa atagctacaa tccagacagt   2160
aagacacttt cagagggtgc aaatttccta tatataaata aagaagaatt gcatccaaat   2220
aaattgcacc tagaaataaa agaaggtgct gaactttttt tattcgggta a            2271
```

<210> SEQ ID NO 3
<211> LENGTH: 225
<212> TYPE: DNA
<213> ORGANISM: Cyanobacterium sp. ABICyano1

<400> SEQUENCE: 3

```
atgaacttta caagaatctt tttaaagggc gatcgcacca tgttaaatga tggtacattt     60
gttcagatat ttgatattta ccatgaccac gcattgggag tgacccttga ccttaagaca    120
gaaaaaatta tttccgatga tgttagggta attactgtca aagacttatt gttcgatggc    180
acttataaag ggtaaaatc ttttatgccc gataatgccc gataa                     225
```

<210> SEQ ID NO 4
<211> LENGTH: 225
<212> TYPE: DNA
<213> ORGANISM: Cyanobacterium sp. ABICyano1

<400> SEQUENCE: 4

```
atgaacttta caagaatctt tttaaagggc gatcgcacca tgttaaatga tggtacattt     60
gttcagatat ttgatattta ccatgaccac gcattgggag tgacccttga ccttaagaca    120
gaaaaaatta tttccgatga tgttagggta attactgtca aagacttatt gttcgatggc    180
acttataaag ggtaaaatc ttttatgccc gataatgccc gataa                      225
```

<210> SEQ ID NO 5
<211> LENGTH: 588
<212> TYPE: DNA
<213> ORGANISM: Cyanobacterium sp. ABICyano1

<400> SEQUENCE: 5

```
atggcttttg gttatgagtt ggtaaaaata ttcaaagagg ttgccactgg tacaaaagca     60
gatattgaaa cccgtcctat ttttaatgaa gctatagaat acttgaaaca ggataatgct    120
aatggaatta ttgccttgaa gctagaccga atcgcacgga atgctttaga tgtattgcgt    180
ttggttcgtg aaaccttaga accacaaaat aaaatgttag tgttactaga tattcaggta    240
gatacttcga caccttcagg aaaaatgatt ttaactgtaa tgagtgccgt tgctgaactc    300
gaaagagaca tgatctatga tcgcactcag gggggtagaa agactaaagc ccaaaagggc    360
gggtatgcct acgggaaacc taaatttggc tataagactg aagaaaagga actaaaagaa    420
gattcagcac aacaggaaac tattaaacta attaagagac accgtaggtc agggaaaagc    480
taccagaaaa tagctgatta tctcaatgcc caaagtattc ccactaaaca aggtaagaaa    540
tggagttcta gcgtcgtcta tcgaatctgt caggaaaaag ctggttaa                  588
```

<210> SEQ ID NO 6
<211> LENGTH: 264
<212> TYPE: DNA
<213> ORGANISM: Cyanobacterium sp. ABICyano1

<400> SEQUENCE: 6

```
atgaacaata aatatttatg gactaaccac gctcggaaac gtttaactga acgatgggaa     60
ataaaagaat catgggttat tgataccatc gaaaatcctg aacgttcaga atttattgtt    120
gatgagtcag gggaaaaata tcattactat aaaagaatag ctaagtttaa gaatagagtg    180
ttagaagtga taacttctgc caactcaaca cccacaagaa taataacctt ttactttaac    240
cgtaacatga ggaaaaattt atga                                            264
```

<210> SEQ ID NO 7
<211> LENGTH: 249
<212> TYPE: DNA
<213> ORGANISM: Cyanobacterium sp. ABICyano1

<400> SEQUENCE: 7

```
atgattgtta cttacgataa tgaagttgac gcaatttatt ttaagttaac ggaaaataaa     60
attgatagca ccgaacctca aacagacagg attatcattg attacgatga aagtaataat    120
attgttggca ttgaggtatt agattttaat tatcttgtca agaaaggttt aaccgttgct    180
gatttacctt tttctgaaga tgaaagatta acagcttctc aatattttaa ttttcctgtt    240
gctatctaa                                                             249
```

<210> SEQ ID NO 8
<211> LENGTH: 12657
<212> TYPE: DNA
<213> ORGANISM: Artificial sequence
<220> FEATURE:
<223> OTHER INFORMATION: Synthetic plasmid sequence pAB722, derived from the endogenous p6.8 plasmid, plus pdc and adh genes.

<400> SEQUENCE: 8

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ggaggatcag ccttatgaat tcttataccg    300
tgggtactta tttagccgaa cgcttagtgc aaattggttt aaaacatcat tttgccgtgg    360
ctggggacta taatttagtg ttattggata acttattatt aaataaaaac atggaacaag    420
tgtattgttg taatgaatta aattgtggtt tttctgctga aggttatgct agagctaaag    480
gtgcagctgc tgctgttgtt acttattctg tgggtgcttt atctgctttt gatgctattg    540
gtggtgctta tgccgaaaat ttacccgtga ttttaatttc tggtgcccct aataataatg    600
atcatgccgc tggacatgtt ttacatcatg ccttaggtaa aaccgattat cattatcaat    660
tagaaatggc caaaaatatt actgctgctg ccgaagctat ttatactcct gaagaagccc    720
ctgccaaaat tgatcatgtg attaaaaccg ccttacgcga aaaaaaaccc gtgtatttag    780
aaattgcctg taatattgct tctatgcctt gtgctgctcc tgggcctgct tctgctttat    840
ttaatgatga agcctctgat gaagctagtt taaatgctgc cgtggaagaa accttaaaat    900
ttattgccaa tcgcgataaa gttgccgtgt tagttggttc taaattaaga gctgctggtg    960
ctgaagaagc tgctgttaaa tttgctgatg ctttaggtgg tgcagttgct actatggctg   1020
ctgccaaatc tttttttccc gaagaaaatc cccattatat tggaactagt tggggagaag   1080
tttcttatcc tggtgtggaa aaaactatga aagaagccga cgctgttatt gctttagccc   1140
ctgtgtttaa tgattattct accactggtt ggactgatat tcccgatccc aaaaaattag   1200
ttttagccga acctcgttct gttgttgtta atggtgttcg ctttccctct gtgcatttaa   1260
aagattattt aacccgctta gcccaaaaag tttctaaaaa aactggtgcc ttagattttt   1320
ttaaatcttt aaatgcgggt gaattaaaaa aagctgctcc tgctgatcct tctgctcctt   1380
tagttaatgc tgaaattgcc cgtcaagttg aagccttatt aacccctaat actaccgtta   1440
ttgccgaaac tggtgattct tggtttaatg cccaacgcat gaaattacct aatggtgccc   1500
gtgttgaata tgaaatgcaa tggggtcata ttggttggtc tgtacctgct gcttttggtt   1560
atgctgttgg tgctcctgaa cgtcgtaata ttttaatggt gggtgatggt tcttttcaat   1620
taactgccca agaagttgcc caaatggttc gcttaaaatt acccgttatt atttttttaa   1680
taaataatta tggttatacc attgaagtga tgattcatga tggccatat aataatatta   1740
aaaattggga ttatgcgggt ttaatggaag tgtttaatgg taatggtggt tatgattctg   1800
gtgctggtaa aggtttaaaa gccaaaactg gtggtgaatt agctgaagct attaaagttg   1860
ccttagccaa tactgatggg ccaaccttaa ttgaatgttt tattggtcgc gaagattgta   1920
ccgaagaatt agttaaatgg ggtaaacgtg ttgctgctgc taattctcgc aaacccgtga   1980
ataaattatt gtaatttttg ggatcaatt cgagctcagc aagtttcatc ccgacccccct   2040
cagggtcggg attttttat tgtactagtt gacataagta aaggcatccc ctgcgtgata   2100
taattacctt cagtttaagg aggtatacac atatgattaa agcctacgct gccctggaag   2160
ccaacggaaa actccaaccc tttgaatacg accccggtgc cctgggtgct aatgaggtgg   2220
```

```
agattgaggt gcagtattgt ggggtgtgcc acagtgattt gtccatgatt aataacgaat   2280
ggggcatttc caattacccc ctagtgccgg gtcatgaggt ggtgggtact gtggccgcca   2340
tgggcgaagg ggtgaaccat gttgaggtgg gggatttagt ggggctgggt tggcattcgg   2400
gctactgcat gacctgccat agttgtttat ctggctacca caacctttgt gccacggcgg   2460
aatcgaccat tgtgggccac tacggtggct ttggcgatcg ggttcgggcc aagggagtca   2520
gcgtggtgaa attacctaaa ggcattgacc tagccagtgc cgggcccctt ttctgtggag   2580
gaattaccgt tttcagtcct atggtggaac tgagtttaaa gcccactgca aaagtggcag   2640
tgatcggcat tgggggcttg ggccatttag cggtgcaatt tctccgggcc tggggctgtg   2700
aagtgactgc ctttacctcc agtgccagga agcaaacgga agtgttggaa ttgggcgctc   2760
accacatact agattccacc aatccagagg cgatcgccag tgcggaaggc aaatttgact   2820
atattatctc cactgtgaac ctgaagcttg actggaactt atacatcagc accctggcgc   2880
cccagggaca tttccacttt gttggggtgg tgttggagcc tttggatcta aatcttttc    2940
cccttttgat gggacaacgc tccgtttctg cctccccagt gggtagtccc gccaccattg   3000
ccaccatgtt ggactttgct gtgcgccatg acattaaacc cgtggtggaa caatttagct   3060
ttgatcagat caacgaggcg atcgcccatc tagaaagcgg caaagcccat tatcgggtag   3120
tgctcagcca tagtaaaaat tagctctgca aaggttgctt ctgggtccgt ggaacgctcg   3180
gttgccgccg ggcgtttttt attcctgcag gatcatcttg ctgaaaaact cgagcgctcg   3240
ttccgcaaag cggtacggag ttagttaggg gctaatgggc attctcccgt acaggaaaga   3300
gttagaagtt attaattatc aacaattctc ctttgcctag tgcatcgtta cctttttaat   3360
taaaacataa ggaaaactaa taatcgtaat aatttaacct caaagtgtaa agaaatgtga   3420
aattctgact tttataacgt taaagaggga aaaattagca gtttaaaata cctagagaat   3480
agtctggggt aagcatagag aattagatta gttaagttaa tcaaattcag aaaaaataat   3540
aatcgtaaat agttaatctg ggtgtataga aaatgatccc cttcatgata agatttaaac   3600
tcgaaaagca aaagccaaaa aactaacttc cattaaaaga agttgttaca tataacgcta   3660
taaagaaaat ttatatattt ggaggatacc aaccatgtct catattcaac gtgaaactag   3720
ttgttctcgc cctcgtttaa attctaatat ggatgccgat ttatatggtt ataaatgggc   3780
tcgtgataat gttggtcaat ctggtgctac tatttatcgt ttatatggta aacctgatgc   3840
tcctgaatta ttcttgaaac atggtaaagg ttctgttgct aatgatgtta ctgatgaaat   3900
ggttcgttta aactggttga ctgaatttat gcctttacct actattaaac attttattcg   3960
tactcccgat gatgcttggt tattaactac tgctattcct ggtaaaactg cttttcaagt   4020
tttagaagaa tatcctgatt ctggtgaaaa tattgttgat gctttagctg tttttttacg   4080
tcgtttacat tctattcccg tttgtaattg tccttttaat tctgatcgtg tttttcgttt   4140
agctcaagct caatctcgta tgaataatgg tttagttgat gcttctgatt ttgatgatga   4200
acgtaatggt tggcctgttg aacaagtttg gaaagaaatg cacaaattgt taccttttc    4260
tcctgattct gttgttactc atggtgattt ttctttagat aatttgatct ttgatgaagg   4320
taaattgatt ggttgtattg atgttggtcg tgttggtatt gctgatcgtt atcaagattt   4380
agctatttta tggaattgtt taggtgaatt ttctccttct ttacagaaac gtttatttca   4440
gaaatatggt attgataatc ctgatatgaa caagttacaa tttcatttaa tgttggacga   4500
gttcttttaa gaattaattc atgaccaaaa tcccttaacg tgagttttcg ttccactgag   4560
```

-continued

```
cgtcagaccc cgtagaaaag atcaaaggat cttcttgaga tccttttttt ctgcgcgtaa   4620
tctgctgcta tttaaattac gtacacgtgt tattactttg ttaacgacaa ttgtcttaat   4680
taactgggcc tcatgggcct tccgctcact gcccgctttc cagtcgggaa acctgtcgtg   4740
ccagctctgc agatgacggt gaaaacctct gacacatgca gctcccggag acggtcacag   4800
cttgtctgta agcggatgcc gggagcagac aagcccgtca gggcgcgtca gcgggtgttg   4860
gcgggtgtcg gggcgcagcc atgacccagt cacgtagcga tagcggagtg tatactggct   4920
taactatgcg gcatcagagc agattgtact gagagtgcac catatgcggt gtgaaatacc   4980
gcacagatgc gtaaggagaa aataccgcat caggcgctct tccgcttcct cgctcactga   5040
ctcgctgcgc tcggtcgttc ggctgcggcg agcggtatca gctcactcaa aggcggtaat   5100
acggttatcc acagaatcag gggataacgc aggaaagaac atgtgagcaa aaggccagca   5160
aaaggccagg aaccgtaaaa aggccgcgtt gctggcgttt ttccataggc tccgcccccc   5220
tgacgagcat cacaaaaatc gacgctcaag tcagaggtgg cgaaacccga caggactata   5280
aagataccag gcgtttcccc ctggaagctc cctcgtgcgc tctcctgttc cgaccctgcc   5340
gcttaccgga tacctgtccg cctttctccc ttcgggaagc gtggcgcttt ctcatagctc   5400
acgctgtagg tatctcagtt cggtgtaggt cgttcgctcc aagctgggct gtgtgcacga   5460
accccccgtt cagcccgacc gctgcgcctt atccggtaac tatcgtcttg agtccaaccc   5520
ggtaagacac gacttatcgc cactggcagc agccactggt aacaggatta gcagagcgag   5580
gtatgtaggc ggtgctacag agttcttgaa gtggtggcct aactacggct acactagaag   5640
gacagtattt ggtatctgcg ctctgctgaa gccagttacc ttcggaaaaa gagttggtag   5700
ctcttgatcc ggcaaacaaa ccaccgctgg tagcggtggt ttttttgttt gcaagcagca   5760
gattacgcgc agaaaaaaag gatctcaaga agatcctttg atcttttcta ctgcagaagc   5820
ttgttagaca ccctgtcatg tattttatat tatttatttc accatacgga ttaagtgaaa   5880
cctaatgaaa atagtacttt cggagcttta actttaatga aggtatgttt ttttatagac   5940
atcgatgtct ggtttaacaa taggaaaaag tagctaaaac tcccatgaat taaagaaata   6000
acaaggtgtc taacaacctg ttattaagaa tgttagaaaa gacttaacat ttgtgttgag   6060
tttttataga cattggtgtc tagacatacg gtagataagg tttgctcaaa aataaaataa   6120
aaaaagattg gactaaaaaa catttaattt agtacaattt aattagttat tttttcgtct   6180
caaattttgc tttgttgagc agaaatttag ataaaaaaat ccccgtgatc agattacaat   6240
gtcgttcatt gtacgatgtg tcgaaaaatc tttacgacac tctaaactga ccacacgggg   6300
gaaaaagaaa actgaactaa taacatcatg atactcggaa aacctagcaa ttctcaaccc   6360
ctaaacaaaa gaaacttcca aaaccctgac catataaagg agtggcaaca atcagcaatc   6420
agtcaagatt tgatagcaga aaatcttgta tcggttgcta atggttttga tgtactattt   6480
atcggcaata aataccgaac taacacgggt gttctgtcac ggcacatatt aaactcctat   6540
tctcatttag aagatggtgg ttcgtatggt agaacatttg acccatttac caataaagaa   6600
atgcagtggg ttcaatttaa accgaataga ccaagaaaag gttctactgg taaggtaatc   6660
aaatatgaat cgccaaaagg tgaacctaca agagttctaa tgccgtttgt gcctatgaaa   6720
atatggcaac ggattagcga taagttcgga gtaccgatta atccgaaaaa agatactcac   6780
ttttgggaat gggtaaagaa taatccatcg ataccgattg ccattacaga aggaaataaa   6840
aaagctaatt gcctattatc ctatggctat cctgctattg cctttgtagg catttggaac   6900
ggattagaga aaataaatga tttctcgaag gaaaagcagt taaaagagga tttgaaatgg   6960
```

```
ttgttatcca acggcaaccg aaatattaat atcatctttg accaagacca gaaacaaaaa   7020
actgtaatta atgtaaacaa agctattttc gctttatctt ctctaataag tagaaatggt   7080
cataaagtta atattgtgca atggttgccg tcaaaaggta aaggaataga tgattatttg   7140
gtagctttac cttttgagaa aagagaaaat catttagaca acttaattaa aattgcacca   7200
tcatttaatt tttggtcaac taaatactta ttcaagtgtc gtaaaccaga tttaaccgta   7260
aattgccgtt atttgagcga tgcagtaaaa gaattacctc aagaggatat agcattaata   7320
gcacctcacg gcacgggtaa aacttcatta gtagctactc acgttaagaa tcggagttat   7380
cacggaagga aaactatttc attggtgcat cttgaaagtt tagccaaagc taatggcaac   7440
gcacttggat tatattaccg aaccgaaaat aatattgaaa agcaatatct tggatttagc   7500
ttatgtgtag atagttgccg tgataagatt aacggcatta caactgatat tatttcaggt   7560
caagattatt gccttttcat tgatgaaatt gaccaagtaa ttccacacat ccttaacagt   7620
gaaactgaag taagtaagta tagatgcacc atcattgaca ctttttctga actggtgaga   7680
aatgctgaac aggtcattat tgctgatgct gatttatccg atgtgacgat tgacctaata   7740
gaaaacatca gaggtaaaaa actatatgta atcaagaatg aatatcagta tcagggaatg   7800
acttttaacg ccgttggttc accattagaa atgatggcaa tgatgggaaa atcggtgtca   7860
gaaggcaaga aattatttat taacaccaca tcccaaaagg caaaaagtaa gtacggcaca   7920
atcgctcttg agtcttatat ttttggtcta aataaagaag caaagatatt aagaatagac   7980
tctgaaacca ctaaaaaccc tgaacatcca gcctataaaa tcattgacca agacttaaat   8040
aatatcctca aagattatga ttatgtcatt gcctcacctt gccttcaaac aggtgtcagt   8100
attaccttaa aagggcattt tgaccagcaa tttaactttt ccagtggaaa cattacacct   8160
cattgctttt tacagcaaat gtggcggttg agggatgcag aaattgaaag attctattat   8220
gtgccgaact catctaacct caatctcatt gggaataagt caagttcacc atcagacctt   8280
ctaaagagca ataacaagat ggcaacggca acggttaacc ttttgggtag aatcgactcc   8340
gaatattccc tagagtatga atcgcacggc atttggcttg agacgtgggc aaaattatca   8400
gcacggcata acagttcaat gcgttgttac tctgaaattc ttacctatct aattacgtct   8460
caagggcata aattaaatat caacattccc tcacctcttg cagatattaa gaagctaaat   8520
gatgaggtaa gtagtaacag ggaaaaggta aaaaatgaga gatactctca gaggttaaac   8580
tcaccagata ttaacgatgc agaagctacc atactcgaat ctaaagagca aaaaatcgga   8640
ttgactctca atgagagatg caccctagaa aagcataaag ttaagaagcg gtatgggaat   8700
gtaaagatgg atattctcac ctttgatgat gatggactat accccaaact cagactattt   8760
tattacctca ccatcggtaa acctcatctc aaggctaatg acagaaaagc tattgccaaa   8820
atgggcaatg acaataaagg caagattcta tcaaaagact tagttaataa aacttactcc   8880
gctcgtgtga aggtcttaga gattcttaaa ctaactgact ttatcgacaa tcttagagat   8940
gaactcttaa taactcccaa taatccagct atcaccgatt ttaataatct tctgctaaga   9000
gctaagaagg atttaagagt attaggagtc aacatcggaa aatatccaat ggccaacatt   9060
aatgccgtac ttactctcat tggtcacaaa ctttctgtaa tgagagatga gttcggaaaa   9120
gagaaaagga taaaagtaga tggtaaatca taccgatgtt atcaacttga aacattacca   9180
gattttacca atgatactct tgactactgg ttagaaaatg atagccaaaa agaagtaaca   9240
gcaacagaaa attactccga aaattttaac ccttcaaata gctacaatcc agacagtaag   9300
```

-continued

```
acactttcag agggtgcaaa tttcctatat ataaataaag aagaattgca tccaaataaa   9360
ttgcacctag aaataaaaga aggtgctgaa cttttttat tcggggtaaa ggtgattgtg   9420
aaaggaatct tggacggggc agtaactata ttctctatgg gtcaagaata cgatttatcc   9480
ctcaatgaac tagaggggat gttaacatca tgaactttac aagaatcttt ttaaagggcg   9540
atcgcaccat gttaaatgat ggtacatttg ttcagatatt tgatatttac catgaccacg   9600
cattgggagt gacccttgac cttaagacag aaaaaattat ttccgatgat gttagggtaa   9660
ttactgtcaa agacttattg ttcgatggca cttataaagg ggtaaaatct tttatgcccg   9720
ataatgcccg ataatgcccg attgatgcta caaaatccca taatcataag cgataatccc   9780
ctaatagctt gtaattcttg aaccgtagcg attttagagt attccaaaaa gaagaaataa   9840
acaccgcaaa atgtcgtatt tcacatatat aaaccaaggt tttttgccct aaaatcttta   9900
tgtttgtagt gtgatgttgg gtcaaaatgg tcagaaaagt tgcaaggttt ttatggatgc   9960
ttacgcgcgc gaggggtaag catccccaaa tagttacttt atcctagtcc atgcccattt  10020
attgccgtcc cgttcggctt taaaaaagtg ccaaaactca caaggtgcaa taaaaagttc  10080
tgtacctttc gcaaccctag ataatctttc aacagttact tttttcccta ttatctcggt  10140
acaaagtttg gctagtttct cttttccctc tttttcaatc aagccttctt gtatgcccaa  10200
ctcattgatt aatctctcta tttttaccat tatttcccgt tcaggtagtt tatcccctaa  10260
atcttcatcg gggggcaatg tagggcattc tgaaggggct ttttcttctg tctggacatt  10320
atctaatatt gaagtaacca aactatcttc agttttttct attcctatta attcatattc  10380
ggttactgta tccgtatcaa tatccgaata actatcttta tccgtattag ctattcggtt  10440
aagtttatcc gttaactcag aaacaagact atatagcggt tttagctttt cttctatcct  10500
gttatctaat acggataagt ttatacggtt atcattatcc gtattagtat cattgggctt  10560
ttttggtagt tctacccccct cataaaccgc ttttattccc aattccaaca gactgataac  10620
agtatccttt ataatgggtt ttttgctgat atggtgaact tttgcccctt ccatcattgc  10680
gatactttct atctcactca tcaacttatc gcttaagtga atctcgtatc tgtttaatcc  10740
cttactggtt ttattcatat ccgtttactt tattcggtta acaattctat tttatacgaa  10800
taaaatatta tacggttaac tttatacgtt taactatttt atctatacgg ataacagtaa  10860
taagttattc gtattagtta tacgtttact tttatccaaa taaaattagt gcatttaaac  10920
taaaagaatg attttatcgg agttgatagc attggattaa cctaaagatg tttataagct  10980
atatctgata agtatttaag gttattttgt tattctgttt attgacatta tcagaataaa  11040
agaatagaat ataattgttg agagataaga ggtttaagtg attatggtta agaagttagt  11100
tggttatgtc agggtcagta gtgaatcgca agaggataac actagcttac agaatcagat  11160
agagagaatt gaagcatatt gtatggcttt tggttatgag ttggtaaaaa tattcaaaga  11220
ggttgccact ggtacaaaag cagatattga aacccgtcct atttttaatg aagctataga  11280
atacttgaaa caggataatg ctaatggaat tattgccttg aagctagacc gaatcgcacg  11340
gaatgcttta gatgtattgc gtttggttcg tgaaacctta gaaccacaaa ataaaatgtt  11400
agtgttacta gatattcagg tagatacttc gacaccttca ggaaaaatga ttttaactgt  11460
aatgagtgcc gttgctgaac tcgaaagaga catgatctat gatcgcactc aggggggtag  11520
aaagactaaa gcccaaaagg gcgggtatgc ctacgggaaa cctaaatttg gctataagac  11580
tgaagaaaag gaactaaaag aagattcagc acaacaggaa actattaaac taattaagag  11640
acaccgtagg tcagggaaaa gctaccagaa aatagctgat tatctcaatg cccaaagtat  11700
```

```
tcccactaaa caaggtaaga aatggagttc tagcgtcgtc tatcgaatct gtcaggaaaa  11760

agctggttaa gtctgtttat agatatttag aatttattga ataaaaatag tatgaacaat  11820

aaatatttat ggactaacca cgctcggaaa cgtttaactg aacgatggga aataaaagaa  11880

tcatgggtta ttgataccat cgaaaatcct gaacgttcag aatttattgt tgatgagtca  11940

ggggaaaaat atcattacta taaaagaata gctaagttta agaatagagt gttagaagtg  12000

ataacttctg ccaactcaac acccacaaga ataataacct tttactttaa ccgtaacatg  12060

aggaaaaatt tatgattgtt acttacgata atgaagttga cgcaatttat tttaagttaa  12120

cggaaaataa aattgatagc accgaacctc aaacagacag gattatcatt gattacgatg  12180

aaagtaataa tattgttggc attgaggtat tagattttaa ttatcttgtc aagaaaggtt  12240

taaccgttgc tgatttacct ttttctgaag atgaaagatt aacagcttct caatatttta  12300

attttcctgt tgctatctaa tccagaaggg gcaataatcc ccttctttca tcgagttaga  12360

cttaatatca caaaagtcat tttcatttta ccgtttcttt tccacagcgt ccgtacgccc  12420

ctcgttaaat ctcaaaaccg acaatttatg atgtttataa aaagttactc actttaataa  12480

gtatttatac tcattaaagg gttattcttt ttttgtagcc tgataggttg ggaaggaata  12540

tttcagatta tcagatttgt tgaatatttt tcgtcagata cgcaaacctt acaaacataa  12600

ttaacaactg aaactattga tatgtctagg ttttagctct atcacaggtt ggatctg     12657
```

```
<210> SEQ ID NO 9
<211> LENGTH: 14290
<212> TYPE: DNA
<213> ORGANISM: Artificial sequence
<220> FEATURE:
<223> OTHER INFORMATION: Synthetic plasmid sequence AB193, derived from
      the endogenous p6.8 plasmid, plus nirA, pdc and adh genes.

<400> SEQUENCE: 9
```

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ggaggatcag ccttatgaat tcttataccg    300

tgggtactta tttagccgaa cgcttagtgc aaattggttt aaaacatcat tttgccgtgg    360

ctggggacta taatttagtg ttattggata acttattatt aaataaaaac atggaacaag    420

tgtattgttg taatgaatta aattgtggtt tttctgctga aggttatgct agagctaaag    480

gtgcagctgc tgctgttgtt acttattctg tgggtgcttt atctgctttt gatgctattg    540

gtggtgctta tgccgaaaat ttacccgtga ttttaatttc tggtgcccct aataataatg    600

atcatgccgc tggacatgtt ttacatcatg ccttaggtaa aaccgattat cattatcaat    660

tagaaatggc caaaaatatt actgctgctg ccgaagctat ttatactcct gaagaagccc    720

ctgccaaaat tgatcatgtg attaaaaccg ccttacgcga aaaaaaaccc gtgtatttag    780

aaattgcctg taatattgct tctatgcctt gtgctgctcc tgggcctgct tctgctttat    840

ttaatgatga agcctctgat gaagctagtt taaatgctgc cgtggaagaa accttaaaat    900

ttattgccaa tcgcgataaa gttgccgtgt tagttggttc taaattaaga gctgctggtg    960

ctgaagaagc tgctgttaaa tttgctgatg ctttaggtgg tgcagttgct actatggctg   1020

ctgccaaatc ttttttcccc gaagaaaatc cccattatat tggaactagt tggggagaag   1080
```

```
tttcttatcc tggtgtggaa aaaactatga aagaagccga cgctgttatt gctttagccc   1140

ctgtgtttaa tgattattct accactggtt ggactgatat tcccgatccc aaaaaattag   1200

ttttagccga acctcgttct gttgttgtta atggtgttcg ctttccctct gtgcatttaa   1260

aagattattt aacccgctta gcccaaaaag tttctaaaaa aactggtgcc ttagattttt   1320

ttaaatcttt aaatgcgggt gaattaaaaa aagctgctcc tgctgatcct tctgctcctt   1380

tagttaatgc tgaaattgcc cgtcaagttg aagccttatt aacccctaat actaccgtta   1440

ttgccgaaac tggtgattct tggtttaatg cccaacgcat gaaattacct aatggtgccc   1500

gtgttgaata tgaaatgcaa tggggtcata ttggttggtc tgtacctgct gcttttggtt   1560

atgctgttgg tgctcctgaa cgtcgtaata ttttaatggt gggtgatggt tcttttcaat   1620

taactgccca agaagttgcc caaatggttc gcttaaaatt acccgttatt attttttttaa   1680

taaataatta tggttatacc attgaagtga tgattcatga tgggccatat aataatatta   1740

aaaattggga ttatgcgggt ttaatggaag tgtttaatgg taatggtggt tatgattctg   1800

gtgctggtaa aggtttaaaa gccaaaactg gtggtgaatt agctgaagct attaaagttg   1860

ccttagccaa tactgatggg ccaaccttaa ttgaatgttt tattggtcgc gaagattgta   1920

ccgaagaatt agttaaatgg ggtaaacgtg ttgctgctgc taattctcgc aaacccgtga   1980

ataaattatt gtaatttttg gggatcaatt cgagctcttt aaaccaagat tagaaaatcc   2040

atttcattaa cgtaaaccaa cataattagg agaaattaat tacaatggtt gttgctgtaa   2100

ataccaccac cacaaaaaaa gtgaaactaa ataaaattga aaaagtaaaa gaagcaaaac   2160

acggtttgga tgttaaggaa gaaatagaaa agtttgctca aatgggttgg gaagcaatgg   2220

atgaagatga cctcattgtt cgtttaaagt ggttggggat tttttttcgc ccagtaactc   2280

cggggaaatt tatgcttagg ttacgcactc ctaatggtat tctcaacagc caacaattac   2340

gcacttttgc ggaaattatt gaacgttatg gggaggatgg aaaagctgat attactaccc   2400

gtcaaaatat tcaattaagg ggagttcatt tacaggatat accagatatt tttcgtaaat   2460

tggaagcggt gggcatgaca tcgattcagt caggaatgga taatgtgcgt aatttaacgg   2520

gttctcctgt tgctggaatt gaccctcatg agttaattga caccagagaa ttaaatcaaa   2580

aattacagga tttgattact aaccatggac agggtagtta tgagtttagt agtctccctc   2640

gtaaattaaa cattgcgatc gaaggtagta aagataattc tattcacgct gaattgaatg   2700

atatagcatt tttacccgcc tataaagatg gtgaattagg ttttaatgtt gtggtggggg   2760

gttacttatc cgctcaaagg tgcgcagagt ctattccgat ggatgtttgg gtaagaccta   2820

atgaagaagt attgaaatta tgcgcggcta ttcttagtgt ttatagtgag tgtgcattgg   2880

aagaaggttt gagggaaaat agagcaaaag cccgtttaat gtggttaatt gataaatggg   2940

gtatgaatcg ttttcgcatt gaagtggaga aaaaactagg acaatcctta caatttgccg   3000

ccccgaaaga tgaaattacc ttagaaaaaa gagatcattt aggggttaat cctcaaaagc   3060

aagagggtta tagttatatc ggtattcata ttcctgttgg gcatttagat gcggagggtt   3120

tatttgaaat tgctcgttta gcggatgttt atggtaacgg agaaattcgg gcaacagtgg   3180

aacaaaattt tattattcct tttgtagcca atgacagggt agaagcattt cttgctgaac   3240

caattttaga acgctatcga gttaatcctt cacctttaag ccgttctgta atttcgtgta   3300

caggggctcg ttattgtaat tttgccttgg tagaaactaa gcagagagcg gtgaaactag   3360

ccacagaatt agataatgaa ctaaatattc cctctaaagt cagaattcat tggacaggtt   3420
```

```
gtcctaactc ttgcggacag gctcaagcag gggacattgg cttaatgggt actaaagcga   3480
aaaaagatgg gcaggtggta gagggtgtta acttatttat gggggg aaaa gtgggcaagg   3540
atgcacattt agggagtctc aaacaaaaaa gtattccctg tgatgatttg aaatccgttt   3600
tgaaggaaat tttaattaat gaatttgggg caacagttaa ataagagctc agcaagtttc   3660
atcccgaccc cctcagggtc gggatttttt tattgtacta gttgacataa gtaaaggcat   3720
cccctgcgtg atataattac cttcagttta aggaggtata cacatatgat taaagcctac   3780
gctgccctgg aagccaacgg aaaactccaa ccctttgaat acgaccccgg tgccctgggt   3840
gctaatgagg tggagattga ggtgcagtat tgtggggtgt gccacagtga tttgtccatg   3900
attaataacg aatggggcat ttccaattac cccctagtgc cgggtcatga ggtggtgggt   3960
actgtggccg ccatgggcga aggggtgaac catgttgagg tgggggattt agtggggctg   4020
ggttggcatt cgggctactg catgacctgc catagttgtt tatctggcta ccacaacctt   4080
tgtgccacgg cggaatcgac cattgtgggc cactacggtg gctttggcga tcgggttcgg   4140
gccaagggag tcagcgtggt gaaattacct aaaggcattg acctagccag tgccgggccc   4200
cttttctgtg gaggaattac cgttttcagt cctatggtgg aactgagttt aaagcccact   4260
gcaaaagtgg cagtgatcgg cattgggggc ttgggccatt tagcggtgca atttctccgg   4320
gcctggggct gtgaagtgac tgcctttacc tccagtgcca ggaagcaaac ggaagtgttg   4380
gaattgggcg ctcaccacat actagattcc accaatccag aggcgatcgc cagtgcggaa   4440
ggcaaatttg actatattat ctccactgtg aacctgaagc ttgactggaa cttatacatc   4500
agcaccctgg cgccccaggg acatttccac tttgttgggg tggtgttgga gcctttggat   4560
ctaaatcttt ttcccctttt gatgggacaa cgctccgttt ctgcctcccc agtgggtagt   4620
cccgccacca ttgccaccat gttggacttt gctgtgcgcc atgacattaa acccgtggtg   4680
gaacaattta gctttgatca gatcaacgag gcgatcgccc atctagaaag cggcaaagcc   4740
cattatcggg tagtgctcag ccatagtaaa aattagctct gcaaaggttg cttctgggtc   4800
cgtggaacgc tcggttgccg ccgggcgttt tttattcctg caggatcatc ttgctgaaaa   4860
actcgagcgc tcgttccgca aagcggtacg gagttagtta ggggctaatg ggcattctcc   4920
cgtacaggaa agagttagaa gttattaatt atcaacaatt ctcctttgcc tagtgcatcg   4980
ttaccttttt aattaaaaca taaggaaaac taataatcgt aataatttaa cctcaaagtg   5040
taaagaaatg tgaaattctg acttttataa cgttaaagag ggaaaaatta gcagtttaaa   5100
atacctagag aatagtctgg ggtaagcata gagaattaga ttagttaagt taatcaaatt   5160
cagaaaaaat aataatcgta aatagttaat ctgggtgtat agaaaatgat ccccttcatg   5220
ataagattta aactcgaaaa gcaaaagcca aaaaactaac ttccattaaa agaagttgtt   5280
acatataacg ctataaagaa aatttatata tttggaggat accaaccatg tctcatattc   5340
aacgtgaaac tagttgttct cgccctcgtt taaattctaa tatggatgcc gatttatatg   5400
gttataaatg ggctcgtgat aatgttggtc aatctggtgc tactatttat cgtttatatg   5460
gtaaacctga tgctcctgaa ttattcttga aacatggtaa aggttctgtt gctaatgatg   5520
ttactgatga aatggttcgt ttaaactggt tgactgaatt tatgccttta cctactatta   5580
aacattttat tcgtactccc gatgatgctt ggttattaac tactgctatt cctggtaaaa   5640
ctgcttttca agttttagaa gaatatcctg attctggtga aaatattgtt gatgctttag   5700
ctgttttttt acgtcgttta cattctattc ccgtttgtaa ttgtcctttt aattctgatc   5760
gtgtttttcg tttagctcaa gctcaatctc gtatgaataa tggtttagtt gatgcttctg   5820
```

```
attttgatga tgaacgtaat ggttggcctg ttgaacaagt ttggaaagaa atgcacaaat   5880
tgttaccttt ttctcctgat tctgttgtta ctcatggtga tttttcttta gataatttga   5940
tctttgatga aggtaaattg attggttgta ttgatgttgg tcgtgttggt attgctgatc   6000
gttatcaaga tttagctatt ttatggaatt gtttaggtga attttctcct tctttacaga   6060
aacgtttatt tcagaaatat ggtattgata atcctgatat gaacaagtta caatttcatt   6120
taatgttgga cgagttcttt taagaattaa ttcatgacca aaatccctta acgtgagttt   6180
tcgttccact gagcgtcaga ccccgtagaa aagatcaaag gatcttcttg agatcctttt   6240
tttctgcgcg taatctgctg ctatttaaat tacgtacacg tgttattact ttgttaacga   6300
caattgtctt aattaactgg gcctcatggg ccttccgctc actgcccgct ttccagtcgg   6360
gaaacctgtc gtgccagctc tgcagatgac ggtgaaaacc tctgacacat gcagctcccg   6420
gagacggtca cagcttgtct gtaagcggat gccgggagca gacaagcccg tcagggcgcg   6480
tcagcgggtg ttggcgggtg tcggggcgca gccatgaccc agtcacgtag cgatagcgga   6540
gtgtatactg gcttaactat gcggcatcag agcagattgt actgagagtg caccatatgc   6600
ggtgtgaaat accgcacaga tgcgtaagga gaaaataccg catcaggcgc tcttccgctt   6660
cctcgctcac tgactcgctg cgctcggtcg ttcggctgcg gcgagcggta tcagctcact   6720
caaaggcggt aatacggtta tccacagaat caggggataa cgcaggaaag aacatgtgag   6780
caaaaggcca gcaaaaggcc aggaaccgta aaaaggccgc gttgctggcg tttttccata   6840
ggctccgccc ccctgacgag catcacaaaa atcgacgctc aagtcagagg tggcgaaacc   6900
cgacaggact ataaagatac caggcgtttc cccctggaag ctccctcgtg cgctctcctg   6960
ttccgaccct gccgcttacc ggatacctgt ccgcctttct cccttcggga agcgtggcgc   7020
tttctcatag ctcacgctgt aggtatctca gttcggtgta ggtcgttcgc tccaagctgg   7080
gctgtgtgca cgaacccccc gttcagcccg accgctgcgc cttatccggt aactatcgtc   7140
ttgagtccaa cccggtaaga cacgacttat cgccactggc agcagccact ggtaacagga   7200
ttagcagagc gaggtatgta ggcggtgcta cagagttctt gaagtggtgg cctaactacg   7260
gctacactag aaggacagta tttggtatct gcgctctgct gaagccagtt accttcggaa   7320
aaagagttgg tagctcttga tccggcaaac aaaccaccgc tggtagcggt ggtttttttg   7380
tttgcaagca gcagattacg cgcagaaaaa aaggatctca agaagatcct ttgatctttt   7440
ctactgcaga agcttgttag acaccctgtc atgtatttta tattatttat ttcaccatac   7500
ggattaagtg aaacctaatg aaaatagtac tttcggagct ttaactttaa tgaaggtatg   7560
ttttttata gacatcgatg tctggtttaa caataggaaa aagtagctaa aactcccatg   7620
aattaaagaa ataacaaggt gtctaacaac ctgttattaa gaatgttaga aaagacttaa   7680
catttgtgtt gagtttttat agacattggt gtctagacat acggtagata aggtttgctc   7740
aaaaataaaa taaaaaaaga ttggactaaa aaacatttaa tttagtacaa tttaattagt   7800
tattttttcg tctcaaattt tgctttgttg agcagaaatt tagataaaaa aatccccgtg   7860
atcagattac aatgtcgttc attgtacgat gtgtcgaaaa atctttacga cactctaaac   7920
tgaccacacg ggggaaaaag aaaactgaac taataacatc atgatactcg gaaaacctag   7980
caattctcaa cccctaaaca aaagaaactt ccaaaaccct gaccatataa aggagtggca   8040
acaatcagca atcagtcaag atttgatagc agaaaatctt gtatcggttg ctaatggttt   8100
tgatgtacta tttatcggca ataaataccg aactaacacg ggtgttctgt cacggcacat   8160
```

```
attaaactcc tattctcatt tagaagatgg tggttcgtat ggtagaacat ttgacccatt   8220
taccaataaa gaaatgcagt gggttcaatt taaaccgaat agaccaagaa aaggttctac   8280
tggtaaggta atcaaatatg aatcgccaaa aggtgaacct acaagagttc taatgccgtt   8340
tgtgcctatg aaaatatggc aacggattag cgataagttc ggagtaccga ttaatccgaa   8400
aaaagatact cacttttggg aatgggtaaa gaataatcca tcgataccga ttgccattac   8460
agaaggaaat aaaaaagcta attgcctatt atcctatggc tatcctgcta ttgcctttgt   8520
aggcatttgg aacggattag agaaaataaa tgatttctcg aaggaaaagc agttaaaaga   8580
ggatttgaaa tggttgttat ccaacggcaa ccgaaatatt aatatcatct ttgaccaaga   8640
ccagaaacaa aaaactgtaa ttaatgtaaa caaagctatt ttcgctttat cttctctaat   8700
aagtagaaat ggtcataaag ttaatattgt gcaatggttg ccgtcaaaag gtaaaggaat   8760
agatgattat ttggtagctt taccttttga gaaaagagaa aatcatttag acaacttaat   8820
taaaattgca ccatcattta atttttggtc aactaaatac ttattcaagt gtcgtaaacc   8880
agatttaacc gtaaattgcc gttatttgag cgatgcagta aaagaattac ctcaagagga   8940
tatagcatta atagcacctc acggcacggg taaaacttca ttagtagcta ctcacgttaa   9000
gaatcggagt tatcacggaa ggaaaactat ttcattggtg catcttgaaa gtttagccaa   9060
agctaatggc aacgcacttg gattatatta ccgaaccgaa aataatattg aaaagcaata   9120
tcttggattt agcttatgtg tagatagttg ccgtgataag attaacggca ttacaactga   9180
tattatttca ggtcaagatt attgcctttt cattgatgaa attgaccaag taattccaca   9240
catccttaac agtgaaactg aagtaagtaa gtatagatgc accatcattg acactttttc   9300
tgaactggtg agaaatgctg aacaggtcat tattgctgat gctgatttat ccgatgtgac   9360
gattgaccta atagaaaaca tcagaggtaa aaaactatat gtaatcaaga atgaatatca   9420
gtatcaggga atgactttta acgccgttgg ttcaccatta gaaatgatgg caatgatggg   9480
aaaatcggtg tcagaaggca agaaattatt tattaacacc acatcccaaa aggcaaaaag   9540
taagtacggc acaatcgctc ttgagtctta tatttttggt ctaaataaag aagcaaagat   9600
attaagaata gactctgaaa ccactaaaaa ccctgaacat ccagcctata aaatcattga   9660
ccaagactta aataatatcc tcaaagatta tgattatgtc attgcctcac cttgccttca   9720
aacaggtgtc agtattacct taaaagggca ttttgaccag caatttaact tttccagtgg   9780
aaacattaca cctcattgct ttttacagca aatgtggcgg ttgagggatg cagaaattga   9840
aagattctat tatgtgccga actcatctaa cctcaatctc attgggaata agtcaagttc   9900
accatcagac cttctaaaga gcaataacaa gatggcaacg gcaacggtta accttttggg   9960
tagaatcgac tccgaatatt ccctagagta tgaatcgcac ggcatttggc ttgagacgtg  10020
ggcaaaatta tcagcacggc ataacagttc aatgcgttgt tactctgaaa ttcttaccta  10080
tctaattacg tctcaagggc ataaattaaa tatcaacatt ccctcacctc ttgcagatat  10140
taagaagcta aatgatgagg taagtagtaa cagggaaaag gtaaaaaatg agagatactc  10200
tcagaggtta aactcaccag atattaacga tgcagaagct accatactcg aatctaaaga  10260
gcaaaaaatc ggattgactc tcaatgagag atgcacccta gaaaagcata aagttaagaa  10320
gcggtatggg aatgtaaaga tggatattct cacctttgat gatgatggac tataccccaa  10380
actcagacta ttttattacc tcaccatcgg taaacctcat ctcaaggcta atgacagaaa  10440
agctattgcc aaaatgggca atgacaataa aggcaagatt ctatcaaaag acttagttaa  10500
taaaacttac tccgctcgtg tgaaggtctt agagattctt aaactaactg actttatcga  10560
```

```
caatcttaga gatgaactct taataactcc caataatcca gctatcaccg attttaataa  10620
tcttctgcta agagctaaga aggatttaag agtattagga gtcaacatcg gaaaatatcc  10680
aatggccaac attaatgccg tacttactct cattggtcac aaactttctg taatgagaga  10740
tgagttcgga aaagagaaaa ggataaaagt agatggtaaa tcataccgat gttatcaact  10800
tgaaacatta ccagatttta ccaatgatac tcttgactac tggttagaaa atgatagcca  10860
aaaagaagta acagcaacag aaaattactc cgaaaatttt aacccttcaa atagctacaa  10920
tccagacagt aagacacttt cagagggtgc aaatttccta tatataaata aagaagaatt  10980
gcatccaaat aaattgcacc tagaaataaa agaaggtgct gaactttttt tattcggggt  11040
aaaggtgatt gtgaaaggaa tcttggacgg ggcagtaact atattctcta tgggtcaaga  11100
atacgattta tccctcaatg aactagaggg gatgttaaca tcatgaactt tacaagaatc  11160
tttttaaagg gcgatcgcac catgttaaat gatggtacat ttgttcagat atttgatatt  11220
taccatgacc acgcattggg agtgaccctt gaccttaaga cagaaaaaat tatttccgat  11280
gatgttaggg taattactgt caaagactta ttgttcgatg gcacttataa aggggtaaaa  11340
tcttttatgc ccgataatgc ccgataatgc ccgattgatg ctacaaaatc ccataatcat  11400
aagcgataat cccctaatag cttgtaattc ttgaaccgta gcgattttag agtattccaa  11460
aaagaagaaa taaacaccgc aaaatgtcgt atttcacata tataaaccaa ggtttttttgc  11520
cctaaaatct ttatgtttgt agtgtgatgt tgggtcaaaa tggtcagaaa agttgcaagg  11580
tttttatgga tgcttacgcg cgcgaggggt aagcatcccc aaatagttac tttatcctag  11640
tccatgccca tttattgccg tcccgttcgg ctttaaaaaa gtgccaaaac tcacaaggtg  11700
caataaaaag ttctgtacct ttcgcaaccc tagataatct ttcaacagtt acttttttttc  11760
ctattatctc ggtacaaagt ttggctagtt tctcttttcc ctctttttca atcaagcctt  11820
cttgtatgcc caactcattg attaatctct ctatttttac cattatttcc cgttcaggta  11880
gtttatcccc taaatcttca tcggggggca atgtagggca ttctgaaggg gctttttctt  11940
ctgtctggac attatctaat attgaagtaa ccaaactatc ttcagttttt tctattccta  12000
ttaattcata ttcggttact gtatccgtat caatatccga ataactatct ttatccgtat  12060
tagctattcg gttaagttta tccgttaact cagaaacaag actatatagc ggttttagct  12120
tttcttctat cctgttatct aatacggata agtttatacg gttatcatta tccgtattag  12180
tatcattggg ctttttttggt agttctaccc cctcataaac cgcttttatt cccaattcca  12240
acagactgat aacagtatcc tttataatgg gttttttgct gatatggtga actttttgccc  12300
cttccatcat tgcgatactt tctatctcac tcatcaactt atcgcttaag tgaatctcgt  12360
atctgtttaa tcccttactg gttttattca tatccgttta ctttattcgg ttaacaattc  12420
tattttatac gaataaaata ttatacggtt aactttatac gtttaactat tttatctata  12480
cggataacag taataagtta ttcgtattag ttatacgttt acttttatcc aaataaaatt  12540
agtgcattta aactaaaaga atgattttat cggagttgat agcattggat taacctaaag  12600
atgtttataa gctatatctg ataagtattt aaggttattt tgttattctg tttattgaca  12660
ttatcagaat aaaagaatag aatataattg ttgagagata agaggtttaa gtgattatgg  12720
ttaagaagtt agttggttat gtcagggtca gtagtgaatc gcaagaggat aacactagct  12780
tacagaatca gatagagaga attgaagcat attgtatggc ttttggttat gagttggtaa  12840
aaatattcaa agaggttgcc actggtacaa aagcagatat tgaaacccgt cctattttta  12900
```

```
atgaagctat agaatacttg aaacaggata atgctaatgg aattattgcc ttgaagctag  12960
accgaatcgc acggaatgct ttagatgtat tgcgtttggt tcgtgaaacc ttagaaccac  13020
aaaataaaat gttagtgtta ctagatattc aggtagatac ttcgacacct tcaggaaaaa  13080
tgattttaac tgtaatgagt gccgttgctg aactcgaaag agacatgatc tatgatcgca  13140
ctcagggggg tagaaagact aaagcccaaa agggcgggta tgcctacggg aaacctaaat  13200
ttggctataa gactgaagaa aaggaactaa aagaagattc agcacaacag gaaactatta  13260
aactaattaa gagacaccgt aggtcaggga aaagctacca gaaaatagct gattatctca  13320
atgcccaaag tattcccact aaacaaggta agaaatggag ttctagcgtc gtctatcgaa  13380
tctgtcagga aaaagctggt taagtctgtt tatagatatt tagaatttat tgaataaaaa  13440
tagtatgaac aataaatatt tatggactaa ccacgctcgg aaacgtttaa ctgaacgatg  13500
ggaaataaaa gaatcatggg ttattgatac catcgaaaat cctgaacgtt cagaatttat  13560
tgttgatgag tcaggggaaa aatatcatta ctataaaaga atagctaagt ttaagaatag  13620
agtgttagaa gtgataactt ctgccaactc aacacccaca agaataataa ccttttactt  13680
taaccgtaac atgaggaaaa atttatgatt gttacttacg ataatgaagt tgacgcaatt  13740
tattttaagt taacggaaaa taaaattgat agcaccgaac ctcaaacaga caggattatc  13800
attgattacg atgaaagtaa taatattgtt ggcattgagg tattagattt taattatctt  13860
gtcaagaaag gtttaaccgt tgctgattta cctttttctg aagatgaaag attaacagct  13920
tctcaatatt ttaattttcc tgttgctatc taatccagaa ggggcaataa tccccttctt  13980
tcatcgagtt agacttaata tcacaaaagt cattttcatt ttaccgtttc ttttccacag  14040
cgtccgtacg cccctcgtta aatctcaaaa ccgacaattt atgatgttta taaaaagtta  14100
ctcactttaa taagtattta tactcattaa agggttattc tttttttgta gcctgatagg  14160
ttgggaagga atatttcaga ttatcagatt tgttgaatat ttttcgtcag atacgcaaac  14220
cttacaaaca taattaacaa ctgaaactat tgatatgtct aggttttagc tctatcacag  14280
gttggatctg                                                         14290
```

```
<210> SEQ ID NO 10
<211> LENGTH: 14506
<212> TYPE: DNA
<213> ORGANISM: Artificial sequence
<220> FEATURE:
<223> OTHER INFORMATION: Synthetic plasmid sequence pAB194, derived from
      the endogenous p6.8 plasmid, plus nirA, pdc and adh genes.

<400> SEQUENCE: 10
```

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ggaggatcag ccttatgaat tcttataccg    300
tgggtactta tttagccgaa cgcttagtgc aaattggttt aaaacatcat tttgccgtgg    360
ctggggacta taatttagtg ttattggata acttattatt aaataaaaac atggaacaag    420
tgtattgttg taatgaatta aattgtggtt tttctgctga aggttatgct agagctaaag    480
gtgcagctgc tgctgttgtt acttattctg tgggtgcttt atctgctttt gatgctattg    540
gtggtgctta tgccgaaaat ttacccgtga ttttaatttc tggtgcccct aataataatg    600
```

```
atcatgccgc tggacatgtt ttacatcatg ccttaggtaa aaccgattat cattatcaat    660
tagaaatggc caaaaatatt actgctgctg ccgaagctat ttatactcct gaagaagccc    720
ctgccaaaat tgatcatgtg attaaaaccg ccttacgcga aaaaaaaccc gtgtatttag    780
aaattgcctg taatattgct tctatgcctt gtgctgctcc tgggcctgct tctgctttat    840
ttaatgatga agcctctgat gaagctagtt taaatgctgc cgtggaagaa accttaaaat    900
ttattgccaa tcgcgataaa gttgccgtgt tagttggttc taaattaaga gctgctggtg    960
ctgaagaagc tgctgttaaa tttgctgatg ctttaggtgg tgcagttgct actatggctg   1020
ctgccaaatc tttttttccc gaagaaaatc cccattatat tggaactagt tggggagaag   1080
tttcttatcc tggtgtggaa aaaactatga aagaagccga cgctgttatt gctttagccc   1140
ctgtgtttaa tgattattct accactggtt ggactgatat tcccgatccc aaaaaattag   1200
ttttagccga acctcgttct gttgttgtta atggtgttcg ctttccctct gtgcatttaa   1260
aagattattt aacccgctta gcccaaaaag tttctaaaaa aactggtgcc ttagattttt   1320
ttaaatcttt aaatgcgggt gaattaaaaa aagctgctcc tgctgatcct tctgctcctt   1380
tagttaatgc tgaaattgcc cgtcaagttg aagccttatt aacccctaat actaccgtta   1440
ttgccgaaac tggtgattct tggtttaatg cccaacgcat gaaattacct aatggtgccc   1500
gtgttgaata tgaaatgcaa tggggtcata ttggttggtc tgtacctgct gcttttggtt   1560
atgctgttgg tgctcctgaa cgtcgtaata ttttaatggt gggtgatggt tcttttcaat   1620
taactgccca agaagttgcc caaatggttc gcttaaaatt acccgttatt attttttttaa  1680
taaataatta tggttatacc attgaagtga tgattcatga tgggccatat aataatatta   1740
aaaattggga ttatgcgggt ttaatggaag tgtttaatgg taatggtggt tatgattctg   1800
gtgctggtaa aggtttaaaa gccaaaactg gtggtgaatt agctgaagct attaaagttg   1860
ccttagccaa tactgatggg ccaaccttaa ttgaatgttt tattggtcgc gaagattgta   1920
ccgaagaatt agttaaatgg ggtaaacgtg ttgctgctgc taattctcgc aaacccgtga   1980
ataaattatt gtaatttttg ggatcaatt cgagctcgaa tgtaaacttt cactaattta    2040
gtgggaaaat ctacggcaaa ataagttata aaataacaga taaagccgtt tttactaaca   2100
ataattgtta atagttgaaa gtctatattt atcttagatt cttcactatt aactaacatt   2160
taaaaatcaa tttaattcct tgcctagttt cttttaaaga aatttaattc cgagggctag   2220
gcaagataaa atccaaaatt gaccagcgta ttttaaacgt tgactctgat tgtgtaacag   2280
gagaattcct aaaaaaagct atggttgttg ctgtaaatac caccaccaca aaaaaagtga   2340
aactaaataa aattgaaaaa gtaaaagaag caaaacacgg tttggatgtt aaggaagaaa   2400
tagaaaagtt tgctcaaatg ggttgggaag caatggatga agatgacctc attgttcgtt   2460
taaagtggtt ggggattttt tttcgcccag taactccggg gaaatttatg cttaggttac   2520
gcactcctaa tggtattctc aacagccaac aattacgcac ttttgcggaa attattgaac   2580
gttatgggga ggatggaaaa gctgatatta ctacccgtca aaatattcaa ttaaggggag   2640
ttcatttaca ggatatacca gatatttttc gtaaattgga agcggtgggc atgacatcga   2700
ttcagtcagg aatggataat gtgcgtaatt taacgggttc tcctgttgct ggaattgacc   2760
ctcatgagtt aattgacacc agagaattaa atcaaaaatt acaggatttg attactaacc   2820
atggacaggg tagttatgag tttagtagtc tccctcgtaa attaaacatt gcgatcgaag   2880
gtagtaaaga taattctatt cacgctgaat tgaatgatat agcattttta cccgcctata   2940
aagatggtga attaggtttt aatgttgtgg tgggggggtta cttatccgct caaaggtgcg  3000
```

```
cagagtctat tccgatggat gtttgggtaa gacctaatga agaagtattg aaattatgcg   3060
cggctattct tagtgtttat agtgagtgtg cattggaaga aggtttgagg gaaaatagag   3120
caaaagcccg tttaatgtgg ttaattgata aatggggtat gaatcgtttt cgcattgaag   3180
tggagaaaaa actaggacaa tccttacaat ttgccgcccc gaaagatgaa attaccttag   3240
aaaaaagaga tcatttaggg gttaatcctc aaaagcaaga gggttatagt tatatcggta   3300
ttcatattcc tgttgggcat ttagatgcgg agggtttatt tgaaattgct cgtttagcgg   3360
atgtttatgg taacggagaa attcgggcaa cagtggaaca aaattttatt attccttttg   3420
tagccaatga cagggtagaa gcatttcttg ctgaaccaat tttagaacgc tatcgagtta   3480
atccttcacc tttaagccgt tctgtaattt cgtgtacagg ggctcgttat tgtaattttg   3540
ccttggtaga aactaagcag agagcggtga aactagccac agaattagat aatgaactaa   3600
atattccctc taaagtcaga attcattgga caggttgtcc taactcttgc ggacaggctc   3660
aagcagggga cattggctta atgggtacta aagcgaaaaa agatgggcag gtggtagagg   3720
gtgttaactt atttatgggg ggaaaagtgg gcaaggatgc acatttaggg agtctcaaac   3780
aaaaaagtat tccctgtgat gatttgaaat ccgttttgaa ggaaatttta attaatgaat   3840
ttggggcaac agttaaataa gagctcagca agtttcatcc cgacccccctc agggtcggga   3900
tttttttatt gtactagttg acataagtaa aggcatcccc tgcgtgatat aattaccttc   3960
agtttaagga ggtatacaca tatgattaaa gcctacgctg ccctggaagc caacggaaaa   4020
ctccaaccct ttgaatacga ccccggtgcc ctgggtgcta atgaggtgga gattgaggtg   4080
cagtattgtg ggtgtgccca cagtgatttg tccatgatta ataacgaatg gggcatttcc   4140
aattaccccc tagtgccggg tcatgaggtg gtgggtactg tggccgccat gggcgaaggg   4200
gtgaaccatg ttgaggtggg ggatttagtg gggctgggtt ggcattcggg ctactgcatg   4260
acctgccata gttgtttatc tggctaccac aacctttgtg ccacggcgga atcgaccatt   4320
gtgggccact acggtggctt tggcgatcgg gttcgggcca agggagtcag cgtggtgaaa   4380
ttacctaaag gcattgacct agccagtgcc gggcccctttt tctgtggagg aattaccgtt   4440
ttcagtccta tggtggaact gagtttaaag cccactgcaa aagtggcagt gatcggcatt   4500
gggggcttgg gccatttagc ggtgcaattt ctccgggcct ggggctgtga agtgactgcc   4560
tttacctcca gtgccaggaa gcaaacggaa gtgttggaat tgggcgctca ccacatacta   4620
gattccacca atccagaggc gatcgccagt gcggaaggca aatttgacta tattatctcc   4680
actgtgaacc tgaagcttga ctggaactta tacatcagca ccctggcgcc ccagggacat   4740
ttccactttg ttggggtggt gttggagcct ttggatctaa atcttttttcc ccttttgatg   4800
ggacaacgct ccgtttctgc ctccccagtg ggtagtcccg ccaccattgc caccatgttg   4860
gactttgctg tgcgccatga cattaaaccc gtggtggaac aatttagctt tgatcagatc   4920
aacgaggcga tcgcccatct agaaagcggc aaagcccatt atcgggtagt gctcagccat   4980
agtaaaaatt agctctgcaa aggttgcttc tgggtccgtg gaacgctcgg ttgccgccgg   5040
gcgtttttta ttcctgcagg atcatcttgc tgaaaaactc gagcgctcgt tccgcaaagc   5100
ggtacggagt tagttagggg ctaatgggca ttctcccgta caggaaagag ttagaagtta   5160
ttaattatca acaattctcc tttgcctagt gcatcgttac ctttttaatt aaaacataag   5220
gaaaactaat aatcgtaata atttaacctc aaagtgtaaa gaaatgtgaa attctgactt   5280
ttataacgtt aaagagggaa aaattagcag tttaaaatac ctagagaata gtctggggta   5340
```

```
agcatagaga attagattag ttaagttaat caaattcaga aaaaataata atcgtaaata   5400
gttaatctgg gtgtatagaa aatgatcccc ttcatgataa gatttaaact cgaaaagcaa   5460
aagccaaaaa actaacttcc attaaaagaa gttgttacat ataacgctat aaagaaaatt   5520
tatatatttg gaggatacca accatgtctc atattcaacg tgaaactagt tgttctcgcc   5580
ctcgtttaaa ttctaatatg gatgccgatt tatatggtta taaatgggct cgtgataatg   5640
ttggtcaatc tggtgctact atttatcgtt tatatggtaa acctgatgct cctgaattat   5700
tcttgaaaca tggtaaaggt tctgttgcta atgatgttac tgatgaaatg gttcgtttaa   5760
actggttgac tgaatttatg cctttaccta ctattaaaca ttttattcgt actcccgatg   5820
atgcttggtt attaactact gctattcctg gtaaaactgc ttttcaagtt ttagaagaat   5880
atcctgattc tggtgaaaat attgttgatg ctttagctgt ttttttacgt cgtttacatt   5940
ctattcccgt ttgtaattgt ccttttaatt ctgatcgtgt tttcgttta gctcaagctc    6000
aatctcgtat gaataatggt ttagttgatg cttctgattt tgatgatgaa cgtaatggtt   6060
ggcctgttga acaagtttgg aaagaaatgc acaaattgtt acctttttct cctgattctg   6120
ttgttactca tggtgatttt tctttagata atttgatctt tgatgaaggt aaattgattg   6180
gttgtattga tgttggtcgt gttggtattg ctgatcgtta tcaagattta gctattttat   6240
ggaattgttt aggtgaattt tctccttctt tacagaaacg tttatttcag aaatatggta   6300
ttgataatcc tgatatgaac aagttacaat ttcatttaat gttggacgag ttcttttaag   6360
aattaattca tgaccaaaat cccttaacgt gagttttcgt tccactgagc gtcagacccc   6420
gtagaaaaga tcaaaggatc ttcttgagat cctttttttc tgcgcgtaat ctgctgctat   6480
ttaaattacg tacacgtgtt attactttgt taacgacaat tgtcttaatt aactgggcct   6540
catgggcctt ccgctcactg cccgctttcc agtcgggaaa cctgtcgtgc cagctctgca   6600
gatgacggtg aaaacctctg acacatgcag ctcccggaga cggtcacagc ttgtctgtaa   6660
gcggatgccg ggagcagaca agcccgtcag ggcgcgtcag cgggtgttgg cgggtgtcgg   6720
ggcgcagcca tgacccagtc acgtagcgat agcggagtgt atactggctt aactatgcgg   6780
catcagagca gattgtactg agagtgcacc atatgcggtg tgaaataccg cacagatgcg   6840
taaggagaaa ataccgcatc aggcgctctt ccgcttcctc gctcactgac tcgctgcgct   6900
cggtcgttcg gctgcggcga gcggtatcag ctcactcaaa ggcggtaata cggttatcca   6960
cagaatcagg ggataacgca ggaaagaaca tgtgagcaaa aggccagcaa aaggccagga   7020
accgtaaaaa ggccgcgttg ctggcgtttt tccataggct ccgcccccct gacgagcatc   7080
acaaaaatcg acgctcaagt cagaggtggc gaaacccgac aggactataa agataccagg   7140
cgtttccccc tggaagctcc ctcgtgcgct ctcctgttcc gaccctgccg cttaccggat   7200
acctgtccgc ctttctccct tcgggaagcg tggcgctttc tcatagctca cgctgtaggt   7260
atctcagttc ggtgtaggtc gttcgctcca agctgggctg tgtgcacgaa ccccccgttc   7320
agcccgaccg ctgcgcctta tccggtaact atcgtcttga gtccaacccg gtaagacacg   7380
acttatcgcc actggcagca gccactggta acaggattag cagagcgagg tatgtaggcg   7440
gtgctacaga gttcttgaag tggtggccta actacggcta cactagaagg acagtatttg   7500
gtatctgcgc tctgctgaag ccagttacct tcggaaaaag agttggtagc tcttgatccg   7560
gcaaacaaac caccgctggt agcggtggtt tttttgtttg caagcagcag attacgcgca   7620
gaaaaaaagg atctcaagaa gatcctttga tcttttctac tgcagaagct tgttagacac   7680
cctgtcatgt attttatatt atttatttca ccatacggat taagtgaaac ctaatgaaaa   7740
```

```
tagtactttc ggagctttaa ctttaatgaa ggtatgtttt tttatagaca tcgatgtctg   7800
gtttaacaat aggaaaaagt agctaaaact cccatgaatt aaagaaataa caaggtgtct   7860
aacaacctgt tattaagaat gttagaaaag acttaacatt tgtgttgagt ttttatagac   7920
attggtgtct agacatacgg tagataaggt ttgctcaaaa ataaaataaa aaaagattgg   7980
actaaaaaac atttaattta gtacaattta attagttatt ttttcgtctc aaattttgct   8040
ttgttgagca gaaatttaga taaaaaaatc cccgtgatca gattacaatg tcgttcattg   8100
tacgatgtgt cgaaaaatct ttacgacact ctaaactgac cacacggggg aaaaagaaaa   8160
ctgaactaat aacatcatga tactcggaaa acctagcaat tctcaacccc taaacaaaag   8220
aaacttccaa aaccctgacc atataaagga gtggcaacaa tcagcaatca gtcaagattt   8280
gatagcagaa aatcttgtat cggttgctaa tggttttgat gtactattta tcggcaataa   8340
ataccgaact aacacgggtg ttctgtcacg gcacatatta aactcctatt ctcatttaga   8400
agatggtggt tcgtatggta gaacatttga cccatttacc aataaagaaa tgcagtgggt   8460
tcaatttaaa ccgaatagac caagaaaagg ttctactggt aaggtaatca aatatgaatc   8520
gccaaaaggt gaacctacaa gagttctaat gccgtttgtg cctatgaaaa tatggcaacg   8580
gattagcgat aagttcggag taccgattaa tccgaaaaaa gatactcact tttgggaatg   8640
ggtaaagaat aatccatcga taccgattgc cattacagaa ggaaataaaa aagctaattg   8700
cctattatcc tatggctatc ctgctattgc ctttgtaggc atttggaacg gattagagaa   8760
aataaatgat ttctcgaagg aaaagcagtt aaaagaggat ttgaaatggt tgttatccaa   8820
cggcaaccga aatattaata tcatctttga ccaagaccag aaacaaaaaa ctgtaattaa   8880
tgtaaacaaa gctattttcg ctttatcttc tctaataagt agaaatggtc ataaagttaa   8940
tattgtgcaa tggttgccgt caaaaggtaa aggaatagat gattatttgg tagctttacc   9000
ttttgagaaa agagaaaatc atttagacaa cttaattaaa attgcaccat catttaattt   9060
ttggtcaact aaatacttat tcaagtgtcg taaaccagat ttaaccgtaa attgccgtta   9120
tttgagcgat gcagtaaaag aattacctca agaggatata gcattaatag cacctcacgg   9180
cacgggtaaa acttcattag tagctactca cgttaagaat cggagttatc acggaaggaa   9240
aactatttca ttggtgcatc ttgaaagttt agccaaagct aatggcaacg cacttggatt   9300
atattaccga accgaaaata atattgaaaa gcaatatctt ggatttagct tatgtgtaga   9360
tagttgccgt gataagatta acggcattac aactgatatt atttcaggtc aagattattg   9420
ccttttcatt gatgaaattg accaagtaat tccacacatc cttaacagtg aaactgaagt   9480
aagtaagtat agatgcacca tcattgacac tttttctgaa ctggtgagaa atgctgaaca   9540
ggtcattatt gctgatgctg atttatccga tgtgacgatt gacctaatag aaaacatcag   9600
aggtaaaaaa ctatatgtaa tcaagaatga atatcagtat cagggaatga cttttaacgc   9660
cgttggttca ccattagaaa tgatggcaat gatgggaaaa tcggtgtcag aaggcaagaa   9720
attatttatt aacaccacat cccaaaaggc aaaaagtaag tacggcacaa tcgctcttga   9780
gtcttatatt tttggtctaa ataaagaagc aaagatatta agaatagact ctgaaaccac   9840
taaaaaccct gaacatccag cctataaaat cattgaccaa gacttaaata atatcctcaa   9900
agattatgat tatgtcattg cctcaccttg ccttcaaaca ggtgtcagta ttaccttaaa   9960
agggcatttt gaccagcaat ttaacttttc cagtggaaac attacacctc attgcttttt  10020
acagcaaatg tggcggttga gggatgcaga aattgaaaga ttctattatg tgccgaactc  10080
```

-continued

```
atctaacctc aatctcattg ggaataagtc aagttcacca tcagaccttc taaagagcaa  10140
taacaagatg gcaacggcaa cggttaacct tttgggtaga atcgactccg aatattccct  10200
agagtatgaa tcgcacggca tttggcttga gacgtgggca aaattatcag cacggcataa  10260
cagttcaatg cgttgttact ctgaaattct tacctatcta attacgtctc aagggcataa  10320
attaaatatc aacattccct cacctcttgc agatattaag aagctaaatg atgaggtaag  10380
tagtaacagg gaaaaggtaa aaaatgagag atactctcag aggttaaact caccagatat  10440
taacgatgca gaagctacca tactcgaatc taaagagcaa aaaatcggat tgactctcaa  10500
tgagagatgc accctagaaa agcataaagt taagaagcgg tatgggaatg taaagatgga  10560
tattctcacc tttgatgatg atggactata ccccaaactc agactatttt attacctcac  10620
catcggtaaa cctcatctca aggctaatga cagaaaagct attgccaaaa tgggcaatga  10680
caataaaggc aagattctat caaaagactt agttaataaa acttactccg ctcgtgtgaa  10740
ggtcttagag attcttaaac taactgactt tatcgacaat cttagagatg aactcttaat  10800
aactcccaat aatccagcta tcaccgattt taataatctt ctgctaagag ctaagaagga  10860
tttaagagta ttaggagtca acatcggaaa atatccaatg gccaacatta atgccgtact  10920
tactctcatt ggtcacaaac tttctgtaat gagagatgag ttcggaaaag agaaaaggat  10980
aaaagtagat ggtaaatcat accgatgtta tcaacttgaa acattaccag attttaccaa  11040
tgatactctt gactactggt tagaaaatga tagccaaaaa gaagtaacag caacagaaaa  11100
ttactccgaa aattttaacc cttcaaatag ctacaatcca gacagtaaga cactttcaga  11160
gggtgcaaat ttcctatata taaataaaga agaattgcat ccaaataaat tgcacctaga  11220
aataaaagaa ggtgctgaac tttttttatt cggggtaaag gtgattgtga aaggaatctt  11280
ggacggggca gtaactatat tctctatggg tcaagaatac gatttatccc tcaatgaact  11340
agaggggatg ttaacatcat gaactttaca agaatctttt taaagggcga tcgcaccatg  11400
ttaaatgatg gtacatttgt tcagatattt gatatttacc atgaccacgc attgggagtg  11460
acccttgacc ttaagacaga aaaaattatt tccgatgatg ttagggtaat tactgtcaaa  11520
gacttattgt tcgatggcac ttataaaggg gtaaaatctt ttatgcccga taatgcccga  11580
taatgcccga ttgatgctac aaaatcccat aatcataagc gataatcccc taatagcttg  11640
taattcttga accgtagcga ttttagagta ttccaaaaag aagaaataaa caccgcaaaa  11700
tgtcgtattt cacatatata aaccaaggtt ttttgcccta aaatctttat gtttgtagtg  11760
tgatgttggg tcaaaatggt cagaaaagtt gcaaggtttt tatggatgct tacgcgcgcg  11820
aggggtaagc atccccaaat agttacttta tcctagtcca tgcccattta ttgccgtccc  11880
gttcggcttt aaaaaagtgc caaaactcac aaggtgcaat aaaaagttct gtacctttcg  11940
caaccctaga taatctttca acagttactt tttttcctat tatctcggta caaagtttgg  12000
ctagtttctc ttttccctct ttttcaatca agccttcttg tatgcccaac tcattgatta  12060
atctctctat ttttaccatt atttcccgtt caggtagttt atcccctaaa tcttcatcgg  12120
ggggcaatgt agggcattct gaaggggctt tttcttctgt ctggacatta tctaatattg  12180
aagtaaccaa actatcttca gtttttttcta ttcctattaa ttcatattcg gttactgtat  12240
ccgtatcaat atccgaataa ctatctttat ccgtattagc tattcggtta agtttatccg  12300
ttaactcaga aacaagacta tatagcggtt ttagcttttc ttctatcctg ttatctaata  12360
cggataagtt tatacggtta tcattatccg tattagtatc attgggcttt tttggtagtt  12420
ctaccccctc ataaaccgct tttattccca attccaacag actgataaca gtatccttta  12480
```

```
taatgggttt tttgctgata tggtgaactt ttgccccttc catcattgcg atactttcta  12540
tctcactcat caacttatcg cttaagtgaa tctcgtatct gtttaatccc ttactggttt  12600
tattcatatc cgtttacttt attcggttaa caattctatt ttatacgaat aaaatattat  12660
acggttaact ttatacgttt aactatttta tctatacgga taacagtaat aagttattcg  12720
tattagttat acgtttactt ttatccaaat aaaattagtg catttaaact aaaagaatga  12780
ttttatcgga gttgatagca ttggattaac ctaaagatgt ttataagcta tatctgataa  12840
gtatttaagg ttattttgtt attctgttta ttgacattat cagaataaaa gaatagaata  12900
taattgttga gagataagag gtttaagtga ttatggttaa gaagttagtt ggttatgtca  12960
gggtcagtag tgaatcgcaa gaggataaca ctagcttaca gaatcagata gagagaattg  13020
aagcatattg tatggctttt ggttatgagt tggtaaaaat attcaaagag gttgccactg  13080
gtacaaaagc agatattgaa acccgtccta tttttaatga agctatagaa tacttgaaac  13140
aggataatgc taatggaatt attgccttga agctagaccg aatcgcacgg aatgctttag  13200
atgtattgcg tttggttcgt gaaaccttag aaccacaaaa taaaatgtta gtgttactag  13260
atattcaggt agatacttcg acaccttcag gaaaaatgat tttaactgta atgagtgccg  13320
ttgctgaact cgaaagagac atgatctatg atcgcactca ggggggtaga aagactaaag  13380
cccaaaaggg cgggtatgcc tacgggaaac ctaaatttgg ctataagact gaagaaaagg  13440
aactaaaaga agattcagca caacaggaaa ctattaaact aattaagaga caccgtaggt  13500
cagggaaaag ctaccagaaa atagctgatt atctcaatgc ccaaagtatt cccactaaac  13560
aaggtaagaa atggagttct agcgtcgtct atcgaatctg tcaggaaaaa gctggttaag  13620
tctgtttata gatatttaga atttattgaa taaaaatagt atgaacaata aatatttatg  13680
gactaaccac gctcggaaac gtttaactga acgatgggaa ataaaagaat catgggttat  13740
tgataccatc gaaaatcctg aacgttcaga atttattgtt gatgagtcag gggaaaaata  13800
tcattactat aaaagaatag ctaagtttaa gaatagagtg ttagaagtga taacttctgc  13860
caactcaaca cccacaagaa taataacctt ttactttaac cgtaacatga ggaaaaattt  13920
atgattgtta cttacgataa tgaagttgac gcaatttatt ttaagttaac ggaaaataaa  13980
attgatagca ccgaacctca aacagacagg attatcattg attacgatga aagtaataat  14040
attgttggca ttgaggtatt agattttaat tatcttgtca agaaaggttt aaccgttgct  14100
gatttacctt tttctgaaga tgaaagatta acagcttctc aatattttaa ttttcctgtt  14160
gctatctaat ccagaagggg caataatccc cttctttcat cgagttagac ttaatatcac  14220
aaaagtcatt ttcattttac cgtttctttt ccacagcgtc cgtacgcccc tcgttaaatc  14280
tcaaaaccga caatttatga tgtttataaa aagttactca ctttaataag tatttatact  14340
cattaaaggg ttattctttt tttgtagcct gataggttgg gaaggaatat ttcagattat  14400
cagatttgtt gaatattttt cgtcagatac gcaaacctta caaacataat taacaactga  14460
aactattgat atgtctaggt tttagctcta tcacaggttg gatctg                 14506
```

<210> SEQ ID NO 11
<211> LENGTH: 14410
<212> TYPE: DNA
<213> ORGANISM: Artificial sequence
<220> FEATURE:
<223> OTHER INFORMATION: Synthetic plasmid sequence pAB195, derived from the endogenous p6.8 plasmid, plus nirA, pdc and adh genes.

<400> SEQUENCE: 11

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ggaggatcag ccttatgaat tcttataccg    300
tgggtactta tttagccgaa cgcttagtgc aaattggttt aaaacatcat tttgccgtgg    360
ctggggacta taatttagtg ttattggata acttattatt aaataaaaac atggaacaag    420
tgtattgttg taatgaatta aattgtggtt tttctgctga aggttatgct agagctaaag    480
gtgcagctgc tgctgttgtt acttattctg tgggtgcttt atctgctttt gatgctattg    540
gtggtgctta tgccgaaaat ttacccgtga ttttaatttc tggtgcccct aataataatg    600
atcatgccgc tggacatgtt ttacatcatg ccttaggtaa aaccgattat cattatcaat    660
tagaaatggc caaaaatatt actgctgctg ccgaagctat ttatactcct gaagaagccc    720
ctgccaaaat tgatcatgtg attaaaaccg ccttacgcga aaaaaaaccc gtgtatttag    780
aaattgcctg taatattgct tctatgcctt gtgctgctcc tggcctgct  tctgctttat    840
ttaatgatga agcctctgat gaagctagtt taaatgctgc cgtggaagaa accttaaaat    900
ttattgccaa tcgcgataaa gttgccgtgt tagttggttc taaattaaga gctgctggtg    960
ctgaagaagc tgctgttaaa tttgctgatg ctttaggtgg tgcagttgct actatggctg   1020
ctgccaaatc ttttttttccc gaagaaaatc cccattatat tggaactagt tggggagaag   1080
tttcttatcc tggtgtggaa aaaactatga aagaagccga cgctgttatt gctttagccc   1140
ctgtgtttaa tgattattct accactggtt ggactgatat tcccgatccc aaaaaaattag   1200
ttttagccga acctcgttct gttgttgtta atggtgttcg ctttccctct gtgcatttaa   1260
aagattattt aacccgctta gcccaaaaag tttctaaaaa aactggtgcc ttagattttt   1320
ttaaatcttt aaatgcgggt gaattaaaaa aagctgctcc tgctgatcct tctgctcctt   1380
tagttaatgc tgaaattgcc cgtcaagttg aagccttatt aacccctaat actaccgtta   1440
ttgccgaaac tggtgattct tggtttaatg cccaacgcat gaaattacct aatggtgccc   1500
gtgttgaata tgaaatgcaa tggggtcata ttggttggtc tgtacctgct gcttttggtt   1560
atgctgttgg tgctcctgaa cgtcgtaata ttttaatggt gggtgatggt tcttttcaat   1620
taactgccca agaagttgcc caaatggttc gcttaaaatt acccgttatt attttttttaa   1680
taaataatta tggttatacc attgaagtga tgattcatga tggccatat  aataatatta   1740
aaaattggga ttatgcgggt ttaatggaag tgtttaatgg taatggtggt tatgattctg   1800
gtgctggtaa aggtttaaaa gccaaaactg gtggtgaatt agctgaagct attaaagttg   1860
ccttagccaa tactgatggg ccaaccttaa ttgaatgttt tattggtcgc gaagattgta   1920
ccgaagaatt agttaaatgg ggtaaacgtg ttgctgctgc taattctcgc aaacccgtga   1980
ataaattatt gtaatttttg gggatcaatt cgagctcatc tcctgatcca cacccggaca   2040
tctccatagt ctgggccagt ctgaggactg gtggatcagg gccgtgaatt tacagtattt   2100
cagttaccgc tctatcctta tccttatccg ctcaagagca gagagttaat aggatccgct   2160
aggatatcgg taccgtattt tggatgataa ggaggatcag ccttatggtt gttgctgtaa   2220
ataccaccac cacaaaaaaa gtgaaactaa ataaaattga aaaagtaaaa gaagcaaaac   2280
acggtttgga tgttaaggaa gaaatagaaa agtttgctca aatgggttgg gaagcaatgg   2340
```

```
atgaagatga cctcattgtt cgtttaaagt ggttggggat ttttttttcgc ccagtaactc   2400
cggggaaatt tatgcttagg ttacgcactc ctaatggtat tctcaacagc caacaattac   2460
gcacttttgc ggaaattatt gaacgttatg gggaggatgg aaaagctgat attactaccc   2520
gtcaaaatat tcaattaagg ggagttcatt tacaggatat accagatatt tttcgtaaat   2580
tggaagcggt gggcatgaca tcgattcagt caggaatgga taatgtgcgt aatttaacgg   2640
gttctcctgt tgctggaatt gaccctcatg agttaattga caccagagaa ttaaatcaaa   2700
aattacagga tttgattact aaccatggac agggtagtta tgagtttagt agtctccctc   2760
gtaaattaaa cattgcgatc gaaggtagta aagataattc tattcacgct gaattgaatg   2820
atatagcatt tttacccgcc tataaagatg gtgaattagg ttttaatgtt gtggtggggg   2880
gttacttatc cgctcaaagg tgcgcagagt ctattccgat ggatgtttgg gtaagaccta   2940
atgaagaagt attgaaatta tgcgcggcta ttcttagtgt ttatagtgag tgtgcattgg   3000
aagaaggttt gagggaaaat agagcaaaag cccgtttaat gtggttaatt gataaatggg   3060
gtatgaatcg ttttcgcatt gaagtggaga aaaaactagg acaatcctta caatttgccg   3120
ccccgaaaga tgaaattacc ttagaaaaaa gagatcattt aggggttaat cctcaaaagc   3180
aagagggtta tagttatatc ggtattcata ttcctgttgg gcatttagat gcggagggtt   3240
tatttgaaat tgctcgttta gcggatgttt atggtaacgg agaaattcgg gcaacagtgg   3300
aacaaaattt tattattcct tttgtagcca atgacagggt agaagcattt cttgctgaac   3360
caattttaga acgctatcga gttaatcctt cacctttaag ccgttctgta atttcgtgta   3420
caggggctcg ttattgtaat tttgccttgg tagaaactaa gcagagagcg gtgaaactag   3480
ccacagaatt agataatgaa ctaaatattc cctctaaagt cagaattcat tggacaggtt   3540
gtcctaactc ttgcggacag gctcaagcag gggacattgg cttaatgggt actaaagcga   3600
aaaaagatgg gcaggtggta gagggtgtta acttatttat ggggggaaaa gtgggcaagg   3660
atgcacattt agggagtctc aaacaaaaaa gtattccctg tgatgatttg aaatccgttt   3720
tgaaggaaat tttaattaat gaatttgggg caacagttaa ataagagctc agcaagtttc   3780
atcccgaccc cctcagggtc gggatttttt tattgtacta gttgacataa gtaaaggcat   3840
cccctgcgtg atataattac cttcagttta aggaggtata cacatatgat taaagcctac   3900
gctgccctgg aagccaacgg aaaactccaa ccctttgaat acgaccccgg tgccctgggt   3960
gctaatgagg tggagattga ggtgcagtat tgtggggtgt gccacagtga tttgtccatg   4020
attaataacg aatggggcat ttccaattac cccctagtgc cgggtcatga ggtggtgggt   4080
actgtggccg ccatgggcga aggggtgaac catgttgagg tgggggattt agtggggctg   4140
ggttggcatt cgggctactg catgacctgc catagttgtt tatctggcta ccacaacctt   4200
tgtgccacgg cggaatcgac cattgtgggc cactacggtg gctttggcga tcgggttcgg   4260
gccaagggag tcagcgtggt gaaattacct aaaggcattg acctagccag tgccgggccc   4320
cttttctgtg gaggaattac cgttttcagt cctatggtgg aactgagttt aaagcccact   4380
gcaaaagtgg cagtgatcgg cattgggggc ttgggccatt tagcggtgca atttctccgg   4440
gcctggggct gtgaagtgac tgcctttacc tccagtgcca ggaagcaaac ggaagtgttg   4500
gaattgggcg ctcaccacat actagattcc accaatccag aggcgatcgc cagtgcggaa   4560
ggcaaatttg actatattat ctccactgtg aacctgaagc ttgactggaa cttatacatc   4620
agcaccctgg cgccccaggg acatttccac tttgttgggg tggtgttgga gcctttggat   4680
ctaaatcttt ttccccttttt gatgggacaa cgctccgttt ctgcctcccc agtgggtagt   4740
```

```
cccgccacca ttgccaccat gttggacttt gctgtgcgcc atgacattaa acccgtggtg   4800
gaacaattta gctttgatca gatcaacgag gcgatcgccc atctagaaag cggcaaagcc   4860
cattatcggg tagtgctcag ccatagtaaa aattagctct gcaaaggttg cttctgggtc   4920
cgtggaacgc tcggttgccg ccgggcgttt tttattcctg caggatcatc ttgctgaaaa   4980
actcgagcgc tcgttccgca aagcggtacg gagttagtta ggggctaatg ggcattctcc   5040
cgtacaggaa agagttagaa gttattaatt atcaacaatt ctcctttgcc tagtgcatcg   5100
ttaccttttt aattaaaaca taaggaaaac taataatcgt aataatttaa cctcaaagtg   5160
taaagaaatg tgaaattctg acttttataa cgttaaagag ggaaaaatta gcagtttaaa   5220
atacctagag aatagtctgg ggtaagcata gagaattaga ttagttaagt taatcaaatt   5280
cagaaaaaat aataatcgta aatagttaat ctgggtgtat agaaaatgat ccccttcatg   5340
ataagattta aactcgaaaa gcaaaagcca aaaaactaac ttccattaaa agaagttgtt   5400
acatataacg ctataaagaa aatttatata tttggaggat accaaccatg tctcatattc   5460
aacgtgaaac tagttgttct cgccctcgtt taaattctaa tatggatgcc gatttatatg   5520
gttataaatg ggctcgtgat aatgttggtc aatctggtgc tactatttat cgtttatatg   5580
gtaaacctga tgctcctgaa ttattcttga aacatggtaa aggttctgtt gctaatgatg   5640
ttactgatga aatggttcgt ttaaactggt tgactgaatt tatgccttta cctactatta   5700
aacattttat tcgtactccc gatgatgctt ggttattaac tactgctatt cctggtaaaa   5760
ctgcttttca agttttagaa gaatatcctg attctggtga aaatattgtt gatgctttag   5820
ctgttttttt acgtcgttta cattctattc ccgtttgtaa ttgtcctttt aattctgatc   5880
gtgtttttcg tttagctcaa gctcaatctc gtatgaataa tggtttagtt gatgcttctg   5940
attttgatga tgaacgtaat ggttggcctg ttgaacaagt ttggaaagaa atgcacaaat   6000
tgttaccttt ttctcctgat tctgttgtta ctcatggtga tttttcttta gataatttga   6060
tctttgatga aggtaaattg attggttgta ttgatgttgg tcgtgttggt attgctgatc   6120
gttatcaaga tttagctatt ttatggaatt gtttaggtga attttctcct tctttacaga   6180
aacgtttatt tcagaaatat ggtattgata atcctgatat gaacaagtta caatttcatt   6240
taatgttgga cgagttcttt taagaattaa ttcatgacca aaatccctta acgtgagttt   6300
tcgttccact gagcgtcaga ccccgtagaa aagatcaaag gatcttcttg agatcctttt   6360
tttctgcgcg taatctgctg ctatttaaat tacgtacacg tgttattact ttgttaacga   6420
caattgtctt aattaactgg gcctcatggg ccttccgctc actgcccgct ttccagtcgg   6480
gaaacctgtc gtgccagctc tgcagatgac ggtgaaaacc tctgacacat gcagctcccg   6540
gagacggtca cagcttgtct gtaagcggat gccgggagca gacaagcccg tcagggcgcg   6600
tcagcgggtg ttggcgggtg tcggggcgca gccatgaccc agtcacgtag cgatagcgga   6660
gtgtatactg gcttaactat gcggcatcag agcagattgt actgagagtg caccatatgc   6720
ggtgtgaaat accgcacaga tgcgtaagga gaaaataccg catcaggcgc tcttccgctt   6780
cctcgctcac tgactcgctg cgctcggtcg ttcggctgcg gcgagcggta tcagctcact   6840
caaaggcggt aatacggtta tccacagaat caggggataa cgcaggaaag aacatgtgag   6900
caaaaggcca gcaaaaggcc aggaaccgta aaaaggccgc gttgctggcg tttttccata   6960
ggctccgccc ccctgacgag catcacaaaa atcgacgctc aagtcagagg tggcgaaacc   7020
cgacaggact ataaagatac caggcgtttc cccctggaag ctccctcgtg cgctctcctg   7080
```

```
ttccgaccct gccgcttacc ggatacctgt ccgcctttct cccttcggga agcgtggcgc   7140
tttctcatag ctcacgctgt aggtatctca gttcggtgta ggtcgttcgc tccaagctgg   7200
gctgtgtgca cgaacccccc gttcagcccg accgctgcgc cttatccggt aactatcgtc   7260
ttgagtccaa cccggtaaga cacgacttat cgccactggc agcagccact ggtaacagga   7320
ttagcagagc gaggtatgta ggcggtgcta cagagttctt gaagtggtgg cctaactacg   7380
gctacactag aaggacagta tttggtatct gcgctctgct gaagccagtt accttcggaa   7440
aaagagttgg tagctcttga tccggcaaac aaaccaccgc tggtagcggt ggtttttttg   7500
tttgcaagca gcagattacg cgcagaaaaa aaggatctca agaagatcct ttgatctttt   7560
ctactgcaga agcttgttag acaccctgtc atgtatttta tattatttat ttcaccatac   7620
ggattaagtg aaacctaatg aaaatagtac tttcggagct ttaactttaa tgaaggtatg   7680
tttttttata gacatcgatg tctggtttaa caataggaaa aagtagctaa aactcccatg   7740
aattaaagaa ataacaaggt gtctaacaac ctgttattaa gaatgttaga aaagacttaa   7800
catttgtgtt gagtttttat agacattggt gtctagacat acggtagata aggtttgctc   7860
aaaaataaaa taaaaaaaga ttggactaaa aaacatttaa tttagtacaa tttaattagt   7920
tatttttttcg tctcaaattt tgctttgttg agcagaaatt tagataaaaa aatccccgtg   7980
atcagattac aatgtcgttc attgtacgat gtgtcgaaaa atctttacga cactctaaac   8040
tgaccacacg gggaaaaaag aaaactgaac taataacatc atgatactcg gaaaacctag   8100
caattctcaa cccctaaaca aaagaaactt ccaaaaccct gaccatataa aggagtggca   8160
acaatcagca atcagtcaag atttgatagc agaaaatctt gtatcggttg ctaatggttt   8220
tgatgtacta tttatcggca ataaataccg aactaacacg ggtgttctgt cacggcacat   8280
attaaactcc tattctcatt tagaagatgg tggttcgtat ggtagaacat ttgacccatt   8340
taccaataaa gaaatgcagt gggttcaatt taaaccgaat agaccaagaa aaggttctac   8400
tggtaaggta atcaaatatg aatcgccaaa aggtgaacct acaagagttc taatgccgtt   8460
tgtgcctatg aaaatatggc aacggattag cgataagttc ggagtaccga ttaatccgaa   8520
aaaagatact cacttttggg aatgggtaaa gaataatcca tcgataccga ttgccattac   8580
agaaggaaat aaaaaagcta attgcctatt atcctatggc tatcctgcta ttgcctttgt   8640
aggcatttgg aacggattag agaaaataaa tgatttctcg aaggaaaagc agttaaaaga   8700
ggatttgaaa tggttgttat ccaacggcaa ccgaaatatt aatatcatct ttgaccaaga   8760
ccagaaacaa aaaactgtaa ttaatgtaaa caaagctatt ttcgctttat cttctctaat   8820
aagtagaaat ggtcataaag ttaatattgt gcaatggttg ccgtcaaaag gtaaaggaat   8880
agatgattat ttggtagctt tacctttga gaaaagagaa aatcatttag acaacttaat   8940
taaaattgca ccatcattta atttttggtc aactaaatac ttattcaagt gtcgtaaacc   9000
agatttaacc gtaaattgcc gttatttgag cgatgcagta aaagaattac ctcaagagga   9060
tatagcatta atagcacctc acggcacggg taaaacttca ttagtagcta ctcacgttaa   9120
gaatcggagt tatcacggaa ggaaaactat ttcattggtg catcttgaaa gtttagccaa   9180
agctaatggc aacgcacttg gattatatta ccgaaccgaa aataatattg aaaagcaata   9240
tcttggattt agcttatgtg tagatagttg ccgtgataag attaacggca ttacaactga   9300
tattatttca ggtcaagatt attgcctttt cattgatgaa attgaccaag taattccaca   9360
catccttaac agtgaaactg aagtaagtaa gtatagatgc accatcattg acactttttc   9420
tgaactggtg agaaatgctg aacaggtcat tattgctgat gctgatttat ccgatgtgac   9480
```

```
gattgaccta atagaaaaca tcagaggtaa aaaactatat gtaatcaaga atgaatatca   9540
gtatcaggga atgactttta acgccgttgg ttcaccatta gaaatgatgg caatgatggg   9600
aaaatcggtg tcagaaggca agaaattatt tattaacacc acatcccaaa aggcaaaaag   9660
taagtacggc acaatcgctc ttgagtctta tatttttggt ctaaataaag aagcaaagat   9720
attaagaata gactctgaaa ccactaaaaa ccctgaacat ccagcctata aaatcattga   9780
ccaagactta aataatatcc tcaaagatta tgattatgtc attgcctcac cttgccttca   9840
aacaggtgtc agtattacct taaaagggca ttttgaccag caatttaact tttccagtgg   9900
aaacattaca cctcattgct ttttacagca aatgtggcgg ttgagggatg cagaaattga   9960
aagattctat tatgtgccga actcatctaa cctcaatctc attgggaata agtcaagttc  10020
accatcagac cttctaaaga gcaataacaa gatggcaacg gcaacggtta accttttggg  10080
tagaatcgac tccgaatatt ccctagagta tgaatcgcac ggcatttggc ttgagacgtg  10140
ggcaaaatta tcagcacggc ataacagttc aatgcgttgt tactctgaaa ttcttaccta  10200
tctaattacg tctcaagggc ataaattaaa tatcaacatt ccctcacctc ttgcagatat  10260
taagaagcta aatgatgagg taagtagtaa cagggaaaag gtaaaaaatg agagatactc  10320
tcagaggtta aactcaccag atattaacga tgcagaagct accatactcg aatctaaaga  10380
gcaaaaaatc ggattgactc tcaatgagag atgcacccta gaaaagcata aagttaagaa  10440
gcggtatggg aatgtaaaga tggatattct cacctttgat gatgatggac tataccccaa  10500
actcagacta ttttattacc tcaccatcgg taaacctcat ctcaaggcta atgacagaaa  10560
agctattgcc aaaatgggca atgacaataa aggcaagatt ctatcaaaag acttagttaa  10620
taaaacttac tccgctcgtg tgaaggtctt agagattctt aaactaactg actttatcga  10680
caatcttaga gatgaactct taataactcc caataatcca gctatcaccg attttaataa  10740
tcttctgcta agagctaaga aggatttaag agtattagga gtcaacatcg gaaaatatcc  10800
aatggccaac attaatgccg tacttactct cattggtcac aaactttctg taatgagaga  10860
tgagttcgga aaagagaaaa ggataaaagt agatggtaaa tcataccgat gttatcaact  10920
tgaaacatta ccagatttta ccaatgatac tcttgactac tggttagaaa atgatagcca  10980
aaaagaagta acagcaacag aaaattactc cgaaaatttt aacccttcaa atagctacaa  11040
tccagacagt aagacacttt cagagggtgc aaatttccta tatataaata aagaagaatt  11100
gcatccaaat aaattgcacc tagaaataaa agaaggtgct gaactttttt tattcggggt  11160
aaaggtgatt gtgaaaggaa tcttggacgg ggcagtaact atattctcta tgggtcaaga  11220
atacgattta tccctcaatg aactagaggg gatgttaaca tcatgaactt tacaagaatc  11280
tttttaaagg gcgatcgcac catgttaaat gatggtacat ttgttcagat atttgatatt  11340
taccatgacc acgcattggg agtgaccctt gaccttaaga cagaaaaaat tatttccgat  11400
gatgttaggg taattactgt caaagactta ttgttcgatg gcacttataa aggggtaaaa  11460
tcttttatgc ccgataatgc ccgataatgc ccgattgatg ctacaaaatc ccataatcat  11520
aagcgataat cccctaatag cttgtaattc ttgaaccgta gcgattttag agtattccaa  11580
aaagaagaaa taaacaccgc aaaatgtcgt atttcacata tataaaccaa ggtttttttgc  11640
cctaaaatct ttatgtttgt agtgtgatgt tgggtcaaaa tggtcagaaa agttgcaagg  11700
tttttatgga tgcttacgcg cgcgaggggt aagcatcccc aaatagttac tttatcctag  11760
tccatgccca tttattgccg tcccgttcgg ctttaaaaaa gtgccaaaac tcacaaggtg  11820
```

```
caataaaaag ttctgtacct ttcgcaaccc tagataatct ttcaacagtt actttttttc  11880
ctattatctc ggtacaaagt ttggctagtt tctcttttcc ctctttttca atcaagcctt  11940
cttgtatgcc caactcattg attaatctct ctatttttac cattatttcc cgttcaggta  12000
gtttatcccc taaatcttca tcgggggggca atgtagggca ttctgaaggg gctttttctt  12060
ctgtctggac attatctaat attgaagtaa ccaaactatc ttcagttttt tctattccta  12120
ttaattcata ttcggttact gtatccgtat caatatccga ataactatct ttatccgtat  12180
tagctattcg gttaagttta tccgttaact cagaaacaag actatatagc ggttttagct  12240
tttcttctat cctgttatct aatacggata agtttatacg gttatcatta tccgtattag  12300
tatcattggg ctttttggt agttctaccc cctcataaac cgcttttatt cccaattcca  12360
acagactgat aacagtatcc tttataatgg gtttttgct gatatggtga acttttgccc  12420
cttccatcat tgcgatactt tctatctcac tcatcaactt atcgcttaag tgaatctcgt  12480
atctgtttaa tcccttactg gttttattca tatccgttta ctttattcgg ttaacaattc  12540
tattttatac gaataaaata ttatacggtt aactttatac gtttaactat tttatctata  12600
cggataacag taataagtta ttcgtattag ttatacgttt acttttatcc aaataaaatt  12660
agtgcattta aactaaaaga atgattttat cggagttgat agcattggat taacctaaag  12720
atgtttataa gctatatctg ataagtattt aaggttattt tgttattctg tttattgaca  12780
ttatcagaat aaaagaatag aatataattg ttgagagata agaggtttaa gtgattatgg  12840
ttaagaagtt agttggttat gtcagggtca gtagtgaatc gcaagaggat aacactagct  12900
tacagaatca gatagagaga attgaagcat attgtatggc ttttggttat gagttggtaa  12960
aaatattcaa agaggttgcc actggtacaa aagcagatat tgaaacccgt cctattttta  13020
atgaagctat agaatacttg aaacaggata atgctaatgg aattattgcc ttgaagctag  13080
accgaatcgc acggaatgct ttagatgtat tgcgtttggt tcgtgaaacc ttagaaccac  13140
aaaataaaat gttagtgtta ctagatattc aggtagatac ttcgacacct tcaggaaaaa  13200
tgattttaac tgtaatgagt gccgttgctg aactcgaaag agacatgatc tatgatcgca  13260
ctcagggggg tagaaagact aaagcccaaa agggcgggta tgcctacggg aaacctaaat  13320
ttggctataa gactgaagaa aaggaactaa aagaagattc agcacaacag gaaactatta  13380
aactaattaa gagacaccgt aggtcaggga aaagctacca gaaaatagct gattatctca  13440
atgcccaaag tattcccact aaacaaggta agaaatggag ttctagcgtc gtctatcgaa  13500
tctgtcagga aaaagctggt taagtctgtt tatagatatt tagaatttat tgaataaaaa  13560
tagtatgaac aataaatatt tatggactaa ccacgctcgg aaacgtttaa ctgaacgatg  13620
ggaaataaaa gaatcatggg ttattgatac catcgaaaat cctgaacgtt cagaatttat  13680
tgttgatgag tcaggggaaa aatatcatta ctataaaaga atagctaagt ttaagaatag  13740
agtgttagaa gtgataactt ctgccaactc aacacccaca agaataataa ccttttactt  13800
taaccgtaac atgaggaaaa atttatgatt gttacttacg ataatgaagt tgacgcaatt  13860
tattttaagt taacggaaaa taaaattgat agcaccgaac ctcaaacaga caggattatc  13920
attgattacg atgaaagtaa taatattgtt ggcattgagg tattagattt taattatctt  13980
gtcaagaaag gtttaaccgt tgctgattta cctttttctg aagatgaaag attaacagct  14040
tctcaatatt ttaattttcc tgttgctatc taatccagaa ggggcaataa tccccttctt  14100
tcatcgagtt agacttaata tcacaaaagt cattttcatt ttaccgtttc ttttccacag  14160
cgtccgtacg cccctcgtta aatctcaaaa ccgacaattt atgatgttta taaaaagtta  14220
```

```
ctcactttaa taagtattta tactcattaa agggttattc tttttttgta gcctgatagg  14280

ttgggaagga atatttcaga ttatcagatt tgttgaatat ttttcgtcag atacgcaaac  14340

cttacaaaca taattaacaa ctgaaactat tgatatgtct aggttttagc tctatcacag  14400

gttggatctg                                                         14410
```

<210> SEQ ID NO 12
<211> LENGTH: 6173
<212> TYPE: DNA
<213> ORGANISM: Artificial sequence
<220> FEATURE:
<223> OTHER INFORMATION: Integrative construct p596, designed for the deletion (knockout) of the nitrate reductase gene narB (oriVT-narB_up-FRT-PcpcB-Gm**-TB0014-FRT-narB_down) from the cyanobacterium sp. ABICyano1 host cell chromosome.

<400> SEQUENCE: 12

```
tcgacttctg caggaagttc ctattctcta gaaagtatag gaacttctga gaaaaagtgt     60

aaacaaatat taagaaaaag atcagaaaaa tttaacaaca cgtaataaaa aaatgcgtca    120

ctacgggtta taaatttaca tgaaaggtta aaacactttt ctgagacgat tttgataaaa    180

aagttgtcaa aaaattaagt ttctttacaa atgcttaaca aaaacttggt tttaagcaca    240

aaataagaga gactaatttg cagaagtttt acaaggaaat cttgaagaaa aagatctaag    300

taaaacgact ctgtttaacc aaaatttaac aaatttaaca aaacaaacta aatctattag    360

gagattaact aaaaccatgg taagatcaag taacgacgta acccagcaag gtagtagacc    420

taaaacaaag ttgggaggct caagtatggg tatcattcgc acttgtaggt tagggcccga    480

tcaagtgaaa tctatgcgag ctgctttaga tctttttggt agagaatttg gtgatgttgc    540

aacttatagt caacatcaac cagattccga ctatttggga aatcttttac gttctaaaac    600

attcattgca ttagcagcat ttgatcagga agctgttgtc ggtgcattag ccgcttatgt    660

tttacccaag tttgaacaac ctcgttctga gatctatatc tacgatttag cggtatctgg    720

cgagcatcgt cgccaaggga tagcaacagc gttaatcaat ttgttaaagc atgaagctaa    780

tgctcttggt gcctatgtga tttacgttca agcggactat ggagatgatc ctgccgtagc    840

cttgtatacc aaacttggaa ttagagaaga agttatgcac tttgatattg atccttctac    900

tgctacttaa caattcgttc aagccgagtc acactggctc accttcggtg ggcctttctg    960

cgtttatata ctagagagag aatataaaaa gccagattat taatccggct tttttattat   1020

ttgaagttcc tattctctag aaagtatagg aacttcattt aaattacgta cacggcggcc   1080

gccttcagtt cggtttaaga atatccgata aggttaggtg tcaggtgtca ggttgcaggt   1140

tgcaggtgag agggggaagt cggggcttag ggttttaggg gggtaggggt gaatatattt   1200

aacgtcagtt cggattaaag caattttatc gttatttcta agaagctata aggttttctg   1260

actacgagaa aataatgctt tcagcttatc caaaactcaa gttaattaaa aaagggcaaa   1320

ggtaaatagt gttggggtga atagtgaata attaataatt aataacttct aactcttaac   1380

ccctaactcc taactcctaa ctcctaactc ctaactcatt tctccctctc tccctattcc   1440

cttatccccc aatcaggact taatttcccg taccaaagtt atactaaccc atcttccttg   1500

atcatcatat tgtctaatta aacgtaatct catattcgtt tctactaacc aaccaaattc   1560

aagaaagaaa ctttgacgat tttcaatttt tacaggagtg gtagaagatg caccatcggg   1620

caaaagcaaa actcgatttt ctttatttcc ctgattaaat gtaatgatgt tatcattgat   1680

agtgcctcca gaagaatagt tcataaaagg ggtttttagg gtttgtttga gagtgtttcc   1740
```

```
ttctcgtttt aaagttaatt gagtttgata tggttcacta ttacgccagt ctggatataa   1800
tgttagcgct tctcctcgcc attctccttc tagttgttca atggtaagat gctccctctc   1860
tattccttct cctccctccc gaaattctcg aataagagta acagagtcga aattactatc   1920
tttgtcaaac aattgtacta atctacaacg gcgatcgcgc cttacgtaac catattctgc   1980
cccgaaaacg gaaaaaggac taaactgttg agagcctttg gcaaaatgac catcttcaaa   2040
taaaaatata ttacgattca ggctactaaa ttcattgact acaggattag ggtttccatc   2100
tctagccaga gtaaatctaa tggttttacc atcatcacta ccgagagtta atttactgga   2160
agtctctttg agtaatttac cgtgaggaga aaactgactg aacgagccta accaaactcc   2220
tgagtttttt agtaaataag accactgtga ggaagacata agacgatatt ttaattaaat   2280
taactgagat tattttgtta taaaactacg aacatcaggc tataatatac tatcataaat   2340
attgctaaaa tttcccttaa ttgatactaa taaaattgtt agaatgaacc agtcaaaaga   2400
aatagataaa gagaatttag ttaaagaggt tgctaaaata aaatactggc atcattacat   2460
agattttggt gcaggggtag aaacaaaaac aggaaaagaa ggacgatttt gtaagaaatt   2520
tcaaaactgg attttaagtg gtattcctca agatttaaca ggaaaaactg ttttagatat   2580
tggtgcatgg gatggttttt attctttttc tgcggaaaaa aggggggcaa aaagagtttt   2640
agccacagat tcttttatct gggaacagag gcaattatat ggtttagatg ataatttttg   2700
gcgtgatttt ggagcgggaa aacagggttt tgaattagca agaaaaatgt ttaattccca   2760
agtagaggat tacaatattg atgttttaga tcttaatcct gaaaaaattg gtacttttga   2820
tgtggtattt tttttagggg ttttatatca catgaaatat cctctttatg ctttagaaaa   2880
agtaagaagt gttaccaaag agttgcttat tttagaaact catataagtt tatttttttag   2940
cttatttcct gtacctttaa tgcgctttta tcctactaat gaattaagta aagatgtaac   3000
aaattggact ggtgcaaata tcgctttggt taaatcatgg ttgttaaccg caggttttag   3060
taaagtggag ttagtcaaat ggcggatatc aatctagaat gacggtgaaa acctctgaca   3120
catgcagctc ccggagacgg tcacagcttg tctgtaagcg gatgccggga gcagacaagc   3180
ccgtcagggc gcgtcagcgg gtgttggcgg gtgtcggggc gcagccatga cccagtcacg   3240
tagcgatagc ggagtgtata ctggcttaac tatgcggcat cagagcagat tgtactgaga   3300
gtgcaccata tgcggtgtga aataccgcac agatgcgtaa ggagaaaata ccgcatcagg   3360
cgctcttccg cttcctcgct cactgactcg ctgcgctcgg tcgttcggct gcggcgagcg   3420
gtatcagctc actcaaaggc ggtaatacgg ttatccacag aatcagggga taacgcagga   3480
aagaacatgt gagcaaaagg ccagcaaaag gccaggaacc gtaaaaaggc cgcgttgctg   3540
gcgtttttcc ataggctccg cccccctgac gagcatcaca aaaatcgacg ctcaagtcag   3600
aggtggcgaa acccgacagg actataaaga taccaggcgt ttccccctgg aagctccctc   3660
gtgcgctctc ctgttccgac cctgccgctt accggatacc tgtccgcctt tctcccttcg   3720
ggaagcgtgg cgctttctca tagctcacgc tgtaggtatc tcagttcggt gtaggtcgtt   3780
cgctccaagc tgggctgtgt gcacgaaccc cccgttcagc ccgaccgctg cgccttatcc   3840
ggtaactatc gtcttgagtc caacccggta agacacgact tatcgccact ggcagcagcc   3900
actggtaaca ggattagcag agcgaggtat gtaggcggtg ctacagagtt cttgaagtgg   3960
tggcctaact acggctacac tagaaggaca gtatttggta tctgcgctct gctgaagcca   4020
gttaccttcg gaaaaagagt tggtagctct tgatccggca aacaaaccac cgctggtagc   4080
```

```
ggtggttttt ttgtttgcaa gcagcagatt acgcgcagaa aaaaaggatc tcaagaagat   4140
cctttgatct tttctaatgc atcattcgcc cgtacaagag ttaggagttt ttaattctta   4200
atttttccct tgcccttttt actttgcctt ttgcccattg ctctttgtat gacttgttgg   4260
agaagtctat tgataactca tggggtcaaa tagagatact atccaaccta attttatcgc   4320
ttctgagatg cgatcgaggg tttcttctcg actaaaacca aaatgggttt cttcctgaag   4380
aatagcagta acgcttaagt gtccattaca acttcttaac aaacgggctt catcttcgct   4440
aatagttctt atttccactt gattatcagg tttgcgccaa atcaaataag gctttctttc   4500
tcctgcaatg aggtgtctgg gttcaatggg gcatttatgg gctttggtga ggggaactaa   4560
gcaataacag gaaaagggaa tgcgagtacc atgttctaat ttggggcgat aaccatgaag   4620
ttttttttact cggagacggt gtaataattc ctttggatta ttttttctta aagtaggggc   4680
tgtttctgct cttcttagtc gccattcggt gagagcaaca tcaattaata gtcttgacca   4740
atcaatagtt tgttcttcta tagtaggtat caaaggctcg aaaaattctg gtttaactac   4800
ggtgagataa tccataaaac tattggcata gtctaaaacg gtgacattat cacaatgact   4860
atgaaggtaa aaatcatcga cgaagcgatc gaataattct gatcccataa tcgcttcaca   4920
ggcaggaaat atctcatgaa aaggtgcgat cgttctcgtt ctagccctat ttaagtataa   4980
gtctaaaacc tcttctgtgt ttctttgatg agcgggaata ataatacttt ctaaccaagg   5040
agaatttttg tctgttctca aacttttgag aaattgctgt tctagcttta aaagggtggg   5100
tgatttcatg aaattttagg aatattaacc aatgtaaaga agaatggata ttttatagac   5160
caagtttatc atatggattc gcaagaaaat aattaagcaa tgattaaaat cagggaaaat   5220
acggaaaaca atacctagat attttcggtt ttctctccct attaaataag aaggatatga   5280
caagataaaa ataacaattg aaaattaaat aaatatcaat tgaaacagaa tttgttagga   5340
ggtaaaagta tggctattgt tcgttttaat cctttgtatg aaattaatag cttacatcgt   5400
caaatgaatc gactactaga tgaaataact gcatgggatg atactcctaa ttcatttctc   5460
aaacctgcag tagaattgtt agataatgac aatagtttaa tgcttaaagt tttagtaccc   5520
ggaattgaca aaaaagatct tgatgtcagt gttacccgtg atagtgtgaa ggtaagtggt   5580
gaataccatc gtcaagaaga aaataaagat actggttact acatttctga gtttaattac   5640
ggtaaatttg aacgcacaat taatttacca ttaccgatca aaaatgacca agtaaaagca   5700
gaatataatg acggtgtctt aacgttaatt ttaccaaaac ttgaagacga gaaaaataag   5760
gtatttaaag ttagtttagg agcagaggaa aaaccagctt tagaatcaga aagtaatggc   5820
taatattgtt ctaaaaaagg tttaatgctt actaaataaa taattaattt gcctgtctca   5880
aaaagacagg ttttttttat gaaagtaata agaaataagt agaagtgagg agttggaaag   5940
ataggattaa gaattaggag ttaactattt tcattcttta ttcttccatt gcccattgag   6000
aaatcatatc taaaatcagc aacgccaaat tttagatgca aaataaccat aaataaaatg   6060
cagaaaaaag aatactttag atcttccgta tcagaagata catttcttaa caaaatctgg   6120
tgacaagatt aaacacacga aatccgaggt tttatatatt gattagtcct agg          6173
```

<210> SEQ ID NO 13
<211> LENGTH: 6162
<212> TYPE: DNA
<213> ORGANISM: Artificial sequence
<220> FEATURE:
<223> OTHER INFORMATION: Synthetic plasmid no. 1872; Integrative construct (oriVT-nirA_up-FRT-PcpcB-Gm**-TB0014-FRT-nirA_down) designed for the deletion (knockout) of the nitrite reductase gene nirA from the cyanobacterium sp. ABICyano1 host cell chromosome.

<400> SEQUENCE: 13

```
tcgacttctg caggaagttc ctattctcta gaaagtatag gaacttctga gaaaaagtgt     60
aaacaaatat taagaaaaag atcagaaaaa tttaacaaca cgtaataaaa aaatgcgtca    120
ctacgggtta taaatttaca tgaaaggtta aaacactttt ctgagacgat tttgataaaa    180
aagttgtcaa aaaattaagt ttctttacaa atgcttaaca aaaacttggt tttaagcaca    240
aaataagaga gactaatttg cagaagtttt acaaggaaat cttgaagaaa aagatctaag    300
taaaacgact ctgtttaacc aaaatttaac aaatttaaca aaacaaacta aatctattag    360
gagattaact aaaaccatgg taagatcaag taacgacgta acccagcaag gtagtagacc    420
taaaacaaag ttgggaggct caagtatggg tatcattcgc acttgtaggt tagggcccga    480
tcaagtgaaa tctatgcgag ctgctttaga tctttttggt agagaatttg gtgatgttgc    540
aacttatagt caacatcaac cagattccga ctatttggga aatcttttac gttctaaaac    600
attcattgca ttagcagcat ttgatcagga agctgttgtc ggtgcattag ccgcttatgt    660
tttacccaag tttgaacaac ctcgttctga gatctatatc tacgatttag cggtatctgg    720
cgagcatcgt cgccaaggga tagcaacagc gttaatcaat ttgttaaagc atgaagctaa    780
tgctcttggt gcctatgtga tttacgttca agcggactat ggagatgatc ctgccgtagc    840
cttgtatacc aaacttggaa ttagagaaga agttatgcac tttgatattg atccttctac    900
tgctacttaa caattcgttc aagccgagtc acactggctc accttcggtg ggcctttctg    960
cgtttatata ctagagagag aatataaaaa gccagattat taatccggct tttttattat   1020
ttgaagttcc tattctctag aaagtatagg aacttcattt aaattacgta cacggcggcc   1080
gcaatttgtc ctcggttaat atattgaata caaataaata tttaaagact tatatactta   1140
actgcccaat acattattaa tttgattctt aatattttgt aactttgact actaaataaa   1200
gacacatttt ctttttacac ataattttaa ttcgtttttt gcatctatca gggatgaagg   1260
cttaggaatt cggagagttc gctacgctcg ttccgcaaag cagtacggag ttagttagga   1320
gcaaatggcc attcgcccgt acaggaagaa gttattaatt atcgactatt tacctttgcc   1380
ttttgcctat tccctgcctt aaccagaaaa ttttagaatg aatcagccct gcctagcttt   1440
gccccttatt ctgcattagt gagataatgg gattaagaga aagttttgtt ataaaatatc   1500
atggatcttg caaacttaag aaacgaatat accctcaatg gtttacaaag aaaacaacta   1560
caagaagatc cttttaaaca atttgaatta tggtttcaac aagcctgtga tgctaatttg   1620
cccgaaccta atgctatgaa tttagcaact gtttccccag aaggacaacc aacgcaaaga   1680
attgtcctgt taaaatattt cgatagaagg ggatttgttt tttttaccaa ctatggaagt   1740
aggaaagccc ttcaaattaa tggtaataat cgagtttctc tattgttttt ttggataggt   1800
ttacagcgtc aagtacaaat ttgtggcagt gctgataaaa tttccactat ggaatcactg   1860
aaatacttta caactcgtcc tcgtggcagt caaattggtg catggtgttc tcaacaaagt   1920
agtataattt cttctcgaaa aatattggag ttacagtttg aggaaattaa acagaaattt   1980
cataatcaag aaattcccct tccagcttct tggggaggtt atcgggtagt gccgaatagt   2040
tttgagtttt ggcaaggacg agaaaataga cttcacgatc gcttctacta cactaaatta   2100
gataataatg attgggaaat taggagatta gccccataaa ttttgatttt tactgccatt   2160
gtttgttttt taattatttt cctcgtgaat ttatccatgt cttaactatc tattaacttt   2220
tacttaatat cttctggtta ctctataggg tgatctacct tgcaaaaatt aaggttttga   2280
```

```
taaatcctca gtaccaagat taaggatatt tatgacaatt aatctaaatt tgataggaac   2340
ttatgctaca ggacagtttg atgagggtgc ggcggaaatc ccagcgtttg atccctctac   2400
taaccgttta tttgtagtca attctcaagc tgtaaccgtt gatgttttag atctttccga   2460
ccctaataac cccgttaaaa tcggggaaat agacgcttca gctttaggag gagtcgcaaa   2520
cagtgttgcc gttaaaaatg gtatagttgc gatcgcgatc gaggctaata taaaaaccga   2580
caacggtagt gttgctttct ttaatagcga tagtgatttc agtaaccctg ttaatcccgt   2640
taatactgta accgttgggg cattacctga catggtaaca ttcaccccag acggaatgaa   2700
agtattaacc gctaatgagg gtgaggctaa tgatgattat agcgttgacc ctgaaggttc   2760
aattagtatt attgatataa gcacaggagt ggaaaatgct tctgttacca atgctaattt   2820
taatgctttc gacagtcaaa aagatgcttt agtcgcacag ggagtacgca tttttggttt   2880
aaatgccagt gtttctcaag atttagaacc tgaatatatt gctttttctg ctgactctca   2940
aactgcatac gtcacactac aagaaaataa tgctttagca gttgtagatg ttaccactgg   3000
tactgtttct ggtattgtac ctttaggatt caaaaactat aatgcttcac ccaatttaga   3060
aacagcattt tttgaagaat cagatatcaa tctagaatga cggtgaaaac ctctgacaca   3120
tgcagctccc ggagacggtc acagcttgtc tgtaagcgga tgccgggagc agacaagccc   3180
gtcagggcgc gtcagcgggt gttggcgggt gtcggggcgc agccatgacc cagtcacgta   3240
gcgatagcgg agtgtatact ggcttaacta tgcggcatca gagcagattg tactgagagt   3300
gcaccatatg cggtgtgaaa taccgcacag atgcgtaagg agaaaatacc gcatcaggcg   3360
ctcttccgct tcctcgctca ctgactcgct gcgctcggtc gttcggctgc ggcgagcggt   3420
atcagctcac tcaaaggcgg taatacggtt atccacagaa tcaggggata acgcaggaaa   3480
gaacatgtga gcaaaaggcc agcaaaaggc caggaaccgt aaaaaggccg cgttgctggc   3540
gtttttccat aggctccgcc cccctgacga gcatcacaaa aatcgacgct caagtcagag   3600
gtggcgaaac ccgacaggac tataaagata ccaggcgttt ccccctggaa gctccctcgt   3660
gcgctctcct gttccgaccc tgccgcttac cggatacctg tccgcctttc tcccttcggg   3720
aagcgtggcg ctttctcata gctcacgctg taggtatctc agttcggtgt aggtcgttcg   3780
ctccaagctg ggctgtgtgc acgaaccccc cgttcagccc gaccgctgcg ccttatccgg   3840
taactatcgt cttgagtcca acccggtaag acacgactta tcgccactgg cagcagccac   3900
tggtaacagg attagcagag cgaggtatgt aggcggtgct acagagttct tgaagtggtg   3960
gcctaactac ggctacacta gaaggacagt atttggtatc tgcgctctgc tgaagccagt   4020
taccttcgga aaaagagttg gtagctcttg atccggcaaa caaaccaccg ctggtagcgg   4080
tggttttttt gtttgcaagc agcagattac gcgcagaaaa aaaggatctc aagaagatcc   4140
tttgatcttt tctaatgcat gtaatgacca tgtttgtaat aagtctggcc cgtgtaattc   4200
tcccgttaaa ccaacacgaa gcgatcgcat cactaaacct tttttaacat ttaaatcctt   4260
agttatttgt ttaataataa cattagcaga gtcaatggtt aaatcctcat ttaaactatc   4320
aataacttgc tctaaaactt cttttactcc aacagaatga ataaattctt gagcttctga   4380
ggataaagaa aaatcattat taaaaaacaa ttgggcttct tttacagcat cagttaaacg   4440
agttaaacta ggggcaatta aagcggtaat ttctaataac caatctttat cagtatcaag   4500
attaaattga taaccagcct cttgccaata agaagttatt aaaggtaata aatcctccgc   4560
aggcatttga tgaagatatt gactattaat ccaatcgagt ttatcccaat caaactttgc   4620
```

```
ccccgcctta ttcactcttt ctaaactaaa cttagtcgcc gcttcatcaa gggtaaaaat   4680
ttcctctcca tctggggaag tccatcccaa taaagtcata taattagcaa tagcaggagc   4740
gacaaaaccc attttccgaa aatcatcaat ggaagtaacc ccatctcgtt tggacagttt   4800
tttcccttca gaattcaaaa ttaagggagt atgagcaaat tctgggactt ttccctctag   4860
ggcttgatat aacaaaatct gttttgctgt attggcaata tgatcttctc ctcgaattac   4920
gtgggtaata ttcatgtcta tatcatccac cactaccgct aaattataca acggttgtcc   4980
gaagcgatcg ccctcttttt caggcattcg ggcaataacc atatcccccc ctaaatcact   5040
accctgccac gttacagagc ctctgattaa gtctttccag acaatttgtt gagaatcatc   5100
aattttaaat ctaatcacag gtttacgccc ttgggcttca aattctgcaa tttcttcagg   5160
ggttaaattg cggtgacgat tatcataacg aggggcttga ttattagctt tttgttgctc   5220
tctcattgcc tctaattctt cgggagtgca ataacaggga taagccaatc ctttattcaa   5280
cagagtttga atagcttgac gatataagtc taatctttct gtttgaaaaa aaggaccttc   5340
gtcccaattt agtcctaacc attgtaagcc cgatttaata ttttcagtat attcagcctt   5400
agagcgttct aaatccgtat cttctactct taggataaac gaaccttgat agcgatgggc   5460
aaataaccaa ttaaaaactg ctgtgcgtgc tgtgccgata tgtaaattac ctgtgggaga   5520
tggtgcaatt ctaactctaa cggacataaa atttaacaat cataaatatt tcttgcagtc   5580
ttctattcta tcgaaatcac tgtgttgggg agtagagatg aggtgatgag gagaggggta   5640
agagcattcg ccagaattta aataaatgag caaaagtcaa taccttgcca ataaaactta   5700
ataaatagct caaaacttta tgaatgcgac tatttgaatt agcactaaaa ccactatata   5760
tttggtttcg atgtaattct atcccacgcc ctccaagctg atttcctgcc gaaaaacttg   5820
cttccctaga aaaaatctcg atcacgaagt ggcgctgcgc gatcgcatct cttgtaatat   5880
tagtagaaat atccccatct acggtcagtt gttatagacc taaattcaat tattaagtta   5940
agcaaaaaaa tagtcttttt ttatctcttt ttaagattac ttgtaaaaaa atggctctat   6000
aactttgagt atgtaaatta ttagtgtttg gtaggcaaga ggcaagaggc aataggcaaa   6060
cccctctgtg tctcccctta aaaggggaga agagcaatag gagattatta gataataatt   6120
tagacaaata gttactaatt ttatatcgag ttcaagggaa ag                       6162
```

<210> SEQ ID NO 14
<211> LENGTH: 8167
<212> TYPE: DNA
<213> ORGANISM: Artificial sequence
<220> FEATURE:
<223> OTHER INFORMATION: Synthetic plasmid no. 2198; Integrative construct (oriVT-ureC_up-FRT-PcpcB-Gm**-TB0014-FRT-ureC_down) designed for the deletion (knockout) of the the urease gene ureC from the cyanobacterium sp. ABICyano1 host cell chromosome.

<400> SEQUENCE: 14

```
tcgacttctg caggaagttc ctattctcta gaaagtatag gaacttctga gaaaaagtgt     60
aaacaaatat taagaaaaag atcagaaaaa tttaacaaca cgtaataaaa aaatgcgtca    120
ctacgggtta taaatttaca tgaaaggtta aaacactttt ctgagacgat tttgataaaa    180
aagttgtcaa aaaattaagt ttctttacaa atgcttaaca aaaacttggt tttaagcaca    240
aaataagaga gactaatttg cagaagtttt acaaggaaat cttgaagaaa aagatctaag    300
taaaacgact ctgtttaacc aaaatttaac aaatttaaca aaacaaacta aatctattag    360
gagattaact aaaaccatgg taagatcaag taacgacgta acccagcaag gtagtagacc    420
```

```
taaaacaaag ttgggaggct caagtatggg tatcattcgc acttgtaggt tagggcccga    480
tcaagtgaaa tctatgcgag ctgctttaga tctttttggt agagaatttg gtgatgttgc    540
aacttatagt caacatcaac cagattccga ctatttggga aatcttttac gttctaaaac    600
attcattgca ttagcagcat ttgatcagga agctgttgtc ggtgcattag ccgcttatgt    660
tttacccaag tttgaacaac ctcgttctga gatctatatc tacgatttag cggtatctgg    720
cgagcatcgt cgccaaggga tagcaacagc gttaatcaat ttgttaaagc atgaagctaa    780
tgctcttggt gcctatgtga tttacgttca agcggactat ggagatgatc ctgccgtagc    840
cttgtatacc aaacttggaa ttagagaaga agttatgcac tttgatattg atccttctac    900
tgctacttaa caattcgttc aagccgagtc acactggctc accttcggtg ggcctttctg    960
cgtttatata ctagagagag aatataaaaa gccagattat taatccggct tttttattat   1020
ttgaagttcc tattctctag aaagtatagg aacttcattt aaattacgta cacggcggcc   1080
gcccataatc gcaaggggca aacccctctg tgtctcccct taaaagggga gaagggtaat   1140
aggcaatggg aataaaaaat tagcaattag caactccgaa cttcgaactc tatctgctta   1200
tcctacataa tttattagta aaaatcatga tcactataac agaaaatact aataataatc   1260
ccgaaaattt agataataat aaagtagttg aaattaaaaa cttagacttt tattttggtc   1320
atggtagtat cagaaagcaa atattattta atattaattt aactctaaaa aaaggagaag   1380
ttgttatctt aaaaggtcct tcaggctcag gaaaaacaac tcttttaacc ctcatggggg   1440
ctttacgcag tgctagttat ggctctttga aagtatttaa tcaagaattg ataaatgctc   1500
ctgaaaaact gcttattaat attagaaaaa atattggtta tatcttccaa gctcataatt   1560
tattaaactc tctcaccgcc cgacaaaatg tacaaatgtc tttagagttg catcctcaat   1620
ttagccatga agaagtaaaa caaaaatcaa tcgaaatgtt gaatgctgtt ggtttaggag   1680
atcgtattaa ctactatcct gaaaatcttt ctggtggtca aaaacaaaga gttgcgatcg   1740
cacgtgcttt agtctctcat ccaaaaatgg tactagcaga tgaacccact gccgctttag   1800
acagtaaatc agggcgagat gtggtggaca ttatgcaaaa gttggctaga cagcaaggct   1860
gtactattct catcgttagc catgatgatc gcattttgga tgtagcagat cgtattattg   1920
aattagaaga tggaaaacta ttgacagaat cccaagtgta acgactagga ctatattttt   1980
gaaaaataaa aaacttctcc taaaaagggg acccccccag gagggggggg gaattaggaa   2040
ttaggaatat atattattat taaacaaaaa tttattgttg tcaataatta cagaggattt   2100
taccttttat ttccttttcc aaccagtaag tattataaga aagagatttt agttgactcg   2160
gagttatttg ccatggctgt tggggggcaa aaacgataaa ctctgccctt tgtccaactt   2220
gtatttttaa tggttcttgg tatagacatt ttaaagcatt aacacttaag gctttccata   2280
attgtgaagc ggataattca ccagtaatca caagattttg ccatagtaaa ggtaaagcta   2340
attctaagcc aattgagcct gatggagcat ctgcaaaggc aacggttttt tcttcgtaag   2400
tataaggagt atgattaata gaaatagcat caatcacgcc tgtttttatc ccttccaata   2460
agcccaaacg atcgatttca gtacccaagg ggggatcaaa acgtaaatga ggattataac   2520
tagcaatggt ttcaatattg aggataagat gatgccaatt aacactccca gtaacaggta   2580
attgttcttc ttttgccctt ttaattaaat ccacgcccct agctgtcgaa atattcatta   2640
agtgaatggg ggtttttgtt aatgccacta tttccaacaa agaagcaata gcaaccgttt   2700
ccgctatctc tggatttccg attaaaccaa gacgaatgga agtgcgacac tctctaacta   2760
ccccttttcc ttttaattgt agatttgtag gacaaagggc aataggtaaa tgaaaaggtt   2820
```

```
gagcatattc taataactta cgtactaact gtaaattgct atggggacga ttatctgtaa   2880
aaccaactac tcctgattct gctaaatctg ctaactcggc aatggtattg ccctctaaat   2940
ttttggttaa actaccccaa caatcaaagt ttgtttctag ggatttagtt ttattttgaa   3000
tccatgtcac catattggga ttatctacaa ctggcaaagt attgggtaaa atcgccaccc   3060
ttgacactcc ccctgctttt gcagaagcat taagggtttg tagagtttct ctttcttcgt   3120
atcccggttc accactatga caaaataaat ctactagggc aggggctaat attaagccat   3180
taccatcaat tattttcgct gaatcgtctg ttaattcaat ctttgggctg atttcttgaa   3240
tcttattatc atcaattaag atgtcagtta cttggtcaaa tccagataca ggatctaaag   3300
ttctaatttg ttgaaaaagc agtgtttgat tcaccttggt tcctatttac aactcaataa   3360
cggtgaaaaa gtatctacct ttaatcggtt aaactttttcc atgcctgagt tactatttta   3420
ctcaaccatc gtctttgtac ttgatctaat atttgatctt ctgccaatac ttctttgatt   3480
aggtcttcta aagattttcc ttcataatgg gtttttttcta ctaaagatgc gatcgcctct   3540
gcgactattt ctgcggacac tttttcgcta caaggataat cgagctgatt ggagtcacaa   3600
gttaaacaag aaatcatatt ttttaccccc ctcgattttt attaacaatt gtaaacactt   3660
tttcattttt taggatgttc agaagtttaa cccattcaaa aacaaaaagg gtgataaata   3720
ctgtttttct taacatttca ctttacatag tatgcaaatc tcgatttcac aaattgataa   3780
aacctcataa aaattctcag gtaaattttt gtaaaaagtt atctattttg taaaatttta   3840
tacagaaata tgcttaaata gagttaagaa agtaaaggag agaagaaaat gagtgcagaa   3900
agtcaagccc gtagtttaat gatgcgtcat cataaattta tcaaaaatcg tcaacagtca   3960
atgttaggac gcaccgcttc agaaattggg atggatataa acggttcaga atactggaat   4020
cctgttcagg gaaaacctaa ttctagtttc cgtgttagtt atgatcgctc ccatgcttct   4080
ttaagttaga tatcaatcta gaatgacggt gaaaacctct gacacatgca gctcccggag   4140
acggtcacag cttgtctgta agcggatgcc gggagcagac aagcccgtca gggcgcgtca   4200
gcgggtgttg gcgggtgtcg gggcgcagcc atgacccagt cacgtagcga tagcggagtg   4260
tatactggct taactatgcg gcatcagagc agattgtact gagagtgcac catatgcggt   4320
gtgaaatacc gcacagatgc gtaaggagaa aataccgcat caggcgctct tccgcttcct   4380
cgctcactga ctcgctgcgc tcggtcgttc ggctgcggcg agcggtatca gctcactcaa   4440
aggcggtaat acggttatcc acagaatcag gggataacgc aggaaagaac atgtgagcaa   4500
aaggccagca aaaggccagg aaccgtaaaa aggccgcgtt gctggcgttt ttccataggc   4560
tccgcccccc tgacgagcat cacaaaaatc gacgctcaag tcagaggtgg cgaaacccga   4620
caggactata aagataccag gcgtttcccc ctggaagctc cctcgtgcgc tctcctgttc   4680
cgaccctgcc gcttaccgga tacctgtccg cctttctccc ttcgggaagc gtggcgcttt   4740
ctcatagctc acgctgtagg tatctcagtt cggtgtaggt cgttcgctcc aagctgggct   4800
gtgtgcacga accccccgtt cagcccgacc gctgcgcctt atccggtaac tatcgtcttg   4860
agtccaaccc ggtaagacac gacttatcgc cactggcagc agccactggt aacaggatta   4920
gcagagcgag gtatgtaggc ggtgctacag agttcttgaa gtggtggcct aactacggct   4980
acactagaag gacagtattt ggtatctgcg ctctgctgaa gccagttacc ttcggaaaaa   5040
gagttggtag ctcttgatcc ggcaaacaaa ccaccgctgg tagcggtggt ttttttgttt   5100
gcaagcagca gattacgcgc agaaaaaaag gatctcaaga agatcctttg atcttttcta   5160
```

-continued

```
atgcataggc aagtcttaac cgttttaatc atttttaata ggaattagca attagtaatt   5220
aattaaaacc tgccacctga cacctaacac ttgaaaccca cctaaaccaa tattcttaaa   5280
acattgacgg aaagataaat taaggcttag tattaacaga aatcggacca ttaaccagag   5340
tttgacaggc taaacggtaa ttttttggtt ttttctttaa ctttctggtc tcaaagtctg   5400
tttttggaga taaatttcc atgccttcga caatttctac cacacaagta gcacattgac    5460
cataaccacc acaattgatc aacttaccac gccatttata tatatcaata ttattctgca   5520
aagcctttc tctaagattg gcaccatcgg cggcaactac ttccttattt tctttaataa    5580
atttaatcgt cggcattttt ttctcctcct atactgttaa gttttatatc acaatataaa   5640
gaaattttaa acaatagact tgtttatata taattgaaac caataagtcg ccttaaattt   5700
tctattgaat tacttgaaga tggtttaaaa ttattcaata ttagctatcc acaacccaaa   5760
atcaatactg attatggtca ttaataattc cagttctttt cgtcgctata cgccccctac   5820
ctgtactctt gaaatttata atcctcaacc tttttgggga aaatggcgtt atcaatcttt   5880
tcctcaatac tttagtttc aactacactt cgatgatcct agaataccaa aagataatag    5940
aagtagtata ataggcgatc gcactttact ggaaaaatta agacaattag tagatgaata   6000
tataaactta tacttggatg atagacaaat agttagagat aatcaaactt gtgatatacc   6060
tcaagatgaa cacacagagt ttatttgttt aagtagagaa tcagattata gccataaact   6120
ttattatcac ggtatagaac cacagagaga aacagtagaa gttatcctga caaataccca   6180
attatttgac ctgattaacg ccctagaagc ctattactat gacgtaacca agagcaatca   6240
agaattagga gaagcgattt cgagtaactt aggattaagt atttttatta cagcccttgt   6300
atgtatcatt ggcggttggt tttggtggcg ttatgaacaa aatttagcac tacaacaaaa   6360
tccgatagat aatcaatctc aatcatcaga agcagaagaa tttgatgatg acatagaaaa   6420
agttattcct ccttctcctc tcgatccaca aagtcttcca tcaatagtaa ccccagaagt   6480
accagaagaa ctaagaaaca gagaatctct cccacctcca gaatcaacca taactcgccc   6540
ccccgacaat aaccctacgg cagaaattcc ccaaaatttt cctgaaaata atagtcaggc   6600
aactctaact atggaaacgc ctccccctcc ttcagttaat gatttgcccc catcaaccgt   6660
aaataataat tctcagggaa tgaatagtca accttctttg tctcagacga tttcattaca   6720
accatcctct tccaactcga atacgattcc ttcatctcct cccaaactta acaaattacc   6780
tgttttatca tcttctaatt cctctgtacc aaaccttaat tcctttacct ctgaagacgt   6840
ttctccttcc caatttgcat taaacaatat aaataaaaca aatgatataa cacctcctat   6900
cgtgatcaaa aatccgactc taccagaaaa tatcaataat ttagacacat ctaagttagt   6960
ggcgaaaaaa cttcccccca ccagtgcaga agtcgaagtt aaacaatact ttatttccca   7020
atggcaaccc cctgaaaatt tacagcagag tattgaatat aggttacaaa tcaattcaga   7080
aggacaatta acaaaagtga ctcctatagg acaagttgca attatttatt tagaccgtac   7140
taatatgcct ttattaggaa aaaaaatagc gtcttcatta gaagaagatt ctcaagcaac   7200
aattcgctta attcttagtc caaatggtaa cgtacaaact tttaaagagt aaagtgaata   7260
tgttacggtt tgttgaaaac gtttttagat gaacgtgaat tcggatttca acctaagttc   7320
gagctaaaat tgtaggttaa gttagctaac aggcaacagt gcttttaatt gatataaaat   7380
gagtctaaat tgattttaaa taaatttttc ctaaatttaa cgattttctc tcatctttat   7440
gaaacatatt tttattactg gtgtaagtag tggattaggt gcttacctaa ccaagaaatt   7500
ggttgaagta ggagattttc aaattacagg gatttctcgc aacaagccag tttatttaac   7560
```

```
ttctgaatat ccgattcaat ggcaaaagtt tgatttaaat caaacagaaa aaattaattc   7620

aactatttcc aagattttaa ataaccaaat tatggatgcc ctaattctca atgttggtat   7680

atgggaaaaa acagctttca gtccagatta tagttttgaa gaaatagaat atggggagat   7740

ttatcaatta atacaagtaa acataactgc caatatagaa ttaattcgct ctattttaaa   7800

acaaggtttc ctgaaaaaag gggtaaaat aatctttata ggatcaactt ggggtcttga   7860

aaatcatggg ggaaaagaag ttgtttttc agccacaaaa tttgccttaa gaggtatggt   7920

tcattccttg agagaaattc taaaacatca aatgataagt cctagtgttc ttaatttagg   7980

ttatctatcg gagagtgaat acccccaacc acaagaaact caaattcctt taattgacgt   8040

atgggaagca attaaatttt tattatccac ttccccctat tcgtgtgtaa aagagattga   8100

tatgcccgga atgtttgatt ctaattgttg agtttttat tataggataa aaaaatggca   8160

atcaatg                                                             8167
```

<210> SEQ ID NO 15
<211> LENGTH: 8201
<212> TYPE: DNA
<213> ORGANISM: Artificial sequence
<220> FEATURE:
<223> OTHER INFORMATION: Synthetic plasmid no. 2235; Integrative construct (oriVT-cobK_up-FRT-PcpcB-Gm**-TB0014-FRT-cobK_down) designed for the deletion (knockout) of the the vitamin B12 gene cobK from the cyanobacterium sp. ABICyano1 host cell chromosome.

<400> SEQUENCE: 15

```
tgagaaaaag tgtaaacaaa tattaagaaa aagatcagaa aaatttaaca acacgtaata     60

aaaaaatgcg tcactacggg ttataaattt acatgaaagg ttaaaacact tttctgagac    120

gattttgata aaaaagttgt caaaaaatta agtttcttta caaatgctta acaaaaactt    180

ggttttaagc acaaaataag agagactaat ttgcagaagt tttacaagga aatcttgaag    240

aaaaagatct aagtaaaacg actctgttta accaaaattt aacaaattta acaaaacaaa    300

ctaaatctat taggagatta actaaaacca tggtaagatc aagtaacgac gtaacccagc    360

aaggtagtag acctaaaaca aagttgggag gctcaagtat gggtatcatt cgcacttgta    420

ggttagggcc cgatcaagtg aaatctatgc gagctgcttt agatcttttt ggtagagaat    480

ttggtgatgt tgcaacttat agtcaacatc aaccagattc cgactatttg ggaaatcttt    540

tacgttctaa aacattcatt gcattagcag catttgatca ggaagctgtt gtcggtgcat    600

tagccgctta tgttttaccc aagtttgaac aacctcgttc tgagatctat atctacgatt    660

tagcggtatc tggcgagcat cgtcgccaag ggatagcaac agcgttaatc aatttgttaa    720

agcatgaagc taatgctctt ggtgcctatg tgatttacgt tcaagcggac tatggagatg    780

atcctgccgt agccttgtat accaaacttg gaattagaga agaagttatg cactttgata    840

ttgatccttc tactgctact taacaattcg ttcaagccga gtcacactgg ctcaccttcg    900

gtgggccttt ctgcgtttat atactagaga gagaatataa aaagccagat tattaatccg    960

gctttttat tatttgaagt tcctattctc tagaaagtat aggaacttca tttaaattac   1020

gtacacggcg gccgctaaat ctgttgagga tgtcaaggag tttttaaaga atttttgaga   1080

aaatctgtta gtaatctaat tttgttcgat agatgtcgat tgataggata aagtgcgaat   1140

aaacttaggg ttttaggaga gtaatcgggt aggattcttc ttaatttccc ttcttgaaga   1200

taagattcga taataaatct tggtaatatt gttataccta aatctgcgat cgcacctttt   1260

gcgagaattt ccccattatt agaacataat cgacttttaa ttttgacgat tttttcttca   1320
```

tctccttttg ttaatctcca taggtgaggg gaattaaaat aaccatattg taaacaaaaa 1380
tgattctcta attcttcagg ggaatttggt tcaccataat tttggatata tccttccgaa 1440
gcacataaaa ttaactcaat ctcagctaat tgatgaacta ttaagctaga ggactctatt 1500
ttatcggtaa ttctaattac catatcataa ccttcggcaa tgggatcaac aaaacgatca 1560
tctaaactaa gttccacttt taagagagga tattctgcca taaaagatgc gatcgtatct 1620
cctaaattaa ttgtgccaaa agtcatggga gcattaatcc tcaatttacc ttgaggacgt 1680
tgctgtaaat tagtaaccgc tatttccgct tcctctaaat ccgctaaaat tcccgtgcaa 1740
cgttcataaa aagctaaacc cgtttgagta ggagtgacat tacgagtatt gcggtgtaat 1800
aactgcaccc ctaaataagt ttccaaatta aaaaccaact tattcactgc cgaacgagat 1860
atacccaaaa tgcgagaagc ctgagcaaaa ctacccgact ccaccactaa cacaaaacct 1920
ctaatctgat taaatttatc catttgtcaa cttttattca acaatcagtt aaatataata 1980
tacattgtca accaaaaaat agagaagtat catagaagat aagaactgta gtttagacta 2040
agaaaaaatt gcaagacaat caataagcta acaaaaatta gcttacggag aaaataaatt 2100
gagttaacta ttccttcaaa gttaggtttt tcgccttttt ttacttttgg attgctgttt 2160
tttaatggtg ggataaactt tagctttgtt tctttttcgc ccttgaggcc agccatggga 2220
ttttccccga cttttaggag aaagggtagg acttccaatc tctatcaata atgaagtcat 2280
agatagagca acccttccag gagttaaatt ctgttgtggt ttttgccacg gcaaatggtg 2340
ttcttggact aaatcctttg agagccataa ttgccaagtg atattgacga ttaaattact 2400
ccatctttga cacctgtcag gagtgcgaaa atttggcaaa gtccaatgca acctctgctt 2460
ggcaaaacga taccagtgtt ctaatccaaa ccttcgctta tattgactcc aaatatactc 2520
caaagataaa aattcctctc ctacccagat taaccaaagt ggacgatgta aactccctgt 2580
ttttttctcc tttaatcttt caattttgaa taaagttaat tgttgtgtgg gggcattata 2640
gaaatgaagt tccgtccatt tactgatgcg tatgagtcct agggatgaat cttccatttc 2700
caatacttta ttactctgag gaaaatcatc acattgattt aacttccact ttgctccatg 2760
ttttttcggt cttcctctac cgctataagg gtctggcttg ctataaaggc ataaattaga 2820
acgtactcga atcaacttac ttatctcaat gtccgccgtc tgttggataa atttgccatt 2880
gccatattca caatctaaga ccactaattt ccgtctattt tctggcaatt ctcgacacac 2940
ttgtttgagt tgccatcggg ctttacttaa aggagtttca aaggatgtta ttctttcatg 3000
tcttaaaggt aatgcccaac ttcctttctc ttttaatggt ggtaaccatg ctatggtgct 3060
atatccttgt cctactactg atgaatttag ggatgaatga gaatattgat aacctctatc 3120
tttcatcgtg ggactatctt tacattccca ctgggtatga tctatgccta ataacgtata 3180
ttctaaagtg tctatttctt gagtgtatcg tttcatcaat ttgttgccat tgggacgact 3240
atcctctatc gcttcatagg tgctacacca ttgcctctgg aaaaaaggcg ataaagaaaa 3300
ttctgccaaa ctacgagcat ttctctggt catgatgctg tccattagct caaatgtggc 3360
atctttactt ttgactaaca tttcataggt atcatgacga aaattttta gtctgttata 3420 tttgttcatg tagagagatt ttaatttgtg attattttat tttctctcta tttttctttt 3480
ttgtcttgtc cttcctcatt tttctctaca tttagtctaa actacagtaa gaaaacaaat 3540
gggaaaaaac gattaaaacc atgattacta ttcgcccaag tgaagaaaga ggaaaagcca 3600
atttaggatg gcttgacagt aaacatactt tttcttttgg tagttactat gatcctaatt 3660

-continued acatgggttt tgccagttta cgagtaatca atgaagacaa aattgcaccc actcaaggct 3720
ttaacaccca tagtcatcaa aacatggaaa taattaccta tgttttagaa ggagaactag 3780
aacataaaga cagtatcggt aatggttcaa ttattcgtcc tggtgatgta caaagaatgt 3840
ctgccggtag aggtatcgcc catagtgaat ttaatccctc atctcaagaa acagtccatc 3900
tactacaaat ttggattcaa ccaaatcaaa taggagttga ccccagttat gaacaaaaat 3960
actttgccga tgatgaaaaa caaggaaaat taagactaat tgcttctgaa gatggtagag 4020
aaggatctgt caaaattcac caagatgcgg atctttatga tatcaatcta gaatgacggt 4080
gaaaacctct gacacatgca gctcccggag acggtcacag cttgtctgta agcggatgcc 4140
gggagcagac aagcccgtca gggcgcgtca gcgggtgttg gcgggtgtcg gggcgcagcc 4200
atgacccagt cacgtagcga tagcggagtg tatactggct taactatgcg gcatcagagc 4260
agattgtact gagagtgcac catatgcggt gtgaaatacc gcacagatgc gtaaggagaa 4320
aataccgcat caggcgctct tccgcttcct cgctcactga ctcgctgcgc tcggtcgttc 4380
ggctgcggcg agcggtatca gctcactcaa aggcggtaat acggttatcc acagaatcag 4440
gggataacgc aggaaagaac atgtgagcaa aaggccagca aaaggccagg aaccgtaaaa 4500
aggccgcgtt gctggcgttt ttccataggc tccgcccccc tgacgagcat cacaaaaatc 4560
gacgctcaag tcagaggtgg cgaaacccga caggactata aagataccag gcgtttcccc 4620
ctggaagctc cctcgtgcgc tctcctgttc cgaccctgcc gcttaccgga tacctgtccg 4680
cctttctccc ttcgggaagc gtggcgcttt ctcatagctc acgctgtagg tatctcagtt 4740
cggtgtaggt cgttcgctcc aagctgggct gtgtgcacga accccccgtt cagcccgacc 4800
gctgcgcctt atccggtaac tatcgtcttg agtccaaccc ggtaagacac gacttatcgc 4860
cactggcagc agccactggt aacaggatta gcagagcgag gtatgtaggc ggtgctacag 4920
agttcttgaa gtggtggcct aactacggct acactagaag gacagtattt ggtatctgcg 4980
ctctgctgaa gccagttacc ttcggaaaaa gagttggtag ctcttgatcc ggcaaacaaa 5040
ccaccgctgg tagcggtggt ttttttgttt gcaagcagca gattacgcgc agaaaaaaag 5100
gatctcaaga agatcctttg atcttttcta atgcattctt cagaatgaaa ttactgctcg 5160
taatattgag tatgctactt tagtgggaag agatcagaga ataattgtta gtgctaataa 5220
taatcgggca ggggaggttt ttgatcccaa tggcttagtt tctcaagtaa ttaataatcc 5280
tcaacaaatt aaaaccactg aaattgtttc ttggcaagat ttacaagcag aaaatcctcc 5340
tttgttgcct cgtctaattc ctaatcaaga tgtggttatt cgttatactt ttactcctgt 5400
ttttaacccc aacaatcggg atcaagtggt aggggtgtta gtttctggag acgtggttaa 5460
cgggaaatat tccattgtat ttgatacgat taatgagttt aaggggggt atagtgcggt 5520 ttatcaggtt aactccgaag ataatatctc tttagctagt tctgctacta atagtgaaga 5580
tacaacgaat cagctaattg ctagtcaaaa attattggag ttagcattag aaaatcccaa 5640
tcaaattgtt tctttcagag ataaagtagg ggacgaaact tttactttta ctgcccagac 5700
cattcaaaat aaagctggtg aacctgtggc tattttagta cgggggactc ctgaaaaagc 5760
acttaatcaa attattgcca atagccttaa aactcaagga caaacggcac taatcgtatt 5820
aattcttaat tttattctga taattgtttt aggaagagtt attgcaaatc gtttagaaca 5880
gttacaaaaa acgaccactc aatttgctga aggtaactat cgagtaaggg caaatattgt 5940
tggacaggat gaaattggtg atttagcgga tacatttaat ttactcgcag aaaatattga 6000
aagtaatgaa actttacttt tattagatgc ggaaaaagcc agtttattcc aagaaattac 6060

```
gggagcgagg gtagttgatg aagatgatat taatcaagtg ttcgatcgca gtttaccaaa   6120
agcaaaagaa attttagaag ttgatcgtct tgttatctat cgctttaagc ctaattggag   6180
tggttatatt agcaatgaag caggagatca agatttaccc agtgctttga gtgagcagtt   6240
aaatgatcct tgtattcctt tatccttaag ggattcttat ataaacggta gagttgtggc   6300
aacagaaaat gtttataccg cagggtttgc tcctgaacat gaagccttga tgcaccgctt   6360
acaaatcaaa tccaatttag ttattcccat catcagtcaa ggacaactat ttgctttatt   6420
gattgcccat cattgtcgtc aacatcatca atggcaagaa aaagaaatct ctttcttaag   6480
tcaaattgct ttacgatacg gggtaatttt agaccgggtt aatatcttaa aagcccaaat   6540
gacttcggca actcgtgcag aacaactcaa agaaataacc cttaatttag ctgaaggttt   6600
aagtccccaa gaggtaatga atacggcagt tttagagact cgtaaagtat tgagatgcga   6660
tcgctctatt gtttatgaat ttgatgaaaa atggcaaggt acaatcattg ctgaatctgt   6720
agcagaaggc tatcctcaag ccctcggtgc gaaaatccat gatccttgtt ttgaagaaga   6780
atatgtagaa aaatatttgc agggcagagt tcaagcaact ccagatattc acaatgcagg   6840
attaacttta tgtcacctaa aacaattaga tccttttgag gtaaaagcca acttagttgc   6900
ccccattatc gttaaccgta aattaatcgg cttattgatt tgtcaccaat gctcaaacat   6960
aagagaatgg gaactatcag aaattgactt tatgactcaa gttgccactc aagtaggact   7020
agctttagaa agagtcaaat tgattgactt acagttacag gcagagcaag aacaaagaca   7080
ggcaaaagag ttattacaac aaagagcgtt agaactatta atgcaagttg accctgtttc   7140
caaaggggat ctaaccattc gtgccactgt tacggaagat gaaatcggta cgattgctga   7200
ctcttataac gccaccattg aaagtttaag acaaattgta tcccaagtac aaaatgcggc   7260
gttagaagta gctcaaacta ccagtaataa tgaaagtgac atggaaattc tgcgcttaga   7320
aattgctgaa caggtagaaa atattgctca agccttacaa acggtaaatg ctatgagtcg   7380
ttctagtaaa attgtggcag aaagtgcgga acaagcggaa gaagccctaa tcaaagctca   7440
agaaagcgtt gctgtgggag attcagcaat gaataaaacc gtgcgctcaa ttatggatat   7500
tcgtgccact gtacaacaag ccgcagatca ggttaaaaaa ctaggggata ccacagaaaa   7560
tatttccaat ttcgtgtctc tgattggcag atttgccgct caaacacacc ttttggcttt   7620
gaaagcctcc attgaagcgg cacgagctgg agagcaagga cagggctttg cggtgattgc   7680
tgatgaggtt cgggctttag cgactcagtc tgctcaggca acggctgaca ttgacaagtt   7740
agtgacggac attctttcag aaacaaaggt ggtggtaact tccatggaag agggcaatga   7800
attagttgtt gagggtagta aactggtaga ggaaacccgc cagagtctta accaaattac   7860
cgccgctacc gtacagatta acgagttagt agaagcgatc gcggcggctg cttttgaaca   7920
gtcagaaaac tcggaggaag ttagtatcac aatgggagat gtggcaaagg tagctgaaaa   7980
aactaattct tcggtaactc aactttctca atcctttatt cagttaaggt ctcttgctag   8040
aaaattagag tctgatgtgg ctaaatttaa ggtcaattag aaaagggtaa ggggcaaagg   8100
gcaaaacccc ctttatcccc cctcttgggg gggagagcaa aggtaattga ttagtcgact   8160
tctgcaggaa gttcctattc tctagaaagt ataggaactt c                        8201
```

<210> SEQ ID NO 16
<211> LENGTH: 278
<212> TYPE: DNA
<213> ORGANISM: Cyanobacterium sp. ABICyano1

<400> SEQUENCE: 16
aattaataac ttcttcctgt acgggcgaat ggccatttgc tcctaactaa ctccgtactg 60
ctttgcggaa cgagcgtagc gaactctccg aattactaag ccttcatccc tgatagatgc 120
aaaaaacgaa ttaaaattat gtgtaaaaag aaaatgtgtc tttatttagt agtcaaagtt 180
acaaaatatt aagaatcaaa ttaataatgt attgggcagt taagtatata agtctttaaa 240
tatttatttg tattcaatat attaaccgag gacaaatt 278

<210> SEQ ID NO 17
<211> LENGTH: 246
<212> TYPE: DNA
<213> ORGANISM: Cyanobacterium sp. ABICyano1

<400> SEQUENCE: 17
ccaatatctt gtcatacata cttatttgcc tcactattag ccctatatgt ctctattgta 60
tttttctttt tctcctattc ctagatcttg taatgaatca ttactctctg aaatatagct 120
actaatttta tggttgtttg taaaatatat taacaaatga acaataaatc atattttgtg 180
ttaatctaat tattagacaa ctactgaatt tatattcaga tattcacaga taggagaatt 240
ttgatt 246

<210> SEQ ID NO 18
<211> LENGTH: 162
<212> TYPE: DNA
<213> ORGANISM: Cyanobacterium sp. ABICyano1

<400> SEQUENCE: 18 tattatttt cgtttatatg cagatttaga ataaacaaaa ttcatttact gcaaattttc 60
aaaaaaatgt gactaaacat acaaaataaa gaaaaaataa agttttaaat ttatgtacat 120
caaacttaag aaatgtttaa attacttaga aatttatagt tc 162

<210> SEQ ID NO 19
<211> LENGTH: 433
<212> TYPE: DNA
<213> ORGANISM: Cyanobacterium sp. ABICyano1

<400> SEQUENCE: 19
tttatatata aactcgaata aaattatcaa tataaagtca aactatatct atcctatttt 60
aactgctatt ggtaagtccc ttaattagtg ttggggtgaa tagattttaa aagggcaaac 120
ccccctttat cctccctcga gagggggag ggcaaaaggc aaggggcaag ggaaaaatta 180
agaattaaga attaaaaact ccgaacacct gtaggggcga atagccattc gcttcccctc 240
atccccccat ctccccaaca ccctaagccc ctactcgtta ctcatttatt tacatcattt 300
atttacatca ttaagaaaag taacaaattt tgacaagtag tcttttgaca ggaaaaagca 360
aattctcgaa gatgaaaaca atagaaaaaa attcaatctt acagtaacga tgaaaaaact 420
tttaggctta att 433

<210> SEQ ID NO 20
<211> LENGTH: 299
<212> TYPE: DNA
<213> ORGANISM: Cyanobacterium sp. ABICyano1

<400> SEQUENCE: 20
tgtctcaaaa agacaggttt tttttatgaa agtaataaga aataagtaga agtgaggagt 60
tggaaagata ggattaagaa ttaggagtta actattttca ttctttattc ttccattgcc 120
cattgagaaa tcatatctaa aatcagcaac gccaaatttt agatgcaaaa taaccataaa 180
taaaatgcag aaaaaagaat actttagatc ttccgtatca gaagatacat ttcttaacaa 240
aatctggtga caagattaaa cacacgaaat ccgaggtttt atatattgat tagtcctag 299

<210> SEQ ID NO 21
<211> LENGTH: 536
<212> TYPE: DNA
<213> ORGANISM: Cyanobacterium sp. ABICyano1

<400> SEQUENCE: 21
attctgtgaa ttgattagat ttgaggtttt ttaagaggtt gattaccttg cctccaaaaa 60
aatcataaca cactaatgct ctatatgaaa gggctttaga cccataggtt tttgagaaaa 120
aaacttgcta actctcggac aatgtcagca taactaaagt caattctttt cgtactttat 180
aattgtctat aatttaatat acaactgttc tgaaactagt ttttctctac attccttagt 240
tttatctgag taaggttgct tgtaacttaa cttcggttgg gcctaaaaat atccgattag 300
gagcaggtgt cagactttaa ttaattatta attattaatt gcttattgcc aaccctcggc 360
gacaccactt tttcatcagc cccagataaa gattgatgtt ttagttttgt ttctttttat 420
cccctaattc aactaataca agtaaaacta aggttgttta tcaaaaatga tggttgatgt 480
ttgggtaaat tttaagatat tatgaaaaga aaatgaataa aaaatgaaaa atcttt 536

<210> SEQ ID NO 22
<211> LENGTH: 320
<212> TYPE: DNA
<213> ORGANISM: Cyanobacterium sp. ABICyano1

<400> SEQUENCE: 22
gaatatctca tccttagctt ctacttatac cttcagcata gttaaaaatc atccctttat 60
tgatggtaat aaaagaacag gttttattag tggagtaacc tttttaatgc tcaatggttc 120
tcactttact gcttctgaag tggaagtagt acatatcatc caaaccttag ctagtggcag 180
aattaccgag gaagaattac aacaatggtt cgtaaggaaa agtaagcaga tgaataatta 240
aagcatcatt tcatcctcat ttcatattct cctgtcacca tggtatggaa gattaggtaa 300
aaatgaggaa aaagtttatt 320

<210> SEQ ID NO 23
<211> LENGTH: 309
<212> TYPE: DNA
<213> ORGANISM: Cyanobacterium sp. ABICyano1

<400> SEQUENCE: 23
atacatggtt ggttcactga cttttacccc agttttctct ttgaacaatt ggcataactc 60
tgaaaaaatc agatcgggct tttgttgaat tatttgttca atcaaagcaa aaccgtgatt 120
gtctattttc tttttttcc caccactcat agataaaaat ttatcccgaa ctcaggttat 180
attaagttcg gatgatcact taagataatt gatcagattg gttaagatag agaaaaattc 240
tttttcatag tgatttcata attgatagtt acaataacga ttattattta gtaaaaagat 300
tttcaaatc 309

<210> SEQ ID NO 24
<211> LENGTH: 330
<212> TYPE: DNA
<213> ORGANISM: Cyanobacterium sp. ABICyano1

<400> SEQUENCE: 24
tggtcaagtt actatatgtt tagaaacaac aaaaaaagaa gtcattataa aaataattga 60
tacaggaatt ggcattaata aagaagaaca aaaattaatt tttaatcgtt tttatcgaat 120
caataaagca agaaatagag agaaaggcag ttgcggatta ggtttagcta ttgcaaatgc 180
gatcgcgctt aatcatggtg gtagaataat tttagaaagt caagaaaatc aaggcagtat 240
ttttaccgtt tatttaccga aaatcatttc atcctaattt catattcttt tgacagaatc 300
aaaggtaaag ataaaaagag agaaacagtc 330

<210> SEQ ID NO 25
<211> LENGTH: 359
<212> TYPE: DNA
<213> ORGANISM: Cyanobacterium sp. ABICyano1

<400> SEQUENCE: 25
cctcaactac aagttctttt atatattact ttaacctgag ttttggataa gctgaaagca 60
ttattttctc gtagtcagaa aaccttatag cttcttagaa ataacgataa aattacctta 120
atccgaactg acgttaaata tattcacccc tatcacccca aaaccctaag cccctacttc 180
cccctttccc ttcatcacct catccccca tcccctaaca cttaacctta ttctttattc 240
ttaaaccgaa ctgaggtgaa gttgcagaat acccatgggg ggttacagca ttgtagaaaa 300
ataaatattc tttcattatt aaggttgttt ggtaaaaata tgtgaaaacc ctaataatt 359

<210> SEQ ID NO 26
<211> LENGTH: 239
<212> TYPE: DNA
<213> ORGANISM: Cyanobacterium sp. ABICyano1

<400> SEQUENCE: 26
ggggacagac atatttttat cataatggta aattcataat aattttagac ttttttttgc 60
aaaaattaat ctcactctct tctttcccta tctcccattg tttcttatat cccaatgccc 120
caatacccaa agctcagaaa ataggtatta gcgaagaggt gttgatcccc tcccctagca 180
aaatatactc ctatatagta aagtgagaaa gtgaagaaat aagatcaagt tcgcaattt 239

<210> SEQ ID NO 27
<211> LENGTH: 290
<212> TYPE: DNA
<213> ORGANISM: Cyanobacterium sp. ABICyano1

<400> SEQUENCE: 27
ttgacgattg tattgactta cgccaaatgg cttaccctca tagtgaatag ttgataatta 60
agaattaaaa atcccgttca cgacagaagg gagtgtaaga gccttcggtg cgaactctca 120
tcttccctga aacctgacac ctgaaacctg acacctgaaa cctgacacct catctcccta 180
atcccctaat tttaatgaaa aaatacccctg agtgggcatt gaaaaaaaag aaaagttgtt 240
cgactatgaa ataagaattc tgcacttcgt gagaaaaaag gaaatgaaat 290

<210> SEQ ID NO 28
<211> LENGTH: 355
<212> TYPE: DNA
<213> ORGANISM: Cyanobacterium sp. ABICyano1

<400> SEQUENCE: 28
ctatttaact aggaaaaggt aaagttaaaa ggacaagggt aaataattaa aaattaagaa 60
ttaagaactt ctaactctca ttactcatta cttatttcct cctctcaccc cttctcctga 120
tcacctcttc tcctcaatac tcggaactca tttccccatg gtgtgacact caaatcaaaa 180
gtctgttatt gactttcaga tgaaatatta ctatgataac aatatccccc ctatgggtat 240
ataaaaatat gagcgatatt agttaaaaat caaatttgga tttttttct gaaaatattt 300 taagattaag taaagataag taaagaaatt ataagcaatt ttgttaaatc atacc 355

<210> SEQ ID NO 29
<211> LENGTH: 619
<212> TYPE: DNA
<213> ORGANISM: Cyanobacterium sp. ABICyano1

<400> SEQUENCE: 29
ctcacactga aaatattgcc acaagaaata aagatcaagc aataatcctg actaaaaagg 60
aataaagtaa ttatcctttt cctgatatgt tatctgactt gttgtttctt agtcatgttc 120
cttccatttt tatttttgtt tttatcattt ttattacaaa aatttcttaa tagggctaaa 180
gcatttagtt agttttttag ctctcaacaa gttgactaat caatataatg ccctaagtta 240
atttgccctt ggtttgacgg aggatattgg aaaaaagaaa cttctcgttg tatttcacag 300
ggaaaagggg gaaattttat taataactaa acaatagaaa ataattattt atttatatta 360
ttttgtgaac aaatgttcaa gaattaaagt gtaataagaa aatttatttt tttatattta 420
tttaaaactt agatataagc ctaaaggtct gaaattatta ttagacaatc aattgattca 480
gaggtaatag ttttttactt aaaaatattt tttcaaaatt atcccctatt tgggtattga 540
aaaataaata aattcaagta ataatataca gaataaagga aaatctaatc ttaaaaattt 600
tgtgtgtgag gaattgaaa 619

<210> SEQ ID NO 30
<211> LENGTH: 496
<212> TYPE: DNA
<213> ORGANISM: Cyanobacterium sp. ABICyano1

<400> SEQUENCE: 30
caaatcacga gaatttatgt agggactatt ttgggttgac ggtggagagt atgtcgccct 60
tgaattatga cccgaagatg aagatgtcgg ggaggtggaa ggacggtctt taagaggttt 120
aacatcaaag ttggtcataa tctctgtccc tgtttgataa ctactattta attttgagtt 180
gttttaggta catcaaaata cccaaatcct tactctcccc tcaatataca acaaaaaaaa 240
ctttttgatt cactttagtc ataaaaatta gaatttatct accgaaatat tacataaatg 300
taatgtatat attttctgat ttattccgtg tgagccatga ttcataattt ataattcata 360
atttctaaat atgcccctac aatggatata gaatgtcatt ttaattatag gtatcataat 420
cgtggtagtt actccggaaa aaactattga atcaaattca gtctcacctg ctacagatag 480
agtagccgtt attctt 496

<210> SEQ ID NO 31
<211> LENGTH: 283
<212> TYPE: DNA
<213> ORGANISM: Cyanobacterium sp. ABICyano1

<400> SEQUENCE: 31
ctacaggggc aagatttggc ggaaatctat atgtggattc tctttcaagt gaagaaggtg 60
cagtgccgac ttatctggac ttattagaat acgatattcg cactattact aatggtttgt 120
tagcaggagt gaacaattaa aaattttttc ctaattgacg aataaaaaat caatgtcaac 180

```
taatagttaa caatactctc tgaaaaccaa aaattgtcaa ccaaaacata acataatttt    240

tacccaaaaa cctcatttat aaactttaag gataaaatca atg                      283


<210> SEQ ID NO 32
<211> LENGTH: 299
<212> TYPE: DNA
<213> ORGANISM: Cyanobacterium sp. ABICyano1

<400> SEQUENCE: 32

gggattagag agttcaaagt taggaatgag gtgtcaggtt ttaggtttca ggtttagggg     60

agcaatgaga aagaggtttc aggtttcagg tgtcaggttg caggtgtcac aggtgatgag    120

gggatggggg atgaggggga aacaagtaag taataagtgt tcggagtttt taattcttaa    180

ttcttaattt ttcctttgcc tcttgccttt tgccttgtct taattactaa tttctaatta    240

aaatgattgt gttttctagt ttagtctcat ggttacttga acccttacag catagtttt     299


<210> SEQ ID NO 33
<211> LENGTH: 416
<212> TYPE: DNA
<213> ORGANISM: Cyanobacterium sp. ABICyano1

<400> SEQUENCE: 33

ttacaaacgg cgggaattat tatggtagta gcgatgttag taaccccggg tgcgatcgca     60

tatttactta cagatcgttt tgatcaaatg ttaatcttat caatagttag tagtgttcta    120

tcttgtgttt taggcactta tttaagttat cattttgatg tttctacggg gggaagtatt    180

gtcgttttaa tgaccataat ttttatttta gcgatgattt ttgctcctaa atatggcatc    240

atcaatcaaa ataccaaaat atattctgct taacttgttt actgatactt caaataatca    300

tataacctat cttccgagtt aaaaataatg gatattatcc aactgaggtc gagaatagag    360

tttctttttt gatagaattt ttttacacca gttattcatt actatcatgg gataat        416


<210> SEQ ID NO 34
<211> LENGTH: 412
<212> TYPE: DNA
<213> ORGANISM: Cyanobacterium sp. ABICyano1

<400> SEQUENCE: 34

taatatagtg attattataa atgcaatgtg aatcaaacct atattttacc gtacattgac     60

catggaactt aatttgaggt gattagtaga gggtgcgatc gccctatttg tcaaataata    120

aagataacat ttgacattgc tgattgaaga cataaaacac agaaaaaatc aggtaaaaat    180

ataaagctaa agtctaaata tggtttactt ttgccttcga cttacaacaa aaaatcatag    240

ctagaatcac caacgcctaa tattttattt agctgaaatt ttgggatgaa ctttttgtaa    300

aaatcggggg tctaaaaata tagcaaccac gatattaaat aactgagtga ttattttaat    360

ctattggggg cttattaact aaatacttgc atttttatgg agggttttaa tt            412


<210> SEQ ID NO 35
<211> LENGTH: 364
<212> TYPE: DNA
<213> ORGANISM: Cyanobacterium sp. ABICyano1

<400> SEQUENCE: 35

aaagattatt ttctacagaa gcaacccttt catcttccga attttcagga atttcctgct     60

tttgtttctg aatattagca taggcggctt ttgcccactc taaagaaggt tgagactgaa    120

tttctgaggt ttcagaagga gcattagatt gtttatcttc aacaacagga ggtttttgtt    180
```

```
caatattttc cttattctct tttttacggc gaaaccaatt aaacataatg attgtgcata    240

aatattcgtt aatatattgt aaccctagaa aggaatcggt ttcaggttta tccccagaga    300

atgtgaacct ttacagaaag taaaaagtct aaaatcgtag caacaataaa tcacagaaat    360

tgag                                                                 364


<210> SEQ ID NO 36
<211> LENGTH: 304
<212> TYPE: DNA
<213> ORGANISM: Cyanobacterium sp. ABICyano1

<400> SEQUENCE: 36

gcgattatca accacgaaaa catacaatta ttatcaaacc tgctgagaaa ttatccacag     60

aaatagatgt ttctgcgaag ggaaaatggg cttttcattg ccatttaatg tatcacatgg    120

atgtgggaat gtttcggact attaatgtta tttcctaaaa aataatagta ttaaagccta    180

aaatttttat aaaaaaattc atgtctttta ttagggtgag cattcttcct ttatgtctcc    240

ttattttacc tctttagagg taactacaaa cttaatcaaa aaatttagat aattaattat    300

atca                                                                 304


<210> SEQ ID NO 37
<211> LENGTH: 490
<212> TYPE: DNA
<213> ORGANISM: Cyanobacterium sp. ABICyano1

<400> SEQUENCE: 37

catctttact tttgactaac atttcatagg tatcatgacg aaaatttttt agtctgttat     60

atttgttcat gtagagagat tttaatttgt gattatttta ttttctctct atttttcttt    120

tttgtcttgt ccttcctcat ttttctctac atttagtcta aactacagct ctttaatctt    180

cagtttctct ttcctcctct tcctcatcaa ggtaatcatc ccaattaata tcttcttctt    240

gttctaattt gggttgagat tgttgtttat caatcatatt tcatactcct aaaactttct    300

tacttattta tcagttactt tttacccatt tatgcaatag tgtagaaatt tttttcgatc    360

gagttaatta atttttattt caaccatatc taaataattc ttgatggaca ttctagttaa    420

ctagaaggtt taagctaaaa ataattattg atattgcctt cggtataact aactatatcc    480

agagaaaaag                                                           490


<210> SEQ ID NO 38
<211> LENGTH: 306
<212> TYPE: DNA
<213> ORGANISM: Cyanobacterium sp. ABICyano1

<400> SEQUENCE: 38

ctcaagagat agttaaaaaa caaatagctt tagtctatca attaatcgaa ttatttttac     60

aaacaaattt tcataaaccc atagaactag aggaggaagt tatttatgtt taaaaatcta    120

aaagagtttt atattcccct aaaacccccct tagtaagagt gactttttttc atcatttgcc    180

tgtaaattct cctcttttaa taagagagct agggtgtttt aaaagaggat tttattgctt    240

tccaattcta actacttcaa aaacttattt tatactcaat aatttattaa tcaagaggaa    300

attacc                                                               306


<210> SEQ ID NO 39
<211> LENGTH: 464
<212> TYPE: DNA
```

<213> ORGANISM: Cyanobacterium sp. ABICyano1

<400> SEQUENCE: 39
tcgagcgctc gttccgcaaa gcggtacgga gttagttagg ggctaatggg cattctcccg 60
tacaggaaag agttagaagt tattaattat caacaattct cctttgccta gtgcatcgtt 120
acctttttaa ttaaaacata aggaaaacta ataatcgtaa taatttaacc tcaaagtgta 180
aagaaatgtg aaattctgac ttttataacg ttaaagaggg aaaaattagc agtttaaaat 240
acctagagaa tagtctgggg taagcataga gaattagatt agttaagtta atcaaattca 300
gaaaaaataa taatcgtaaa tagttaatct gggtgtatag aaaatgatcc ccttcatgat 360
aagatttaaa ctcgaaaagc aaaagccaaa aaactaactt ccattaaaag aagttgttac 420
atataacgct ataaagaaaa tttatatatt tggaggatac caac 464

<210> SEQ ID NO 40
<211> LENGTH: 541
<212> TYPE: DNA
<213> ORGANISM: Cyanobacterium sp. ABICyano1

<400> SEQUENCE: 40
aatagttgat aattactcgt tactcattac tcacttaaac ctgccacctg atacctgcca 60
cctctccccc catcacctca tcccctcaac attccgaacc ccttgacact ttgaactaaa 120
attgtattaa agtgcaaatc tggacggggt taaccagtgt gacttataat agtaaacgct 180 gtttttttata ataaataagc taaatattta aaaactatga gtaaatatac actaaatggt 240
actagacgta agcagaaaag aacctccggt ttccgcgccc gtatgagaac caaaaatggt 300
agaaaagtaa ttcaagctcg tcgtaataag ggtagaaaaa gattagcagt ataaaattac 360
tgttaaataa ggaagctaag tttagcattt taagtttgat attactaatc attaaattta 420
ctgtgaaata taggtgggac taccatcaaa gcatcgactg aaacggcgtt taaatttcca 480
atctgtttat caacagggta ttcgccgctc tagtcgttat tttattgtcc gagggttacg 540
g 541

<210> SEQ ID NO 41
<211> LENGTH: 569
<212> TYPE: DNA
<213> ORGANISM: Cyanobacterium sp. ABICyano1

<400> SEQUENCE: 41
ctccgcttaa aaaatttcat ttttcgatca aaaaagacaa attattacta attagctcat 60
ggcaataaat aatcagtagt aatctgtttt cacattttat tgttaatttt tattattgct 120
aatatcaacc ttttctactt ctgcttaata ttttatttat gctcaatggg aaaatctgaa 180
ataagattga gaacagtgtt accaatagaa gtatttaagg tttaaagcat accttaaaga 240
taacattttt ttttgaaaag agtcaaatta tttttgaaag gctgatattt ttgatattta 300
ctaatatttt atttatttct ttttccctta aaataagagc taaatctgtt tttattatca 360
tttatcaagc tctattaata cctcaacttt ttcaagaaaa aataataata atttttccct 420
ctattctcat gaccttttag gaaaattaat tttagaaaaa ctattgacaa acccataaaa 480
aatgagataa gattatagat tgtcactggt attttatact agaggcaaat tatatttata 540
tatacaaaaa tgctgtataa aaaacatct 569

<210> SEQ ID NO 42
<211> LENGTH: 163

```
<212> TYPE: DNA
<213> ORGANISM: Cyanobacterium sp. ABICyano1

<400> SEQUENCE: 42

agtaaagatt atcaccaaca tctgaaacct gacttcatca actgaggaaa taaccactgt     60

ggctgtgttt aaaatcgact gcgtagcaag taaaactcaa aaaaatcaag gtcaatacgg    120

aaagtttgtg cttgaaccct tagaaaaagg acaaggcata act                      163


<210> SEQ ID NO 43
<211> LENGTH: 301
<212> TYPE: DNA
<213> ORGANISM: Cyanobacterium sp. ABICyano1

<400> SEQUENCE: 43

ctacatcaac taatcaaaag ttaagaaaaa agatagaaac gcccatgaat attaaagatt     60

aatctgtgtc ctttaacttt ttatcccctt aaaagagcat aactaaaaca ttgatagatt    120

ttataaagaa aagtaacaaa atcttgactt aaatgagaaa ggattaaaaa ccaaagcctt    180

atctgaggga atgttaaaca aattttaaat attgttaagc aagaaccaca atggtgacaa    240

atagccctta tcatcttcag taatgtagta gtttaagtat ttgtcgagag aggaatccct    300

c                                                                    301


<210> SEQ ID NO 44
<211> LENGTH: 299
<212> TYPE: DNA
<213> ORGANISM: Cyanobacterium sp. ABICyano1

<400> SEQUENCE: 44

gatcgaattt ttgactattt aataatttct ttactattca taatatctca aaagacttct     60

atctttttaa gtaaactacc tcctctaaga ataaacactt attgactata ttccttttta    120

gttataaaat ggcatttaaa gttactcaaa atatttgcaa tcattctaca aaacatagtg    180

tatttccttg tattaagcgt attgtgtcct gttagataat gtaggaaaga ttgtgagttg    240

ataggtgata aatacataac tcattagaca acaagataaa gttgtaggag ttctaaatt     299


<210> SEQ ID NO 45
<211> LENGTH: 261
<212> TYPE: DNA
<213> ORGANISM: Cyanobacterium sp. ABICyano1

<400> SEQUENCE: 45

aagagtttgg catttttatt ggtaagacta ttctgagaaa aatgtgacaa tttgttaaaa     60

tatttgctag aaatagaaaa agtaatttgg caaagatact taaatcgtat cgaaaaacgg    120

agttacatta actctaactc atgctatatt aagaaaagtt aattgcagat cagtattatt    180

gctgagtagc agtgccgtct ccaataatat aaagagagac aatataaaag taaaacttga    240

caagttaaaa aaagaaagat t                                              261


<210> SEQ ID NO 46
<211> LENGTH: 396
<212> TYPE: DNA
<213> ORGANISM: Cyanobacterium sp. ABICyano1

<400> SEQUENCE: 46

aactttagat attcgtagtt ggcaatgtcg taaatgcgga acaatacatg gaaaacatat     60

agatttgtaa tgagaaaaag tgtaaacaaa tattaagaaa aagatcagaa aaatttaaca    120
```

```
acacgtaata aaaaaatgcg tcactacggg ttataaattt acatgaaagg ttaaaacact    180

tttctgagac gattttgata aaaaagttgt caaaaaatta agtttcttta caaatgctta    240

acaaaaactt ggttttaagc acaaaataag agagactaat ttgcagaagt tttacaagga    300

aatcttgaag aaaaagatct aagtaaaacg actctgttta accaaaattt aacaaattta    360

acaaaacaaa ctaaatctat taggagatta actaca                              396
```

<210> SEQ ID NO 47
<211> LENGTH: 1710
<212> TYPE: DNA
<213> ORGANISM: Artificial sequence
<220> FEATURE:
<223> OTHER INFORMATION: Pyruvate decarboxylase gene from Zymomonas mobilis; further codon optimized for maximal expression in Cyanobacterium sp. ABICyano1.

<400> SEQUENCE: 47

```
atgaattctt ataccgtggg tacttattta gccgaacgct tagtgcaaat tggtttaaaa     60

catcattttg ccgtggctgg ggactataat ttagtgttat tggataactt attattaaat    120

aaaaacatgg aacaagtgta ttgttgtaat gaattaaatt gtggtttttc tgctgaaggt    180

tatgctagag ctaaaggtgc agctgctgct gttgttactt attctgtggg tgctttatct    240

gcttttgatg ctattggtgg tgcttatgcc gaaaatttac ccgtgatttt aatttctggt    300

gcccctaata ataatgatca tgccgctgga catgttttac atcatgcctt aggtaaaacc    360

gattatcatt atcaattaga aatggccaaa aatattactg ctgctgccga agctatttat    420

actcctgaag aagcccctgc caaaattgat catgtgatta aaaccgcctt acgcgaaaaa    480

aaacccgtgt atttagaaat tgcctgtaat attgcttcta tgccttgtgc tgctcctggg    540

cctgcttctg ctttatttaa tgatgaagcc tctgatgaag ctagtttaaa tgctgccgtg    600

gaagaaacct taaaatttat tgccaatcgc gataaagttg ccgtgttagt tggttctaaa    660

ttaagagctg ctggtgctga agaagctgct gttaaatttg ctgatgcttt aggtggtgca    720

gttgctacta tggctgctgc caaatctttt tttcccgaag aaaatcccca ttatattgga    780

actagttggg gagaagtttc ttatcctggt gtggaaaaaa ctatgaaaga agccgacgct    840

gttattgctt tagcccctgt gtttaatgat tattctacca ctggttggac tgatattccc    900

gatcccaaaa aattagtttt agccgaacct cgttctgttg ttgttaatgg tgttcgcttt    960

ccctctgtgc atttaaaaga ttatttaacc cgcttagccc aaaaagtttc taaaaaaact   1020

ggtgccttag attttttttaa atctttaaat gcgggtgaat taaaaaaagc tgctcctgct   1080

gatccttctg ctcctttagt taatgctgaa attgcccgtc aagttgaagc cttattaacc   1140

cctaatacta ccgttattgc cgaaactggt gattcttggt ttaatgccca acgcatgaaa   1200

ttacctaatg gtgcccgtgt tgaatatgaa atgcaatggg gtcatattgg ttggtctgta   1260

cctgctgctt ttggttatgc tgttggtgct cctgaacgtc gtaatatttt aatggtgggt   1320

gatggttctt ttcaattaac tgcccaagaa gttgcccaaa tggttcgctt aaaattaccc   1380

gttattattt ttttaataaa taattatggt tataccattg aagtgatgat tcatgatggg   1440

ccatataata atattaaaaa ttgggattat gcgggtttaa tggaagtgtt taatggtaat   1500

ggtggttatg attctggtgc tggtaaaggt ttaaaagcca aaactggtgg tgaattagct   1560

gaagctatta aagttgcctt agccaatact gatgggccaa ccttaattga atgttttatt   1620

ggtcgcgaag attgtaccga agaattagtt aaatggggta aacgtgttgc tgctgctaat   1680

tctcgcaaac ccgtgaataa attattgtaa                                    1710
```

<210> SEQ ID NO 48
<211> LENGTH: 569
<212> TYPE: PRT
<213> ORGANISM: zymomonas mobilis

<400> SEQUENCE: 48

```
Met Asn Ser Tyr Thr Val Gly Thr Tyr Leu Ala Glu Arg Leu Val Gln
1               5                   10                  15

Ile Gly Leu Lys His His Phe Ala Val Ala Gly Asp Tyr Asn Leu Val
            20                  25                  30

Leu Leu Asp Asn Leu Leu Leu Asn Lys Asn Met Glu Gln Val Tyr Cys
        35                  40                  45

Cys Asn Glu Leu Asn Cys Gly Phe Ser Ala Glu Gly Tyr Ala Arg Ala
    50                  55                  60

Lys Gly Ala Ala Ala Ala Val Val Thr Tyr Ser Val Gly Ala Leu Ser
65                  70                  75                  80

Ala Phe Asp Ala Ile Gly Gly Ala Tyr Ala Glu Asn Leu Pro Val Ile
                85                  90                  95

Leu Ile Ser Gly Ala Pro Asn Asn Asn Asp His Ala Ala Gly His Val
            100                 105                 110

Leu His His Ala Leu Gly Lys Thr Asp Tyr His Tyr Gln Leu Glu Met
        115                 120                 125

Ala Lys Asn Ile Thr Ala Ala Ala Glu Ala Ile Tyr Thr Pro Glu Glu
    130                 135                 140

Ala Pro Ala Lys Ile Asp His Val Ile Lys Thr Ala Leu Arg Glu Lys
145                 150                 155                 160

Lys Pro Val Tyr Leu Glu Ile Ala Cys Asn Ile Ala Ser Met Pro Cys
                165                 170                 175

Ala Ala Pro Gly Pro Ala Ser Ala Leu Phe Asn Asp Glu Ala Ser Asp
            180                 185                 190

Glu Ala Ser Leu Asn Ala Ala Val Glu Glu Thr Leu Lys Phe Ile Ala
        195                 200                 205

Asn Arg Asp Lys Val Ala Val Leu Val Gly Ser Lys Leu Arg Ala Ala
    210                 215                 220

Gly Ala Glu Glu Ala Ala Val Lys Phe Ala Asp Ala Leu Gly Gly Ala
225                 230                 235                 240

Val Ala Thr Met Ala Ala Ala Lys Ser Phe Phe Pro Glu Glu Asn Pro
                245                 250                 255

His Tyr Ile Gly Thr Ser Trp Gly Glu Val Ser Tyr Pro Gly Val Glu
            260                 265                 270

Lys Thr Met Lys Glu Ala Asp Ala Val Ile Ala Leu Ala Pro Val Phe
        275                 280                 285

Asn Asp Tyr Ser Thr Thr Gly Trp Thr Asp Ile Pro Asp Pro Lys Lys
    290                 295                 300

Leu Val Leu Ala Glu Pro Arg Ser Val Val Val Asn Gly Val Arg Phe
305                 310                 315                 320

Pro Ser Val His Leu Lys Asp Tyr Leu Thr Arg Leu Ala Gln Lys Val
                325                 330                 335

Ser Lys Lys Thr Gly Ala Leu Asp Phe Phe Lys Ser Leu Asn Ala Gly
            340                 345                 350

Glu Leu Lys Lys Ala Ala Pro Ala Asp Pro Ser Ala Pro Leu Val Asn
        355                 360                 365

Ala Glu Ile Ala Arg Gln Val Glu Ala Leu Leu Thr Pro Asn Thr Thr
```

```
    370                 375                 380

Val Ile Ala Glu Thr Gly Asp Ser Trp Phe Asn Ala Gln Arg Met Lys
385                 390                 395                 400

Leu Pro Asn Gly Ala Arg Val Glu Tyr Glu Met Gln Trp Gly His Ile
                405                 410                 415

Gly Trp Ser Val Pro Ala Ala Phe Gly Tyr Ala Val Gly Ala Pro Glu
            420                 425                 430

Arg Arg Asn Ile Leu Met Val Gly Asp Gly Ser Phe Gln Leu Thr Ala
        435                 440                 445

Gln Glu Val Ala Gln Met Val Arg Leu Lys Leu Pro Val Ile Ile Phe
    450                 455                 460

Leu Ile Asn Asn Tyr Gly Tyr Thr Ile Glu Val Met Ile His Asp Gly
465                 470                 475                 480

Pro Tyr Asn Asn Ile Lys Asn Trp Asp Tyr Ala Gly Leu Met Glu Val
                485                 490                 495

Phe Asn Gly Asn Gly Gly Tyr Asp Ser Gly Ala Gly Lys Gly Leu Lys
            500                 505                 510

Ala Lys Thr Gly Gly Glu Leu Ala Glu Ala Ile Lys Val Ala Leu Ala
        515                 520                 525

Asn Thr Asp Gly Pro Thr Leu Ile Glu Cys Phe Ile Gly Arg Glu Asp
    530                 535                 540

Cys Thr Glu Glu Leu Val Lys Trp Gly Lys Arg Val Ala Ala Ala Asn
545                 550                 555                 560

Ser Arg Lys Pro Val Asn Lys Leu Leu
                565
```

<210> SEQ ID NO 49
<211> LENGTH: 1011
<212> TYPE: DNA
<213> ORGANISM: Synechocystis PCC 6803

<400> SEQUENCE: 49

```
atgattaaag cctacgctgc cctggaagcc aacggaaaac tccaaccctt tgaatacgac      60

cccggtgccc tgggtgctaa tgaggtggag attgaggtgc agtattgtgg ggtgtgccac     120

agtgatttgt ccatgattaa taacgaatgg ggcatttcca attacccccct agtgccgggt     180

catgaggtgg tgggtactgt ggccgccatg ggcgaagggg tgaaccatgt tgaggtgggg     240

gatttagtgg ggctgggttg gcattcgggc tactgcatga cctgccatag ttgtttatct     300

ggctaccaca acctttgtgc cacggcggaa tcgaccattg tgggccacta cggtggcttt     360

ggcgatcggg ttcgggccaa gggagtcagc gtggtgaaat tacctaaagg cattgaccta     420

gccagtgccg ggcccctttt ctgtggagga attaccgttt tcagtcctat ggtggaactg     480

agtttaaagc ccactgcaaa agtggcagtg atcggcattg gggggcttggg ccatttagcg     540

gtgcaatttc tccgggcctg gggctgtgaa gtgactgcct ttacctccag tgccaggaag     600

caaacggaag tgttggaatt gggcgctcac cacatactag attccaccaa tccagaggcg     660

atcgccagtg cggaaggcaa atttgactat attatctcca ctgtgaacct gaagcttgac     720

tggaacttat acatcagcac cctggcgccc cagggacatt tccactttgt tggggtggtg     780

ttggagcctt tggatctaaa tctttttccc cttttgatgg gacaacgctc cgtttctgcc     840

tccccagtgg gtagtcccgc caccattgcc accatgttgg actttgctgt gcgccatgac     900

attaaacccg tggtggaaca atttagcttt gatcagatca acgaggcgat cgcccatcta     960

gaaagcggca aagcccatta tcgggtagtg ctcagccata gtaaaaatta g            1011
```

<210> SEQ ID NO 50
<211> LENGTH: 336
<212> TYPE: PRT
<213> ORGANISM: Synechocystis PCC 6803

<400> SEQUENCE: 50

```
Met Ile Lys Ala Tyr Ala Ala Leu Glu Ala Asn Gly Lys Leu Gln Pro
1               5                   10                  15

Phe Glu Tyr Asp Pro Gly Ala Leu Gly Ala Asn Glu Val Glu Ile Glu
            20                  25                  30

Val Gln Tyr Cys Gly Val Cys His Ser Asp Leu Ser Met Ile Asn Asn
        35                  40                  45

Glu Trp Gly Ile Ser Asn Tyr Pro Leu Val Pro Gly His Glu Val Val
    50                  55                  60

Gly Thr Val Ala Ala Met Gly Glu Gly Val Asn His Val Glu Val Gly
65                  70                  75                  80

Asp Leu Val Gly Leu Gly Trp His Ser Gly Tyr Cys Met Thr Cys His
                85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
    130                 135                 140

Pro Leu Phe Cys Gly Gly Ile Thr Val Phe Ser Pro Met Val Glu Leu
145                 150                 155                 160

Ser Leu Lys Pro Thr Ala Lys Val Ala Val Ile Gly Ile Gly Gly Leu
                165                 170                 175

Gly His Leu Ala Val Gln Phe Leu Arg Ala Trp Gly Cys Glu Val Thr
            180                 185                 190

Ala Phe Thr Ser Ser Ala Arg Lys Gln Thr Glu Val Leu Glu Leu Gly
        195                 200                 205

Ala His His Ile Leu Asp Ser Thr Asn Pro Glu Ala Ile Ala Ser Ala
    210                 215                 220

Glu Gly Lys Phe Asp Tyr Ile Ile Ser Thr Val Asn Leu Lys Leu Asp
225                 230                 235                 240

Trp Asn Leu Tyr Ile Ser Thr Leu Ala Pro Gln Gly His Phe His Phe
                245                 250                 255

Val Gly Val Val Leu Glu Pro Leu Asp Leu Asn Leu Phe Pro Leu Leu
            260                 265                 270

Met Gly Gln Arg Ser Val Ser Ala Ser Pro Val Gly Ser Pro Ala Thr
        275                 280                 285

Ile Ala Thr Met Leu Asp Phe Ala Val Arg His Asp Ile Lys Pro Val
    290                 295                 300

Val Glu Gln Phe Ser Phe Asp Gln Ile Asn Glu Ala Ile Ala His Leu
305                 310                 315                 320

Glu Ser Gly Lys Ala His Tyr Arg Val Val Leu Ser His Ser Lys Asn
                325                 330                 335
```

<210> SEQ ID NO 51
<211> LENGTH: 1008
<212> TYPE: DNA
<213> ORGANISM: Artificial sequence
<220> FEATURE:
<223> OTHER INFORMATION: Alcohol dehydrogenase sequence 916 from Synechococcus PCC 7002, codon optimzed for optimal expression in Cyanobacterium sp. ABICyano1.

<400> SEQUENCE: 51

```
atgcctatga tcaaagcctt cgcagttcat gagtctgatg gagatttaca gccttttgaa      60
tatgatcctg gtgcattatt atctgatcaa gttgagatcg aagttaaata ttgtggaatt     120
tgtcattctg atttatctat gatctctaat gaatggggta tgacccaata ccctttagta     180
cctggacatg aggtagtagg tgcaatcgcc aaagtaggtg aaaatgttaa aaatttatct     240
gttggtcaaa ttgtaggatt aggttggcac gcaggttatt gtaacgaatg tcctcaatgt     300
actactggtg atcaaaattt atgtgctact gctcaaggaa ctattgtagg acatcatgga     360
ggtttcgctg aaaaagttcg cgctgctgca aattctgtag ttcccatccc tgaaggaatc     420
gatttagaag ctgctggacc tttattttgt ggaggtatca ccgtttttaa tcctttagta     480
caatatggaa tccaacccac tgcaaaagtt gctgtaattg gaattggagg tttaggtcac     540
atggctgttc aattcttaaa cgcttggggt tgtgaagtta ccgcttttac cagttctgaa     600
gcaaaaatca ctgaggcttt agaattaggt gctcatcaca ctttaaacag tcgtgaccct     660
gaagccatcg cagccgctgc tggacagttt gatttaatca tttctaccgt taacgttaaa     720
ttagattgga atgcctattt aagtacttta aaacctcacg gtcgtttaca cttcgtaggt     780
gctactttag atcccttaga cattaacgtt tttgctttaa tcatgcagca acgttctatc     840
tctggtagtc ctgttggatc tcctgcaacc atcgcaaaaa tgttagaatt tgcaaaatta     900
cataaaattc aacctaaaat tgaaaccttt aaatttgaag atgttaacca ggctattgca     960
cgtttaaaaa gtggtgaagc ccactatcgt attgtattat gtagataa                 1008
```

<210> SEQ ID NO 52
<211> LENGTH: 335
<212> TYPE: PRT
<213> ORGANISM: Synechococcus sp. PCC 7002

<400> SEQUENCE: 52

```
Met Pro Met Ile Lys Ala Phe Ala Val His Glu Ser Asp Gly Asp Leu
1               5                   10                  15

Gln Pro Phe Glu Tyr Asp Pro Gly Ala Leu Leu Ser Asp Gln Val Glu
            20                  25                  30

Ile Glu Val Lys Tyr Cys Gly Ile Cys His Ser Asp Leu Ser Met Ile
        35                  40                  45

Ser Asn Glu Trp Gly Met Thr Gln Tyr Pro Leu Val Pro Gly His Glu
    50                  55                  60

Val Val Gly Ala Ile Ala Lys Val Gly Glu Asn Val Lys Asn Leu Ser
65                  70                  75                  80

Val Gly Gln Ile Val Gly Leu Gly Trp His Ala Gly Tyr Cys Asn Glu
                85                  90                  95

Cys Pro Gln Cys Thr Thr Gly Asp Gln Asn Leu Cys Ala Thr Ala Gln
            100                 105                 110

Gly Thr Ile Val Gly His His Gly Gly Phe Ala Glu Lys Val Arg Ala
        115                 120                 125

Ala Ala Asn Ser Val Val Pro Ile Pro Glu Gly Ile Asp Leu Glu Ala
    130                 135                 140

Ala Gly Pro Leu Phe Cys Gly Gly Ile Thr Val Phe Asn Pro Leu Val
145                 150                 155                 160

Gln Tyr Gly Ile Gln Pro Thr Ala Lys Val Ala Val Ile Gly Ile Gly
                165                 170                 175
```

```
Gly Leu Gly His Met Ala Val Gln Phe Leu Asn Ala Trp Gly Cys Glu
            180                 185                 190

Val Thr Ala Phe Thr Ser Ser Glu Ala Lys Ile Thr Glu Ala Leu Glu
        195                 200                 205

Leu Gly Ala His His Thr Leu Asn Ser Arg Asp Pro Glu Ala Ile Ala
    210                 215                 220

Ala Ala Ala Gly Gln Phe Asp Leu Ile Ile Ser Thr Val Asn Val Lys
225                 230                 235                 240

Leu Asp Trp Asn Ala Tyr Leu Ser Thr Leu Lys Pro His Gly Arg Leu
                245                 250                 255

His Phe Val Gly Ala Thr Leu Asp Pro Leu Asp Ile Asn Val Phe Ala
            260                 265                 270

Leu Ile Met Gln Gln Arg Ser Ile Ser Gly Ser Pro Val Gly Ser Pro
        275                 280                 285

Ala Thr Ile Ala Lys Met Leu Glu Phe Ala Lys Leu His Lys Ile Gln
    290                 295                 300

Pro Lys Ile Glu Thr Phe Lys Phe Glu Asp Val Asn Gln Ala Ile Ala
305                 310                 315                 320

Arg Leu Lys Ser Gly Glu Ala His Tyr Arg Ile Val Leu Cys Arg
                325                 330                 335


<210> SEQ ID NO 53
<211> LENGTH: 1017
<212> TYPE: DNA
<213> ORGANISM: Artificial sequence
<220> FEATURE:
<223> OTHER INFORMATION: Alcohol dehydrogenase from Lyngbya sp., further
      codon optimized for optimal expression in Cyanobacterium sp.
      ABICyano1.

<400> SEQUENCE: 53

atgagtgaaa ctaaatttaa agcctatgcc gtaatgaatc ctggtgaaaa attacaaccc      60

tgggaatatg aacctgctcc tttacaggta gatgaaattg aagtaagagt tactcacaat     120

ggtttatgtc acactgactt acacatgaga gataatgact ggaatgttag tgagttcccc     180

ttagtagcag gtcatgaagt tgttggtgaa gtaaccgctg ttggtgaaaa agtaaccagt     240

cgtaaaaaag gtgatagagt tggtgtaggt tggattcgta attcttgtcg cgcttgtgac     300

cattgtttac aaggagaaga gaacatttgt agagagggtt atactggttt aattgttggt     360

catcacggtg gatttgctga tcgtgtacgt gtacctgctg acttcactta taaaattcct     420

gatgctttag atagtgcatc tgctgctcct ttattatgtg ccggtattac cgtttacact     480

cctttaagaa cctacattaa acatcccggt atgaaagtag gtgttatggg tattggagga     540

ttaggacatt tagctattaa atttgctcgt gcaatgggag cagaagttac tgcctttagt     600

accagtccta ataaagaagc ccaagccaaa gaatttggtg ctcatcattt ccaacaatgg     660

ggtactgctg aagaaatgaa agctgttgcc ggtaattttg atttagtttt atctaccatc     720

tctgctgaaa ctgactggga tgctgccttc tctttattag caaataacgg tgttttatgt     780

ttcgtaggta ttcccgttag ttctttaaat gttcctttaa ttcctttaat tttcggacaa     840

aaatctgttg taggttctgt agttggagga agaagattca tggcagaaat gttagagttc     900

gccgctgtaa atcagattaa acctatgatc gaaactatgc ccttatctca agtaaatgaa     960

gctatggata aagttgccgc caataaagcc agatatagaa ttgtattatt atctgaa       1017


<210> SEQ ID NO 54
```

```
<211> LENGTH: 339
<212> TYPE: PRT
<213> ORGANISM: Lyngbya sp.

<400> SEQUENCE: 54

Met Ser Glu Thr Lys Phe Lys Ala Tyr Ala Val Met Asn Pro Gly Glu
1               5                   10                  15

Lys Leu Gln Pro Trp Glu Tyr Glu Pro Ala Pro Leu Gln Val Asp Glu
            20                  25                  30

Ile Glu Val Arg Val Thr His Asn Gly Leu Cys His Thr Asp Leu His
        35                  40                  45

Met Arg Asp Asn Asp Trp Asn Val Ser Glu Phe Pro Leu Val Ala Gly
    50                  55                  60

His Glu Val Val Gly Glu Val Thr Ala Val Gly Glu Lys Val Thr Ser
65                  70                  75                  80

Arg Lys Lys Gly Asp Arg Val Gly Val Gly Trp Ile Arg Asn Ser Cys
                85                  90                  95

Arg Ala Cys Asp His Cys Leu Gln Gly Glu Glu Asn Ile Cys Arg Glu
            100                 105                 110

Gly Tyr Thr Gly Leu Ile Val Gly His His Gly Gly Phe Ala Asp Arg
        115                 120                 125

Val Arg Val Pro Ala Asp Phe Thr Tyr Lys Ile Pro Asp Ala Leu Asp
    130                 135                 140

Ser Ala Ser Ala Ala Pro Leu Leu Cys Ala Gly Ile Thr Val Tyr Thr
145                 150                 155                 160

Pro Leu Arg Thr Tyr Ile Lys His Pro Gly Met Lys Val Gly Val Met
                165                 170                 175

Gly Ile Gly Gly Leu Gly His Leu Ala Ile Lys Phe Ala Arg Ala Met
            180                 185                 190

Gly Ala Glu Val Thr Ala Phe Ser Thr Ser Pro Asn Lys Glu Ala Gln
        195                 200                 205

Ala Lys Glu Phe Gly Ala His His Phe Gln Gln Trp Gly Thr Ala Glu
    210                 215                 220

Glu Met Lys Ala Val Ala Gly Asn Phe Asp Leu Val Leu Ser Thr Ile
225                 230                 235                 240

Ser Ala Glu Thr Asp Trp Asp Ala Ala Phe Ser Leu Leu Ala Asn Asn
                245                 250                 255

Gly Val Leu Cys Phe Val Gly Ile Pro Val Ser Ser Leu Asn Val Pro
            260                 265                 270

Leu Ile Pro Leu Ile Phe Gly Gln Lys Ser Val Val Gly Ser Val Val
        275                 280                 285

Gly Gly Arg Arg Phe Met Ala Glu Met Leu Glu Phe Ala Ala Val Asn
    290                 295                 300

Gln Ile Lys Pro Met Ile Glu Thr Met Pro Leu Ser Gln Val Asn Glu
305                 310                 315                 320

Ala Met Asp Lys Val Ala Ala Asn Lys Ala Arg Tyr Arg Ile Val Leu
                325                 330                 335

Leu Ser Glu


<210> SEQ ID NO 55
<211> LENGTH: 101
<212> TYPE: DNA
<213> ORGANISM: Artificial sequence
<220> FEATURE:
<223> OTHER INFORMATION: Synthetic PCR template sequence for intergenic
      sequence
```

<400> SEQUENCE: 55
gtaatttttg gggatcaatt cgagctcttt aaaccaagat tagaaaatcc atttcattaa 60
cgtaaaccaa cataattagg agaaattaat tacaatgcaa t 101

<210> SEQ ID NO 56
<211> LENGTH: 316
<212> TYPE: DNA
<213> ORGANISM: Artificial sequence
<220> FEATURE:
<223> OTHER INFORMATION: Synthetic PCR template sequence for intergenic sequence

<400> SEQUENCE: 56
gtaatttttg gggatcaatt cgagctcgaa tgtaaacttt cactaattta gtgggaaaat 60
ctacggcaaa ataagttata aaataacaga taaagccgtt tttactaaca ataattgtta 120
atagttgaaa gtctatattt atcttagatt cttcactatt aactaacatt taaaaatcaa 180
tttaattcct tgcctagttt cttttaaaga aatttaattc cgagggctag gcaagataaa 240
atccaaaatt gaccagcgta ttttaaacgt tgactctgat tgtgtaacag gagaattcct 300
aaaaaaagct atgcaa 316

<210> SEQ ID NO 57
<211> LENGTH: 220
<212> TYPE: DNA
<213> ORGANISM: Artificial sequence
<220> FEATURE:
<223> OTHER INFORMATION: Synthetic PCR template sequence for intergenic sequence

<400> SEQUENCE: 57
gtaatttttg gggatcaatt cgagctcatc tcctgatcca cacccggaca tctccatagt 60
ctgggccagt ctgaggactg gtggatcagg gccgtgaatt tacagtattt cagttaccgc 120
tctatcctta tccttatccg ctcaagagca gagagttaat aggatccgct aggatatcgg 180
taccgtattt tggatgataa ggaggatcag ccttatgcaa 220

<210> SEQ ID NO 58
<211> LENGTH: 39
<212> TYPE: DNA
<213> ORGANISM: Artificial sequence
<220> FEATURE:
<223> OTHER INFORMATION: Synthetic PCR primer sequence.

<400> SEQUENCE: 58
tttggggatc aattcgagct ctttaaacca agattagaa 39

<210> SEQ ID NO 59
<211> LENGTH: 39
<212> TYPE: DNA
<213> ORGANISM: Artificial sequence
<220> FEATURE:
<223> OTHER INFORMATION: Synthetic PCR primer sequence.

<400> SEQUENCE: 59
gtatttacag caacaaccat tgtaattaat ttctcctaa 39

<210> SEQ ID NO 60
<211> LENGTH: 40
<212> TYPE: DNA
<213> ORGANISM: Artificial sequence
<220> FEATURE:

<223> OTHER INFORMATION: Synthetic PCR primer sequence.

<400> SEQUENCE: 60
ttggggatca attcgagctc gaatgtaaac tttcactaat 40

<210> SEQ ID NO 61
<211> LENGTH: 51
<212> TYPE: DNA
<213> ORGANISM: Artificial sequence
<220> FEATURE:
<223> OTHER INFORMATION: Synthetic PCR primer sequence.

<400> SEQUENCE: 61
gtatttacag caacaaccat agcttttttt aggaattctc ctgttacaca a 51

<210> SEQ ID NO 62
<211> LENGTH: 35
<212> TYPE: DNA
<213> ORGANISM: Artificial sequence
<220> FEATURE:
<223> OTHER INFORMATION: Synthetic PCR primer sequence.

<400> SEQUENCE: 62
ggatcaattc gagctcatct cctgatccac acccg 35

<210> SEQ ID NO 63
<211> LENGTH: 46
<212> TYPE: DNA
<213> ORGANISM: Artificial sequence
<220> FEATURE:
<223> OTHER INFORMATION: Synthetic PCR primer sequence.

<400> SEQUENCE: 63
gtatttacag caacaaccat aaggctgatc ctccttatca tccaaa 46

<210> SEQ ID NO 64
<211> LENGTH: 40
<212> TYPE: DNA
<213> ORGANISM: Artificial sequence
<220> FEATURE:
<223> OTHER INFORMATION: Synthetic PCR primer sequence.

<400> SEQUENCE: 64
ttaggagaaa ttaattacaa tggttgttgc tgtaaatacc 40

<210> SEQ ID NO 65
<211> LENGTH: 40
<212> TYPE: DNA
<213> ORGANISM: Artificial sequence
<220> FEATURE:
<223> OTHER INFORMATION: Synthetic PCR primer sequence.

<400> SEQUENCE: 65
gagaattcct aaaaaaagct atggttgttg ctgtaaatac 40

<210> SEQ ID NO 66
<211> LENGTH: 40
<212> TYPE: DNA
<213> ORGANISM: Artificial sequence
<220> FEATURE:
<223> OTHER INFORMATION: Synthetic PCR primer sequence.

<400> SEQUENCE: 66
tgataaggag gatcagcctt atggttgttg ctgtaaatac 40

<210> SEQ ID NO 67
<211> LENGTH: 40
<212> TYPE: DNA
<213> ORGANISM: Artificial sequence
<220> FEATURE:
<223> OTHER INFORMATION: Synthetic PCR primer sequence.

<400> SEQUENCE: 67
ggtcgggatg aaacttgctg agctcttatt taactgttgc 40

<210> SEQ ID NO 68
<211> LENGTH: 17660
<212> TYPE: DNA
<213> ORGANISM: Artificial sequence
<220> FEATURE:
<223> OTHER INFORMATION: Synthetic plasmid derived from p6.8; contains pdc, adh, and nirA genes in one operon.

<400> SEQUENCE: 68
tcgacaatta ataacttctt cctgtacggg cgaatggcca tttgctccta actaactccg 60
tactgctttg cggaacgagc gtagcgaact ctccgaatta ctaagccttc atccctgata 120
gatgcaaaaa acgaattaaa attatgtgta aaaagaaaat gtgtctttat ttagtagtca 180
aagttacaaa atattaagaa tcaaattaat aatgtattgg gcagttaagt atataagtct 240
ttaaatattt atttgtattc aatatattaa ggaggatcag ccttatgaat tcttataccg 300
tgggtactta tttagccgaa cgcttagtgc aaattggttt aaaacatcat tttgccgtgg 360
ctggggacta taatttagtg ttattggata acttattatt aaataaaaac atggaacaag 420
tgtattgttg taatgaatta aattgtggtt tttctgctga aggttatgct agagctaaag 480
gtgcagctgc tgctgttgtt acttattctg tgggtgcttt atctgctttt gatgctattg 540
gtggtgctta tgccgaaaat ttacccgtga ttttaatttc tggtgcccct aataataatg 600
atcatgccgc tggacatgtt ttacatcatg ccttaggtaa aaccgattat cattatcaat 660
tagaaatggc caaaaatatt actgctgctg ccgaagctat ttatactcct gaagaagccc 720
ctgccaaaat tgatcatgtg attaaaaccg ccttacgcga aaaaaaaccc gtgtatttag 780
aaattgcctg taatattgct tctatgcctt gtgctgctcc tgggcctgct tctgctttat 840
ttaatgatga agcctctgat gaagctagtt taaatgctgc cgtggaagaa accttaaaat 900
ttattgccaa tcgcgataaa gttgccgtgt tagttggttc taaattaaga gctgctggtg 960
ctgaagaagc tgctgttaaa tttgctgatg ctttaggtgg tgcagttgct actatggctg 1020
ctgccaaatc tttttttccc gaagaaaatc cccattatat tggaactagt tggggagaag 1080
tttcttatcc tggtgtggaa aaaactatga aagaagccga cgctgttatt gctttagccc 1140
ctgtgtttaa tgattattct accactggtt ggactgatat tcccgatccc aaaaaattag 1200
ttttagccga acctcgttct gttgttgtta atggtgttcg ctttccctct gtgcatttaa 1260
aagattattt aacccgctta gcccaaaaag tttctaaaaa aactggtgcc ttagattttt 1320
ttaaatcttt aaatgcgggt gaattaaaaa aagctgctcc tgctgatcct tctgctcctt 1380
tagttaatgc tgaaattgcc cgtcaagttg aagccttatt aacccctaat actaccgtta 1440
ttgccgaaac tggtgattct tggtttaatg cccaacgcat gaaattacct aatggtgccc 1500
gtgttgaata tgaaatgcaa tggggtcata ttggttggtc tgtacctgct gcttttggtt 1560
atgctgttgg tgctcctgaa cgtcgtaata ttttaatggt gggtgatggt tcttttcaat 1620
taactgccca agaagttgcc caaatggttc gcttaaaatt acccgttatt atttttttaa 1680
taaataatta tggttatacc attgaagtga tgattcatga tgggccatat aataatatta 1740

```
aaaattggga ttatgcgggt ttaatggaag tgtttaatgg taatggtggt tatgattctg   1800
gtgctggtaa aggtttaaaa gccaaaactg gtggtgaatt agctgaagct attaaagttg   1860
ccttagccaa tactgatggg ccaaccttaa ttgaatgttt tattggtcgc gaagattgta   1920
ccgaagaatt agttaaatgg ggtaaacgtg ttgctgctgc taattctcgc aaacccgtga   1980
ataaattatt gtaatttaaa ccaagattag aaaatccatt tcattaacgt aaaccaacat   2040
aattaggagg atcagcacaa tgagtgaaac taaatttaaa gcctatgccg taatgaatcc   2100
tggtgaaaaa ttacaaccct gggaatatga acctgctcct ttacaggtag atgaaattga   2160
agtaagagtt actcacaatg gtttatgtca cactgactta cacatgagag ataatgactg   2220
gaatgttagt gagttcccct tagtagcagg tcatgaagtt gttggtgaag taaccgctgt   2280
tggtgaaaaa gtaaccagtc gtaaaaaagg tgatagagtt ggtgtaggtt ggattcgtaa   2340
ttcttgtcgc gcttgtgacc attgtttaca aggagaagag aacatttgta gagagggtta   2400
tactggttta attgttggtc atcacggtgg atttgctgat cgtgtacgtg tacctgctga   2460
cttcacttat aaaattcctg atgctttaga tagtgcatct gctgctcctt tattatgtgc   2520
cggtattacc gtttacactc ctttaagaac ctacattaaa catcccggta tgaaagtagg   2580
tgttatgggt attggaggat taggacattt agctattaaa tttgctcgtg caatgggagc   2640
agaagttact gcctttagta ccagtcctaa taaagaagcc caagccaaag aatttggtgc   2700
tcatcatttc caacaatggg gtactgctga agaaatgaaa gctgttgccg gtaattttga   2760
tttagtttta tctaccatct ctgctgaaac tgactgggat gctgccttct ctttattagc   2820
aaataacggt gttttatgtt tcgtaggtat tcccgttagt tctttaaatg ttcctttaat   2880
tcctttaatt ttcggacaaa aatctgttgt aggttctgta gttggaggaa gaagattcat   2940
ggcagaaatg ttagagttcg ccgctgtaaa tcagattaaa cctatgatcg aaactatgcc   3000
cttatctcaa gtaaatgaag ctatggataa agttgccgcc aataaagcca gatatagaat   3060
tgtattatta tctgaataat tttggggat caattcgagc tctatattaa ggaggatcag   3120
ccttatggtt gttgctgtaa ataccaccac cacaaaaaaa gtgaaactaa ataaaattga   3180
aaaagtaaaa gaagcaaaac acggtttgga tgttaaggaa gaaatagaaa agtttgctca   3240
aatgggttgg gaagcaatgg atgaagatga cctcattgtt cgtttaaagt ggttggggat   3300
ttttttcgc ccagtaactc cggggaaatt tatgcttagg ttacgcactc ctaatggtat   3360
tctcaacagc caacaattac gcacttttgc ggaaattatt gaacgttatg gggaggatgg   3420
aaaagctgat attactaccc gtcaaaatat tcaattaagg ggagttcatt tacaggatat   3480
accagatatt tttcgtaaat tggaagcggt gggcatgaca tcgattcagt caggaatgga   3540
taatgtgcgt aatttaacgg gttctcctgt tgctggaatt gaccctcatg agttaattga   3600
caccagagaa ttaaatcaaa aattacagga tttgattact aaccatggac agggtagtta   3660
tgagtttagt agtctccctc gtaaattaaa cattgcgatc gaaggtagta aagataattc   3720
tattcacgct gaattgaatg atatagcatt tttacccgcc tataaagatg gtgaattagg   3780
ttttaatgtt gtggtggggg gttacttatc cgctcaaagg tgcgcagagt ctattccgat   3840
ggatgtttgg gtaagaccta atgaagaagt attgaaatta tgcgcggcta ttcttagtgt   3900
ttatagtgag tgtgcattgg aagaaggttt gagggaaaat agagcaaaag cccgtttaat   3960
gtggttaatt gataaatggg gtatgaatcg ttttcgcatt gaagtggaga aaaaactagg   4020
acaatcctta caatttgccg ccccgaaaga tgaaattacc ttagaaaaaa gagatcattt   4080
```

```
aggggttaat cctcaaaagc aagagggtta tagttatatc ggtattcata ttcctgttgg   4140
gcatttagat gcggagggtt tatttgaaat tgctcgttta gcggatgttt atggtaacgg   4200
agaaattcgg gcaacagtgg aacaaaattt tattattcct tttgtagcca atgacagggt   4260
agaagcattt cttgctgaac caattttaga acgctatcga gttaatcctt cacctttaag   4320
ccgttctgta atttcgtgta caggggctcg ttattgtaat tttgccttgg tagaaactaa   4380
gcagagagcg gtgaaactag ccacagaatt agataatgaa ctaaatattc cctctaaagt   4440
cagaattcat tggacaggtt gtcctaactc ttgcggacag gctcaagcag ggacattgg    4500
cttaatgggt actaaagcga aaaaagatgg gcaggtggta gagggtgtta acttatttat   4560
ggggggaaaa gtgggcaagg atgcacattt agggagtctc aaacaaaaaa gtattccctg   4620
tgatgatttg aaatccgttt tgaaggaaat tttaattaat gaatttgggg caacagttaa   4680
ataactagat ctacttctaa actgaaacaa atttgagggt aggcttcatt gtctgccctt   4740
atttttttat ttaggaaaag tgaacagact aaagagtgtt ggctctattg ctttgagtat   4800
gtaaattagg cgttgctgaa ttaaggtatg atttttgacc cctgcaggat catcttgctg   4860
aaaaactcga gaagttccta ttctctagaa agtataggaa cttcccaata tcttgtcata   4920
catacttatt tgcctcacta ttagccctat atgtctctat tgtatttttc tttttctcct   4980
attcctagat cttgtaatga atcattactc tctgaaatat agctactaat tttatggttg   5040
tttgtaaaat atattaacaa atgaacaata aatcatattt tgtgttaatc taattattag   5100
acaactactg aatttatatt cagatattca cagataggag aattttgagc atgccacaat   5160
ttggtatatt atgtaaaaca ccacctaagg tgcttgttcg tcagtttgtg gaaaggtttg   5220
aaagaccttc aggtgagaaa atagcattat gtgctgctga actaacctat ttatgttgga   5280
tgattacaca taacggaaca gcaatcaaga gagccacatt catgagctat aatactatca   5340
taagcaattc gctgagtttc gatattgtca ataaatcact ccagtttaaa tacaagacgc   5400
aaaaagcaac aattctggaa gcctcattaa agaaattgat tcctgcttgg gaatttacaa   5460
ttattcctta ctatggacaa aaacatcaat ctgatatcac tgatattgta agtagtttgc   5520
aattacagtt cgaatcatcg gaagaagcag ataagggaaa tagccacagt aaaaaaatgc   5580
ttaaagcact tctaagtgag ggtgaaagca tctgggagat cactgagaaa atactaaatt   5640
cgtttgagta tacttcgaga tttacaaaaa caaaaacttt ataccaattc ctcttcctag   5700
ctactttcat caattgtgga agattcagcg atattaagaa cgttgatccg aaatcattta   5760
aattagtcca aaataagtat ctgggagtaa taatccagtg tttagtgaca gagacaaaga   5820
caagcgttag taggcacata tacttcttta gcgcaagggg taggatcgat ccacttgtat   5880
atttggatga atttttgagg aattctgaac cagtcctaaa acgagtaaat aggaccggca   5940
attcttcaag caataaacag gaataccaat tattaaaaga taacttagtc agatcgtaca   6000
ataaagcttt gaagaaaaat gcgccttatt caatctttgc tataaaaaat ggcccaaaat   6060
ctcacattgg aagacatttg atgacctcat ttctttcaat gaagggccta acggagttga   6120
ctaatgttgt gggaaattgg agcgataagc gtgcttctgc cgtggccagg acaacgtata   6180
ctcatcagat aacagcaata cctgatcact acttcgcact agtttctcgg tactatgcat   6240
atgatccaat atcaaaggaa atgatagcat tgaaggatga gactaatcca attgaggagt   6300
ggcagcatat agaacagcta aagggtagtg ctgaaggaag catacgatac cccgcatgga   6360
atgggataat atcacaggag gtactagact acctttcatc ctacataaat agacgcatat   6420
aacgcaaaaa accccgcttc ggcggggttt tttcgcggcc gcattctgtg aattgattag   6480
```

```
atttgaggtt ttttaagagg ttgattacct tgcctccaaa aaatcataac acactaatgc   6540
tctatatgaa agggctttag acccataggt ttttgagaaa aaaacttgct aactctcgga   6600
caatgtcagc ataactaaag tcaattcttt tcgtacttta taattgtcta taatttaata   6660
tacaactgtt ctgaaactag tttttctcta cattccttag ttttatctga gtaaggttgc   6720
ttgtaactta acttcggttg ggcctaaaaa tatccgatta ggagcaggtg tcagacttta   6780
attaattatt aattattaat tgcttattgc caaccctcgg cgacaccact ttttcatcag   6840
ccccagataa agattgatgt tttagttttg tttcttttta tcccctaatt caactaatac   6900
aagtaaaact aaggttgttt atcaaaaatg atggttgatg tttgggtaaa ttttaagata   6960
ttatgaaaag aaaatgaata aaaaatgaaa aatccatatg tctttaaaag agaaaaccca   7020
aagtttattc gctaatgctt ttggataccc tgccacccat accattcaag ctcctggtcg   7080
tgttaattta attggtgagc atactgatta taatgatggt ttcgtattac cctgtgctat   7140
cgactatcaa actgtaattt cttgtgctcc tagagacgac cgtaaagttc gtgttatggc   7200
agccgattat gaaaaccaat tagatgaatt ttctttagat gcccccattg tagctcacga   7260
aaactatcag tgggcaaatt atgtacgtgg tgttgttaaa cacttacaat taagaaacaa   7320
ttcttttggt ggtgtagaca tggtaatcag tggtaacgtt ccccaaggag caggtttaag   7380
ttctagtgct tctttagagg tagctgttgg aaccgtttta caacagttat atcatttacc   7440
tttagatggt gcccaaatcg cattaaatgg tcaagaggcc gagaatcaat tcgttggttg   7500
taattgtggt attatggatc aattaatctc tgctttaggt aaaaaagacc atgctttatt   7560
aatcgattgt cgttctttag gtactaaagc cgtttctatg cctaaaggtg ttgcagtagt   7620
tatcatcaac tctaatttta aacgtacttt agtaggaagt gaatacaaca ctcgtcgtga   7680
acaatgtgaa actggtgccc gtttttccca acaacctgct ttaagagatg ttaccattga   7740
agaatttaat gccgttgccc atgaattaga tcctatcgtt gctaaacgtg ttagacatat   7800
tttaaccgaa aacgccagaa ctgtagaagc cgcaagtgca ttagaacaag gagacttaaa   7860
aagaatggga gaattaatgg ccgaatctca cgcttctatg agagatgatt ttgaaattac   7920
cgttcctcaa attgacacct tagtagaaat cgttaaagct gtaatcggtg acaaaggtgg   7980
tgttagaatg actggtggag gttttggtgg ttgtattgtt gctttaattc ctgaagagtt   8040
agttcccgca gtacaacaag ccgttgcaga acaatacgaa gcaaaaactg gaattaaaga   8100
aactttttac gtttgtaaac ctagtcaggg tgctggtcaa tgttaactag cataacccct   8160
tggggcctct aaacgggtct tgaggggttt tttgctcgat cgagcgctcg ttccgcaaag   8220
cggtacggag ttagttaggg gctaatgggc attctcccgt acaggaaaga gttagaagtt   8280
attaattatc aacaattctc ctttgcctag tgcatcgtta ccttttttaat taaaacataa   8340
ggaaaactaa taatcgtaat aatttaacct caaagtgtaa agaaatgtga aattctgact   8400
tttataacgt taaagaggga aaaattagca gtttaaaata cctagagaat agtctggggt   8460
aagcatagag aattagatta gttaagttaa tcaaattcag aaaaaataat aatcgtaaat   8520
agttaatctg ggtgtataga aaatgatccc cttcatgata agatttaaac tcgaaaagca   8580
aaagccaaaa aactaacttc cattaaaaga agttgttaca tataacgcta taaagaaaat   8640
ttatatattt ggaggatacc aaccatgtct catattcaac gtgaaactag ttgttctcgc   8700
cctcgtttaa attctaatat ggatgccgat ttatatggtt ataaatgggc tcgtgataat   8760
gttggtcaat ctggtgctac tatttatcgt ttatatggta aacctgatgc tcctgaatta   8820
```

```
ttcttgaaac atggtaaagg ttctgttgct aatgatgtta ctgatgaaat ggttcgttta   8880
aactggttga ctgaatttat gcctttacct actattaaac attttattcg tactcccgat   8940
gatgcttggt tattaactac tgctattcct ggtaaaactg cttttcaagt tttagaagaa   9000
tatcctgatt ctggtgaaaa tattgttgat gctttagctg tttttttacg tcgtttacat   9060
tctattcccg tttgtaattg tccttttaat tctgatcgtg tttttcgttt agctcaagct   9120
caatctcgta tgaataatgg tttagttgat gcttctgatt ttgatgatga acgtaatggt   9180
tggcctgttg aacaagtttg gaaagaaatg cacaaattgt taccttttc tcctgattct   9240
gttgttactc atggtgattt ttctttagat aatttgatct ttgatgaagg taaattgatt   9300
ggttgtattg atgttggtcg tgttggtatt gctgatcgtt atcaagattt agctatttta   9360
tggaattgtt taggtgaatt ttctccttct ttacagaaac gtttatttca gaaatatggt   9420
attgataatc ctgatatgaa caagttacaa tttcatttaa tgttggacga gttcttttaa   9480
gaattaattc atgaccaaaa tcccttaacg tgagttttcg ttccactgag cgtcagaccc   9540
cgtagaaaag atcaaaggat cttcttgaga tcctttttt ctgcgcgtaa tctgctgcta   9600
tttaaattac gtacacgtgt tattactttg ttaacgagaa gttcctattc tctagaaagt   9660
ataggaactt caattgtctt aattaactgg gcctcatggg ccttccgctc actgcccgct   9720
ttccagtcgg gaaacctgtc gtgccagctc tgcagatgac ggtgaaaacc tctgacacat   9780
gcagctcccg gagacggtca cagcttgtct gtaagcggat gccgggagca gacaagcccg   9840
tcagggcgcg tcagcgggtg ttggcgggtg tcggggcgca gccatgaccc agtcacgtag   9900
cgatagcgga gtgtatactg gcttaactat gcggcatcag agcagattgt actgagagtg   9960
caccatatgc ggtgtgaaat accgcacaga tgcgtaagga gaaaataccg catcaggcgc  10020
tcttccgctt cctcgctcac tgactcgctg cgctcggtcg ttcggctgcg gcgagcggta  10080
tcagctcact caaaggcggt aatacggtta tccacagaat caggggataa cgcaggaaag  10140
aacatgtgag caaaaggcca gcaaaaggcc aggaaccgta aaaaggccgc gttgctggcg  10200
tttttccata ggctccgccc ccctgacgag catcacaaaa atcgacgctc aagtcagagg  10260
tggcgaaacc cgacaggact ataaagatac caggcgtttc cccctggaag ctccctcgtg  10320
cgctctcctg ttccgaccct gccgcttacc ggatacctgt ccgcctttct cccttcggga  10380
agcgtggcgc tttctcatag ctcacgctgt aggtatctca gttcggtgta ggtcgttcgc  10440
tccaagctgg gctgtgtgca cgaacccccc gttcagcccg accgctgcgc cttatccggt  10500
aactatcgtc ttgagtccaa cccggtaaga cacgacttat cgccactggc agcagccact  10560
ggtaacagga ttagcagagc gaggtatgta ggcggtgcta cagagttctt gaagtggtgg  10620
cctaactacg gctacactag aaggacagta tttggtatct gcgctctgct gaagccagtt  10680
accttcggaa aaagagttgg tagctcttga tccggcaaac aaaccaccgc tggtagcggt  10740
ggtttttttg tttgcaagca gcagattacg cgcagaaaaa aaggatctca agaagatcct  10800
ttgatctttt ctactgcaga agcttgttag acaccctgtc atgtatttta tattatttat  10860
ttcaccatac ggattaagtg aaacctaatg aaaatagtac tttcggagct ttaactttaa  10920
tgaaggtatg ttttttata gacatcgatg tctggtttaa caataggaaa aagtagctaa  10980
aactcccatg aattaaagaa ataacaaggt gtctaacaac ctgttattaa gaatgttaga  11040
aaagacttaa catttgtgtt gagtttttat agacattggt gtctagacat acggtagata  11100
aggtttgctc aaaaataaaa taaaaaaaga ttggactaaa aacatttaa tttagtacaa  11160
tttaattagt tattttttcg tctcaaattt tgctttgttg agcagaaatt tagataaaaa  11220
```

```
aatccccgtg atcagattac aatgtcgttc attgtacgat gtgtcgaaaa atctttacga  11280
cactctaaac tgaccacacg gggaaaaag aaaactgaac taataacatc atgatactcg  11340
gaaaacctag caattctcaa cccctaaaca aaagaaactt ccaaaaccct gaccatataa  11400
aggagtggca acaatcagca atcagtcaag atttgatagc agaaaatctt gtatcggttg  11460
ctaatggttt tgatgtacta tttatcggca ataaataccg aactaacacg ggtgttctgt  11520
cacggcacat attaaactcc tattctcatt tagaagatgg tggttcgtat ggtagaacat  11580
ttgacccatt taccaataaa gaaatgcagt gggttcaatt taaaccgaat agaccaagaa  11640
aaggttctac tggtaaggta atcaaatatg aatcgccaaa aggtgaacct acaagagttc  11700
taatgccgtt tgtgcctatg aaaatatggc aacggattag cgataagttc ggagtaccga  11760
ttaatccgaa aaaagatact cacttttggg aatgggtaaa gaataatcca tcgataccga  11820
ttgccattac agaaggaaat aaaaaagcta attgcctatt atcctatggc tatcctgcta  11880
ttgcctttgt aggcatttgg aacggattag agaaaataaa tgatttctcg aaggaaaagc  11940
agttaaaaga ggatttgaaa tggttgttat ccaacggcaa ccgaaatatt aatatcatct  12000
ttgaccaaga ccagaaacaa aaaactgtaa ttaatgtaaa caaagctatt ttcgctttat  12060
cttctctaat aagtagaaat ggtcataaag ttaatattgt gcaatggttg ccgtcaaaag  12120
gtaaaggaat agatgattat ttggtagctt tacctttga gaaaagagaa aatcatttag  12180
acaacttaat taaaattgca ccatcattta atttttggtc aactaaatac ttattcaagt  12240
gtcgtaaacc agatttaacc gtaaattgcc gttatttgag cgatgcagta aaagaattac  12300
ctcaagagga tatagcatta atagcacctc acggcacggg taaaacttca ttagtagcta  12360
ctcacgttaa gaatcggagt tatcacggaa ggaaaactat ttcattggtg catcttgaaa  12420
gtttagccaa agctaatggc aacgcacttg gattatatta ccgaaccgaa aataatattg  12480
aaaagcaata tcttggattt agcttatgtg tagatagttg ccgtgataag attaacggca  12540
ttacaactga tattatttca ggtcaagatt attgcctttt cattgatgaa attgaccaag  12600
taattccaca catccttaac agtgaaactg aagtaagtaa gtatagatgc accatcattg  12660
acactttttc tgaactggtg agaaatgctg aacaggtcat tattgctgat gctgatttat  12720
ccgatgtgac gattgaccta atagaaaaca tcagaggtaa aaaactatat gtaatcaaga  12780
atgaatatca gtatcaggga atgactttta acgccgttgg ttcaccatta gaaatgatgg  12840
caatgatggg aaaatcggtg tcagaaggca agaaattatt tattaacacc acatcccaaa  12900
aggcaaaaag taagtacggc acaatcgctc ttgagtctta tatttttggt ctaaataaag  12960
aagcaaagat attaagaata gactctgaaa ccactaaaaa ccctgaacat ccagcctata  13020
aaatcattga ccaagactta aataatatcc tcaaagatta tgattatgtc attgcctcac  13080
cttgccttca aacaggtgtc agtattacct taaaagggca ttttgaccag caatttaact  13140
tttccagtgg aaacattaca cctcattgct ttttacagca aatgtggcgg ttgagggatg  13200
cagaaattga aagattctat tatgtgccga actcatctaa cctcaatctc attgggaata  13260
agtcaagttc accatcagac cttctaaaga gcaataacaa gatggcaacg gcaacggtta  13320
accttttggg tagaatcgac tccgaatatt ccctagagta tgaatcgcac ggcatttggc  13380
ttgagacgtg ggcaaaatta tcagcacggc ataacagttc aatgcgttgt tactctgaaa  13440
ttcttaccta tctaattacg tctcaagggc ataaattaaa tatcaacatt ccctcacctc  13500
ttgcagatat taagaagcta aatgatgagg taagtagtaa cagggaaaag gtaaaaaatg  13560
```

```
agagatactc tcagaggtta aactcaccag atattaacga tgcagaagct accatactcg  13620
aatctaaaga gcaaaaaatc ggattgactc tcaatgagag atgcacccta gaaaagcata  13680
aagttaagaa gcggtatggg aatgtaaaga tggatattct cacctttgat gatgatggac  13740
tataccccaa actcagacta ttttattacc tcaccatcgg taaacctcat ctcaaggcta  13800
atgacagaaa agctattgcc aaaatgggca atgacaataa aggcaagatt ctatcaaaag  13860
acttagttaa taaaacttac tccgctcgtg tgaaggtctt agagattctt aaactaactg  13920
actttatcga caatcttaga gatgaactct taataactcc caataatcca gctatcaccg  13980
attttaataa tcttctgcta agagctaaga aggatttaag agtattagga gtcaacatcg  14040
gaaaatatcc aatggccaac attaatgccg tacttactct cattggtcac aaactttctg  14100
taatgagaga tgagttcgga aaagagaaaa ggataaaagt agatggtaaa tcataccgat  14160
gttatcaact tgaaacatta ccagatttta ccaatgatac tcttgactac tggttagaaa  14220
atgatagcca aaaagaagta acagcaacag aaaattactc cgaaaatttt aacccttcaa  14280
atagctacaa tccagacagt aagacacttt cagagggtgc aaatttccta tatataaata  14340
aagaagaatt gcatccaaat aaattgcacc tagaaataaa agaaggtgct gaactttttt  14400
tattcggggt aaaggtgatt gtgaaaggaa tcttggacgg ggcagtaact atattctcta  14460
tgggtcaaga atacgattta tccctcaatg aactagaggg gatgttaaca tcatgaactt  14520
tacaagaatc tttttaaagg gcgatcgcac catgttaaat gatggtacat ttgttcagat  14580
atttgatatt taccatgacc acgcattggg agtgaccctt gaccttaaga cagaaaaaat  14640
tatttccgat gatgttaggg taattactgt caaagactta ttgttcgatg gcacttataa  14700
aggggtaaaa tcttttatgc ccgataatgc ccgataatgc ccgattgatg ctacaaaatc  14760
ccataatcat aagcgataat cccctaatag cttgtaattc ttgaaccgta gcgattttag  14820
agtattccaa aaagaagaaa taaacaccgc aaaatgtcgt atttcacata tataaaccaa  14880
ggtttttgc cctaaaatct ttatgtttgt agtgtgatgt tgggtcaaaa tggtcagaaa  14940
agttgcaagg tttttatgga tgcttacgcg cgcgaggggt aagcatcccc aaatagttac  15000
tttatcctag tccatgccca tttattgccg tcccgttcgg ctttaaaaaa gtgccaaaac  15060
tcacaaggtg caataaaaag ttctgtacct ttcgcaaccc tagataatct ttcaacagtt  15120
actttttttc ctattatctc ggtacaaagt ttggctagtt tctcttttcc ctctttttca  15180
atcaagcctt cttgtatgcc caactcattg attaatctct ctatttttac cattatttcc  15240
cgttcaggta gtttatcccc taaatcttca tcggggggca atgtagggca ttctgaaggg  15300
gctttttctt ctgtctggac attatctaat attgaagtaa ccaaactatc ttcagttttt  15360
tctattccta ttaattcata ttcggttact gtatccgtat caatatccga ataactatct  15420
ttatccgtat tagctattcg gttaagttta tccgttaact cagaaacaag actatatagc  15480
ggttttagct tttcttctat cctgttatct aatacggata agtttatacg gttatcatta  15540
tccgtattag tatcattggg ctttttttggt agttctaccc cctcataaac cgcttttatt  15600
cccaattcca acagactgat aacagtatcc tttataatgg gttttttgct gatatggtga  15660
acttttgccc cttccatcat tgcgatactt tctatctcac tcatcaactt atcgcttaag  15720
tgaatctcgt atctgtttaa tcccttactg gttttattca tatccgttta ctttattcgg  15780
ttaacaattc tattttatac gaataaaata ttatacggtt aactttatac gtttaactat  15840
tttatctata cggataacag taataagtta ttcgtattag ttatacgttt acttttatcc  15900
aaataaaatt agtgcattta aactaaaaga atgattttat cggagttgat agcattggat  15960
```

```
taacctaaag atgtttataa gctatatctg ataagtattt aaggttattt tgttattctg  16020

tttattgaca ttatcagaat aaaagaatag aatataattg ttgagagata agaggtttaa  16080

gtgattatgg ttaagaagtt agttggttat gtcagggtca gtagtgaatc gcaagaggat  16140

aacactagct tacagaatca gatagagaga attgaagcat attgtatggc ttttggttat  16200

gagttggtaa aaatattcaa agaggttgcc actggtacaa aagcagatat tgaaacccgt  16260

cctattttta atgaagctat agaatacttg aaacaggata atgctaatgg aattattgcc  16320

ttgaagctag accgaatcgc acggaatgct ttagatgtat tgcgtttggt tcgtgaaacc  16380

ttagaaccac aaaataaaat gttagtgtta ctagatattc aggtagatac ttcgacacct  16440

tcaggaaaaa tgattttaac tgtaatgagt gccgttgctg aactcgaaag agacatgatc  16500

tatgatcgca ctcagggggg tagaaagact aaagcccaaa agggcgggta tgcctacggg  16560

aaacctaaat ttggctataa gactgaagaa aaggaactaa aagaagattc agcacaacag  16620

gaaactatta aactaattaa gagacaccgt aggtcaggga aaagctacca gaaaatagct  16680

gattatctca atgcccaaag tattcccact aaacaaggta agaaatggag ttctagcgtc  16740

gtctatcgaa tctgtcagga aaaagctggt taagtctgtt tatagatatt tagaatttat  16800

tgaataaaaa tagtatgaac aataaatatt tatggactaa ccacgctcgg aaacgtttaa  16860

ctgaacgatg ggaaataaaa gaatcatggg ttattgatac catcgaaaat cctgaacgtt  16920

cagaatttat tgttgatgag tcaggggaaa aatatcatta ctataaaaga atagctaagt  16980

ttaagaatag agtgttagaa gtgataactt ctgccaactc aacacccaca agaataataa  17040

ccttttactt taaccgtaac atgaggaaaa atttatgatt gttacttacg ataatgaagt  17100

tgacgcaatt tattttaagt taacggaaaa taaaattgat agcaccgaac ctcaaacaga  17160

caggattatc attgattacg atgaaagtaa taatattgtt ggcattgagg tattagattt  17220

taattatctt gtcaagaaag gtttaaccgt tgctgattta cctttttctg aagatgaaag  17280

attaacagct tctcaatatt ttaattttcc tgttgctatc taatccagaa ggggcaataa  17340

tccccttctt tcatcgagtt agacttaata tcacaaaagt cattttcatt ttaccgtttc  17400

ttttccacag cgtccgtacg cccctcgtta aatctcaaaa ccgacaattt atgatgttta  17460

taaaaagtta ctcactttaa taagtattta tactcattaa agggttattc tttttttgta  17520

gcctgatagg ttgggaagga atatttcaga ttatcagatt tgttgaatat ttttcgtcag  17580

atacgcaaac cttacaaaca taattaacaa ctgaaactat tgatatgtct aggttttagc  17640

tctatcacag gttggatctg                                              17660
```

<210> SEQ ID NO 69
<211> LENGTH: 20
<212> TYPE: DNA
<213> ORGANISM: Artificial sequence
<220> FEATURE:
<223> OTHER INFORMATION: Synthetic PCR forward primer sequence targeting genomic enolase.

<400> SEQUENCE: 69

```
ccggcacaga tgtagcttta                                                  20
```

<210> SEQ ID NO 70
<211> LENGTH: 20
<212> TYPE: DNA
<213> ORGANISM: Artificial sequence
<220> FEATURE:
<223> OTHER INFORMATION: Synthetic PCR  reverse primer sequence targeting enolase

<400> SEQUENCE: 70
aaactcactg ggagaatggg 20

<210> SEQ ID NO 71
<211> LENGTH: 20
<212> TYPE: DNA
<213> ORGANISM: Artificial sequence
<220> FEATURE:
<223> OTHER INFORMATION: Synthetic PCR forward primer sequence targeting pyruvate decarboxylase (PDC).

<400> SEQUENCE: 71
gcgataaagt tgccgtgtta 20

<210> SEQ ID NO 72
<211> LENGTH: 20
<212> TYPE: DNA
<213> ORGANISM: Artificial sequence
<220> FEATURE:
<223> OTHER INFORMATION: Synthetic PCR reverse primer sequence targeting pyruvate decarboxylase (PDC)

<400> SEQUENCE: 72
ccacctaaag catcagcaaa 20

<210> SEQ ID NO 73
<211> LENGTH: 20
<212> TYPE: DNA
<213> ORGANISM: Artificial sequence
<220> FEATURE:
<223> OTHER INFORMATION: Synthetic PCR forward primer sequence targeting nitrite reductase (nirA)

<400> SEQUENCE: 73
aattatgcgc ggctattctt 20

<210> SEQ ID NO 74
<211> LENGTH: 20
<212> TYPE: DNA
<213> ORGANISM: Artificial sequence
<220> FEATURE:
<223> OTHER INFORMATION: Synthetic PCR reverse primer sequence targeting nitrite reductase (nirA)

<400> SEQUENCE: 74
aaccacatta aacgggcttt 20

<210> SEQ ID NO 75
<211> LENGTH: 148
<212> TYPE: DNA
<213> ORGANISM: Artificial sequence
<220> FEATURE:
<223> OTHER INFORMATION: Synthetic ssDNA oligonucleotide sequence (PDCopt1 oligo)

<400> SEQUENCE: 75
gaagaaacct taaaatttat tgccaatcgc gataaagttg ccgtgttagt tggttctaaa 60
ttaagagctg ctggtgctga agaagctgct gttaaatttg ctgatgcttt aggtggtgca 120
gttgctacta tggctgctgc caaatctt 148

<210> SEQ ID NO 76
<211> LENGTH: 122
<212> TYPE: DNA
<213> ORGANISM: Artificial sequence

```
<220> FEATURE:
<223> OTHER INFORMATION: synthetic ssDNA oligonucleotide sequence
      (nirA_oligo).

<400> SEQUENCE: 76

atgaagaagt attgaaatta tgcgcggcta ttcttagtgt ttatagtgag tgtgcattgg     60

aagaaggttt gagggaaaat agagcaaaag cccgtttaat gtggttaatt gataaatggg    120

gt                                                                   122


<210> SEQ ID NO 77
<211> LENGTH: 67
<212> TYPE: DNA
<213> ORGANISM: Cyanobacterium sp.

<400> SEQUENCE: 77

tttaaaccaa gattagaaaa tccatttcat taacgtaaac caacataatt aggagaaatt     60

aattaca                                                               67


<210> SEQ ID NO 78
<211> LENGTH: 283
<212> TYPE: DNA
<213> ORGANISM: Cyanobacterium sp.

<400> SEQUENCE: 78

gaatgtaaac tttcactaat ttagtgggaa aatctacggc aaaataagtt ataaaataac     60

agataaagcc gtttttacta acaataattg ttaatagttg aaagtctata tttatcttag    120

attcttcact attaactaac atttaaaaat caatttaatt ccttgcctag tttcttttaa    180

agaaatttaa ttccgagggc taggcaagat aaaatccaaa attgaccagc gtattttaaa    240

cgttgactct gattgtgtaa caggagaatt cctaaaaaaa gct                      283


<210> SEQ ID NO 79
<211> LENGTH: 187
<212> TYPE: DNA
<213> ORGANISM: Artificial Sequence
<220> FEATURE:
<223> OTHER INFORMATION: Synthetic intergenic sequence

<400> SEQUENCE: 79

atctcctgat ccacacccgg acatctccat agtctgggcc agtctgagga ctggtggatc     60

agggccgtga atttacagta tttcagttac cgctctatcc ttatccttat ccgctcaaga    120

gcagagagtt aataggatcc gctaggatat cggtaccgta ttttggatga taaggaggat    180

cagcctt                                                              187
```